US010667688B2

(12) United States Patent
Khachaturian et al.

(10) Patent No.: US 10,667,688 B2
(45) Date of Patent: Jun. 2, 2020

(54) MULTI-VITAL SIGN DETECTOR OF SPO2 BLOOD OXYGENATION AND HEART RATE FROM A PHOTOPLETHYSMOGRAM SENSOR AND RESPIRATION RATE, HEART RATE VARIABILITY AND BLOOD PRESSURE FROM A MICRO DYNAMIC LIGHT SCATTERING SENSOR IN AN ELECTRONIC MEDICAL RECORDS SYSTEM

(71) Applicant: ARC Devices Ltd., Dublin (IE)

(72) Inventors: Mark Khachaturian, Boca Raton, FL (US); Michael Smith, Lakeway, TX (US); Irwin Gross, Boca Raton, FL (US); Christine Tengler Cherepy, Boca Raton, FL (US)

(73) Assignee: ARC Devices Ltd., Dublin (IE)

( * ) Notice: Subject to any disclaimer, the term of this patent is extended or adjusted under 35 U.S.C. 154(b) by 150 days.

(21) Appl. No.: 16/024,784

(22) Filed: Jun. 30, 2018

(65) Prior Publication Data
US 2018/0303342 A1    Oct. 25, 2018

Related U.S. Application Data

(63) Continuation of application No. 15/438,751, filed on Feb. 21, 2017, now Pat. No. 10,492,684.

(51) Int. Cl.
*A61B 5/00*     (2006.01)
*A61B 5/024*    (2006.01)
(Continued)

(52) U.S. Cl.
CPC ............ *A61B 5/0008* (2013.01); *A61B 5/002* (2013.01); *A61B 5/02241* (2013.01);
(Continued)

(58) Field of Classification Search
None
See application file for complete search history.

(56) References Cited

U.S. PATENT DOCUMENTS 3,647,299 A    3/1972  Lavallee et al.
4,063,551 A    12/1977 Sweeney
(Continued)

FOREIGN PATENT DOCUMENTS

CN    1271562 A    11/2000
CN    102198004 A    9/2011
(Continued)

OTHER PUBLICATIONS

Cepada, ICDAI-DMSS: Iligan City Diabetes Association Inc. Diabetes Monitoring Support System, Department of Information Technology School of Computer Studies, Mindanao State University—Iligan Institute of Technology, Mar. 2011, downloaded from the Internet on Feb. 4, 2018.
(Continued)

*Primary Examiner* — Brian T Gedeon
(74) *Attorney, Agent, or Firm* — Michael G. Smith, Esq.

(57) ABSTRACT

In some implementations, an apparatus includes a first microprocessor, a digital infrared sensor operably coupled to the first microprocessor, an ambient temperature sensor operably coupled to the first microprocessor, a battery operably coupled to the first microprocessor, a multi-vital-sign finger cuff that is detachable and removable from the apparatus and that includes: a printed circuit board, a SpO2 subsystem that is operably coupled to the printed circuit board and that includes a photoplethysmogram sensor and that is operably coupled to the printed circuit board, the photoplethysmogram sensor includes one infrared detector that detects infrared energy at two different transmitted wavelengths, red and near infrared, and a micro dynamic light scattering sensor, the micro dynamic light scattering sensor includes two photo diode receivers and one laser transmitter.

20 Claims, 45 Drawing Sheets

(51) Int. Cl.
  *G06F 1/16* (2006.01)
  *A61B 5/022* (2006.01)
  *G16H 40/40* (2018.01)
  *G16H 10/60* (2018.01)
  *G16H 40/63* (2018.01)
  *A61B 5/145* (2006.01)
  *A61B 5/01* (2006.01)
  *A61B 5/08* (2006.01)
  *A61B 5/1495* (2006.01)
  *A61B 5/0402* (2006.01)
  *A61B 5/103* (2006.01)

(52) U.S. Cl.
  CPC ...... *A61B 5/02416* (2013.01); *A61B 5/02427* (2013.01); *A61B 5/02433* (2013.01); *A61B 5/14542* (2013.01); *A61B 5/6898* (2013.01); *A61B 5/7275* (2013.01); *A61B 5/7278* (2013.01); *A61B 5/743* (2013.01); *G06F 1/1632* (2013.01); *G16H 10/60* (2018.01); *G16H 40/40* (2018.01); *G16H 40/63* (2018.01); *A61B 5/0077* (2013.01); *A61B 5/01* (2013.01); *A61B 5/0402* (2013.01); *A61B 5/0816* (2013.01); *A61B 5/1032* (2013.01); *A61B 5/1495* (2013.01); *A61B 5/746* (2013.01); *A61B 2505/07* (2013.01); *A61B 2560/0252* (2013.01); *A61B 2560/0425* (2013.01); *A61B 2562/028* (2013.01); *A61B 2562/0219* (2013.01); *A61B 2562/0257* (2013.01)

(56) References Cited

U.S. PATENT DOCUMENTS

| | | |
|---|---|---|
| 4,086,915 A | 5/1978 | Kofsky et al. |
| 4,095,117 A | 6/1978 | Nagy |
| 4,281,645 A | 8/1981 | Jobsis |
| 4,315,150 A | 2/1982 | Darringer et al. |
| 4,322,012 A | 3/1982 | Conti |
| 4,394,773 A | 7/1983 | Ruell |
| 4,602,642 A | 7/1986 | O'Hara et al. |
| 4,634,294 A | 1/1987 | Christol et al. |
| 4,709,690 A | 12/1987 | Haber |
| 4,797,840 A | 1/1989 | Fraden |
| 4,956,867 A | 9/1990 | Zurek et al. |
| 5,017,018 A | 5/1991 | Iuchi et al. |
| 5,067,162 A | 11/1991 | Driscoll, Jr. et al. |
| 5,077,476 A | 12/1991 | Rosenthal |
| 5,133,605 A | 7/1992 | Nakamura |
| 5,150,969 A | 9/1992 | Goldberg et al. |
| 5,272,340 A | 12/1993 | Anbar |
| 5,325,442 A | 6/1994 | Knapp |
| 5,351,303 A | 9/1994 | Willmore |
| 5,368,038 A | 11/1994 | Fraden |
| 5,398,681 A | 3/1995 | Kupershmidt |
| 5,689,576 A | 11/1997 | Schneider et al. |
| 5,737,439 A | 4/1998 | Lapsley et al. |
| 5,743,644 A | 4/1998 | Kobayashi |
| 5,909,501 A | 6/1999 | Thebaud |
| 5,940,526 A | 8/1999 | Setlak et al. |
| 5,953,441 A | 9/1999 | Setlak |
| 6,001,066 A | 12/1999 | Canfield et al. |
| 6,095,682 A | 8/2000 | Hollander et al. |
| 6,118,890 A | 9/2000 | Senior |
| 6,134,340 A | 10/2000 | Hsu et al. |
| 6,213,952 B1 | 4/2001 | Finarov et al. |
| 6,241,288 B1 | 6/2001 | Bergenek et al. |
| 6,286,994 B1 | 9/2001 | Boesel et al. |
| 6,289,114 B1 | 9/2001 | Mainguet |
| 6,292,685 B1 | 9/2001 | Pompei |
| 6,327,376 B1 | 12/2001 | Harkin |
| 6,343,141 B1 | 1/2002 | Okada et al. |
| 6,358,216 B1 | 3/2002 | Kraus et al. |
| 6,445,938 B1 | 9/2002 | Berman et al. |
| 6,466,202 B1 | 10/2002 | Suso et al. |
| 6,483,929 B1 | 11/2002 | Murakami et al. |
| 6,505,059 B1 | 1/2003 | Kollias et al. |
| 6,546,122 B1 | 4/2003 | Russo |
| 6,560,352 B2 | 5/2003 | Rowe et al. |
| 6,587,701 B1 | 7/2003 | Stranc et al. |
| 6,728,560 B2 | 4/2004 | Kollias et al. |
| 6,742,927 B2 | 6/2004 | Bellifemine |
| 6,751,342 B2 | 6/2004 | Shepard |
| 6,757,412 B1 | 6/2004 | Parsons |
| 6,819,950 B2 | 11/2004 | Mills |
| 6,832,000 B2 | 12/2004 | Herman et al. |
| 6,985,763 B2 | 1/2006 | Boas et al. |
| 7,092,376 B2 | 8/2006 | Schuman |
| 7,140,768 B2 | 11/2006 | Prabhakar |
| 7,214,953 B2 | 5/2007 | Setlak et al. |
| 7,321,701 B2 | 1/2008 | Setlak et al. |
| 7,339,685 B2 | 3/2008 | Carlson et al. |
| 7,346,386 B2 | 3/2008 | Pompei |
| 7,351,974 B2 | 4/2008 | Setlak |
| 7,358,514 B2 | 4/2008 | Setlak et al. |
| 7,358,515 B2 | 4/2008 | Setlak et al. |
| 7,361,919 B2 | 4/2008 | Setlak |
| 7,433,729 B2 | 10/2008 | Setlak et al. |
| 7,520,668 B2 | 4/2009 | Chen |
| 7,572,056 B2 | 8/2009 | Lane |
| 7,651,266 B2 | 1/2010 | Bellifemine |
| 7,671,351 B2 | 3/2010 | Setlak et al. |
| 7,787,938 B2 | 8/2010 | Pompei |
| 7,915,601 B2 | 3/2011 | Setlak et al. |
| 8,128,280 B2 | 3/2012 | Bellifemine |
| 8,194,942 B2 | 6/2012 | Tobe et al. |
| 8,213,689 B2 | 7/2012 | Yagnik et al. |
| 8,249,547 B1 | 8/2012 | Fellner |
| 8,401,285 B1 | 3/2013 | Rezaee et al. |
| 8,452,382 B1 | 5/2013 | Roth |
| 8,493,482 B2 | 7/2013 | Cote et al. |
| 8,517,603 B2 | 8/2013 | Fraden |
| 8,527,038 B2 | 9/2013 | Moon et al. |
| 8,617,081 B2 | 12/2013 | Mestha et al. |
| 8,693,739 B2 | 4/2014 | Weng et al. |
| 8,849,379 B2 | 9/2014 | Abreu |
| 8,950,935 B1 | 2/2015 | Khachaturian et al. |
| 8,965,090 B1 | 2/2015 | Khachaturian et al. |
| D723,951 S | 3/2015 | Gross et al. |
| D723,952 S | 3/2015 | Gross et al. |
| 9,008,458 B2 | 4/2015 | Pack |
| D738,757 S | 9/2015 | Gross et al. |
| 9,149,216 B2 | 10/2015 | Eisen et al. |
| 9,262,826 B2 | 2/2016 | Khachaturian et al. |
| 9,282,896 B2 | 3/2016 | Crawley et al. |
| 9,305,350 B2 | 4/2016 | Crawley et al. |
| 9,321,394 B2 | 4/2016 | Bouffay et al. |
| 9,324,144 B2 | 4/2016 | Khachaturian et al. |
| 9,330,459 B2 | 5/2016 | Crawley et al. |
| 9,406,125 B2 | 8/2016 | Khachaturian et al. |
| 9,442,065 B2 | 9/2016 | Gulati et al. |
| 9,478,025 B2 | 10/2016 | Khachaturian et al. |
| 9,494,567 B2 | 11/2016 | Islam |
| 9,495,744 B2 | 11/2016 | Khachaturian et al. |
| 9,497,534 B2 | 11/2016 | Prest et al. |
| 9,501,824 B2 | 11/2016 | Khachaturian et al. |
| 9,508,141 B2 | 11/2016 | Khachaturian et al. |
| 9,591,968 B2 | 3/2017 | Gross et al. |
| 9,629,545 B2 | 4/2017 | Gross et al. |
| 9,629,546 B2 | 4/2017 | Gross et al. |
| 9,629,547 B2 | 4/2017 | Gross et al. |
| 9,636,018 B2 | 5/2017 | Gross et al. |
| 9,636,457 B2 | 5/2017 | Newberry et al. |
| 9,642,527 B2 | 5/2017 | Gross et al. |
| 9,642,528 B2 | 5/2017 | Gross et al. |
| 9,642,538 B2 | 5/2017 | Newberry |
| 9,642,578 B2 | 5/2017 | Newberry |
| 9,651,533 B2 | 5/2017 | Islam |
| 9,691,146 B2 | 6/2017 | Khachaturian et al. |
| 9,713,425 B2 | 7/2017 | Gross et al. |
| 9,721,339 B2 | 8/2017 | Khachaturian et al. |
| 9,743,834 B2 | 8/2017 | Gross et al. |

(56) References Cited

U.S. PATENT DOCUMENTS

| | | |
|---|---|---|
| 9,750,409 B2 | 9/2017 | Gross et al. |
| 9,750,410 B2 | 9/2017 | Gross et al. |
| 9,750,411 B2 | 9/2017 | Gross et al. |
| 9,750,412 B2 | 9/2017 | Gross et al. |
| 9,757,032 B2 | 9/2017 | Gross et al. |
| 9,757,040 B2 | 9/2017 | Islam |
| 9,775,517 B2 | 10/2017 | Gross et al. |
| 9,775,518 B2 | 10/2017 | Gross et al. |
| 9,782,073 B2 | 10/2017 | Gross et al. |
| 9,782,074 B2 | 10/2017 | Gross et al. |
| 9,788,723 B2 | 10/2017 | Gross et al. |
| 9,788,767 B1 | 10/2017 | Newberry |
| 9,795,297 B2 | 10/2017 | Gross et al. |
| 9,801,543 B2 | 10/2017 | Gross et al. |
| 9,854,973 B2 | 1/2018 | Crawley et al. |
| 9,861,286 B1 | 1/2018 | Islam |
| 9,872,620 B2 | 1/2018 | Gross et al. |
| 9,881,369 B2 | 1/2018 | Crawley et al. |
| 9,885,698 B2 | 2/2018 | Islam |
| 9,888,849 B2 | 2/2018 | Gross et al. |
| 9,888,850 B2 | 2/2018 | Gross et al. |
| 9,888,851 B2 | 2/2018 | Gross et al. |
| 9,888,852 B2 | 2/2018 | Gross et al. |
| 9,895,061 B2 | 2/2018 | Gross et al. |
| 9,895,062 B2 | 2/2018 | Gross et al. |
| 9,931,035 B2 | 4/2018 | Gross et al. |
| 9,974,438 B2 | 5/2018 | Gross et al. |
| 10,074,175 B2 | 9/2018 | Khachaturian et al. |
| 2001/0005424 A1 | 6/2001 | Marksteiner |
| 2002/0067845 A1 | 6/2002 | Griffis |
| 2002/0076089 A1 | 6/2002 | Muramatsu et al. |
| 2002/0077850 A1 | 6/2002 | McMenimen et al. |
| 2002/0138768 A1 | 9/2002 | Murakami et al. |
| 2002/0143257 A1 | 10/2002 | Newman et al. |
| 2002/0172410 A1 | 11/2002 | Shepard |
| 2003/0069486 A1 | 4/2003 | Sueppel et al. |
| 2003/0069487 A1 | 4/2003 | Mortara |
| 2003/0078622 A1 | 4/2003 | Cansell et al. |
| 2003/0123714 A1 | 7/2003 | O'Gorman et al. |
| 2003/0126448 A1 | 7/2003 | Russo |
| 2003/0169910 A1 | 9/2003 | Reisman et al. |
| 2003/0190062 A1 | 10/2003 | Noro et al. |
| 2004/0013162 A1 | 1/2004 | Beerwerth |
| 2004/0019293 A1 | 1/2004 | Schweitzer et al. |
| 2004/0097818 A1 | 5/2004 | Schmid et al. |
| 2004/0116822 A1 | 6/2004 | Lindsey |
| 2004/0120383 A1 | 6/2004 | Kennedy et al. |
| 2004/0153341 A1 | 8/2004 | Brandt et al. |
| 2004/0186357 A1 | 9/2004 | Soderberg et al. |
| 2004/0193068 A1 | 9/2004 | Burton et al. |
| 2005/0023991 A1 | 2/2005 | Kemper |
| 2005/0043602 A1 | 2/2005 | Freger et al. |
| 2005/0054908 A1 | 3/2005 | Blank et al. |
| 2005/0203350 A1 | 9/2005 | Beck |
| 2005/0206518 A1 | 9/2005 | Welch et al. |
| 2005/0209515 A1 | 9/2005 | Hockersmith et al. |
| 2005/0288571 A1 | 12/2005 | Perkins et al. |
| 2006/0004271 A1 | 1/2006 | Peyser et al. |
| 2006/0030759 A1 | 2/2006 | Weiner et al. |
| 2006/0045316 A1 | 3/2006 | Hauke et al. |
| 2006/0110015 A1 | 5/2006 | Rowe |
| 2006/0116555 A1 | 6/2006 | Pavlidis et al. |
| 2006/0155589 A1 | 7/2006 | Lane et al. |
| 2006/0195024 A1 | 8/2006 | Benni |
| 2006/0209631 A1 | 9/2006 | Melese et al. |
| 2006/0225737 A1 | 10/2006 | Lobbi |
| 2006/0238333 A1 | 10/2006 | Welch et al. |
| 2006/0278293 A1 | 12/2006 | Weber et al. |
| 2006/0293921 A1 | 12/2006 | McCarthy et al. |
| 2007/0013511 A1 | 1/2007 | Weiner et al. |
| 2007/0049834 A1 | 3/2007 | Tao et al. |
| 2007/0069887 A1 | 3/2007 | Welch et al. |
| 2007/0080233 A1 | 4/2007 | Forster et al. |
| 2007/0135866 A1 | 6/2007 | Baker et al. |
| 2007/0142731 A1 | 6/2007 | Ye et al. |
| 2007/0183475 A1 | 8/2007 | Hutcherson |
| 2007/0185390 A1 | 8/2007 | Perkins et al. |
| 2007/0189358 A1 | 8/2007 | Lane et al. |
| 2008/0033308 A1 | 2/2008 | Cen et al. |
| 2008/0064967 A1 | 3/2008 | Ide |
| 2008/0149701 A1 | 6/2008 | Lane |
| 2008/0175301 A1 | 7/2008 | Chen |
| 2008/0208019 A1 | 8/2008 | Nitzan |
| 2008/0281167 A1 | 11/2008 | Soderberg et al. |
| 2008/0281168 A1 | 11/2008 | Gibson et al. |
| 2008/0300473 A1 | 12/2008 | Benni |
| 2009/0062674 A1 | 3/2009 | Jin et al. |
| 2009/0100333 A1 | 4/2009 | Xiao |
| 2009/0103469 A1 | 4/2009 | Smith et al. |
| 2009/0105549 A1 | 4/2009 | Smith et al. |
| 2009/0105566 A1 | 4/2009 | Smith et al. |
| 2009/0105567 A1 | 4/2009 | Smith et al. |
| 2009/0131774 A1 | 5/2009 | Sweitzer et al. |
| 2009/0141124 A1 | 6/2009 | Liu et al. |
| 2009/0172591 A1 | 7/2009 | Pomper |
| 2009/0175317 A1 | 7/2009 | Chan et al. |
| 2009/0177248 A1 | 7/2009 | Roberts |
| 2009/0182526 A1 | 7/2009 | Quinn et al. |
| 2009/0196475 A1 | 8/2009 | Demirli et al. |
| 2009/0221880 A1 | 9/2009 | Soderberg et al. |
| 2010/0049077 A1 | 2/2010 | Sadleir et al. |
| 2010/0056928 A1 | 3/2010 | Zuzak |
| 2010/0094098 A1 | 4/2010 | Smith et al. |
| 2010/0094145 A1 | 4/2010 | Ye et al. |
| 2010/0121164 A1 | 5/2010 | Donars et al. |
| 2010/0191472 A1 | 7/2010 | Doniger et al. |
| 2010/0265986 A1 | 10/2010 | Mullin et al. |
| 2010/0280331 A1 | 11/2010 | Kaufman et al. |
| 2010/0284436 A1 | 11/2010 | Lane et al. |
| 2010/0298650 A1 | 11/2010 | Moon et al. |
| 2010/0322282 A1 | 12/2010 | Lane et al. |
| 2010/0324380 A1 | 12/2010 | Perkins et al. |
| 2011/0047298 A1 | 2/2011 | Eaton et al. |
| 2011/0054267 A1 | 3/2011 | Fidacaro et al. |
| 2011/0112791 A1 | 5/2011 | Pak et al. |
| 2011/0121978 A1 | 5/2011 | Schwörer et al. |
| 2011/0140896 A1 | 6/2011 | Menzel |
| 2011/0148622 A1 | 6/2011 | Judy et al. |
| 2011/0152629 A1 | 6/2011 | Eaton et al. |
| 2011/0158283 A1 | 6/2011 | Meyerson et al. |
| 2011/0178376 A1 | 7/2011 | Judy et al. |
| 2011/0199203 A1 | 8/2011 | Hsu |
| 2011/0224518 A1 | 9/2011 | Tindi et al. |
| 2011/0228810 A1 | 9/2011 | O'Hara et al. |
| 2011/0228811 A1 | 9/2011 | Fraden |
| 2011/0230731 A1 | 9/2011 | Rantala et al. |
| 2011/0237906 A1 | 9/2011 | Kabakov |
| 2011/0251493 A1 | 10/2011 | Poh et al. |
| 2011/0275978 A1 | 11/2011 | Hyde et al. |
| 2011/0276698 A1 | 11/2011 | Bigioi et al. |
| 2011/0285248 A1 | 11/2011 | Cewers |
| 2011/0286644 A1 | 11/2011 | Kislal |
| 2011/0291837 A1 | 12/2011 | Rantala |
| 2011/0291838 A1 | 12/2011 | Rantala |
| 2012/0004516 A1 | 1/2012 | Eng et al. |
| 2012/0005248 A1 | 1/2012 | Garudadri et al. |
| 2012/0022348 A1 | 1/2012 | Droitcour et al. |
| 2012/0026119 A1 | 2/2012 | Judy et al. |
| 2012/0053422 A1 | 3/2012 | Rantala |
| 2012/0094600 A1 | 4/2012 | DelloStritto et al. |
| 2012/0096367 A1 | 4/2012 | DelloStritto et al. |
| 2012/0130197 A1 | 5/2012 | Kugler et al. |
| 2012/0130251 A1 | 5/2012 | Huff |
| 2012/0130252 A1 | 5/2012 | Pohjanen et al. |
| 2012/0136559 A1 | 5/2012 | Rothschild |
| 2012/0150482 A1 | 6/2012 | Yildizyan et al. |
| 2012/0154152 A1 | 6/2012 | Rantala et al. |
| 2012/0165617 A1 | 6/2012 | Vesto et al. |
| 2012/0179011 A1 | 7/2012 | Moon et al. |
| 2012/0242844 A1 | 9/2012 | Walker et al. |
| 2012/0271130 A1 | 10/2012 | Benni |
| 2012/0302905 A1 | 11/2012 | Kaski |
| 2012/0319848 A1 | 12/2012 | Coffeng |
| 2012/0330126 A1 | 12/2012 | Hoppe et al. |

(56) References Cited

U.S. PATENT DOCUMENTS

| | | |
|---|---|---|
| 2013/0002420 A1 | 1/2013 | Perkins et al. |
| 2013/0006093 A1 | 1/2013 | Raleigh et al. |
| 2013/0023772 A1 | 1/2013 | Kinsley et al. |
| 2013/0035599 A1 | 2/2013 | De Bruijn et al. |
| 2013/0060098 A1 | 3/2013 | Thomsen et al. |
| 2013/0085348 A1 | 4/2013 | Devenyi et al. |
| 2013/0085708 A1 | 4/2013 | Sattler |
| 2013/0085758 A1 | 4/2013 | Csoma et al. |
| 2013/0086122 A1 | 4/2013 | Devenyi et al. |
| 2013/0109927 A1 | 5/2013 | Menzel |
| 2013/0109929 A1 | 5/2013 | Menzel |
| 2013/0110311 A1 | 5/2013 | Ver Steeg et al. |
| 2013/0137939 A1 | 5/2013 | He et al. |
| 2013/0138003 A1 | 5/2013 | Kaski |
| 2013/0162423 A1 | 6/2013 | Rowe et al. |
| 2013/0172770 A1 | 7/2013 | Muehlsteff |
| 2013/0178719 A1 | 7/2013 | Balji et al. |
| 2013/0211265 A1 | 8/2013 | Bedingham et al. |
| 2013/0215928 A1 | 8/2013 | Bellifemine |
| 2013/0245457 A1 | 9/2013 | Kinsley et al. |
| 2013/0245462 A1 | 9/2013 | Capdevila et al. |
| 2013/0245467 A1 | 9/2013 | St. Pierre et al. |
| 2013/0245488 A1 | 9/2013 | Quinn et al. |
| 2013/0245489 A1 | 9/2013 | Mullin et al. |
| 2013/0265327 A1 | 10/2013 | Vann et al. |
| 2013/0267792 A1 | 10/2013 | Petersen et al. |
| 2013/0267793 A1 | 10/2013 | Meador et al. |
| 2013/0267861 A1 | 10/2013 | Vassallo et al. |
| 2013/0267873 A1 | 10/2013 | Fuchs |
| 2013/0268283 A1 | 10/2013 | Vann et al. |
| 2013/0271283 A1 | 10/2013 | Judy et al. |
| 2013/0271591 A1 | 10/2013 | Van Leest et al. |
| 2013/0296716 A1 | 11/2013 | Kurzenberger |
| 2013/0307536 A1 | 11/2013 | Feng et al. |
| 2013/0310669 A1 | 11/2013 | Nitzan |
| 2013/0322729 A1 | 12/2013 | Mestha et al. |
| 2013/0334298 A1 | 12/2013 | Sakpal et al. |
| 2013/0342691 A1 | 12/2013 | Lewis et al. |
| 2014/0003461 A1 | 1/2014 | Roth |
| 2014/0003462 A1 | 1/2014 | Roth |
| 2014/0031637 A1 | 1/2014 | Fidacaro et al. |
| 2014/0032241 A1 | 1/2014 | Coffeng |
| 2014/0058213 A1 | 2/2014 | Abu-Tarif et al. |
| 2014/0171805 A1 | 2/2014 | Mullin et al. |
| 2014/0064327 A1 | 3/2014 | Roth |
| 2014/0064328 A1 | 3/2014 | Roth |
| 2014/0064333 A1 | 3/2014 | Roth |
| 2014/0072190 A1 | 3/2014 | Wu et al. |
| 2014/0072228 A1 | 3/2014 | Rubinstein |
| 2014/0072229 A1 | 3/2014 | Wadhwa |
| 2014/0073860 A1 | 3/2014 | Uriti |
| 2014/0088434 A1 | 3/2014 | Roth |
| 2014/0088435 A1 | 3/2014 | Roth |
| 2014/0088436 A1 | 3/2014 | Roth |
| 2014/0088446 A1 | 3/2014 | St. Pierre et al. |
| 2014/0112367 A1 | 4/2014 | Roth |
| 2014/0112940 A1 | 4/2014 | Lane |
| 2014/0114600 A1 | 4/2014 | Roth |
| 2014/0121481 A1 | 5/2014 | Abrams et al. |
| 2014/0155759 A1 | 6/2014 | Kaestle et al. |
| 2014/0189576 A1 | 7/2014 | Carmi |
| 2014/0221766 A1 | 8/2014 | Kinast |
| 2014/0221796 A1 | 8/2014 | Lia et al. |
| 2014/0232516 A1 | 8/2014 | Stivoric et al. |
| 2014/0235963 A1 | 8/2014 | Edwards et al. |
| 2014/0243648 A1 | 8/2014 | Dubielczyk |
| 2014/0247058 A1 | 9/2014 | Mortara |
| 2014/0253709 A1 | 9/2014 | Bresch et al. |
| 2014/0291527 A1 | 10/2014 | Okudo et al. |
| 2014/0321505 A1 | 10/2014 | Rill et al. |
| 2014/0330098 A1 | 11/2014 | Merritt et al. |
| 2014/0331298 A1 | 11/2014 | Baker et al. |
| 2015/0025344 A1 | 1/2015 | Benni |
| 2015/0036350 A1 | 2/2015 | Palikaras et al. |
| 2015/0045663 A1 | 2/2015 | Palikaras et al. |
| 2015/0073828 A1 | 3/2015 | Mortara et al. |
| 2015/0077268 A1 | 3/2015 | Lane et al. |
| 2015/0088538 A1 | 3/2015 | Dykes et al. |
| 2015/0094914 A1 | 4/2015 | Abreu |
| 2015/0109617 A1 | 4/2015 | Gilbert et al. |
| 2015/0110153 A1 | 4/2015 | Hoblit et al. |
| 2015/0126847 A1 | 5/2015 | Balji et al. |
| 2015/0148622 A1 | 5/2015 | Moyer et al. |
| 2015/0150453 A1 | 6/2015 | Abreu |
| 2015/0157275 A1 | 6/2015 | Swamy et al. |
| 2015/0182114 A1 | 7/2015 | Wang et al. |
| 2015/0182172 A1 | 7/2015 | Shelley et al. |
| 2015/0201872 A1 | 7/2015 | Benni |
| 2015/0257653 A1 | 9/2015 | Hyde et al. |
| 2015/0265159 A1 | 9/2015 | Lane et al. |
| 2015/0272452 A1 | 10/2015 | Mullin et al. |
| 2015/0282747 A1 | 10/2015 | Thiele |
| 2015/0308946 A1 | 10/2015 | Duffy et al. |
| 2015/0327811 A1 | 11/2015 | Mortara |
| 2015/0339805 A1 | 11/2015 | Ohba |
| 2015/0366471 A1 | 12/2015 | LeBoeuf et al. |
| 2016/0000335 A1 | 1/2016 | Khachaturian et al. |
| 2016/0007922 A1 | 1/2016 | Sen et al. |
| 2016/0018257 A1 | 1/2016 | Mirov et al. |
| 2016/0035084 A1 | 2/2016 | Khachaturian et al. |
| 2016/0051171 A1 | 2/2016 | Pikov et al. |
| 2016/0058347 A1 | 3/2016 | Reichgott et al. |
| 2016/0066863 A1 | 3/2016 | Thaveeprungsriporn et al. |
| 2016/0100781 A1 | 4/2016 | Bechtel et al. |
| 2016/0117813 A1 | 4/2016 | Gross et al. |
| 2016/0136367 A1 | 5/2016 | Varney |
| 2016/0150978 A1 | 6/2016 | Yuen et al. |
| 2016/0302666 A1 | 10/2016 | Shaya |
| 2016/0361002 A1 | 12/2016 | Palikaras et al. |
| 2017/0014035 A1 | 1/2017 | Newberry |
| 2017/0014056 A1 | 1/2017 | Newberry |
| 2017/0014572 A1 | 1/2017 | Newberry et al. |
| 2017/0071550 A1 | 3/2017 | Newberry |
| 2017/0106139 A1 | 4/2017 | Adamczyk et al. |
| 2017/0181678 A1 | 6/2017 | Newberry |
| 2017/0189629 A1 | 7/2017 | Newberry |
| 2017/0215751 A1 | 8/2017 | Newberry |
| 2017/0215793 A1 | 8/2017 | Newberry |
| 2017/0215811 A1 | 8/2017 | Newberry |
| 2017/0274146 A1 | 9/2017 | Newberry et al. |
| 2017/0281065 A1 | 10/2017 | Newberry |
| 2017/0325698 A1 | 11/2017 | Allec et al. |
| 2018/0020964 A1 | 1/2018 | Newberry |
| 2018/0055454 A1 | 3/2018 | Newberry |
| 2018/0108275 A1 | 4/2018 | Newberry et al. |
| 2018/0116604 A1 | 5/2018 | Newberry |
| 2018/0116605 A1 | 5/2018 | Newberry |
| 2018/0125431 A1 | 5/2018 | Newberry |
| 2018/0153418 A1 | 6/2018 | Sullivan et al. |
| 2018/0214088 A1 | 8/2018 | Newberry |
| 2018/0235532 A1 | 8/2018 | Newberry |
| 2018/0303433 A1 | 10/2018 | Newberry |
| 2018/0310891 A1 | 11/2018 | Fine et al. |
| 2019/0060568 A1 | 2/2019 | Newberry et al. |
| 2019/0076601 A1 | 3/2019 | Newberry et al. |
| 2019/0105001 A1 | 4/2019 | Newberry |
| 2019/0134308 A1 | 5/2019 | Newberry |
| 2019/0167206 A1 | 6/2019 | Newberry |

FOREIGN PATENT DOCUMENTS

| | | |
|---|---|---|
| CN | 202619644 U | 4/2013 |
| CN | 203861234 U | 10/2014 |
| CN | 105662434 A | 4/2016 |
| CN | 105919601 A | 9/2016 |
| CN | 206342477 U | 7/2017 |
| CN | 206443702 U | 8/2017 |
| DE | 19827343 A1 | 12/1999 |
| EP | 0404562 A2 | 11/1991 |
| EP | 0537383 A1 | 4/1993 |
| EP | 0630203 B1 | 12/1994 |
| EP | 2045590 A1 | 4/2009 |
| EP | 2380493 A1 | 10/2011 |
| EP | 2674735 A1 | 12/2013 |

(56) References Cited

FOREIGN PATENT DOCUMENTS

| | | |
|---|---|---|
| EP | 2836107 A1 | 2/2015 |
| EP | 2997886 A1 | 3/2016 |
| GB | 2291498 A | 1/1996 |
| GB | 2500719 A1 | 10/2013 |
| GB | 1322906.7 A | 1/2015 |
| GB | 2521620 A | 1/2015 |
| GB | 2523741 A | 9/2015 |
| GB | 2528044 A | 1/2016 |
| GB | 2561771 A | 10/2018 |
| JP | 2002527136 A | 8/2002 |
| WO | 1992002792 A1 | 2/1992 |
| WO | 1998001730 A1 | 1/1998 |
| WO | 1999039166 A1 | 8/1999 |
| WO | 1999067611 A1 | 12/1999 |
| WO | 2000021437 A3 | 7/2001 |
| WO | 2005024710 A1 | 3/2005 |
| WO | 2005024712 A1 | 3/2005 |
| WO | 2005078636 A3 | 1/2006 |
| WO | 2008053474 A2 | 5/2008 |
| WO | 2011013132 A1 | 2/2011 |
| WO | 2011063266 A2 | 5/2011 |
| WO | 2012093311 A1 | 7/2012 |
| WO | 2013144559 A1 | 10/2013 |
| WO | 2013144652 A1 | 10/2013 |
| WO | 2014082071 A1 | 5/2014 |
| WO | 2015049268 A1 | 4/2015 |
| WO | 2015128657 A1 | 9/2015 |
| WO | 2015154105 A1 | 10/2015 |
| WO | 2016005050 A1 | 1/2016 |
| WO | 2016040540 A1 | 3/2016 |
| WO | 2016054079 A1 | 4/2016 |
| WO | 2016120870 A1 | 8/2016 |
| WO | 2017120615 A3 | 7/2017 |
| WO | 2017125397 A1 | 7/2017 |

OTHER PUBLICATIONS

Israel Avner Gal, Non-invasive Glucose Measurement, 16th Annual Diabetes Technology Meeting, Bethesda, Maryland, Nov. 10-12, 2012, Diabetes Technology Society, 1157 Chess Drive, Suite 100, Foster City, CA 94404, downloaded from www.diabetestechnology.com on Nov. 16, 2017.

Glucotrack, Product Features, downloaded from www.glucotrack.com/glucotrack-product-features.html.

Shenzhen Creative Industry Co., Ltd., User Manual for Spot-Check Monitor, Ver. 1.3, Jan. 27, 2015, 2/F, Block 3, Nanyou Tian'an Industry Town, 518054 Shenzhen, GD, P.R. China, downloaded from the Internet.

Bindal, Wireless Glucose Monitoring System, downloaded from https://www.scribd.com/document/37054329/Wireless-Glucose-Monitoring-System.

Newberry, Non-Invasive Glucose: Method for Diabetic Health Monitoring using Nitric Oxide Sensing, draft 1.0, Aug. 2017, Sanmina Corp., 13000 S. Memorial Parkway, Huntsville, AL 35803.

Sourceforge, Pulse capture Extract PPG signal from video image of the face, Feb. 10, 2016, https://sourceforge.net/projects/pulsecapture/.

Covidien, Filac 3000 EZ-EZA Electronic Thermometer Operating Manual, 2012, http://www.covidien.com/ImageServer.aspx?contentID=31819&contenttype=application/pdf, retrieved from the Internet on Jul. 24, 2015.

R Fisher, S. Perkins, A. Waiker and E. Wolfart, Frequency Filter, Image Processing Learning Resources, 2003, retrieved from the Internet on Jun. 24, 2014 at http://homepages.inf.ed.ac.uk/rbf/HIPR2/freqfilt.htm.

Gautama, T. and Van Hulle, M., "A phase-based approach to the estimation of the optical flow field using spatial filtering", Neural Netlvorks, IEEE Transactions, 13(5): 1127-1136 (Sep. 2002).

Rubinstein, M., et al., "Motion denoising with application to time-lapse photography," IEEE Computer Vision and Pattern Recognition, CVPR, pp. 313-320 (Jun. 2011).

Wang J., et al., "The cartoon animation filter," ACM Trans. Graph., 25: 1169-1173 (2006).

O. Arikan, Interactive Motion Generation from Examples, ACM Transactions on Graphics (TOG), Proceedings of ACM SIGGRAPH 2002, vol. 21 Issue 3, Jul. 2002, pp. 483-490, ACM New York, NY, USA, ISBN:1-58113-521-1, doi 10.1145/566654.566606, retrieved from the Internet on Jul. 9, 2014 from http://www.okanarikan.com/Papers/SynthesisFromExamples/paper.pdf.

Balakrishnan, Guha, Fredo Durand, and John Guttag. "Detecting pulse from head motions in video." Computer Vision and Pattern Recognition (CVPR), 2013 IEEE Conference on. IEEE, 2013.

Sunghyun Cho, Video deblurring for hand-held cameras using patch-based synthesis, ACM Transactions on Graphics (TOG)—SIGGRAPH 2012 Conference Proceedings, vol. 31 Issue 4, Jul. 2012, Article No. 64, ACM New York, NY, USA, ISSN: 0730-0301 EISSN: 1557-7368 doi 10.1145/2185520/185561, published on Jul. 1, 2012, retrieved from the Internet on Jul. 9, 2014 from http://juew.org/publication/video_deblur.pdf.

Eduardo S.L. Gastal, Adaptive Manifolds for Real-Time High-Dimensional Filtering, ACM Transactions on Graphics (TOG)—SIGGRAPH 2012 Conference Proceedings, vol. 31 Issue 4, Jul. 2012, Article No. 33, ACM New York, NY, USA, ISSN: 0730-0301 EISSN: 1557-7368, doi10.1145/2185520.2185529, retrieved from the Internet on on Jul. 9, 2013 from http://inf.ufrgs.br/~eslgastal/AdaptiveManifolds/Gastal_Oliveira_SIGGRAPH2012_Adaptive_Manifolds.pdf.

C. Liu, Motion magnification, ACM SIGGRAPH 2005, pp. 519-526, 2005, retrieved from http://people.csail.mit.edu/celiu/pdfs/motionmag.pdf on Jul. 9, 2014.

Poveda, Carlos G. Juan, Fundamentals of Microwave Technology for Non-Invasive Blood Glucose Monitoring and Review of the Most Significant Works Developed, Revista Doctorado UMH vol. 1, n°1, 2015—Articulo p6, PhD Program on Industrian and Telecommunication Technologies (TECNIT) nBio Research Group at Systems Engineering Department, Miguel Hernández University, Elche, Spain, Apr. 2015, retrieved from https://www.researchgate.net/publication/298715332 on Nov. 2, 2018.

Saha et al., A Glucose Sensing System Based on Transmission Measurements at Millimetre Waves using Micro strip Patch Antennas, Scientific Reports, 7: 6855, DOI:10.1038/s41598-017-06926-1, Jul. 31, 2017, retrieved from https://www.ncbi.nlm.nih.gov/pmc/articles/PMC5537249/pdf/41598_2017_Article_6926.pdf on Nov. 2, 2018.

Timoner Samson J., and Dennis M. Freeman. "Multi-image gradient-based algorithms for motion estimation." Optical engineering 40.9 (2001): 2003-2016.

Todd, Catherine, et al., Towards Non-Invasive Extraction and Determination of Blood Glucose Levels, Bioengineering 2017, 4, 82, Sep. 27, 2017, retrieved from https://www.ncbi.nlm.nih.gov/pmc/articles/PMC5746749/pdf/bioengineering-04-00082.pdf on Nov. 2, 2018.

Verkruysse, Wim, Lars O. Svaasand, and J. Stuart Nelson. "Remote plethysmographic imaging using ambient light." Optics express 16.26 (2008): 21434-21445.

Hao-Yu Wu, Eulerian Video Magnification for Revealing Subtle Changes in the World, ACM Transactions on Graphics (TOG)—SIGGRAPH 2012 Conference Proceedings, vol. 31 Issue 4, Jul. 2012, Article No. 65, ACM New York, NY, USA, ISSN: 0730-0301 EISSN: 1557-7368 doi 10.1145/2185520.2185561, published on Jul. 1, 2012, retrieved from the Internet on Jul. 9, 2014 from http://people.csail.mit.edu/billf/publications/Eulearian_Video_Magnification.pdf.

Pitzer et al., Detection of Hypoglycemia With the GlucoWatch Biographer, Diabetes Care, vol. 24, No. 5, May 2001, pp. 881-885, retrieved from the Internet from http://citeseerx.ist.psu.edu/viewdoc/download?doi=10.1.1.915.1360&rep=rep1&type=pdf on Nov. 9, 2018.

Islam, S. M. R., et al., "Internet of Things for Health Care: A Comprehensive Survey", Jun. 1, 2015, Digital Object Identifier 10.1109/Access.2015.2437951, IEEE Access vol. 3, 2015, retrieved from the Internet on Oct. 1, 2018.

(56) References Cited

OTHER PUBLICATIONS

Hassanalieragh Moon, et al., Health Monitoring and Management Using Internet-of-Things (IoT) Sensing with Cloud-based Processing: Opportunities and Challenges, 2015 IEEE International Conference on Services Computing, pp. 285-292, 978-1-4673-7281-7/15, DOI 10.1109/SCC.2015.47, retrieved from the Internet on Oct. 1, 2018.

Gravina et al., Multi-Sensor Fusion in Body Sensor Networks: State-of-the-art and research challenges, DOI: 10.1016/j.inffus.2016.09.005, Information Fusion, Sep. 13, 2016, retrieved from the Internet on Oct. 1, 2018 at https://www.researchgate.net/publication/308129451.

Thennadil et al., Comparison of Glucose Concentration in Interstitial Fluid, and Capillary and Venous Blood During Rapid Changes in Blood Glucose Levels, Diabetes Technology & Therapeutics, vol. 3, No. 3, 2001, Mary Ann Liebert, Inc., retrieved from the Internet on Oct. 2, 2018 from http://thenemiirblog.ubiquilight.com/pdf/GlucoseInterstitialvCapillaryvVenous.pdf.

Caduff et al., First human experiments with a novel non-invasive, non-optical continuous glucose monitoring system, Biosensors and Bioelectronics xxx (2003) 1-9, retrieved from the Internet on Oct. 2, 2018.

Klonoff, David C., Noninvasive Blood Glucose Monitoring, Diabetes Care, vol. 20, No. 3, Mar. 1997, pp. 433-437, DOI: 10.2337/diacare.20.3.433, Source: PubMed, retrieved from the Internet on Oct. 2, 2018.

Rossetti et el., Estimating Plasma Glucose from Interstitial Glucose: The Issue of Calibration Algorithms in Commercial Continuous Glucose Monitoring Devices, Sensors 2010, 10, 10936-10952; doi:10.3390/s101210936, ISSN 1424-8220, retrieved from www.mdpi.com/journal/sensors on Oct. 2, 2018.

Khalil et al., Non-Invasive Glucose Measurement Technologies: An Update from 1999 to the Dawn of the New Millennium, Diabetes Technology & Therapeutics, vol. 6, No. 5, 2004, Mary Ann Liebert, Inc., retrieved from the Internet on Oct. 2, 2018 from http://bme240.eng.uci.edu/students/06s/eclin/articles/long.pdf.

Yole, "Non-Invasive Glucose Monitoring Patent Landscape", KnowMade, 2405 route des Dolines, 06902 Sophia Antipolis, France, Tel: +33 489 89 16 20, http://www.knowmade.com, retrieved from the Internet on Oct. 2, 2018, published Sep. 2015.

Berger, Andrew J., Multicomponent blood analysis by near-infrared Raman spectroscopy, Applied Optics, vol. 38, No. 13, May 1, 1999, pp. 2916-2926, retrieved from the Internet on Oct. 2, 2018.

Darwish et al., Wearable and Implantable Wireless Sensor Network Solutions for Healthcare Monitoring, Sensors 2011, 11, 5561-5595; doi:10.3390/s110605561, ISSN 1424-8220, retrieved from www.mdpi.com/journal/sensors on Oct. 2, 2018.

Oliver et al., Glucose sensors: a review of current and emerging technology, Diabetic Medicine, 26, pp. 197-210, 2009 Diabetes UK, retrieved from https://onlinelibrary.wiley.com/doi/epdf/10.1111/j.1464-5491.2008.02642.x on Oct. 2, 2018.

Jurik, Andrew D. et al., Remote Medical Monitoring, University of Virginia, retrieved from http://www.cs.virginia.edu/jurik/docs/jurik-rmm-2008.pdf on Oct. 1, 2018.

Tura, Andrew et al., A Low Frequency Electromagnetic Sensor for Indirect Measurement of Glucose Concentration: In Vitro Experiments in Different Conductive Solutions, Sensors 2010, 10, 5346-5358; doi:10.3390/s100605346, ISSN 1424-8220, retrieved from www.mdpi.com/journal/sensors on Oct. 2, 2018.

Stephen F. Mallin, Noninvasive Prediction of Glucose by Near-Infrared Diffuse Reflectance Spectroscopy, Clinical Chemistry 45:9, 1651-1658 (1999), Oak Ridge Conference, retrieved from the Internet on Oct. 2, 2018 from http://clinchem.aaccjnls.org/content/clinchem/45/9/1651.full.pdf.

Pfützner, Andreas et al., Evaluation of System Accuracy of the GlucoMen LX Plus Blood Glucose Monitoring System With Reference to ISO 15197:2013, Journal of Diabetes Science and Technology 2016, vol. 10(2) 618-619, Diabetes Technology Society, DOI: 10.1177/1932296815613803, retrieved from https://www.ncbi.nlm.nih.gov/pmc/articles/PMC4773971/pdf/10.1177_1932296815613803.pdf on Nov. 2, 2018.

Yitzhak Mendelson, Pulse Oximetry: Theory and Applications for Noninvasive Monitoring, Clin.Chem. 38/9, 1601-1607, (1992), retrieved from the Internet on Oct. 2, 2018.

Yali Zheng, Unobtrusive Sensing and Wearable Devices for Health Informatics, IEEE Transactions on Biomedical Engineering, Mar. 2014, DOI: 10.1109/TBME.2014.2309951, retrieved from the Internet on Oct. 1, 2018 from https://www.researchgate.net/publication/260419901.

John L. Smith, The Pursuit of Noninvasive Glucose: "Hunting the Deceitful Turkey", Fourth Edition, 2015, retrieved from the Internet on Oct. 1, 2018 from http://www.mendosa.com/The%20Pursuit%20of%20Noninvsive%20Glucose,%20Fourth%20Edition.pdf.

Vashist, Sandeep Kumar, Non-Invasive Glucose Monitoring Technology in Diabetes Management: A Review, Analytica Chimica Acta 750 (2012) 16-27, NUS Nanosience and Nanotechnology Initiative (NUSNNI) NanoCore, National University of Singapore, T-Lab Level 11, 5A Engineering Drive 1, Singapore 117580, Singapore, Elsevier B. V., Apr. 2, 2012, retrieved from the Internet on Oct. 2, 2016.

Yilmaz, Tuba et al., Detecting Vital Signs with Wearable Wireless Sensors, Sensors 2010, 10, 10837-10862; doi:10.3390/s101210837, ISSN 1424-8220, Dec. 2, 2010, retrieved from www.mdpi.com/journal/sensors on Oct. 2, 2018.

Pfützner, Andreas, Journal of Diabetes Science and Technology 2016, vol. 10(1) 101-103, Diabetes Technology Society, DOI: 10.1177/1932296815619183, retrieved from retrieved from www.mdpi.com/journal/sensors on Nov. 2, 2018.

Stankovic, John A., Wireless Sensor Networks, Department of Computer Science, University of Virginia Charlottesville, Virginia 22904, Jun. 19, 2006, retrieved from https://www.cs.virginia.edu/~stankovic/psfiles/wsn.pdf on Oct. 1, 2018.

Choi, Heungjae et al., Design and In Vitro Interference Test of Microwave Noninvasive Blood Glucose Monitoring Sensor, IEEE Trans Microw Theory Tech. Oct. 1, 2015; 63(10 Pt 1): 3016-3025, doi: 10.1109/TMTT.2015.2472019, PMCID: PMC4641327, EMSID: EMS65843, PMID: 26568639, retrieved from the Internet on Oct. 2, 2018.

Lai, Xiaochen et al., A Survey of Body Sensor Networks, Sensors 2013, 13, 5406-5447; doi:10.3390/s130505406, ISSN 1424-8220, retrieved from www.mdpi.com/journal/sensors on Oct. 1, 2018.

Bruen et al., Glucose Sensing for Diabetes Monitoring: Recent Developments, Sensors DOI:10.3390/s17081866, Aug. 12, 2017,retrieved from https://pdfs.semanticscholar.org/9a8b/8f1abdd11eae279204c81dbb5525fe473106.pdf?_ga=2.60896047.2075682402.1541162314-1823527149.1541162314 on Nov. 2, 2018.

Facchinetti, Andrea, Continuous Glucose Monitoring Sensors: Past, Present and Future Algorithmic Challenges, Sensors 2016, 16(12), 2093; https://doi.org/10.3390/s16122093, Dec. 9, 2016, retrieved from https://pdfs.semanticscholar.org/6dc7/75fb79fc7ca85d795d8f520d79a03ea45311.pdf?_ga=2.91420569.2075682402.1541162314-1823527149.1541162314 on Nov. 2, 2018.

Larin, Kirill V., et al., Noninvasive Blood Glucose Monitoring With Optical Coherence Tomography, Diabetes Care, vol. 25, No. 12, Dec. 2002, retrieved from the Internet on Oct. 2, 2018.

Chung et al., Simultaneous Measurements of Glucose, Glutamine, Ammonia, Lactate, and Glutamate in Aqueous Solutions by Near-Infrared Spectroscopy, DOI: 10.1366/0003702963906447, Applied Spectroscopy, Feb. 1996, retrieved from www.researchgate.com on Oct. 2, 2018.

Routh, Fourier Transform, Glucose Sensing Neurons in the Ventromedial Hypothalamus, Sensors 2010, 10, 9002-9025; doi:10.3390/s101009002, ISSN 1424-8220, www.mdpi.com/journal/sensors, Aug. 10, 2010, retrieved from the Internet on Oct. 2, 2018 at https://www.researchgate.net/publication/47369031_Glucose_Sensing_Neurons_in_the_Ventromedial_Hypothalamus/download, p. 9009.

Bandodkar et al., Tattoo-Based Noninvasive Glucose Monitoring: A Proof-of-Concept Study, dx.doi.org/10.1021/ac504300n, Anal. Chem. 2015, 87, 394-398, American Chemical Society, retrieved from the Internet on Oct. 2, 2018 at https://pubs.acs.org/doi/pdf/10.1021/ac504300n.

Grose, Julianne H. et al., The Role of PAS Kinase in PASsing the Glucose Signal, Sensors 2010, 10, 5668-5682; doi:10.3390/s100605668, ISSN 1424-8220, www.mdpi.com/journal/sensors, Jun. 4, 2010, retrieved from the Internet on Oct. 2, 2018.

Fernandez, Clara Rodriguez, Needle-Free Diabetes Monitoring: An Interview with the Founder of GlucoWise, Nov. 28, 2016, Labiotech IG, retrieved from the Internet on Oct. 1, 2018.

MULTI-VITAL-SIGN SMARTPHONE SYSTEM 300

DISPLAY OF A MVS SMARTPHONE
1100

DISPLAY OF A MVS SMARTPHONE
1200

FIG. 36
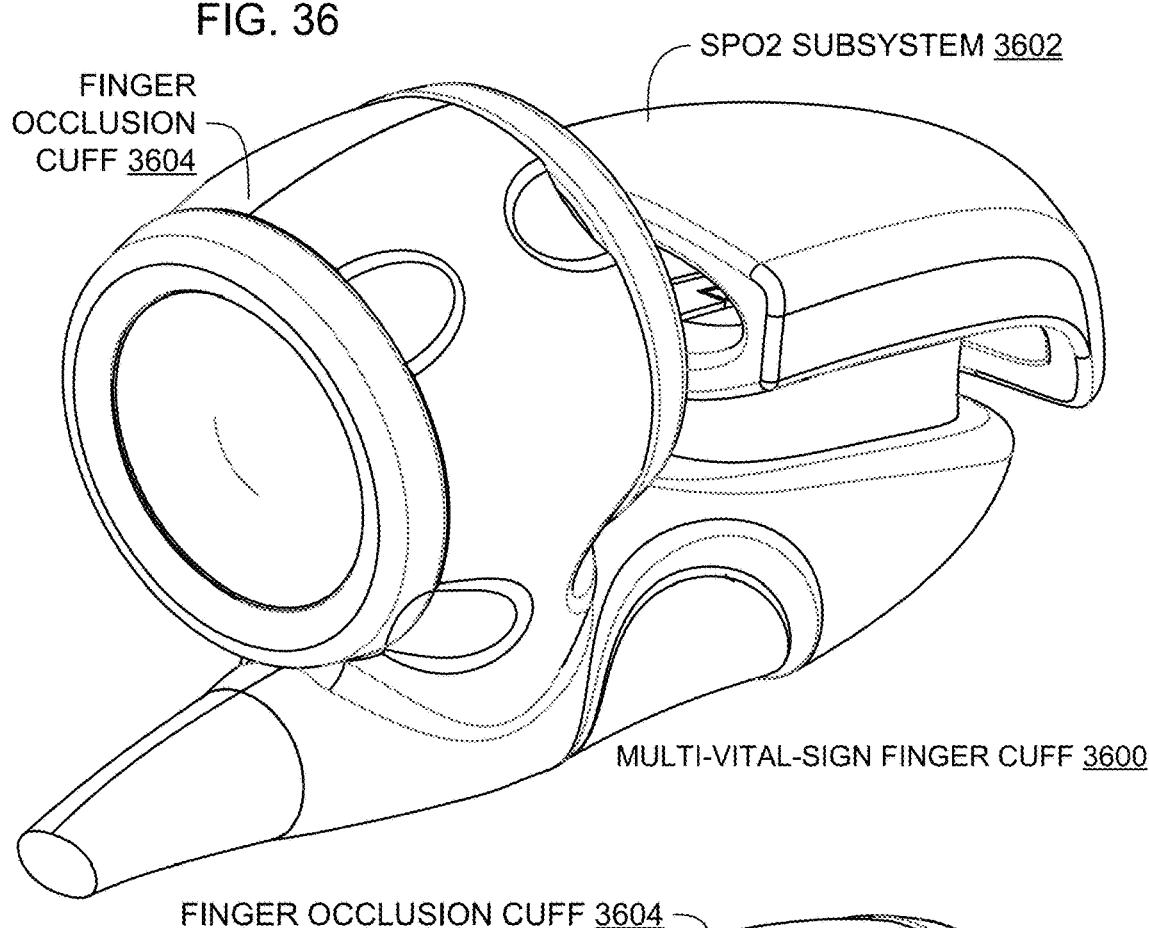
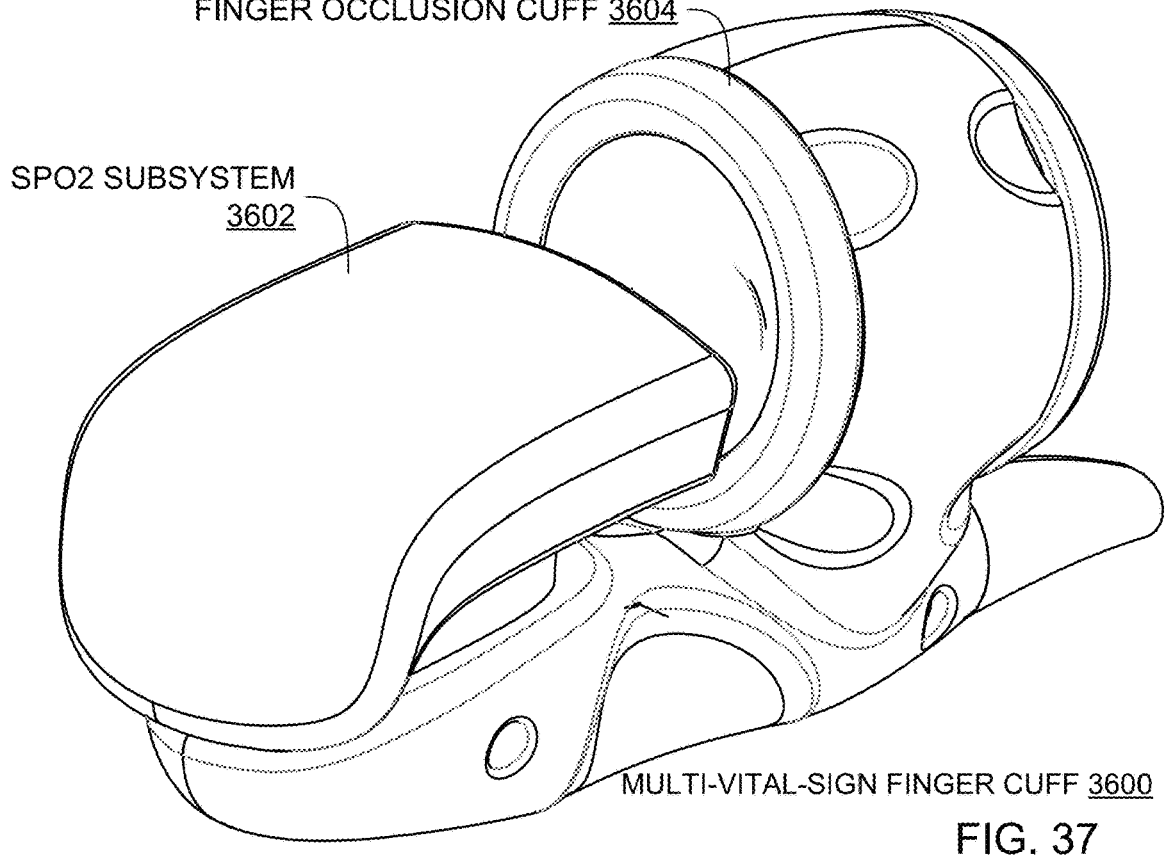
FIG. 37

FIG. 39
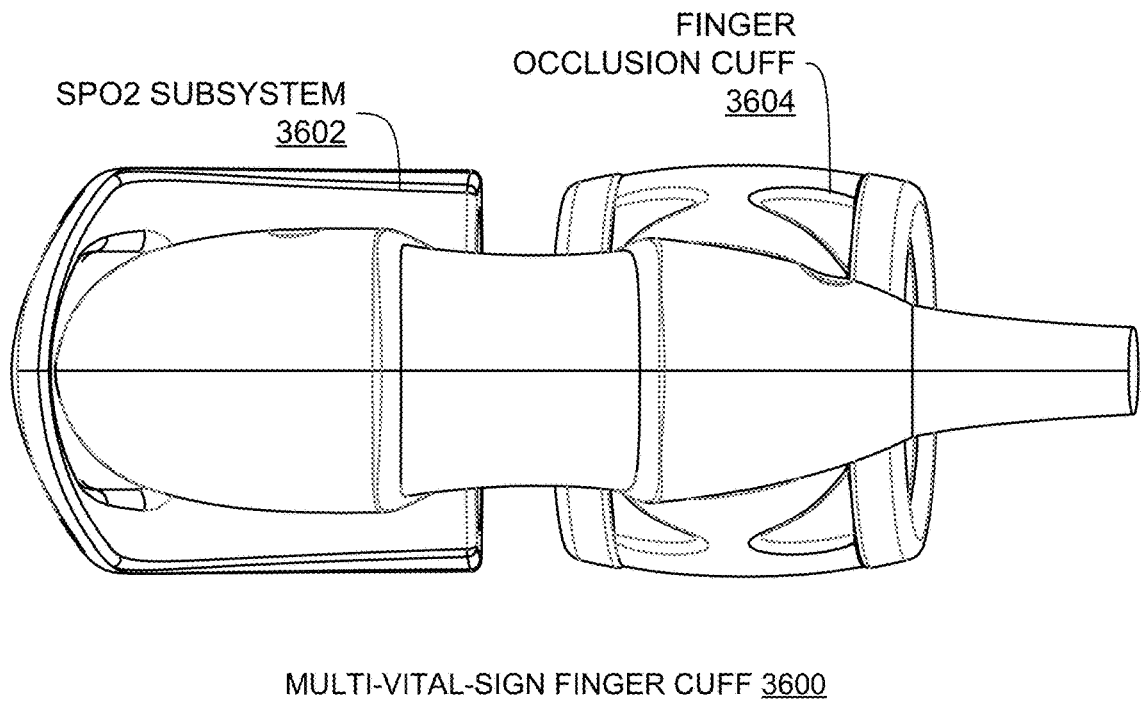
MULTI-VITAL-SIGN FINGER CUFF 3600
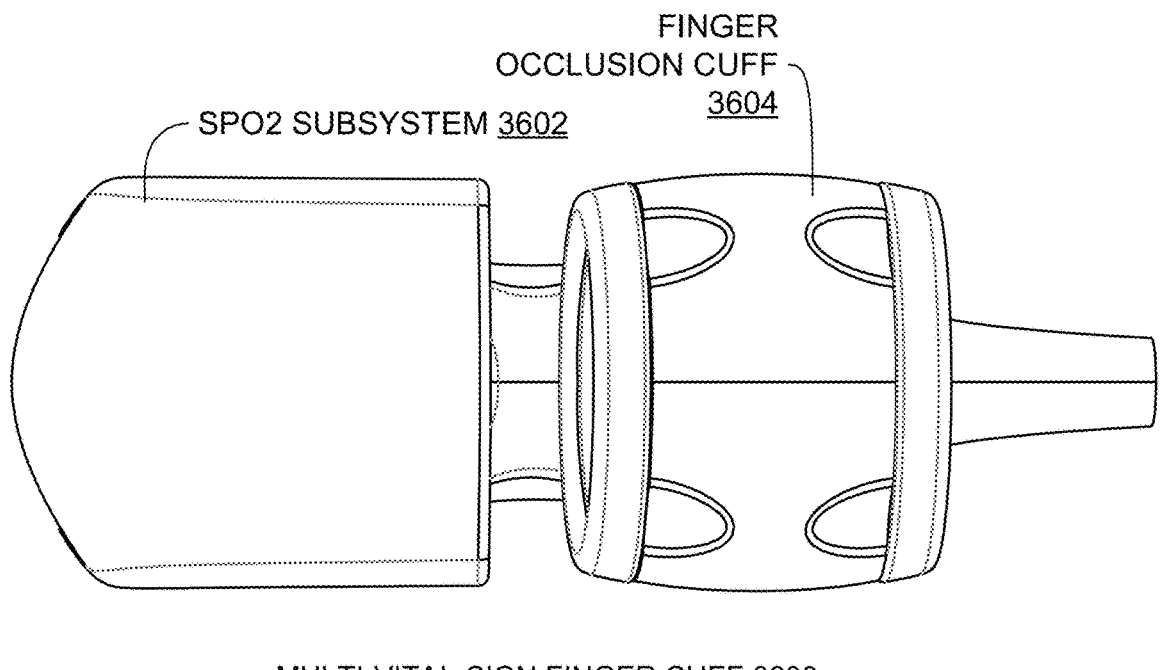
MULTI-VITAL-SIGN FINGER CUFF 3600
FIG. 40

FIG. 41
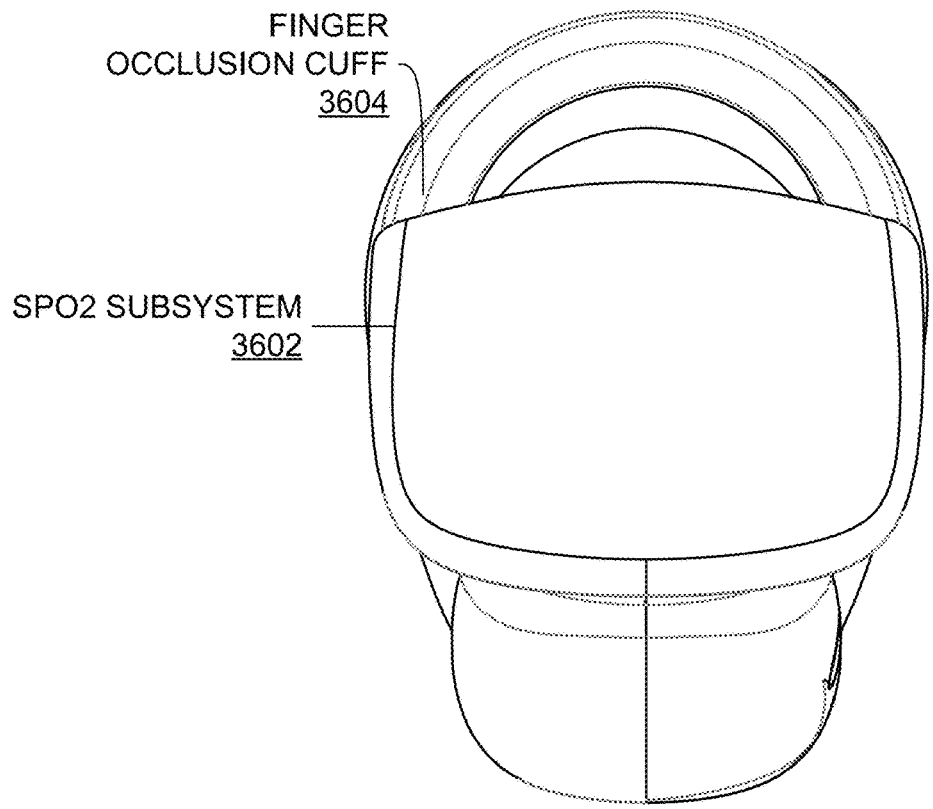
MULTI-VITAL-SIGN FINGER CUFF 3600
FINGER OCCLUSION CUFF 3604
SPO2 SUBSYSTEM 3602
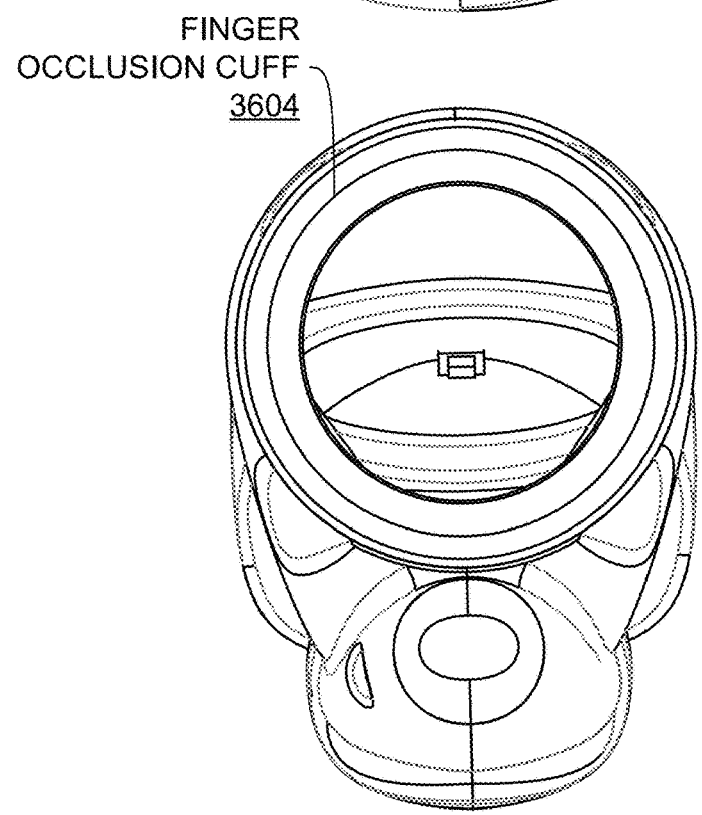
FINGER OCCLUSION CUFF 3604
MULTI-VITAL-SIGN FINGER CUFF 3600
FIG. 42

MULTI-VITAL SIGN DETECTOR OF SPO2 BLOOD OXYGENATION AND HEART RATE FROM A PHOTOPLETHYSMOGRAM SENSOR AND RESPIRATION RATE, HEART RATE VARIABILITY AND BLOOD PRESSURE FROM A MICRO DYNAMIC LIGHT SCATTERING SENSOR IN AN ELECTRONIC MEDICAL RECORDS SYSTEM

FIELD

This disclosure relates generally to detecting multiple vital signs and communicating detected multiple vital signs to a medical records system.

BACKGROUND

Prior techniques of capturing multiple vital signs from human subjects have implemented problematic sensors and have been very cumbersome in terms of affixing the sensors to the patient, recording, storing and forwarding the vital signs to appropriate parties.

BRIEF DESCRIPTION

In one aspect, a device measures temperature, heart rate at rest, heart rate variability, respiration, SpO2, blood flow, blood pressure, total hemoglobin (SpHb), PVi, methemoglobin (SpMet), acoustic respiration rate (RRa), carboxyhemoglobin (SpCO), oxygen reserve index (ORi), oxygen content (SpOC) and/or EEG of a human.

In another aspect, An apparatus includes first microprocessor, a digital infrared sensor operably coupled to the first microprocessor, an ambient temperature sensor operably coupled to the first microprocessor, a battery operably coupled to the first microprocessor, a multi-vital-sign finger cuff that is detachable and removable from the apparatus and that includes a printed circuit board, a SpO2 subsystem that is operably coupled to the printed circuit board and that includes a photoplethysmogram sensor and that is operably coupled to the printed circuit board, the photoplethysmogram sensor includes one infrared detector that detects infrared energy at two different transmitted wavelengths, red and near infrared, and a micro dynamic light scattering sensor, the micro dynamic light scattering sensor includes two photo diode receivers and one laser transmitter.

Apparatus, systems, and methods of varying scope are described herein. In addition to the aspects and advantages described in this summary, further aspects and advantages will become apparent by reference to the drawings and by reading the detailed description that follows.

BRIEF DESCRIPTION OF THE DRAWINGS

FIG. 3-1 through 3-5 are isometric diagrams of a mechanical design of a multi-vital-sign smartphone system;

FIG. 4 is a block diagram of a multi-vital-sign smartphone system;

FIG. 5 is a block diagram of a multi-vital-sign smartphone system;

FIG. 36-43 are drawings of various views of a multi-vital-sign finger cuff;

DETAILED DESCRIPTION

In the following detailed description, reference is made to the accompanying drawings that form a part hereof, and in which is shown by way of illustration specific implementations which may be practiced. These implementations are described in sufficient detail to enable those skilled in the art to practice the implementations, and it is to be understood that other implementations may be utilized and that logical, mechanical, electrical and other changes may be made without departing from the scope of the implementations. The following detailed description is, therefore, not to be taken in a limiting sense.

The detailed description is divided into eleven sections. In the first section, an overview is shown. In the second section, apparatus of an electronic medical records capture system are described. In the third section, implementations of apparatus of multi-vital-sign smartphone systems are described. In the fourth section, implementations of non-touch table-based temperature correlation thermometers are described. In the fifth section, implementations of interoperability device manager components of an EMR System are described. In the sixth section, methods of digital infrared sensors in multi-vital-sign smartphone systems are described. In the seventh section, implementations of apparatus of biological vital sign variation amplification detectors are described. In the eighth section, implementations of methods of biological vital sign amplification are described. In the ninth section, implementations of methods of non-touch table-based temperature correlation are described. In the tenth section, hardware and operating environments in which implementations may be practiced are described. Finally, in the eleventh section, a conclusion of the detailed description is provided.

1. Overview

Figure 1:
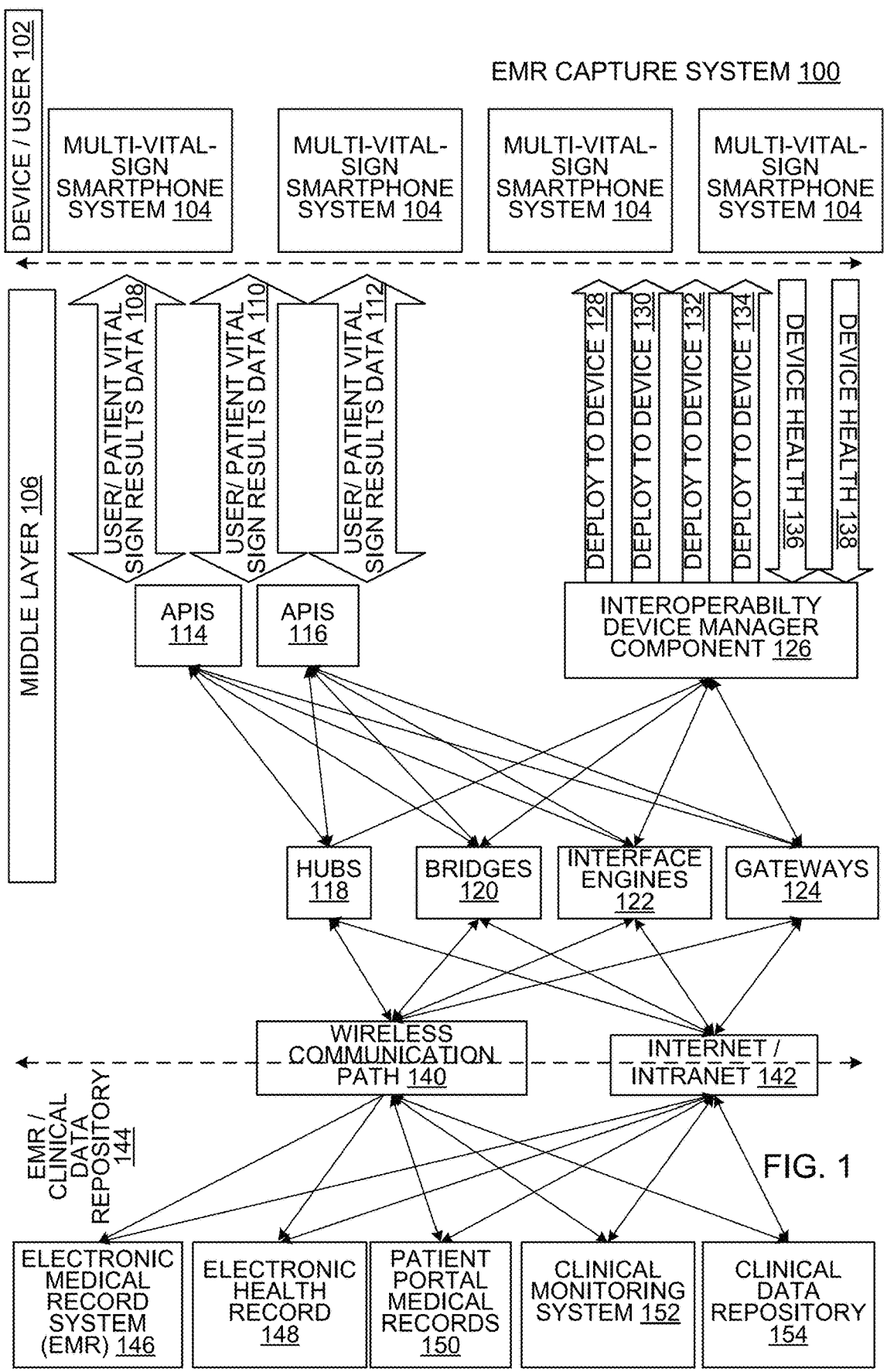
FIG. 1 is a block diagram of an overview of an electronic medical records (EMR) capture system.

FIG. 1 is a block diagram of apparatus of an electronic medical records (EMR) capture system 100, according to an implementation.

EMR capture system 100 includes a device/user layer 102 that further includes one or more multi-vital-sign smartphone system(s) 104. Examples of the multi-vital-sign smartphone system(s) 104 are shown in FIG. 4-10.

EMR capture system 100 includes a middle layer 106 that communicates with the multi-vital-sign smartphone system(s) 104 in the device/user layer 102. The middle layer 106 includes user/patient vital sign results data 108 that is communicated via cellular communication paths, such as 3G, 4G or a 5G or a WiFi® communication path, user/patient vital sign results data 110 that is communicated via a WiFi® communication path and user/patient vital sign results data 112 that is communicated via a Bluetooth® communication path. The middle layer 106 further includes a first set of application program interfaces 114 and optionally a second set of application program interfaces 116 that the user/patient vital sign results data 108, 110 and 112 is communicated to and from the multi-vital-sign smartphone system(s) 104 in the device/user layer 102 between one or more hubs 118, bridges 120, interface engines 122 and gateways 124 in the middle layer 106. The middle layer 106 further includes an interoperability device manager component 126 that deploys data such as primary communication protocol, configuration settings, firmware modifications and representations of an authorized location to the multi-vital-sign smartphone system(s) 104 in the device/user layer 102. The interoperability device manager component 126 sends the data via a 3G, 4G or 5G cellular communication path 128, a WiFi® communication path 130, a Bluetooth® communication path 132 and/or a near-field communication (NFC) path 134. The interoperability device manager component 126 receives the device health data via 3G, 4G or 5G cellular communication path 136 or a WiFi® communication path 138 from the multi-vital-sign smartphone system(s) 104 in the device/user layer 102.

The one or more hubs 118, bridges 120, interface engines 122 and gateways 124 in the middle layer 106 communicate via 3G, 4G or 5G cellular communication path 140 and/or an internet/intranet communication path 142 to an EMR/clinical data repository 144. The EMR/clinical data repository 144 includes an EMR system 146, an electronic health record 148, patient portal medical records 150, a clinical monitoring system 152 and a clinical data repository 154. The EMR system 146 is located within or controlled by a hospital facility. The electronic health record 148 is a patient file that is managed or controlled by an ambulatory medical facility or a private medical office. One example of Bluetooth® protocol is Bluetooth® Core Specification Version 2.1 published by the Bluetooth® SIG, Inc. Headquarters, 5209 Lake Washington Blvd Nebr., Suite 350, Kirkland, Wash. 98033.

Figure 2:
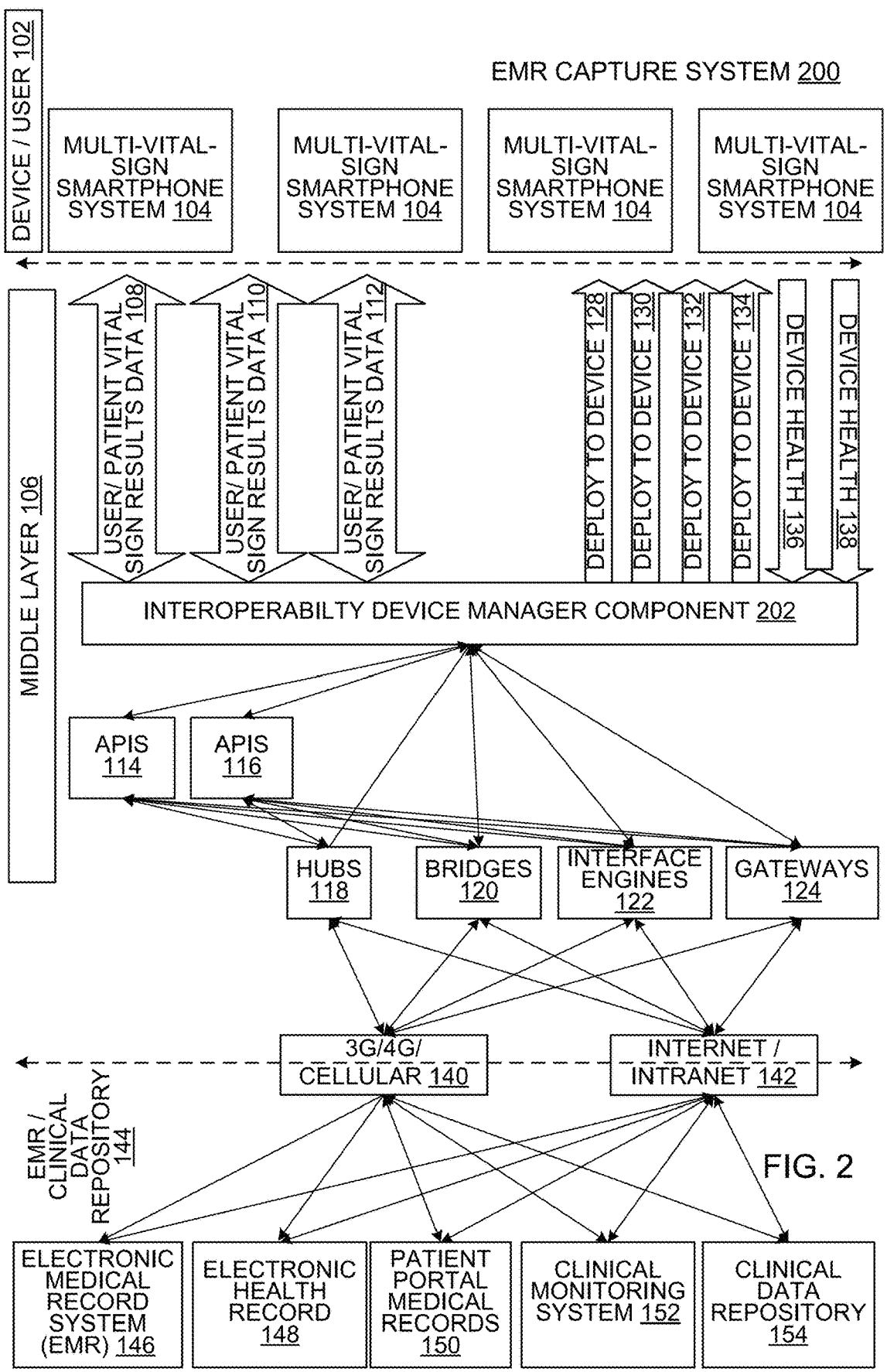
FIG. 2 is a block diagram of apparatus of an EMR capture system, according to an implementation in which an interoperability manager component manages all communications in the middle layer.

FIG. 2 is a block diagram of apparatus of an EMR capture system 200, according to an implementation in which an interoperability manager component manages all communications in the middle layer. In EMR capture system 200, an interoperability manager component 202 manages all communications in the middle layer 106 between the device/user layer 102 and the first set of application program interfaces 114 and the optional second set of application program interfaces 116. In EMR capture system 200, the operation of the device/user layer 102 and the EMR/clinical data repository 144 is the same as in the EMR capture system 100.

Figure 38:
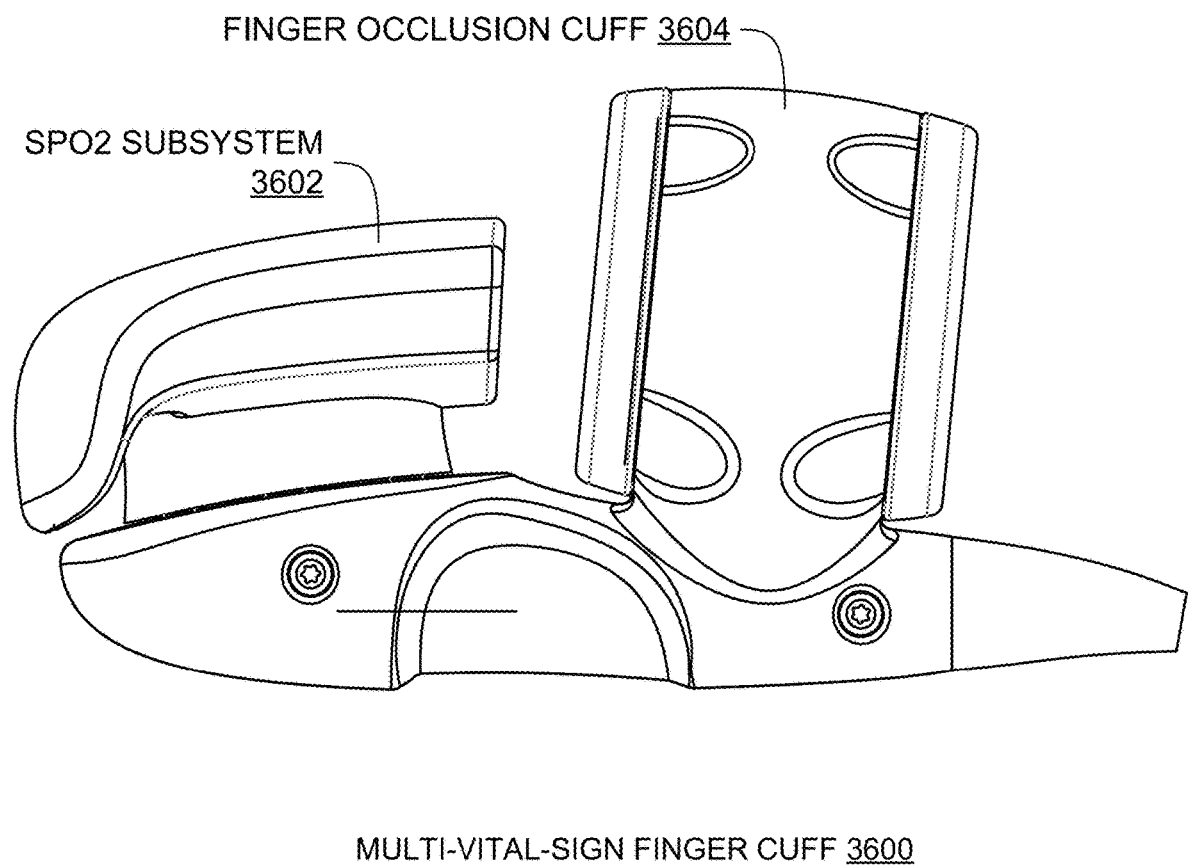
Figure 43:
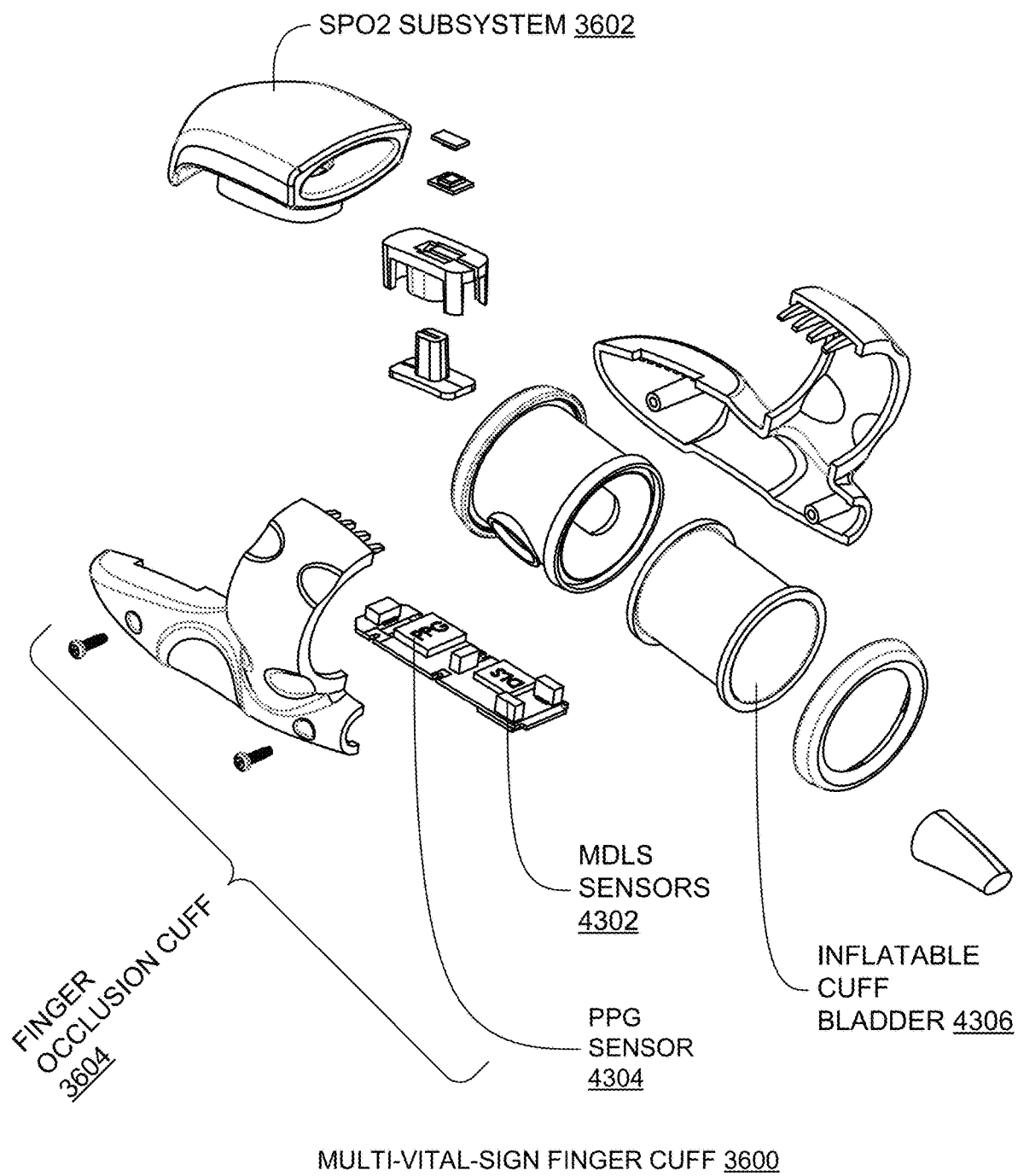

Some other implementations of an electronic medical records capture system includes a bridge that transfers patient measurement records (PMRs) 150 from multi-vital-sign smartphone system(s) 104 to EMR systems in hospital and clinical environments. Each PMR 150 includes patient measurement data, such as biological vital sign 1736 in FIG. 17-19, estimated body core temperature 1720 in FIG. 17, estimated body core temperature 1812 in FIGS. 17 and 21, biological vital sign 1736 in FIG. 17-19, and heartrate 3810, respiratory rate 3816 and EKG 3830 in FIG. 38. Examples of multi-vital-sign smartphone system(s) 104 include the multi-vital-sign smartphone system in FIG. 4, the multivital-sign smartphone systems in FIG. 17-19, and the multi-vital-sign smartphone system 3200. In some implementations, the multi-vital-sign smartphone system(s) 104 includes a temperature estimation table that is stored in memory. The temperature estimation table is a lookup table that correlates a sensed forehead temperature to a body core temperature. The correlation of sensed forehead temperature to body core temperature is a significant advance in the technology of the multi-vital-sign smartphone systems in FIG. 17-19 and the multi-vital-sign smartphone system 3200 in FIG. 32, because the correlation has been developed to a highly accurate degree, to an extent of accuracy that surpasses all other multi-vital-sign smartphone systems, apparatus that estimates a body core temperature, apparatus of variation amplification, hand-held devices, multi-vital-sign smartphone systems and tablets, that for the first time provides sufficient accuracy to be used in medical clinics. The EMR data capture system includes two important aspects: 1. A server bridge to control the flow of patient measurement data from multi-vital-sign smartphone system(s) 104 to one or more and to manage local multi-vital-sign smartphone system(s) 104. 2. The transfer of patient measurement data in a PMR 150, anonymous, and other patient status information to a cloud based EMR/clinical data repository 144. The bridge controls and manages the flow of patient measurement data to an EMR/clinical data repository 144 and another EMR/clinical data repository 144 and provides management services to multi-vital-sign smartphone system(s) 104. The bridge provides an interface to: a wide range of proprietary EMR/clinical data repository 144, location specific services, per hospital, for verification of active operator, and if necessary, patient identifications, and a cloud based EMR/clinical data repository 144) of one or more multi-vital-sign smartphone system(s) 104, for the purpose of storing all measurement records in an anonymous manner for analysis. A setup, management and reporting mechanism also provided. The bridge accepts communications from multi-vital-sign smartphone system(s) 104 to: Data format conversion and transferring patient measurement records to EMR/clinical data repository 144, manage the firmware and configuration settings of the multi-vital-sign smartphone system(s) 104, determine current health and status of the multi-vital-sign smartphone system(s) 104, support device level protocol for communications, TCP/IP. The support device level protocol supports the following core features: authentication of connected device and bridge, transfer of patient measurement records to bridge with acknowledgement and acceptance by the bridge or EMR acceptance, support for dynamic update of configuration information and recovery of health and status of the multi-vital-sign smartphone system(s) 104, support for firmware update mechanism of firmware of multi-vital-sign smartphone system(s) 104. The EMR data capture system provides high availability, 24/7/365, with 99.99% availability. The EMR data capture system provides a scalable server system to meet operational demands in hospital operational environments for one or both of the following deployable cases: 1) A local network at an operational site in which the bridge provides all features and functions in a defined operational network to manage a system of up to 10,000+ multi-vital-sign smartphone system(s) 104. 2) Remote or cloud based EMR/clinical data repository 144 in which the bridge provides all services to many individual hospital or clinical sites spread over a wide geographical area, for 1,000,000+ multi-vital-sign smartphone system(s) 104. The bridge provides a central management system for the multi-vital-sign smartphone system(s) 104 that provides at least the following functions: 1) configuration management and update of the multi-vital-sign smartphone system(s) 104 2) device level firmware for all of the multi-vital-sign smartphone system(s) 104 and 3) management and reporting methods for the multi-vital-sign smartphone system(s) 104. The management and reporting methods for the multi-vital-sign smartphone system(s) 104 provides (but not limited to) health and status of the multi-vital-sign smartphone system(s) 104, battery level, replacement warning of the multi-vital-sign smartphone system(s) 104, check/calibration nearing warning of the multi-vital-sign smartphone system(s) 104, rechecking due to rough handling or out of calibration period of the multi-vital-sign smartphone system(s) 104, history of use, number of measurements, frequency of use etc. of the multi-vital-sign smartphone system(s) 104, display of current device configuration of the multi-vital-sign smartphone system(s) 104, Date/time of last device communications with each of the multi-vital-sign smartphone system(s) 104. The bridge provides extendable features, via software updates, to allow for the addition of enhanced features without the need for additional hardware component installation at the installation site. The bridge provides a device level commission mechanism and interface for the initial setup, configuration and test of multi-vital-sign smartphone system(s) 104 on the network. The bridge supports multi-vital-sign smartphone systems that are not hand-held. Coverage of the EMR data capture system in a hospital can include various locations, wards, ER rooms, offices, physician's Offices etc. or anywhere where automatic management of patient biological vital sign information is required to be saved to a remote EMR system. The multi-vital-sign smartphone system(s) 104 can communicate with a third party bridge to provide access to data storage services, EMR systems, multi-vital-sign smartphone system cloud storage system etc. Networking setup, configuration, performance characteristics etc. are also determined and carried out by the third party bridge or another third party, for the operational environments. The multi-vital-sign smartphone system can support the network protocols for communication with the third party bridge devices. In some implementations the bridge is a remote cloud based bridge. The remote cloud based bridge and the EMR/clinical data repositories 144 are operably coupled to the network via the Internet.

Implementation Details of the Overview Section In some implementations, a push data model is supported by the EMR data capture system between the multi-vital-sign smartphone system(s) 104 and the bridge in which connection and data are initially pushed from the multi-vital-sign smartphone system(s) 104 to the bridge. Once a connection has been established and the multi-vital-sign smartphone system(s) 104 and the bridge, such as an authenticated communication channel, then the roles may be reversed where the bridge controls the flow of information between the multi-vital-sign smartphone system(s) 104 and the EMR/clinical data repository 144. In some implementations, the multi-vital-sign smartphone system(s) 104 are connected via a wireless communication path, such as a WiFi® connection to WiFi® access point(s). In other implementations, the multi-vital-sign smartphone system(s) 104 are connected to a docking station via a wireless or physical wired connection, such as local WiFi®, Bluetooth®, Bluetooth® Low Energy, serial, USB, etc., in which case the docking station then acts as a local pass-through connection and connects to the bridge via a LAN interface and/or cellular or WiFi® link from the docking station to the bridge. In some implementations, the multi-vital-sign smartphone system(s) 104 are connected via a 3G, 4G or a 5G cellular data communication path to a cellular communication tower which is operably coupled to a cell service provider's cell network which is operably coupled to a bridge/access point/transfer to a LAN or WLAN. In some implementations one or more multi-vital-sign smartphone system(s) 104 are connected a smartphone via a communication path such as a Bluetooth® communication path, a 3G, 4G or a 5G cellular data communication path, a USB communication path, a WiFi® communication path, or a WiFi® direct communication path to the cell phone; and the smartphone is connected to a cellular communication tower via a 3G, 4G or a 5G cellular data communication path, the cell tower being operably coupled to a cell service provider's cell network which is operably coupled to a bridge/access point/transfer to a LAN or WLAN. In some implementations, the portable multi-vital-sign smartphone system(s) 104 includes a battery with limited battery power and lifetime that in some implementations needs to be conserved in order to reduce the intervals at which the battery needs to be recharged. These portable multi-vital-sign smartphone system(s) 104 support various power saving modes and as such each device is responsible for the initiation of a connection to the wireless network or a wired network and the subsequent connection to the bridge that meets their own specific operational requirements, which provides the multi-vital-sign smartphone system(s) 104 additional control over their own power management usage and lifetime. In some implementations in which the multi-vital-sign smartphone system(s) 104 attempt connection to the bridge, the bridge is allocated a static Internet protocol (IP) address to reduce the IP discovery burden on the multi-vital-sign smartphone system(s) 104 and thus connect the multi-vital-sign smartphone system to the bridge more quickly. More specifically, the multi-vital-sign smartphone system(s) 104 are not required to support specific discovery protocols or domain name service (DNS) in order to determine the IP address of the bridge. It is therefore important in some implementations that the bridge IP address is static and does not change over the operational lifetime of EMR data capture system on the network. In other implementations, a propriety network discovery protocol using UDP or TCP communications methods is implemented. In other implementations, the multi-vital-sign smartphone system(s) 104 have a HTTP address of a remote sever that acts as a discovery node for the multi-vital-sign smartphone system(s) 104 to obtain a connection to a remote system or to obtain that remote systems network address. In some implementations installation of a new multi-vital-sign smartphone system(s) 104 on the network requires configuration of the multi-vital-sign smartphone system(s) 104 for the bridge of IP address and other essential network configuration and security information. Commissioning of a multi-vital-sign smartphone system(s) 104 on the network in some implementations is carried out from a management interface on the bridge. In this way a single management tool can be used over all lifecycle phases of a multi-vital-sign smartphone system(s) 104 on the network, such as deployment, operational and decommissioning. In some implementations the initial network configuration of the multi-vital-sign smartphone system(s) 104 does not require the multi-vital-sign smartphone system(s) 104 to support any automated network level configuration protocols, WPS, Zeroconfi etc. Rather the bridge supports a dual network configuration, one for operational use on the operational network of the hospital or clinic, or other location, and an isolated local network, with local DHCP server, for out of the box commissioning of a new multi-vital-sign smartphone system(s) 104 and for diagnostic test of the multi-vital-sign smartphone system(s) 104. Multi-vital-sign smartphone system(s) 104 can be factory configured for known network settings and contain a default server IP address on the commissioning network. In addition the multi-vital-sign smartphone system(s) 104 are required in some implementations to support a protocol based command to reset the multi-vital-sign smartphone system(s) 104 to network factory defaults for test purposes. In some situations, the firmware revision(s) of the multi-vital-sign smartphone system(s) 104 are not consistent between all of the multi-vital-sign smartphone systems 104 in the operational environment. Therefore the bridge is backwards compatible with all released firmware revisions from firmware and protocol revision, data content and device settings view point of the multi-vital-sign smartphone system(s) 104. As a result, different revision levels of multi-vital-sign smartphone system(s) 104 can be supported at the same time on the network by the bridge for all operations.

2. Apparatus of Multi-Vital-Sign Smartphone Systems

FIG. 3-1 through 3-5 are isometric diagrams of a mechanical design of a multi-vital-sign smartphone system 300, according to an implementation.

The multi-vital-sign smartphone system 300 includes a multi-vital-sign smartphone 304 that is inserted into a cradle of a multi-vital-signs finger cuff smartphone accessory 302. The multi-vital-signs finger cuff smartphone accessory 302 includes a multi-vital-sign finger cuff that includes a SpO2 subsystem 306 and a finger occlusion cuff 308. The multi-vital-signs finger cuff smartphone accessory 302 also includes a camera 310 or a digital infrared sensor 312. In some implementations, the multi-vital-signs finger cuff smartphone accessory 302 operably couples to the multi-vital-sign smartphone 304 via the direct connect charging contacts 712 of the multi-vital-signs finger cuff smartphone accessory in FIG. 7 and a charging port on the end of the multi-vital-sign smartphone 304 in which the multi-vital-signs finger cuff smartphone accessory 302 receives power and control signals from the multi-vital-sign smartphone 304 and through which data from the multi-vital-signs finger cuff smartphone accessory 302 is transmitted to the multi-vital-sign smartphone 304. In some implementations, the multi-vital-signs finger cuff smartphone accessory 302 operably couples to the multi-vital-sign smartphone 304 via the direct connect charging contacts 712 of the multi-vital-signs finger cuff smartphone accessory in FIG. 7 and a charging port on the back of the multi-vital-sign smartphone 304 in which the multi-vital-signs finger cuff smartphone accessory 302 receives power and control signals from the multi-vital-sign smartphone 304 and through which data from the multi-vital-signs finger cuff smartphone accessory 302 is transmitted to the multi-vital-sign smartphone 304. In some implementations, the multi-vital-signs finger cuff smartphone accessory 302 operably couples to the multi-vital-sign smartphone 304 via the Bluetooth® or other wireless communication modules of the multi-vital-signs finger cuff smartphone accessory 302 and the multi-vital-sign smartphone 304 in which the multi-vital-signs finger cuff smartphone accessory 302 includes a battery and receives control signals from the multi-vital-sign smartphone 304 and through which data from the multi-vital-signs finger cuff smartphone accessory 302 is transmitted to the multi-vital-sign smartphone 304.

Figures 1, 3:
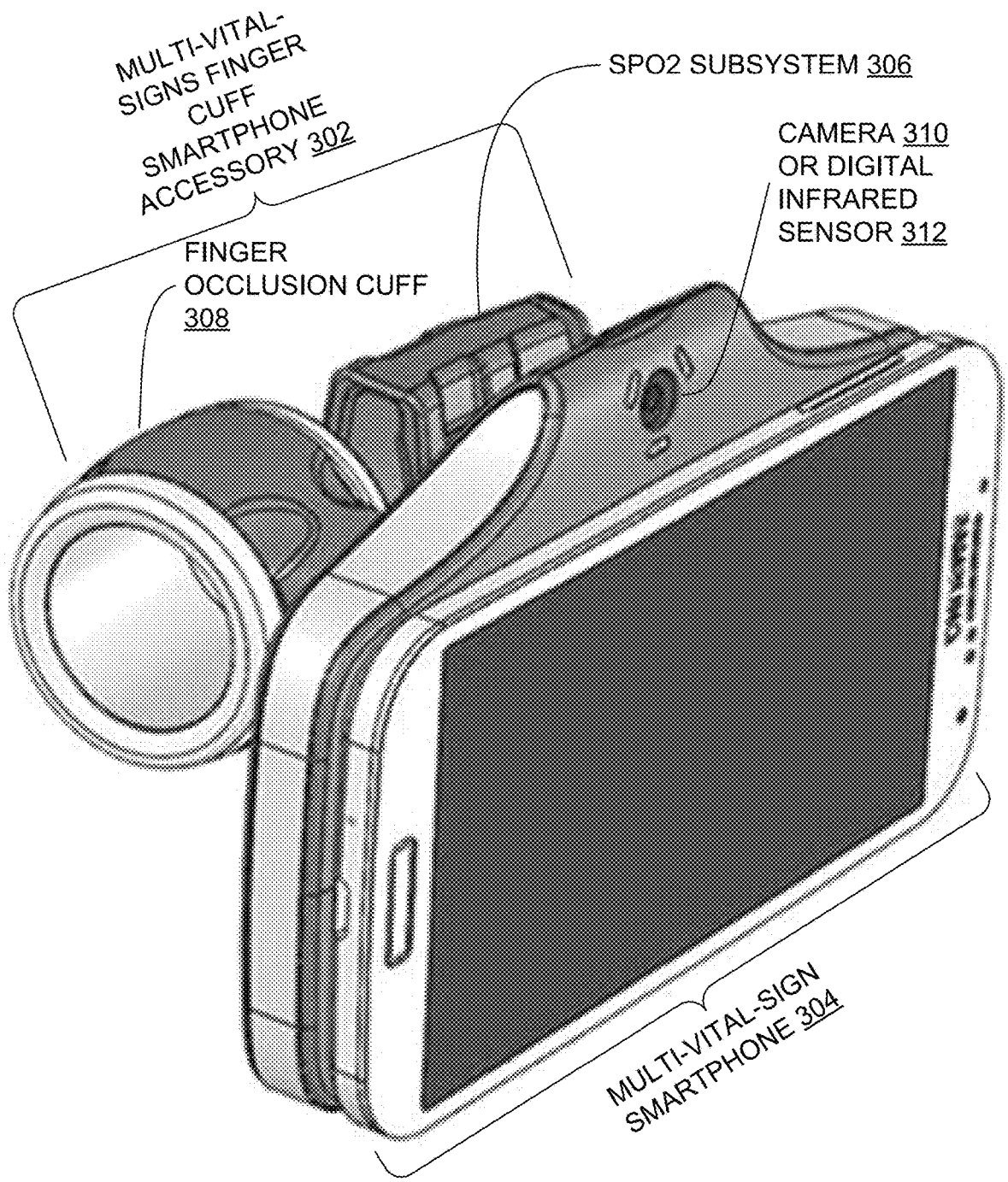
Figures 2, 3:
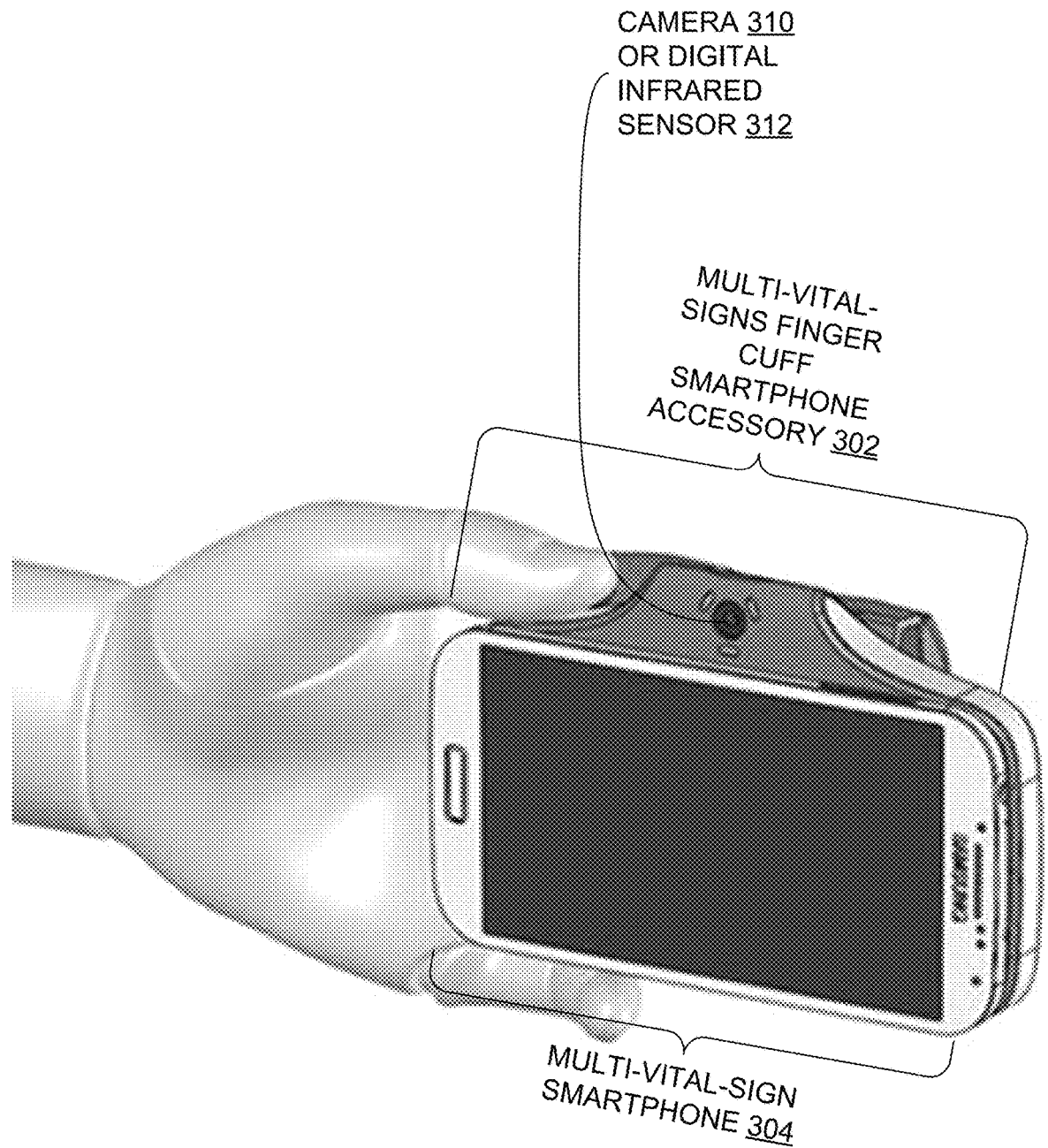
Figure 3:
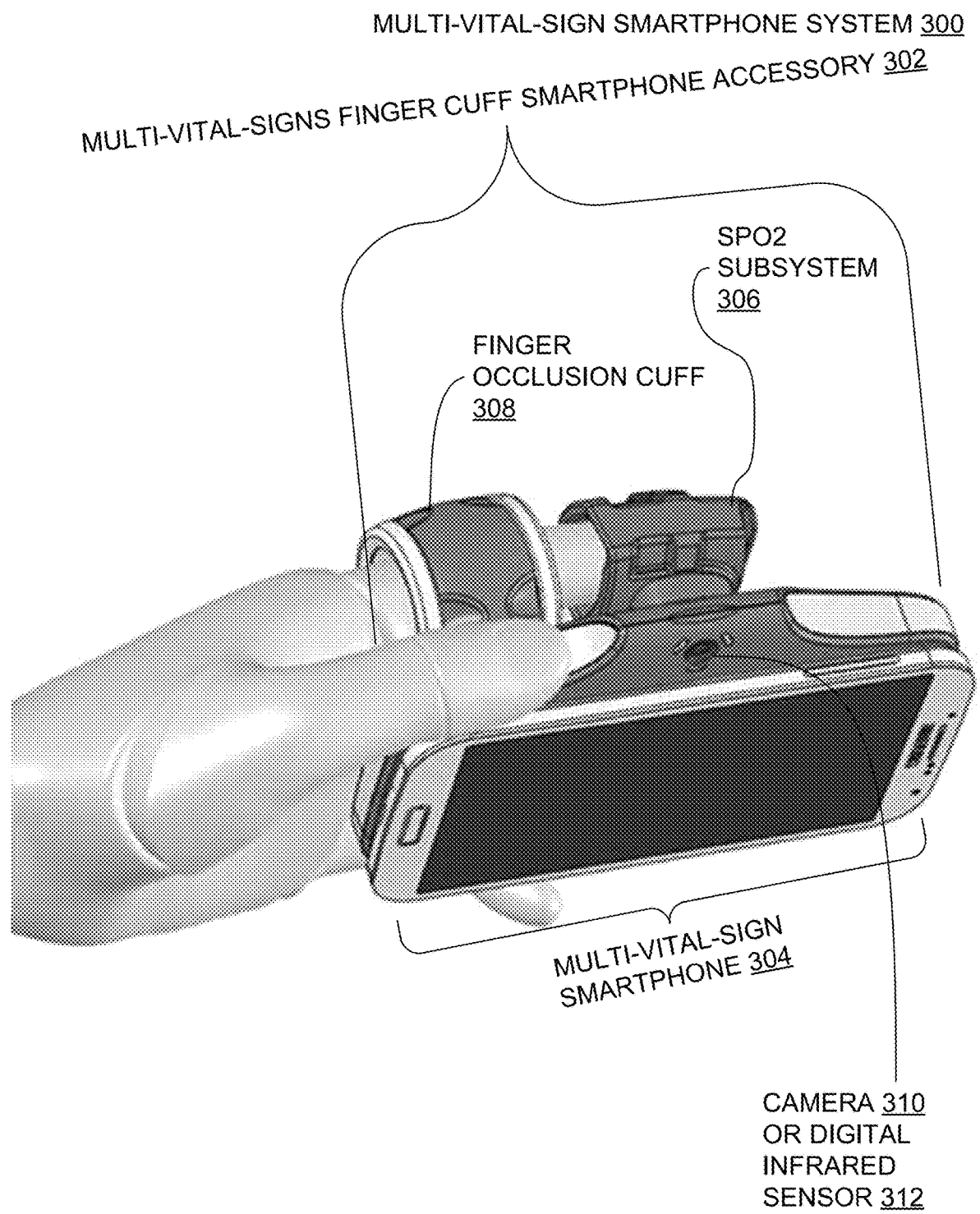
Figures 3, 4:
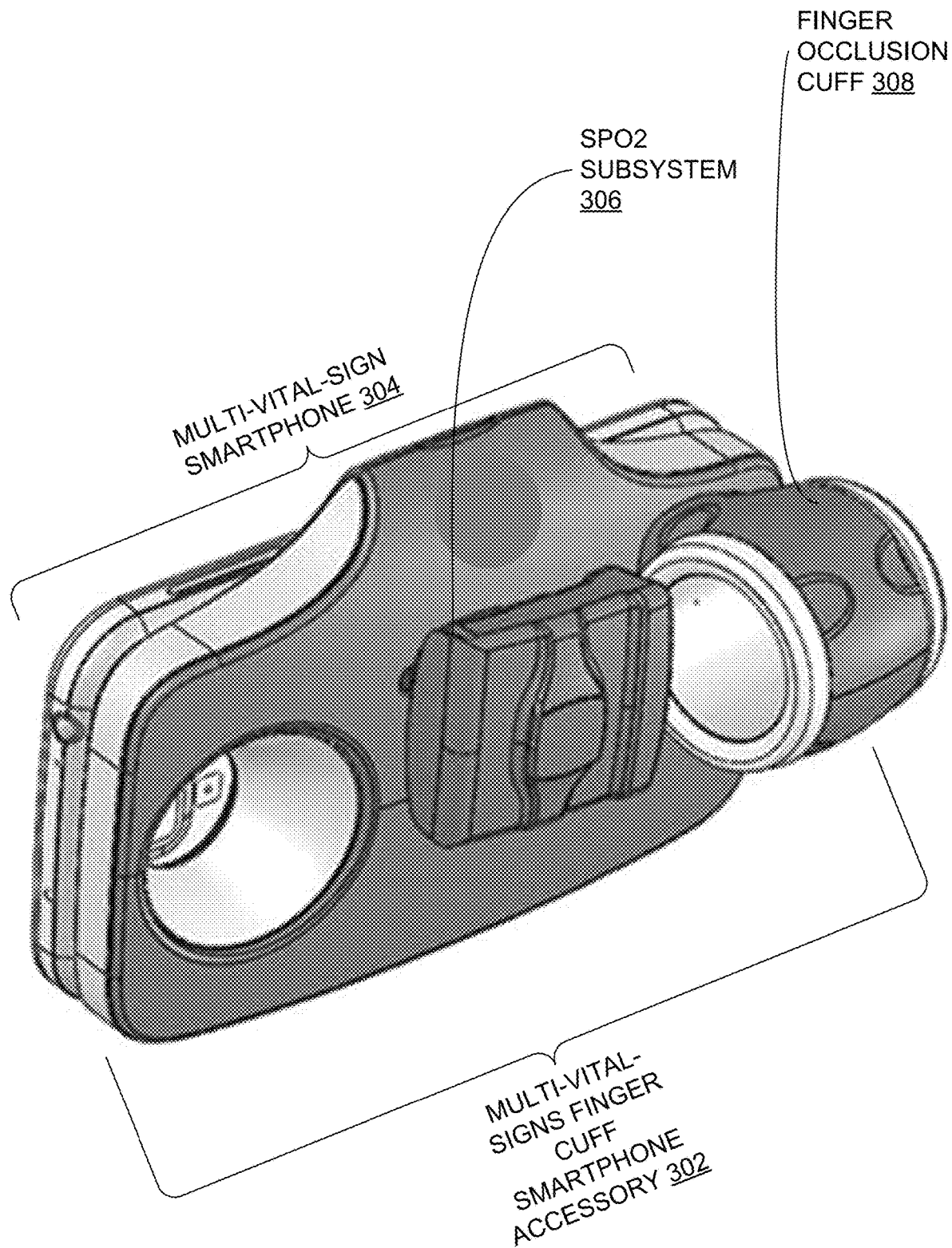

FIG. 4 is a block diagram of a multi-vital-sign smartphone system 400, according to an implementation. The MVS system 400 includes three communicatively coupled devices; a multi-vital-signs finger cuff smartphone accessory (MVSFCSA) 402, a multi-vital-sign smartphone (MVS Smartphone) 404 and a multi-vital-sign finger cuff 406. The MVS system 400 is one examples of the multi-vital-sign smartphone system(s) 104. In some implementations, the MVS system 400 captures, stores and exports raw data from all supported sensors in the multi-vital-sign finger cuff 406. MVS system 400 provides a flexible human vital sign measurement methodology that supports different measurement methods and techniques. The MVS system 400 can be used in a clinical setting or a home setting for the collection of human vital signs. The 'Parameter' in 'Multi-vital-signs finger cuff smartphone accessory' refers to the vital-signs that are measured by the multi-vital-signs finger cuff smartphone accessory 402, such as temperature, heart rate at rest, heart rate variability, respiration, SpO2, blood flow, blood pressure, total hemoglobin (SpHb), PVi, methemoglobin (SpMet), acoustic respiration rate (RRa), carboxyhemoglobin (SpCO), oxygen reserve index (ORi), oxygen content (SpOC) and/or EEG of a human. SpO2 is peripheral capillary oxygen saturation, an estimate of the amount of oxygen in the blood. More specifically, SpO2 is the percentage of oxygenated haemoglobin (haemoglobin containing oxygen) compared to the total amount of haemoglobin in the blood (oxygenated and non-oxygenated haemoglobin). The MVSFCSA 402 can be configured to detect blood pressure only, SpO2 only, heart rate only, respiration only, or any combination of vital signs that the MVSFCSA is capable of detecting. The MVS Smartphone 404 includes non-slip/slide exterior surface material.

The multi-vital-sign finger cuff 406 and the MVSFCSA 402 are operably coupled to each other through an air line 408 and a communication path 410, such as high speed serial link. A high speed serial link is especially important because the cable of a serial link is quite a bit a bit thinner and more flexible than a parallel cable, which provides a lighter cable that can be more easily wrapped around the MVSFCSA 402. A cuff bladder of the multi-vital-sign finger cuff 406 expands and contracts in response to air pressure from the air line 408.

Some implementations of the multi-vital-sign finger cuff 406 include a finger occlusion cuff 416 and a SpO2 subsystem 418. The multi-vital-sign finger cuff 3600 in FIG. 36-43 is one example of the multi-vital-sign finger cuff 406. The finger occlusion cuff 416 and a SpO2 subsystem 418 are shown in greater detail in FIG. 36-43. In some implementations, the finger occlusion cuff 416 includes at least one miniaturized dynamic light scattering (mDLS) sensor and the SpO2 subsystem 418 includes a photoplethysmogram (PPG) sensor. SpO2 subsystem 3602 in FIG. 36-43 is one example of the SpO2 subsystem 418. SpO2 subsystem 418 and the finger occlusion cuff 416 are operably coupled to a common board in the multi-vital-sign finger cuff 406 and the common board is operably coupled through the communication path 410 to a printed circuit board that is in the base of MVSFCSA 402.

In some implementations, the multi-vital-sign finger cuff 406 integrates a photoplethysmogram (PPG) sensor and at least one miniaturized dynamic light scattering (mDLS) sensor into a single sensor. Both of the which are attached to the multi-vital-sign finger cuff 406. The PPG and mDLS implementation of the multi-vital-sign finger cuff 406 measures the following primary and secondary human vital sign measurements through a PPG sensor from either an index finger or a middle finger; on both the left and right hands at heart height to ensure an accurate measurement: Primary human vital sign measurements such as blood pressure (diastolic and systolic), SpO2, heart rate and respiration rate. Secondary human vital sign measurements include heart rate variability and blood flow. The MVSFCSA 402 can estimate the following vital signs: heart rate at rest, heart rate variability, respiration rate, SpO2, blood flow, blood pressure, total hemoglobin (SpHb), PVi, methemoglobin (SpMet), acoustic respiration rate (RRa), carboxyhemoglobin (SpCO), oxygen reserve index (ORi), oxygen content (SpOC) and EEG. The heart rate at rest is estimated from data from the PPG sensor. The respiration rate and heart rate variability and the blood pressure diastolic is estimated from data from the mDLS sensor and the PPG sensor. The respiration and the blood pressure systolic is estimated from data from the mDLS sensor. The SpO2 blood flow is estimated from data from the PPG sensor. The PPG sensor optically measures light that passes through tissue from two IR light emitters. The PPG sensor includes one infrared detector that detects infrared energy at two different transmitted wavelength; red and near infrared. Signal fluctuations of the light are generally attributed to the fluctuations of the local blood volume due to the arterial blood pressure wave, which means that the amount of blood in the illuminated perfused tissue fluctuates at the rate of heartbeats. So does the light transmission or light refraction. Therefore, PPG data is an indirect method of the estimation of the blood volume changes. The blood pressure is estimated from data from the mDLS sensor in conjunction with a blood pressure finger cuff which mimics pressure cycle to create an occlusion like the arm cuff. The biological target is illuminated by a laser, the signal is collected by a detector and the time dependency of the laser speckle characteristics are analyzed. The typical mDLS geometry is designed to create direct signal scattering reflection of the signal into the detector. Each mDLS sensor includes two photo diode receivers and one laser transmitter.

In some implementations, the multi-vital-sign finger cuff 406 is replaceable, detachable and removable from the MVSFCSA 402. In some implementations, the multi-vital-sign finger cuff 406 is integrated into the MVSFCSA 402. The multi-vital-sign finger cuff 406 that is replaceable, detachable and removable from the MVSFCSA 402 is beneficial in two ways: 1) the multi-vital-sign finger cuff 406 is replaceable in the event of damage 2) the multi-vital-sign finger cuff 406 can be detached from the MVSFCSA 402 and then attached to a custom connector cable (pneumatic & electrical) that allows a patient to wear the multi-vital-sign finger cuff 406 for continuous monitoring, and (3) servicing the device. The replaceable multi-vital-sign finger cuff 406 can have photo optic component(s) (e.g. 2× mDLS and PPG) that are cleanable between patients and replaceable in the event of failure of the inflatable cuff or the photo optic component(s). In some implementations, the cuff bladder of the removable multi-vital-sign finger cuff 406 is translucent or transparent to transparent to the mDLS laser wavelengths and which in some implementations allows the position of the multi-vital-sign finger cuff 406 to be adjusted in relation to specific parts of human anatomy for optimal function of the sensors and comfort to the patient.

The MVSFCSA 402 and the MVS Smartphone 404 can be operably coupled to each other through a communication path 412 and a 4 point electrical recharge interface (I/F) line 414 to exchange data and control signals. In some implementations, the 4 point electrical recharge interface (I/F) line 414 is a 3 point electrical recharge interface (I/F) line. The MVSFCSA 402 and the MVS Smartphone 404 do not need to be physically attached to each other for measurement operation by either the MVSFCSA 402 or the MVS Smartphone 404. In some implementations, the MVSFCSA 402 has at least one universal serial bus (USB) port(s) for bi-directional communication, command, control, status and data transfer with another devices with both standard and propriety protocols using USB infrastructure. USB protocol is defined by the USB Implementers Forum at 5440 SW Westgate Dr. Portland Oreg. 94221. In some implementations, the MVS Smartphone 404 has at least one USB port(s) for communication with other devices via USB, such as connected to a MVSFCSA 402 for the purposes of transferring the raw sensor data from the device to a computer for analysis.

Figures 3, 4, 5:
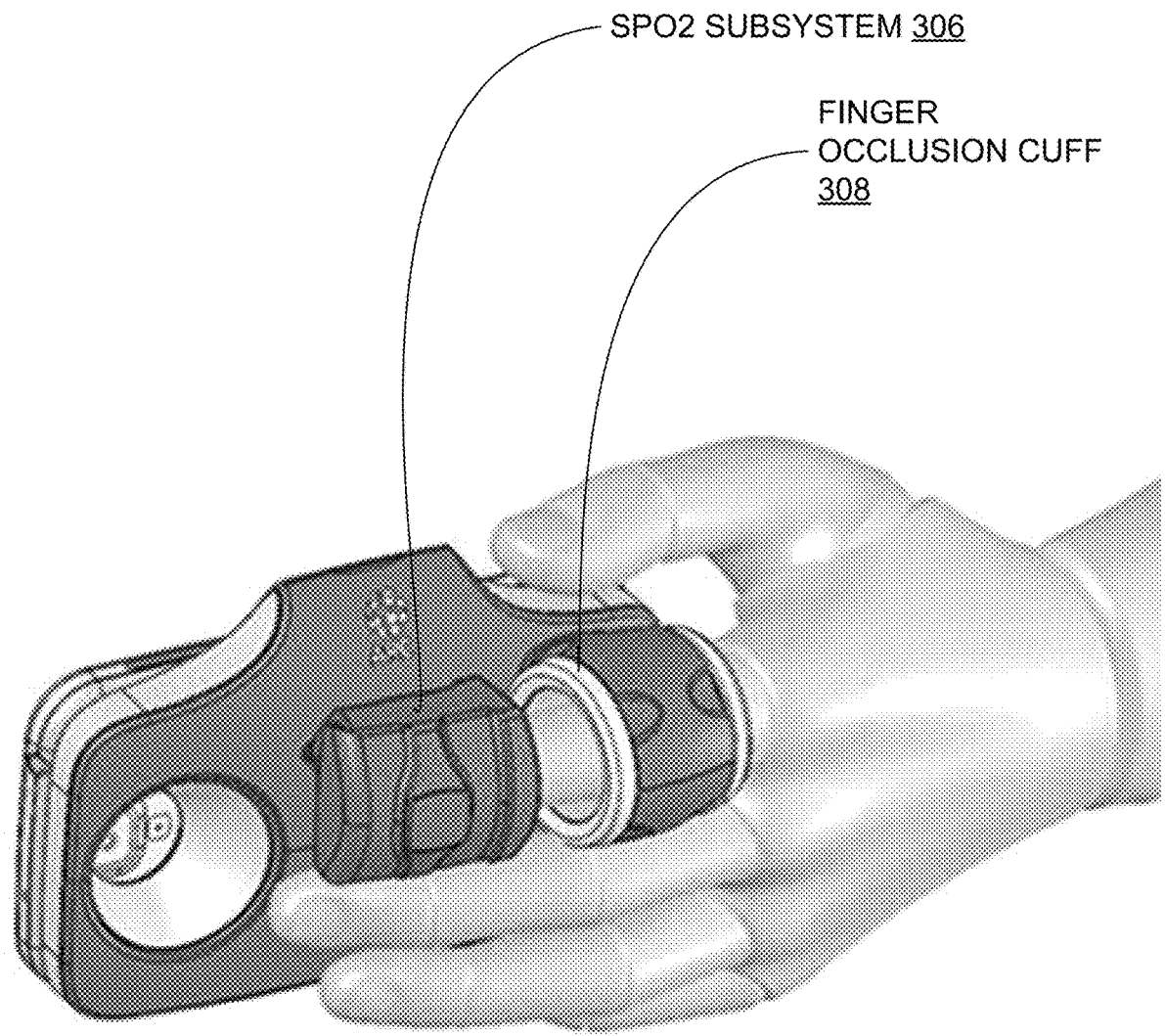
Figure 4:
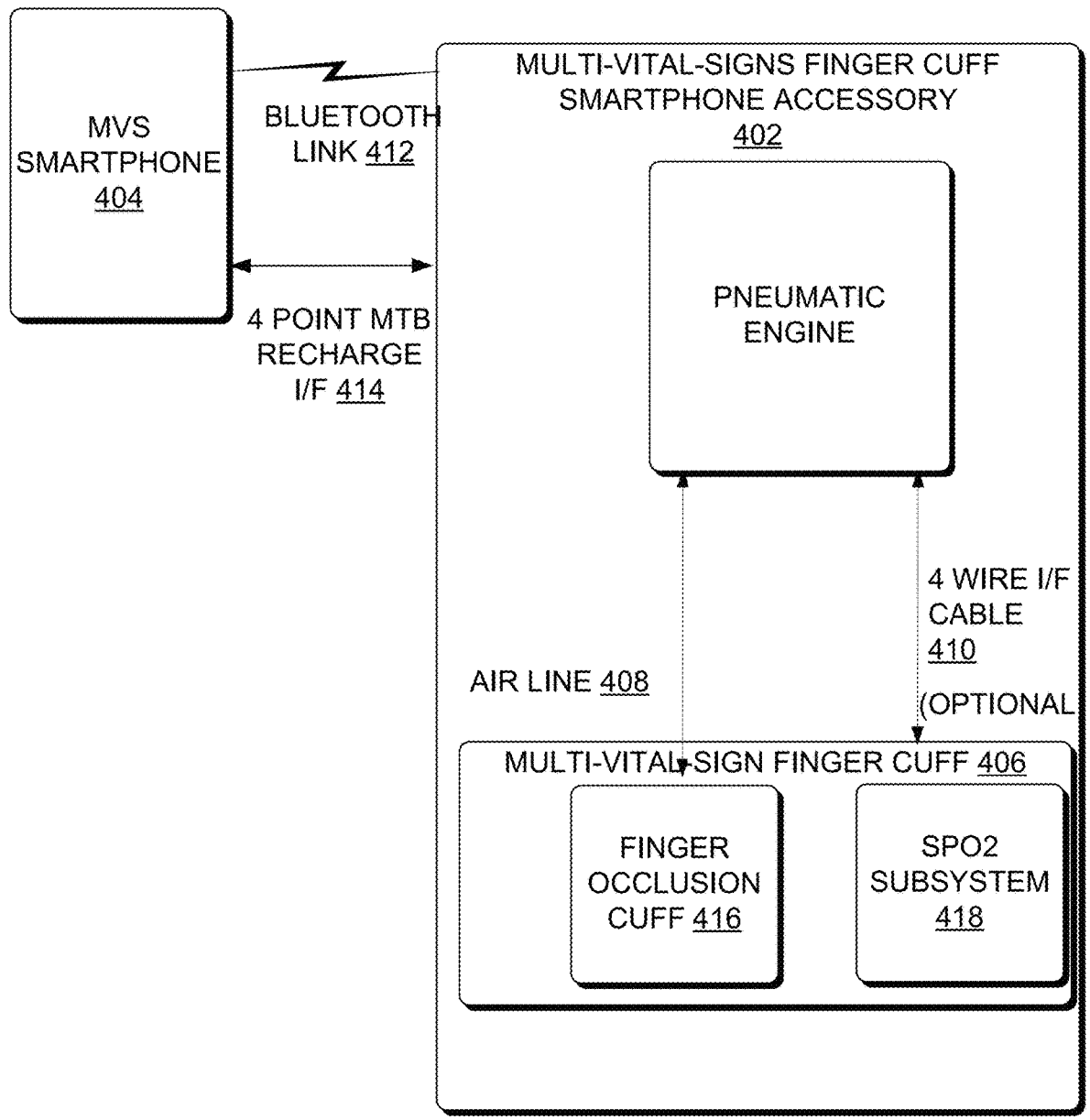
Figure 5:
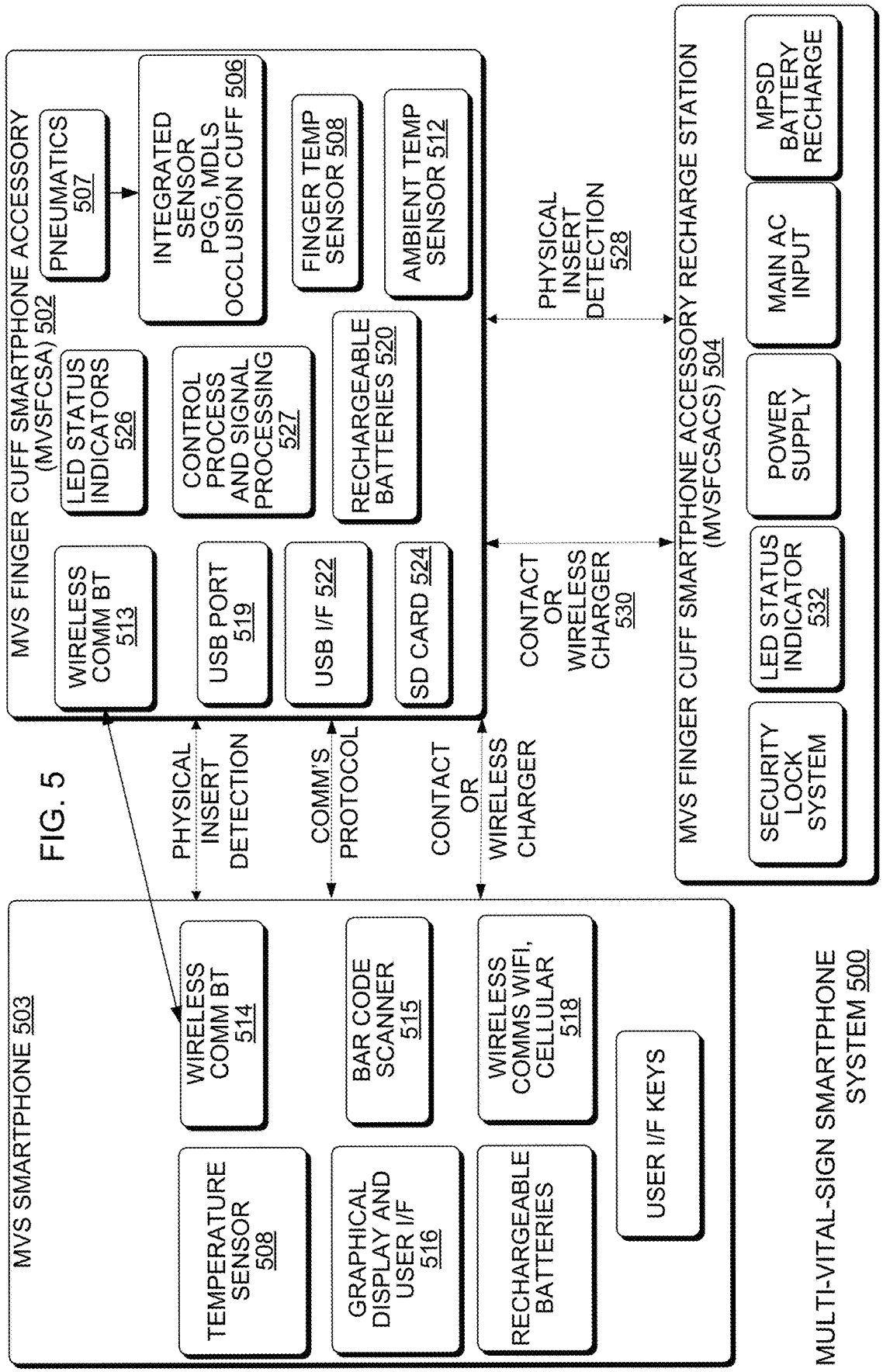

FIG. 5 is a block diagram of a multi-vital-sign smartphone system 500, according to an implementation. The MVS smartphone system 500 includes three communicatively coupled devices; a multi-vital-signs finger cuff smartphone accessory (MVSFCSA) 502, a multi-vital-sign smartphone (MVS Smartphone) 503 and a multi-vital-signs finger cuff smartphone accessory Recharge Station (MVSFCSARS) 504. MVSFCSA 502 is one implementation of MVSFCSA 402 in FIG. 4. MVS Smartphone 503 is one implementation of MVS Smartphone 404 in FIG. 4. The MVS smartphone system 500, the MVSFCSA 502 and the MVS Smartphone 504 are all examples of the multi-vital-sign smartphone system(s) 104. The MVS Smartphone 503 captures, stores and exports raw data from all supported sensors in the system. More specifically, the MVS Smartphone 503 extracts and displays vital sign parameters and transfers the parameters to either a remote third party, hub, bridge etc, or a device manager, or directly to remote EMR/HER/Hospital systems or other third party local or cloud based systems. MVS smartphone system 500 provides a flexible human vital sign measurement methodology that supports different measurement methods and techniques. The MVS smartphone system 500 can be used in a clinical setting for the collection of human vital signs.

Figure 6:
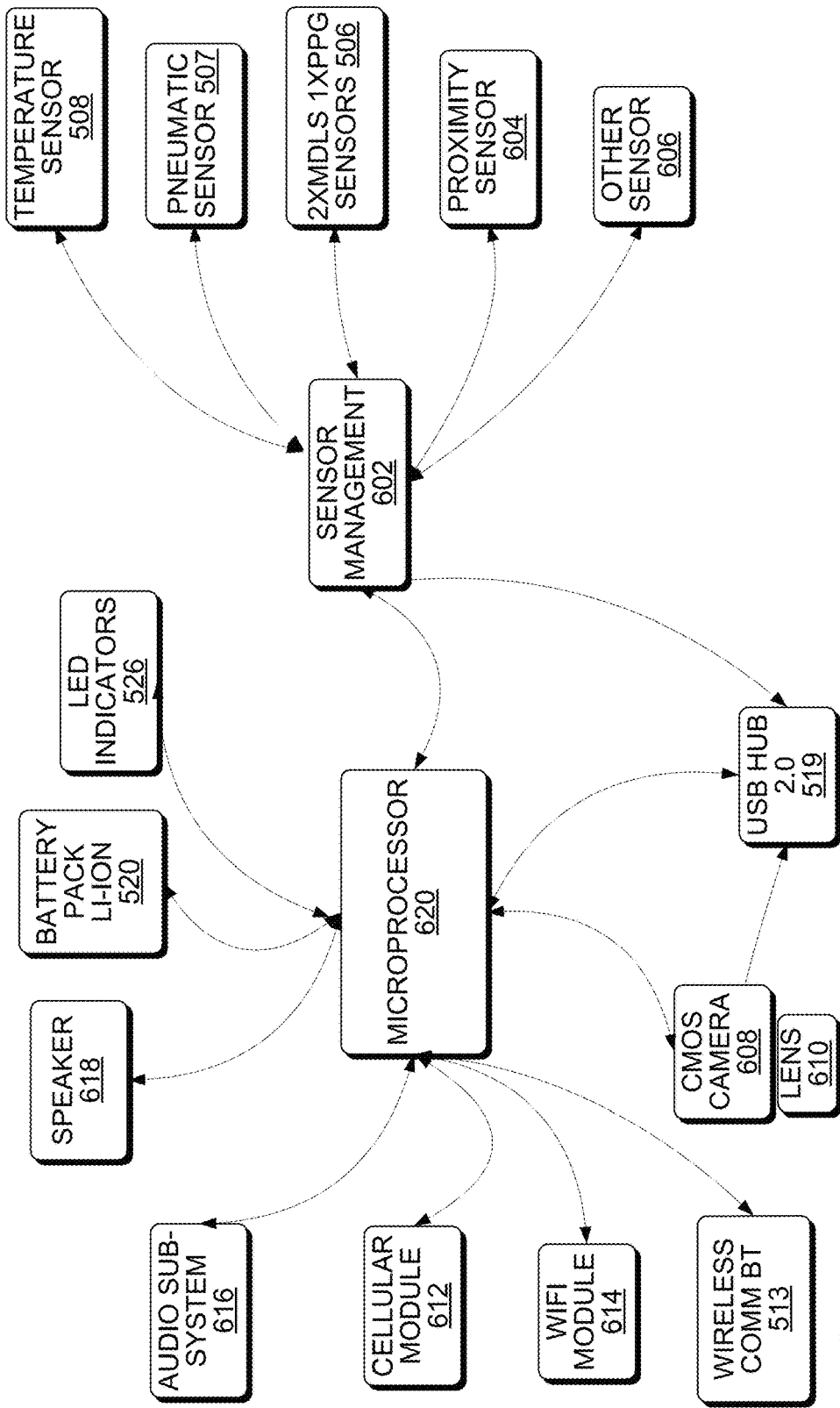
FIG. 6 is a block diagram of a multi-vital-signs finger cuff smartphone accessory.
Figure 7:
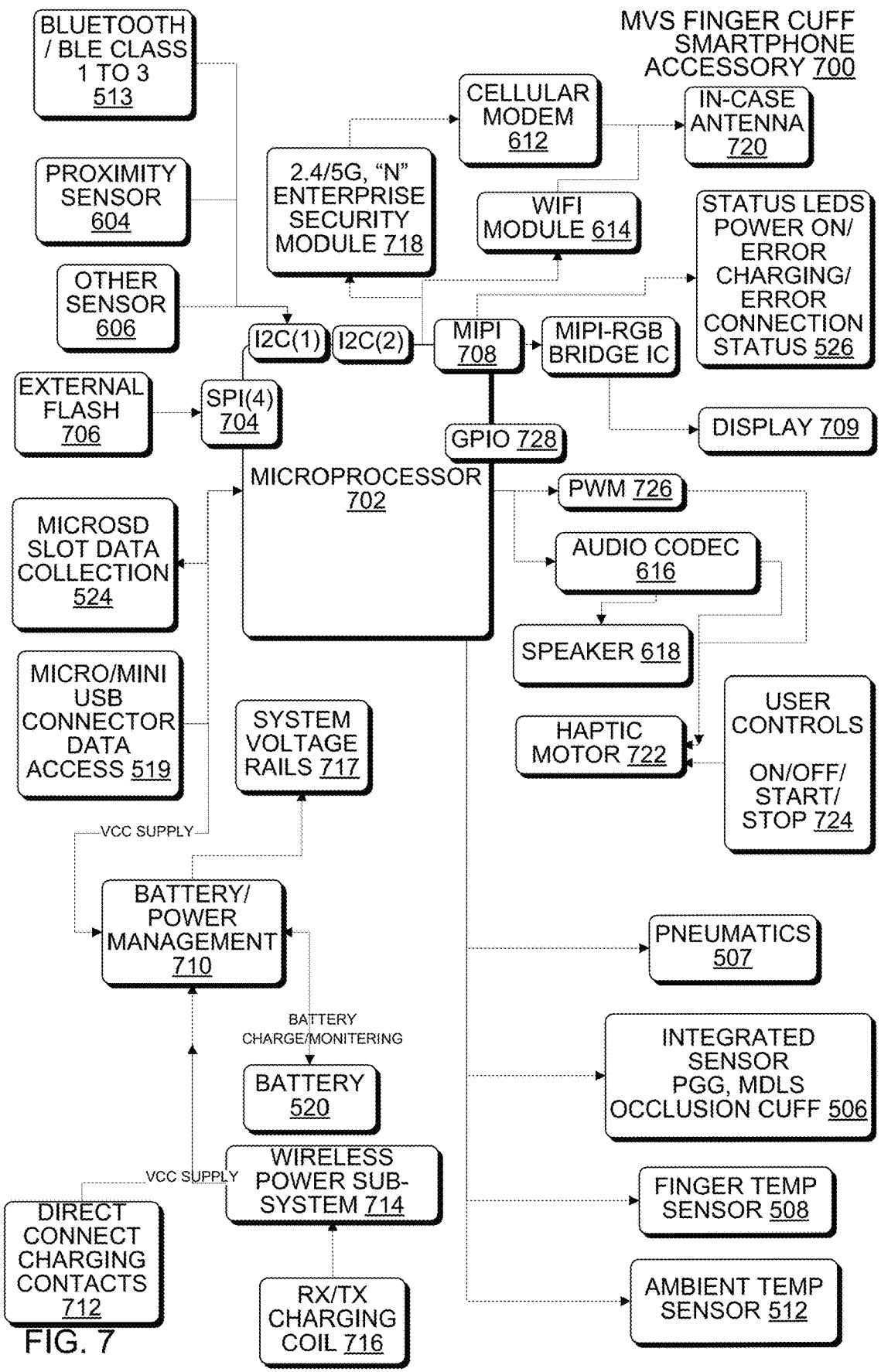
FIG. 7 is a block diagram of a multi-vital-signs finger cuff smartphone accessory.

Some implementations of the MVSFCSA 502 include a multi-vital-sign finger cuff 506 that is fixed into the MVSFCSA 502, rather than the replaceable, detachable and removable multi-vital-sign finger cuff 406 in FIG. 4. The multi-vital-sign finger cuff 506 includes a PPG sensor and at least one mDLS sensor. The multi-vital-sign finger cuff 506 is powered via an air line (e.g. 406 in FIG. 4) by a pneumatic engine 507 that provides air pressure to inflate the cuff bladder of the multi-vital-sign finger cuff 506 and the controlled release of that pressure. In some implementations, the air line 408 is ⅙" (4.2 mm) in diameter. The multi-vital-sign finger cuff 506 in FIG. 5-7 is the same as the mDLS sensors 811 and 814 in FIG. 8, and/or 1742 in FIG. 17-19.

In some implementations, a body surface temperature of a human is also sensed by an infrared finger temperature sensor 508 that is integrated into the MVSFCSA 502 in which the body surface temperature is collected and managed by the MVSFCSA 502. One example of the pneumatic engine 507 is the pneumatic system components 900 in FIG. 9.

In some implementations, a single stage measurement process is required to measure all vital signs in one operation by the MVS Smartphone 503 by the replaceable, detachable and removable multi-vital-sign finger cuff 406 or the multi-vital-sign finger cuff 506 or the infrared finger temperature sensor 508. However, in some implementations, a two stage measurement process is performed in which the MVSFCSA 502 measures some vital signs through the replaceable, detachable and removable multi-vital-sign finger cuff 406 or the multi-vital-sign finger cuff 506; and in the second stage, the body surface temperature is measured through an infrared finger temperature sensor 508 in the MVS Smartphone device 503. One implementation of the infrared finger temperature sensor 508 is digital infrared sensor 2100 in FIG. 21.

The MVSFCSA 502 operates in two primary modes, the modes of operation based on who takes the measurements, a patient or an operator. The two modes are: 1) Operator Mode in which an operator operates the MVSFCSA 502 to take a set of vital sign measurements of another human. The operator is typically clinical staff or a home care giver. 2) Patient Mode in which a patient uses the MVSFCSA 502 to take a set of vital sign measurements of themselves. In some implementations, the MVSFCSA 502 provides both the main measurement modes for patient and operator. The primary measurement areas on the human to be measured are 1) Left hand, index and middle finger, 2) right hand, index and middle finger, and 3) human forehead temperature (requires the other device to perform temperature measurement). The MVSFCSA 502 is portable, light weight, hand held and easy to use in primary and secondary modes of operation in all operational environments.

Given the complex nature of integration into hospital networks, in some implementations, in some implementations the MVSFCSA 502 does not include site communication infrastructure, rather the collected data (vital sign) is extracted from the MVSFCSA 502 via a USB port or by a USB mass storage stick that is inserted into the MVSFCSA 502 or by connecting the MVSFCSA 502 directly to a PC system as a mass storage device itself.

The Multi-Vital-Sign Smartphone (MVS Smartphone) device 503, when connected to a wireless Bluetooth® communication component 513 of the MVSFCSA 502 via a wireless Bluetooth® communication component 514, is a slave to the MVSFCSA 502. The MVS Smartphone 503 reports status, measurement process, and measurement measurements to the user via the MVSFCSA 502. The MVS Smartphone 503 provides a user input method to the MVSFCSA 502 via a graphical user interface on a LCD display 516 which displays data representative of the measurement process and status. In one implementation, the wireless Bluetooth® communication component 513 of the MVSFCSA 502 includes communication capability with cellular communication paths (3G, 4G and/or 5G) and/or WiFi® communication paths and the MVSFCSA 502 is not a slave to the captures vital sign data and transmits the vital sign data via the wireless Bluetooth® communication component 513 in the MVSFCSA 502 to the middle layer 106 in FIG. 1 or the MVS Smartphone 503 transmits the vital sign data via the communication component 518 of the MVS Smartphone 503 to the bridge 120, a WiFi® access point, a cellular communications tower, a bridge 120 in FIG. 1.

In some implementations, the MVS Smartphone 503 provides communications with other devices via a communication component 518 of the MVS Smartphone 503. The communication component 518 has communication capability with cellular communication paths (3G, 4G and/or 5G) and/or WiFi® communication paths. For example, the MVSFCSA 502 captures vital sign data and transmits the vital sign data via the wireless Bluetooth® communication component 513 in the MVSFCSA 502 to the wireless Bluetooth® communication component 514 in the MVS Smartphone 503, and the MVS Smartphone 503 transmits the vital sign data via the communication component 518 of the MVS Smartphone 503 to the middle layer 106 in FIG. 1 or the MVS Smartphone 503 transmits the vital sign data via the communication component 518 of the MVS Smartphone 503 to the bridge 120, a WiFi® access point, a cellular communications tower, a bridge 120 in FIG. 1.

In some implementations, when the MVS Smartphone 503 is connected to the MVSFCSA 502, the MVS Smartphone 503 performs human bar code scan or identification entry as requested by MVSFCSA 502, the MVS Smartphone 503 performs an operator bar code scan or identification entry as requested by MVSFCSA 502, the MVS Smartphone 503 performs human temperature measurement as requested by MVSFCSA 502, the MVS Smartphone 503 displays information that is related to the MVSFCSA 502 direct action, the MVS Smartphone 503 starts when the MVSFCSA 502 is started, and the MVS Smartphone 503 is shutdown under the direction and control of the MVSFCSA 502, and the MVS Smartphone 503 has a self-test mode that determines the operational state of the MVSFCSA 502 and sub systems, to ensure that the MVSFCSA 502 is functional for the measurement. In other implementations, when the MVS Smartphone 503 is connected to the MVSFCSA 502, the MVS Smartphone 503 performs human bar code scan or identification entry as requested by MVS Smartphone 503, the MVS Smartphone 503 performs an operator bar code scan or identification entry as requested by MVS Smartphone 503, the MVS Smartphone 503 performs human temperature measurement as requested by MVS Smartphone 503 and the MVS Smartphone 503 displays information that is related to the MVSFCSA 502 direct action. In some implementations, the information displayed by the MVS Smartphone 503 includes date/time, human identification number, human name, vitals measurement such as blood pressure (diastolic and systolic), SpO2, heart rate, temperature, respiratory rate, MVSFCSA 502 free memory slots, battery status of the MVS Smartphone 503, battery status of the MVSFCSA 502, device status of the MVSFCSA 502, errors of the MVS Smartphone 503, device measurement sequence, measurement quality assessment measurement, mode of operation, subject and operator identification, temperature, measurement, display mode and device revision numbers of the MVS Smartphone 503 and the MVSFCSA 502. In some implementations, when a body surface temperature of a human is also sensed by an infrared sensor in the multi-vital-sign smartphone (MVS Smartphone) device 503, the body surface temperature is collected and managed by the MVSFCSA 502. In other implementations, when a body surface temperature of a human is sensed by an infrared sensor in the multi-vital-sign smartphone (MVS Smartphone) device 503, the body surface temperature is not collected and managed by the MVSFCSA 502.

In some implementations, the multi-vital-signs finger cuff smartphone accessory (MVSFCSA) 502 includes the following sensors and sensor signal capture and processing components that are required to extract the required primary and secondary human vital signs measurements: the multi-vital-sign finger cuff 506 that includes a PPG sensor and two mDLS sensors, the infrared finger temperature sensor 508 and an ambient temperature sensor 512, and in some further implementation, non-disposable sensors for other human measurements. In some implementations, data sample rates for PPG sensor is 2×200 Hz×24 bit=9600 bits/sec, for each of the mDLS sensors is 32 kHz×24 bit=1,572,864 bit/sec and for the ambient temperature sensor is less than 1000 bps. Two mDLS sensors are included in the MVSFCSA 502 to ensure that one or both sensors delivers a good quality signal, thus increasing the probability of obtaining a good signal from a mDLS sensor.

The MVS Smartphone 503 performs concurrent two stage measurement processes for all measurements. The measurement process performed by the MVS Smartphone 503 is controlled and guided from the MVS Smartphone 503 via the GUI on the MVSFCSA 502. The measurements are sequenced and configured to minimize time required to complete all measurements. In some implementations, the MVS Smartphone 503 calculates the secondary measurements of heart rate variability and blood flow. The MVS Smartphone 503 commands and controls the MVSFCSA 502 via a wireless Bluetooth® protocol communication line 412 and in some further implementations, the MVSFCSA 502 communicates to other devices through Bluetooth® protocol communication line (not shown), in addition to the communications with the MVS Smartphone 503, which could also be concurrent. In some further implementations, the MVS Smartphone 503 communicates to other devices through Bluetooth® protocol communication line (not shown), in addition to the communications with the MVSFCSA 502 device, which could also be concurrent.dd MVSFCSA 502 includes a USB port 519 for interface with the MVS Smartphone 503 only, such as the MVS Smartphone 503, to perform the following functions: recharge the internal rechargeable batteries 520 of the MVSFCSA 502, export sensor data sets to a windows based computer system, firmware update of the MVSFCSA 502 via an application to control and manage the firmware update of the MVSFCSA 502 and configuration update of the MVSFCSA 502. The MVSFCSA 502 does not update the MVS Smartphone 503 firmware. The MVSFCSA 502 also includes internal rechargeable batteries 520 that can be recharged via a USB port 522, which provides charge, and the MVSFCSA 502 also includes an external direct DC input providing a fast recharge. The internal batteries of the MVSFCSA 502 can be recharged when the MVSFCSA 502 is powered-off but while connected to USB or DC input. In some implementations, the MVSFCSA 502 can recharge the MVS Smartphone 503 from its internal power source over a wireless charging connection. In some implementations, the internal rechargeable batteries 520 provide sufficient operational life of the MVSFCSA 502 on a single charge to perform at least 2 days of full measurements before recharging of the internal rechargeable batteries 520 of the MVSFCSA 502 is required.

In some implementations, the MVSFCSA 502 includes an internal non-volatile, non-user removable, data storage device 524 for up to 20 human raw measurement data sets. The data storage device 524 can be removed by a technician when the data storage device 524 is determined to be faulty. A human measurement set contains all measurement data and measurements acquired by the MVSFCSA 502, including the temperature measurement from the MVS Smartphone 503. The internal memory is protected against data corruption in the event of an abrupt power loss event. The MVSFCSA 502 and the MVS Smartphone 503 have a human-form fit function sensor and device industrial/mechanical design. The MVSFCSA 502 also includes anti-microbial exterior material to and an easy clean surface for all sensor and device surfaces. The MVSFCSA 502 stores in the data storage device 524 an "atomic" human record structure that contains the entire data set recording for a single human measurement containing all human raw sensor signals and readings, extracted human vitals, and system status information. The MVSFCSA 502 includes self-test components that determine the operational state of the MVSFCSA 502 and sub systems, to ensure that the MVSFCSA 502 is functional for measurement. The MVSFCSA 502 includes a clock function for date and time. In some implementations. The date and time of the MVSFCSA 502 is be updated from the MVS Smartphone 503. In some implementations, the MVSFCSA 502 includes user input controls, such as a power on/off switch (start/stop), an emergency stop control to bring the multi-vital-sign finger cuff to a deflated condition. In some implementations, all other input is supported via the MVS Smartphone 503 via on screen information of the MVS Smartphone 503. In some implementations, the MVSFCSA 502 includes visual indicators 526 such as a fatal fault indicator that indicates device has failed and will not power up, a device fault indicator (that indicates the MVSFCSA 502 has a fault that would affect the measurement function), battery charging status indicator, battery charged status indicator, a battery fault status indicator.

The components (e.g. 506, 507, 508, 512, 513, 519, 520, 522, 524 and 526) in the MVSFCSA 502 are controlled by a control process and signal processing component 527. The control process and signal processing component 527 can implemented by a microprocessor or by a FPGA.

The Multi-vital-signs finger cuff smartphone accessory Recharge Station (MVSFCSARS) 504, provides electrical power to recharge the MVSFCSA 502. The MVSFCSARS 504 can provide electrical power to recharge the batteries of the MVSFCSA 502 either via a physical wired connection ' or via a wireless charger 530. In some implementations, the MVSFCSARS 504 does not provide electrical power to the MVSFCSA 502 because the MVSFCSA 502 includes internal rechargeable batteries 520 that can be recharged via either USB port 522 or a DC input.

MVS Smartphone 503 includes a connection status indicator (connected/not connected, fault detected, charging/not charging), a connected power source status indicator, (either USB or DC input) and a power On/Off status indicator. The visual indicators are visible in low light conditions in the home and clinical environment.

The MVSFCSA 502 is hand held and portable. The MVSFCSA 502 includes non-slip/slide exterior surface material.

FIG. 6 is a block diagram of a multi-vital-signs finger cuff smartphone accessory (MVSFCSA) 600, according to an implementation. MVSFCSA 600 is one implementation of MVSFCSA 402 in FIG. 4 and MVSFCSA 600 is one implementation of MVSFCSA 502 in FIG. 5. The MVSFCSA 600 captures, stores and exports raw data from all supported sensors in the system. MVSFCSA 600 supports a variety measurement methods and techniques. The MVSFCSA 600 can be used in a clinical setting for the collection of human vital signs.

A sensor management component 602 controls and receives data from a multi-vital-sign finger cuff 506, a pump, valve, and pressure sensor (shown in FIG. 9) an infrared finger temperature sensor 508, a proximity sensor 604 and another sensor 606d. The sensor management component 602 can be implemented in the control process and signal processing component 527 in FIG. 5, which can be implemented by a microprocessor or by a FPGA.

MVSFCSA 600 also includes a CMOS camera 608 that is operably coupled to a USB port 519. The CMOS camera captures images that are processed for reading a barcode to identify the patient and by motion amplification components for determining heart rate, respiratory rate, and blood pressure, a lens 610 is coupled to the CMOS camera 608.

The multi-vital-sign finger cuff 506 is integrated into the MVSFCSA 600, rather than the replaceable, detachable and removable multi-vital-sign finger cuff 406 in FIG. 4. The multi-vital-sign finger cuff 506 includes a PPG sensor and at least one mDLS sensor. The multi-vital-sign finger cuff 506 is powered via an air line (e.g. 408 in FIG. 4) by the pneumatic engine 507 that provides air pressure to inflate and deflate the cuff bladder of the multi-vital-sign finger cuff 506 and real time measurement.

In some implementations, a body surface temperature of a human is also sensed by the infrared finger temperature sensor 508 that is integrated into the MVSFCSA 600 in which the body surface temperature is collected and managed by the MVSFCSA 600.

In some implementations, a single stage measurement process is required to measure all vital signs in one operation by the MVSFCSA 600 by the replaceable, detachable and removable multi-vital-sign finger cuff 406 or the multi-vital-sign finger cuff 506 or the infrared finger temperature sensor 508. However, in some implementations, a two stage measurement process is performed in which the MVSFCSA 600 measures some vital signs through the replaceable, detachable and removable multi-vital-sign finger cuff 406 or the multi-vital-sign finger cuff 506; and in the second stage, the body surface temperature is measured through an infrared finger temperature sensor 508 in the MVS Smartphone device 503.

The MVSFCSA 600 operates in two primary modes, the modes of operation based on who takes the measurements, a patient or an operator. The two modes are: 1) Operator Mode in which an operator operates the MVSFCSA 600 to take a set of vital sign measurements of another human. The operator is typically clinical staff or a home care giver. 2) Patient Mode in which a patient uses the MVSFCSA 600 to take a set of vital sign measurements of themselves. In some implementations, the MVSFCSA 600 provides both the main measurement modes for patient and operator. The primary measurement areas on the human to be measured are 1) face 2) forehead 3) Left hand, index and middle finger and 4) right hand, index and middle finger. The MVSFCSA 600 is portable, light weight, hand held and easy to use in primary and secondary modes of operation in all operational environments.

Given the complex nature of integration into hospital networks, in some implementations, the MVSFCSA 600 does not include site communication infrastructure, rather the collected data (vital sign) is extracted from the MVSFCSA 600 via a USB port or by a USB mass storage stick that is inserted into the MVSFCSA 600 or by connecting the MVSFCSA 600 directly to a PC system as a mass storage device itself.

The Multi-Vital-Sign Smartphone (MVS Smartphone) device 503, when connected to a wireless Bluetooth® communication component 513 of the MVSFCSA 600 via a wireless Bluetooth® communication component 514, is a slave to the MVSFCSA 600. The MVS Smartphone 503 reports status, measurement process, and measurement measurements to the user via the MVSFCSA 600.

When the MVS Smartphone 503 is connected to the MVSFCSA 600, the MVS Smartphone 503 performs patient bar code scan or identification entry as requested by MVSFCSA 600, the MVS Smartphone 503 performs an operator bar code scan or identification entry as requested by MVSFCSA 600, the MVS Smartphone 503 performs human temperature measurement as requested by MVSFCSA 600, the MVS Smartphone 503 displays information that is related to the MVSFCSA 600 direct action, the MVSFCSA 600 starts when the MVS Smartphone 503 is started, and the MVSFCSA 600 is shutdown under the direction and control of the MVS Smartphone 503. In some implementations, the information displayed by the MVS Smartphone 503 includes battery status of the MVSFCSA 600, device status of the MVSFCSA 600, MVSFCSA 600 display mode and device revision numbers of the MVS Smartphone 503 and the MVSFCSA 600. In some implementations, when a body surface temperature of a human is also sensed by an infrared finger temperature sensor 508 in the multi-vital-sign smartphone (MVS Smartphone) device 503, the body surface temperature is collected and managed by the MVSFCSA 600.

In some implementations, the multi-vital-signs finger cuff smartphone accessory (MVSFCSA) 600 includes the following sensors and sensor signal capture and processing components that are required to extract the required primary and secondary human vital signs measurements: the multi-vital-sign finger cuff 506 that includes a PPG sensor and two mDLS sensors, the infrared finger temperature sensor 508, a proximity sensor 604 and another non-disposable sensor(s) for other human measurements sensor 606 or ambient temperature sensor 512.

The MVSFCSA 600 performs concurrent two stage measurement processes for all measurements. The measurement process performed by the MVSFCSA 600 is controlled and guided from the MVSFCSA 600 via the GUI on the MVS Smartphone 503. The measurements are sequenced and configured to minimize time required to complete all measurements. In some implementations, the MVSFCSA 600 calculates the secondary measurements of heart rate variability and blood flow. The MVSFCSA 600 commands and controls the MVS Smartphone 503 via a wireless Bluetooth® protocol communication line 412 and in some further implementations, the MVS Smartphone 503 communicates to the communications with the MVSFCSA 600, which could also be concurrent.

In some implementations, the MVSFCSA 600 includes a USB On-the-Go port 519 for interface with slave devices only, such as the MVS Smartphone 503, to perform the following functions: recharge the internal rechargeable batteries 520, export sensor data sets to a windows based computer system, firmware update of the MVSFCSA 600 via an application to control and manage the firmware update of the MVSFCSA 600 and configuration update of the MVSFCSA 600. The MVSFCSA 600 does update the MVS Smartphone 503 firmware. The internal batteries of the MVSFCSA 600 can be recharged when the MVSFCSA 600 is powered-off but while connected to USB or DC input. In some implementations, the MVSFCSA 600 can recharge the MVS Smartphone 503 from its internal power source over a wireless charging connection. In some implementations, the internal rechargeable batteries 520 provide sufficient operational life of the MVSFCSA 600 on a single charge to perform at least 2 days of full measurements before recharging of the internal rechargeable batteries 520 of the MVSFCSA 600 is required.

In some implementations, the MVSFCSA 600 includes visual indicators 526 such as a fatal fault indicator that indicates the MVSFCSA 600 has failed and will not power up, a device fault indicator (that indicates the MVSFCSA 600 has a fault that would affect the measurement function), a battery charging status indicator, a battery charged status indicator, and/or a battery fault status indicator.

The MVSFCSA 600 also includes a cellular communication module 612 (this could be integrated into the processor) for communications via cell communication frequencies and a WiFi® communication module 614 (this could be integrated into the processor) for communications via WIF communication frequencies. In some implementations, the MVSFCSA 600 also includes an audio sub-system d616 that controls at one or more speakers 618 to enunciate information to an operator or patient via tones, polymorphic and general music/speech capability.

MVSFCSA 600 includes a microprocessor 620 that controls and communicates with the sensor management component 602, the CMOS camera 608, the lens 610, the cellular communication module 612, the WiFi® communication module 614, the audio sub-system 616, speakers 618, the USB port 519, the batteries 520 and the visual indicators 526. In some implementations, the sensor management component 602 is a component of the microprocessor 620.

The MVSFCSA 600 is hand held and portable. The MVSFCSA 600 includes non-slip/slide exterior surface material.

FIG. 7 is a block diagram of a multi-vital-signs finger cuff smartphone accessory (MVSFCSA) 700, according to an implementation. MVSFCSA 700 is one implementation of MVSFCSA 402 in FIG. 4, MVSFCSA 700 is one implementation of MVSFCSA 502 in FIG. 5 and MVSFCSA 700 is one implementation of MVSFCSA 600 in FIG. 6. The MVSFCSA 700 captures, stores and exports raw data from all supported sensors in the system. MVSFCSA 700 supports a variety measurement methods and techniques. The MVSFCSA 700 can be used in a clinical setting for the collection of human vital signs.

A microprocessor 702 controls and receives data from a multi-vital-sign finger cuff 506, a pneumatic engine 507, an infrared finger temperature sensor 508, a proximity sensor 604 and another sensor 606. The sensor management component 602 in FIG. 7 can be implemented in the control process and signal processing component 527 in FIG. 5, which can be implemented by a microprocessor or by a FPGA. In some implementations the microprocessor 702 is an advanced reduced instruction set processor.

The multi-vital-sign finger cuff 506 is integrated into the MVSFCSA 700, rather than the replaceable, detachable and removable multi-vital-sign finger cuff 406 in FIG. 4. The multi-vital-sign finger cuff 506 includes a PPG sensor and at least one mDLS sensor. The multi-vital-sign finger cuff 506 is powered via an air line (e.g. 406 in FIG. 4) by the pneumatic engine 507 that provides air pressure to inflate the cuff bladder of the multi-vital-sign finger cuff 506 and the that provides control signal to deflate the cuff bladder of the multi-vital-sign finger cuff 506.

In some implementations, a body surface temperature of a human is also sensed by the infrared finger temperature sensor 508 that is integrated into the MVSFCSA 700 in which the body surface temperature is collected and managed by the MVSFCSA 700.

In some implementations, a single stage measurement process is required to measure all vital signs in one operation by the MVSFCSA 700 by the replaceable, detachable and removable multi-vital-sign finger cuff 406 or the multi-vital-sign finger cuff 506 or the infrared finger temperature sensor 508. However, in some implementations, a two stage measurement process is performed in which the MVSFCSA 700 measures some vital signs through the replaceable, detachable and removable multi-vital-sign finger cuff 406 or the multi-vital-sign finger cuff 506; and in the second stage, the body surface temperature is measured through an infrared finger temperature sensor 508 in the MVS Smartphone device 503.

The Multi-Vital-Sign Smartphone (MVS Smartphone) device 503, when connected to a wireless Bluetooth® communication component 513 of the MVSFCSA 700 via a wireless Bluetooth® communication component 514, is a slave to the MVSFCSA 700. The MVS Smartphone 503 reports status, measurement process, and measurement measurements to the user via the MVSFCSA 700.

In some implementations, the measurement process performed by the MVSFCSA 700 is controlled and guided from the MVSFCSA 700 via the GUI on the MVS Smartphone 503. The measurements are sequenced and configured to minimize time required to complete all measurements. In some implementations, the MVSFCSA 700 calculates the secondary measurements of heart rate variability and blood flow. The MVSFCSA 700 commands and controls the MVS Smartphone 503 via a wireless Bluetooth® protocol communication line 412 and in some further implementations, the MVS Smartphone 503 communicates to the communications with the MVSFCSA 700, which could also be concurrent.

MVSFCSA 700 includes a USB port 519 that is operably coupled to the microprocessor 702 for interface with slave devices only, such as the MVS Smartphone 503, to perform the following functions: recharge the internal rechargeable batteries 520, export sensor data sets to a windows based computer system, firmware update of the MVSFCSA 700 via an application to control and manage the firmware update of the MVSFCSA 700 and configuration update of the MVSFCSA 700.

In some implementation recharging the internal rechargeable batteries 520 via the USB port 519 is controlled by a battery power management module 710. The battery power management module 710 receives power from a direct connect charging contact(s) 712 and/or a wireless power subsystem 714 that receives power from a RX/TX charging coil 716. The internal rechargeable batteries 520 of the MVSFCSA 700 can be recharged when the MVSFCSA 700 is powered-off but while connected to USB port 519 or DC input via the direct connect charging contacts 712. In some implementations, the MVSFCSA 700 can recharge the MVS Smartphone 503 from its internal power source over a wireless charging connection. In some implementations, the internal rechargeable batteries 520 provide sufficient operational life of the MVSFCSA 700 on a single charge to perform at least 2 full days of measurements before recharging of the internal rechargeable batteries 520 of the MVSFCSA 700 is required. In some implementations, system voltage rails 717 are operably coupled to the battery power management module 710.

In some implementations, the MVSFCSA 700 includes an internal non-volatile, non-user removable, data storage device 524 for up to 2 full days of human raw measurement data sets. In some implementations, the MVSFCSA 700 includes a Serial Peripheral Interface (SPI) 704 that is configured to connect to an eternal flash storage system 706.

In some implementations, the MVSFCSA 700 includes a Mobile Industry Processor Interface (MIPI) 708 that is operably connected to the microprocessor 702 and a display screen 709. The microprocessor 702 is also operably coupled to the visual indicators 526.

The MVSFCSA 700 also includes a WiFi® communication module 614 for communications via WiFi® communication frequencies and the MVSFCSA 700 also includes an enterprise security module 718 a cellular communication module 612 for communications via cell phone communication frequencies. The WiFi® communication module 614 and the cellular communication module 612 are operably coupled to an antenna that is located with a case/housing of the MVSFCSA 700.

The MVSFCSA 700 also includes an audio sub-system 616 that controls at one or more speakers 618 to enunciate information to an operator or patient. In some implementations, the microprocessor 702 also controls a haptic motor 722 through the audio sub-system 616. User controls 724 also control the haptic motor 722. A pulse-width modulator 726 that is operably coupled to a general-purpose input/output (GPIO) 728 (that is operably coupled to the microprocessor 702) provides control to the haptic motor 722.

The MVSFCSA 700 is hand held and portable. The MVSFCSA 700 includes non-slip/slide exterior surface material.

In some further implementations the MVSFCSA 600 in FIG. 6 and MVSFCSA 700 in FIG. 7 perform continuous spot monitoring on a predetermined interval with automatic transfer to remote systems via WiFi®, cellular or Bluetooth® communication protocols, with and without the use of a MVS Smartphone device, and alarm monitoring and integration into clinical or other real time monitoring systems, integration with the sensor box, with the MVSFCSA acting as a hub, for third party sensors, such as ECG, or from direct connect USB or wireless devices, e.g. Bluetooth® patches.

Wireless/network systems (WiFi®, cellular 3G, 4g or 5G) or Bluetooth®) are quite often unreliable. Therefore in some implementations, the MVS Smartphone devices and the MVSFCSA devices manage vital sign measurements for later transmission.

Figure 8:
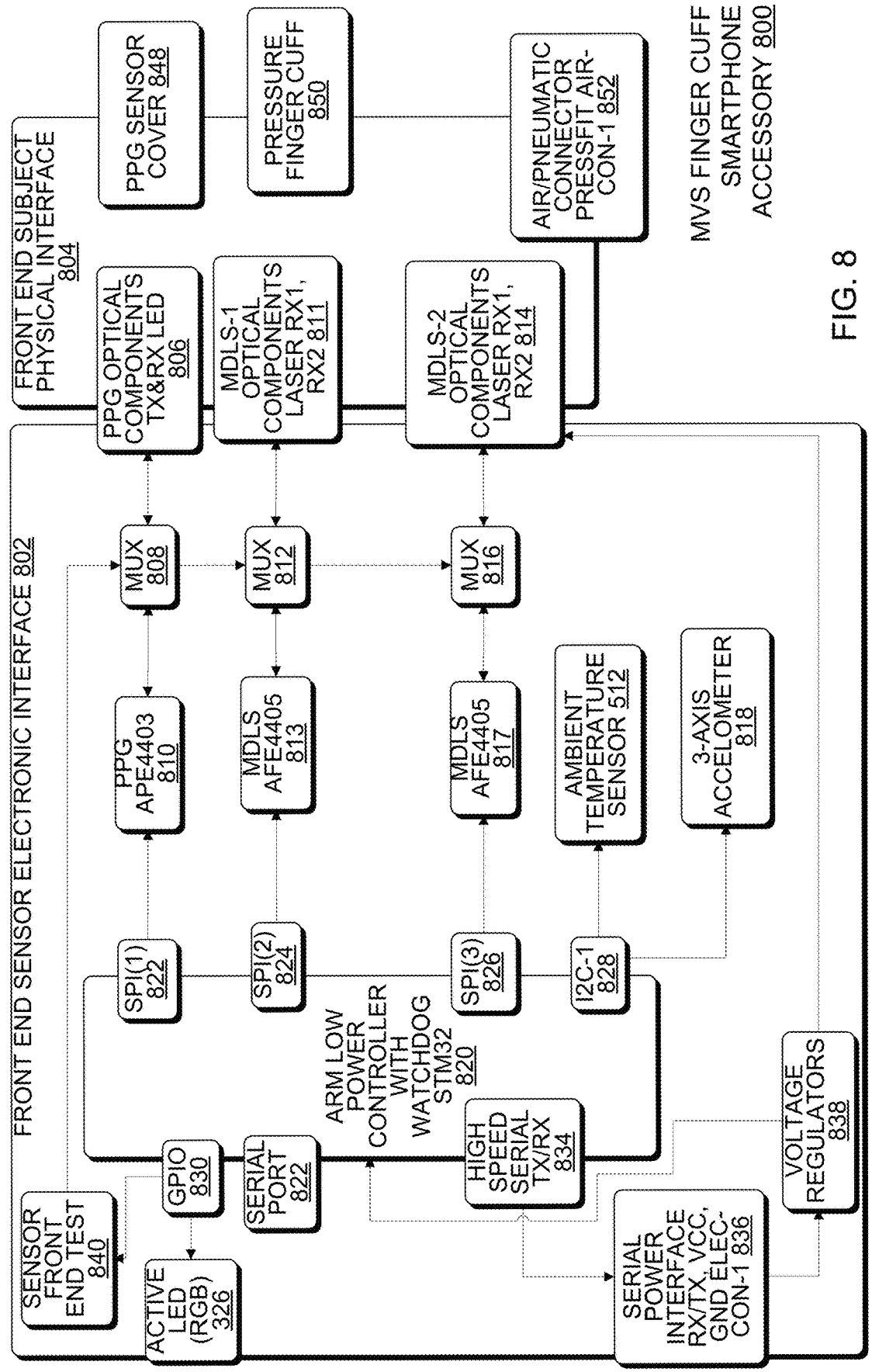
FIG. 8 is a block diagram of a front end of a multi-vital-sign finger cuff.

FIG. 8 is a block diagram of a front end of a multi-vital-sign finger cuff 800, according to an implementation. The front end of a multi-vital-sign finger cuff 800 is one implementation of a portion of a multi-vital-sign finger cuff 406 in FIG. 4. The front end of a multi-vital-sign finger cuff 800 captures, stores and exports raw data from all supported sensors in the system. The front end of a multi-vital-sign finger cuff 800 supports a variety measurement methods and techniques. The front end of a multi-vital-sign finger cuff 800 can be used in a clinical setting for the collection of human vital signs.

The front end of a multi-vital-sign finger cuff 800 includes a front-end sensor electronic interface 802 that is mechanically coupled to a front-end subject physical interface 804. The front-end sensor electronic interface 802 includes a PPG sensor 806 that is electrically coupled to a multiplexer 808 and to a PPG controller 810. The front-end sensor electronic interface 802 includes a mDLS sensor 811 that is electrically coupled to a multiplexer 812 which is coupled to a mDLS controller 813. The front-end sensor electronic interface 802 includes a mDLS sensor 814 that is electrically coupled to a multiplexer 816 and mDLS controller 817. The front-end sensor electronic interface 802 includes an ambient temperature sensor 512. The front-end sensor electronic interface 802 includes a 3-axis accelerator 818.

The PPG controller 810 is electrically coupled to a controller 820 through a Serial Peripheral Interface (SPI) 822. The mDLS controller 813 is electrically coupled to the controller 820 through a SPI 824. The mDLS sensor 814 is electrically coupled to the controller 820 through a SPI 826. The ambient temperature sensor 512 is electrically coupled to the controller 820 through a I2C interface 828. The 3-axis accelerator 818 is electrically coupled to the controller 820 through the I2C interface 828.

Visual indicator(s) 526 are electrically coupled to the controller 820 through a general-purpose input/output (GPIO) interface 830. A serial port 832 and a high speed serial port 834 are electrically coupled to the controller 820 and a serial power interface 836 is electrically coupled to the high speed serial port 834. A voltage regulator 838 is electrically coupled to the controller 820. A sensor front-end test component is electrically coupled to the controller 820 through the GPIO interface 830.

A PPG sensor cover 848 is mechanically coupled to the PPG sensor 806, a finger pressure cuff 850 is mechanically coupled to the front-end subject physical interface 804 and a pneumatic connector 852 is mechanically coupled to the finger pressure cuff 850.

Figure 9:
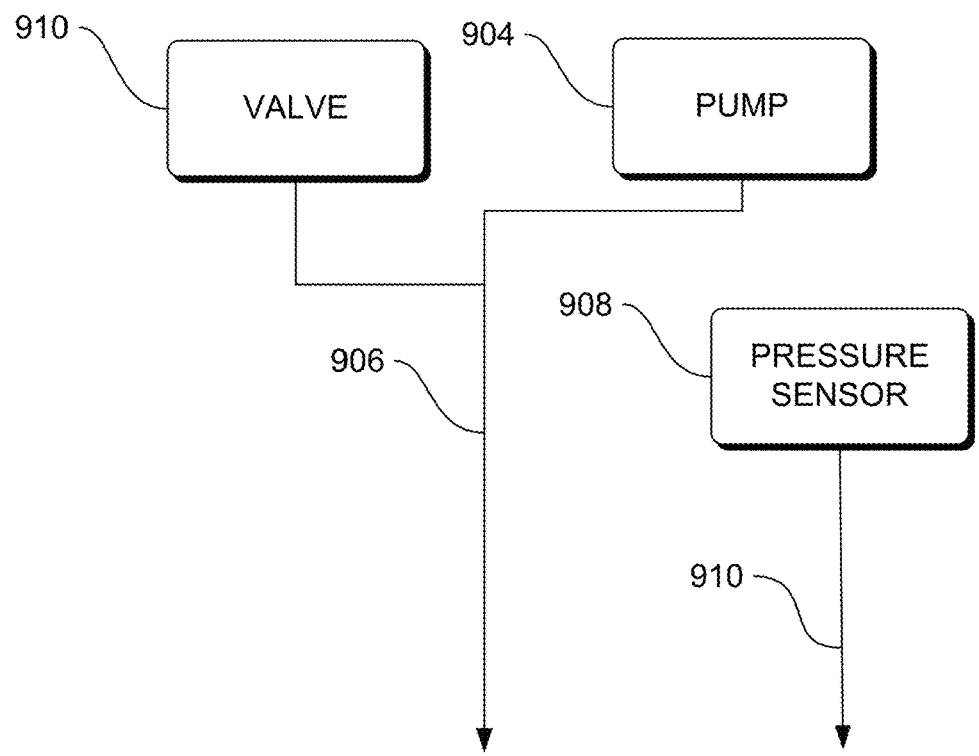
FIG. 9 is a block diagram of pneumatic system components that are internal to the multi-vital-signs finger cuff smartphone accessory.

FIG. 9 is a block diagram of a pneumatic system components 900, according to an implementation. The pneumatic system components 900 is one component of the multi-vital-sign finger cuff 406 in Fig. The pneumatic system components 900 are in the MVSFCSA 402, 502, 600, 700 and the front end of a multi-vital-sign finger cuff 800.

The pneumatic system components 900 includes a pneumatic pump 904 that is mechanically coupled to an inflatable cuff bladder, such as inflatable cuff bladder 1206 that provides air pressure to inflate the inflatable cuff bladder in the finger occlusion cuff 416 in FIG. 4. The inflatable cuff bladder 1206 is mechanically coupled to the pneumatic pump 904 via an air line 906, such as air line 408. The inflatable cuff bladder 1206 is mechanically coupled to a pressure sensor 908 that measures pneumatic pressure in the inflatable cuff bladder 1206. The air line 906 is mechanically coupled to a valve 910 that controls pressure from the pneumatic pump 904 to the inflatable cuff bladder 1206. The pneumatic system components 900 is one implementation of the pneumatic engine 507.

Figure 10:
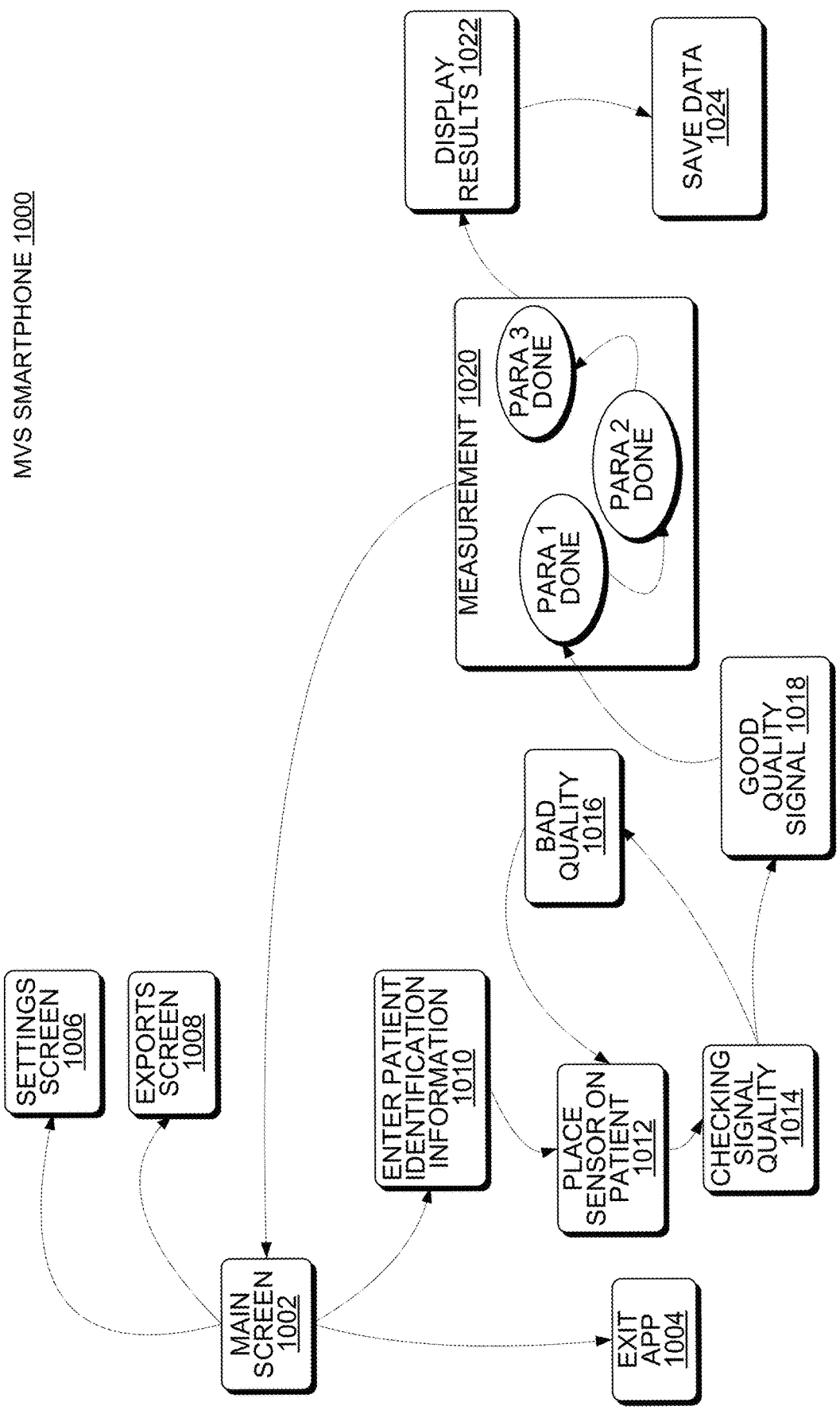
FIG. 10 is a data flow diagram of the multi-vital-Sign smartphone.

FIG. 10 is a data flow diagram 1000 of the multi-vital-sign smartphone (MVS Smartphone) device 503, according to an implementation. Data flow diagram 1000 is a process of the MVSFCSA 502 via a graphical user interface on a LCD display 516 on the MVS Smartphone device 503.

Figure 11:
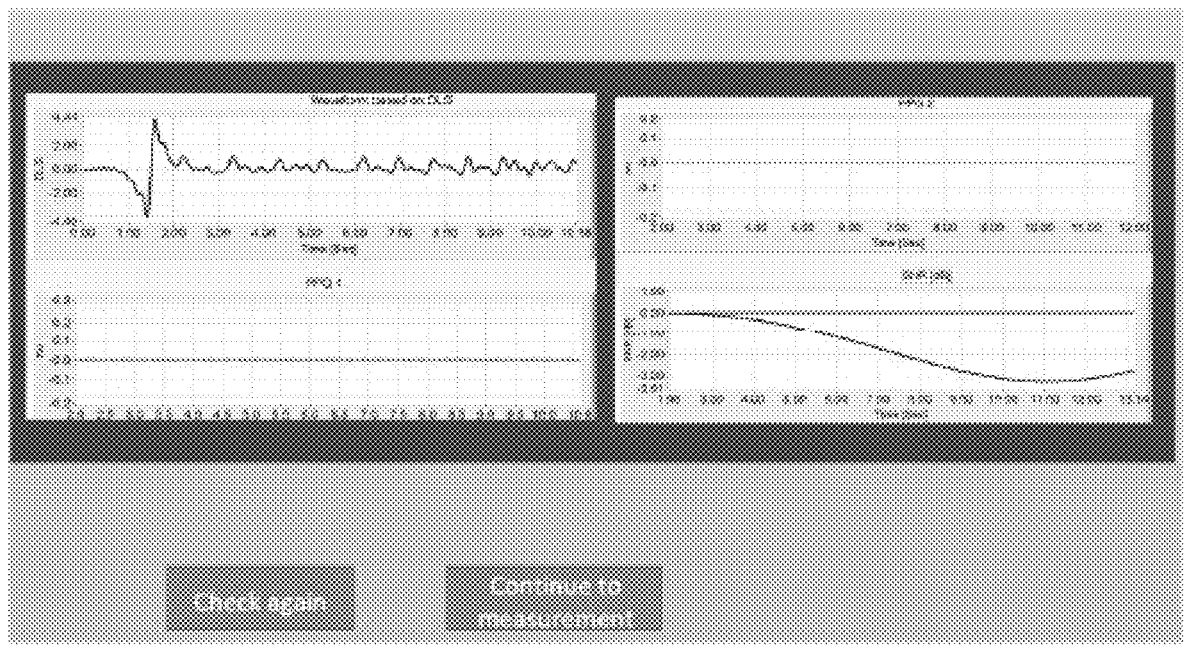
FIG. 11 is a display screen of the multi-vital-sign smartphone indicating that signal quality from the sensors is below a predetermined minimum threshold.
Figure 12:
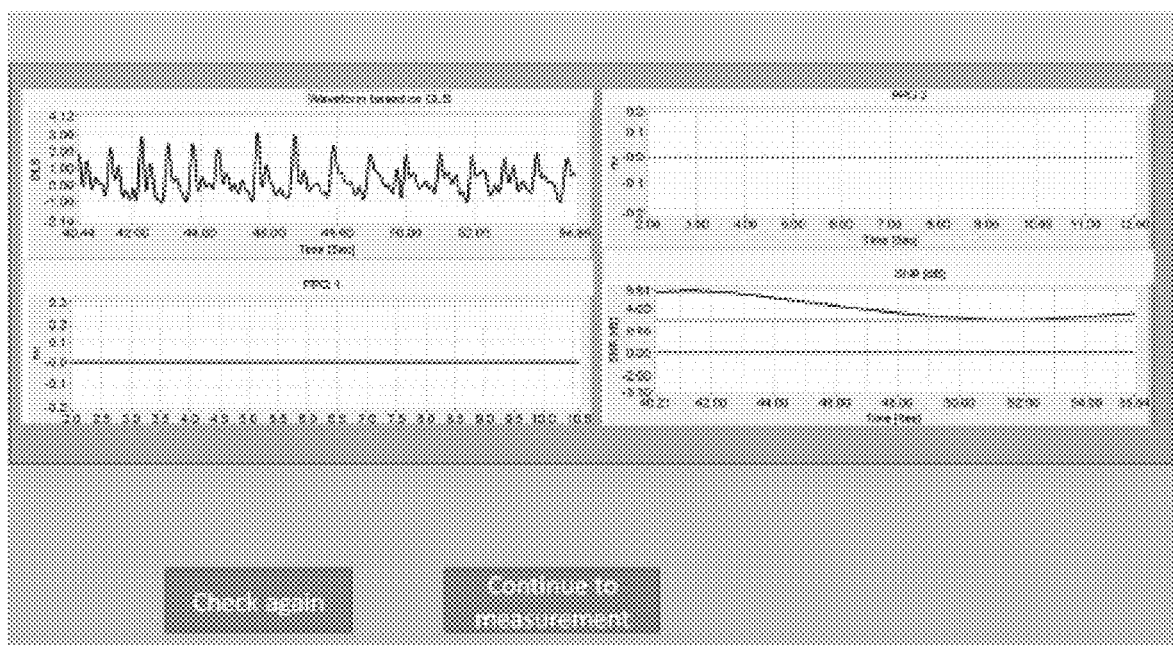
FIG. 12 is a display screen of the multi-vital-sign smartphone indicating that signal quality from the sensors is at or above a predetermined minimum threshold.
Figure 13:
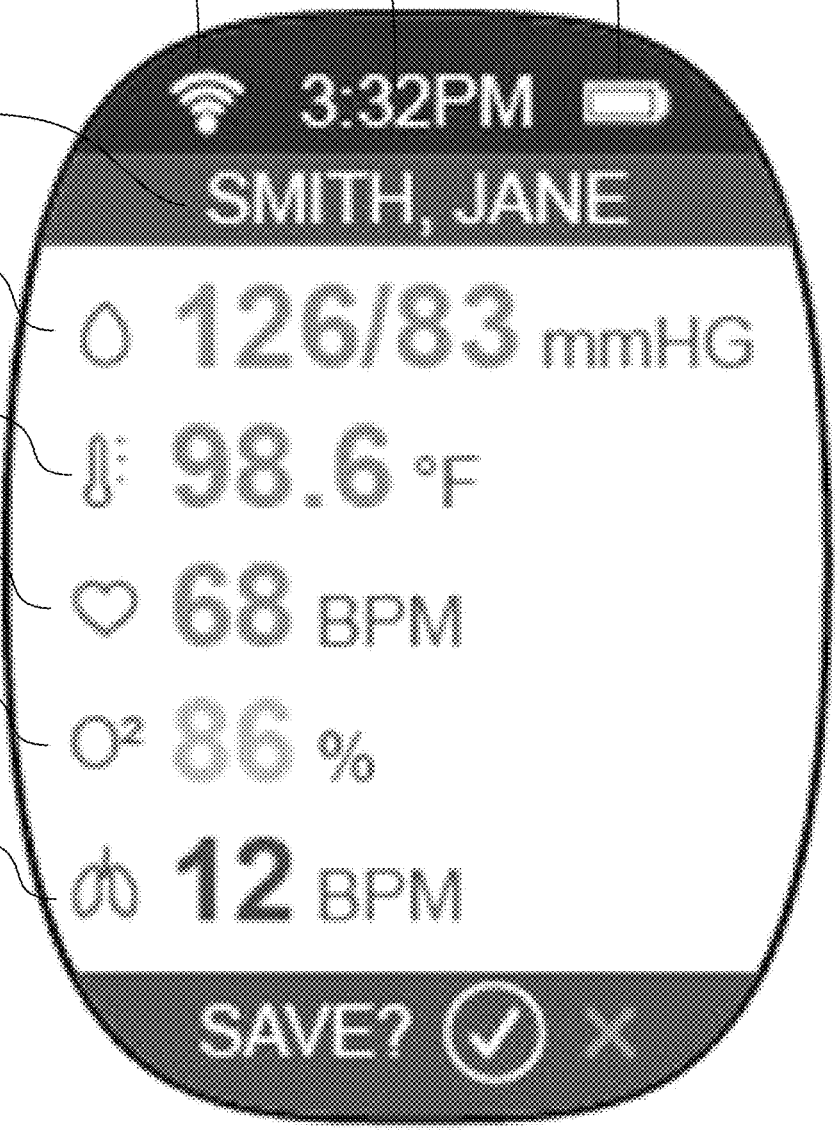
FIG. 13 is a display screen of the multi-vital-sign smartphone showing results of successful multi-vital sign measurements.

In data flow diagram 1000, a main screen 1002 is displayed by the MVS Smartphone device 503 that provides options to exit the application 1004, display configuration settings 1006, display data export settings 1008 or display patient identification entry screen 1010. The configuration settings display 1006 provides options for the configuration/management of the MVS Smartphone device 503. In some implementations, the data flow diagram 1000 includes low power operation and sleep, along startup, initialization, self check and measurement capability of the MVS Smartphone device 503. The display of data export settings 1008 provides options to take individual measurement of a given vital sign. After the patient identification entry screen 1010 or and alternatively, bar code scanning of both operator and subject, has been completed, one or more sensors are placed on the patient 1012, the MVS Smartphone device 503 verifies 1014 that signal quality from the sensors is at or above a predetermined minimum threshold. If the verification 1014 fails 1016 as shown in FIG. 11, then the process resumes where one or more sensors are placed on the patient 1012. If the verification 1014 succeeds 1018 as shown in FIG. 12, then measurement 1020 using the one or more sensors is performed and thereafter the results of the measurements are displayed 1022 as shown in FIG. 13 and thereafter the results of the measurements are saved to EMR or clinical cloud 1024, and then the process continues at the main screen 1002. The "para n done" actions the measurement 1020 are indications that the sensing of the required parameters is complete.

FIG. 11 is a display screen 1100 of the multi-vital-sign smartphone (MVS Smartphone) device 503 indicating that signal quality from the sensors is below a predetermined minimum threshold, according to an implementation.

FIG. 12 is a display screen 1200 of the multi-vital-sign smartphone (MVS Smartphone) device 503 indicating that signal quality from the sensors is at or above a predetermined minimum threshold, according to an implementation.

FIG. 13 is a display screen 1300 of the multi-vital-sign smartphone (MVS Smartphone) device 503 showing results of successful multi-vital sign measurements, according to an implementation. The display screen 1300 includes display of the level of WiFi® connectivity 1302 or the level of Bluetooth® connectivity or the level of cellular connectivity, the current time 1304, battery charge level 1306, the patient name 1308 of the patient whose vital signs are measured, measured blood pressure 1310 (systolic and diastolic in terms of millimeters of mercury) of the patient, measured core temperature 1312, measured heartrate in beats per minute 1314, measured SpO2 levels 1316 in the patient bloodstream and measured respiratory rate 1318 in terms of breaths per minute of the patient.

Figure 14:
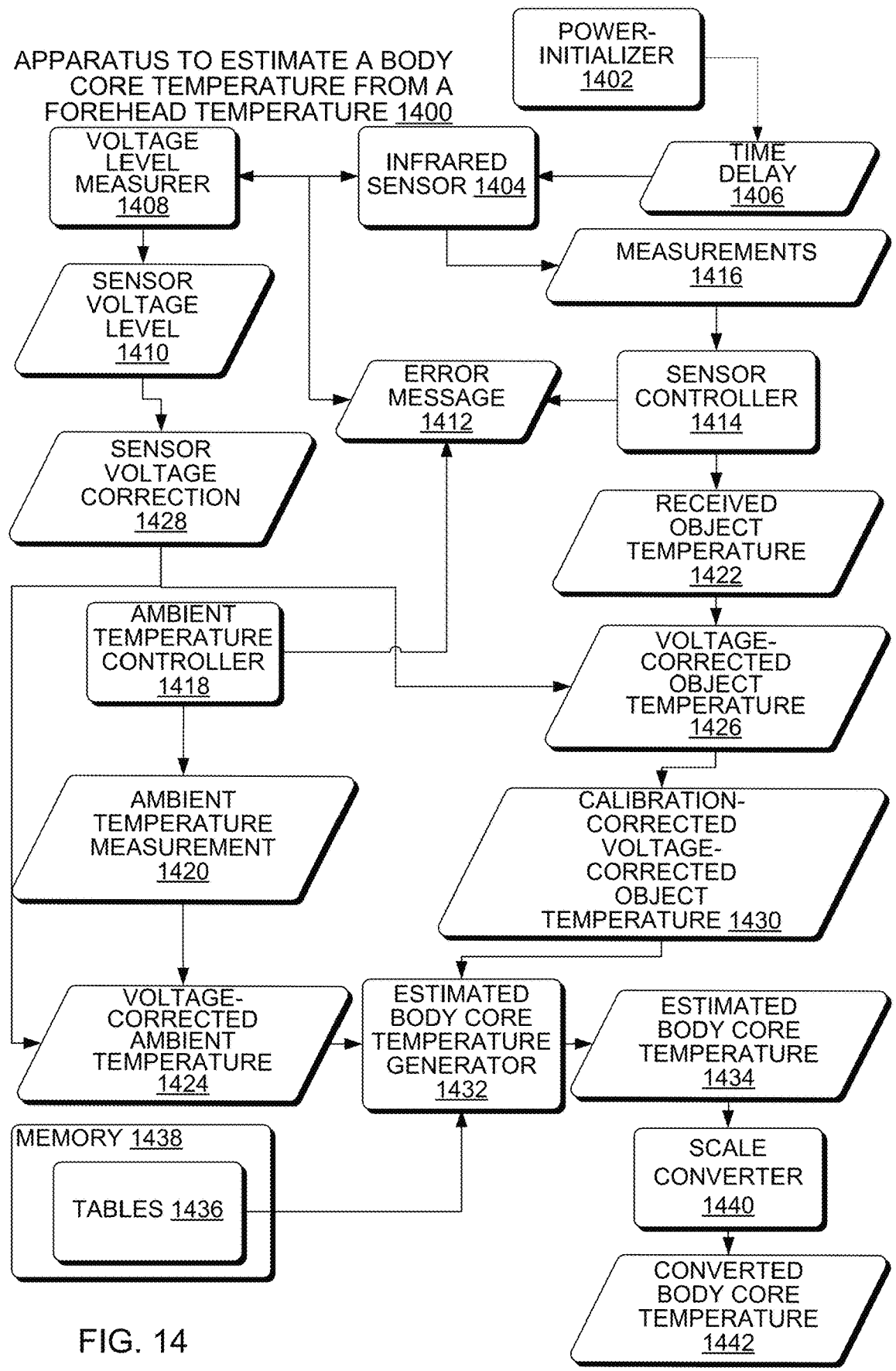
FIG. 14 is a block diagram of an apparatus to estimate a body core temperature from a forehead temperature sensed by an infrared sensor.

FIG. 14 is a block diagram of an apparatus 1400 to estimate a body core temperature from a forehead temperature sensed by an infrared sensor, according to an implementation. Apparatus 1400 includes a power-initializer 1402 for the infrared sensor 1404 and a time delay 1406 that delays subsequent processing for a period of time specified by the time delay 1406 after power initialization of the infrared sensor 1404 by the power-initializer 1402, such as a delay of a minimum of 340 ms (+20 ms) to a maximum of 360 ms.

Apparatus 1400 includes a voltage level measurer 1408 of the infrared sensor 1404 that outputs a representation of the sensor voltage level 1410 of the infrared sensor 1404. When the sensor voltage level 1410 is below 2.7V or is above 3.5V, a reading error message 1412 is generated and displayed.

Apparatus 1400 also includes a sensor controller 1414 that initiates four infrared measurements 1416 of the forehead surface by the infrared sensor 1404 and receives the four infrared measurements 1416. In some implementations, each of the four infrared measurements 1416 of the forehead surface are performed by the infrared sensor 1404 with a period of at least 135 ms (+20 ms) to a maximum of 155 ms between each of the infrared measurements 1416.

If one of the up to 15 infrared measurements 1416 of the forehead surface by the infrared sensor 1404 that is received is invalid, a reading error message 1412 is displayed.

Apparatus 1400 also includes an ambient temperature controller 1418 that initiates an ambient temperature (Ta) measurement 1420 and receives the ambient temperature (Ta) measurement 1420. If the ambient temperature (Ta) measurement 1420 of the ambient temperature is invalid, a reading error message 1412 is displayed. The ambient temperature controller 1418 compares the ambient temperature (Ta) measurement 1420 to a range of acceptable values, such as the numerical range of 283.15K (10° C.) to 313.15° K (40° C.). If the ambient temperature (Ta) measurement 1420 is outside of this range, a reading error message 1412 is displayed. The sensor controller 1414 compares all four of the infrared measurements 1416 of the forehead surface by the infrared sensor 1404 to determine whether or not are all four are within 1 Kelvin degree of each other. If all four infrared measurements of the forehead surface by the infrared sensor 1404 are not within 1 Kelvin degree of each other, a reading error message 1412 is displayed.

The sensor controller 1414 averages the four infrared measurements of the forehead surface to provide a received object temperature (Tobj) 1422 when all four infrared measurements of the forehead surface by the infrared sensor 1404 are within 1 degree Kelvin of each other. The sensor controller 1414 also generates a voltage-corrected ambient temperature (COvTa) 1424 and a voltage-corrected object temperature (COvTobj) 1426 by applying a sensor voltage correction 1428 to the ambient temperature (Ta) and the object temperature (Tobj) 1422, respectively. For example, the sensor voltage correction 1428 in Kelvin=object temperature (Tobj)−(voltage at sensor−3.00)*0.65. In some implementations, a sensor calibration offset is applied to the voltage-corrected object temperature (COvTobj), resulting in a calibration-corrected voltage-corrected object temperature (COcaCOvTobj) 1430. For example, a sensor calibration offset of 0.60 Kelvin is added to each voltage-corrected object temperature (COvTobj) from the infrared sensor 1404 of a particular manufacturer.

An estimated body core temperature generator 1432 reads an estimated body core temperature 1434 from one or more tables 1436 that are stored in a memory 1438 (such as memory 1438 in FIG. 14) that correlates the calibration-corrected voltage-corrected object temperature (COcaCOvTobj) to the body core temperature in reference to the voltage-corrected ambient temperature (COvTa) 1424. One implementation of the estimated body core temperature generator 1432 in FIG. 14 is apparatus 1500 in FIG. 15. The tables 1436 are also known as body core temperature correlation tables.

A scale converter 1440 converts the estimated body core temperature 1434 from Kelvin to ° C. or ° F., resulting in a converted body core temperature 1442. There is a specific algorithm for pediatrics (<=8 years old) to account for the different physiological response of children in the febrile >101 degF range.

Figure 15:
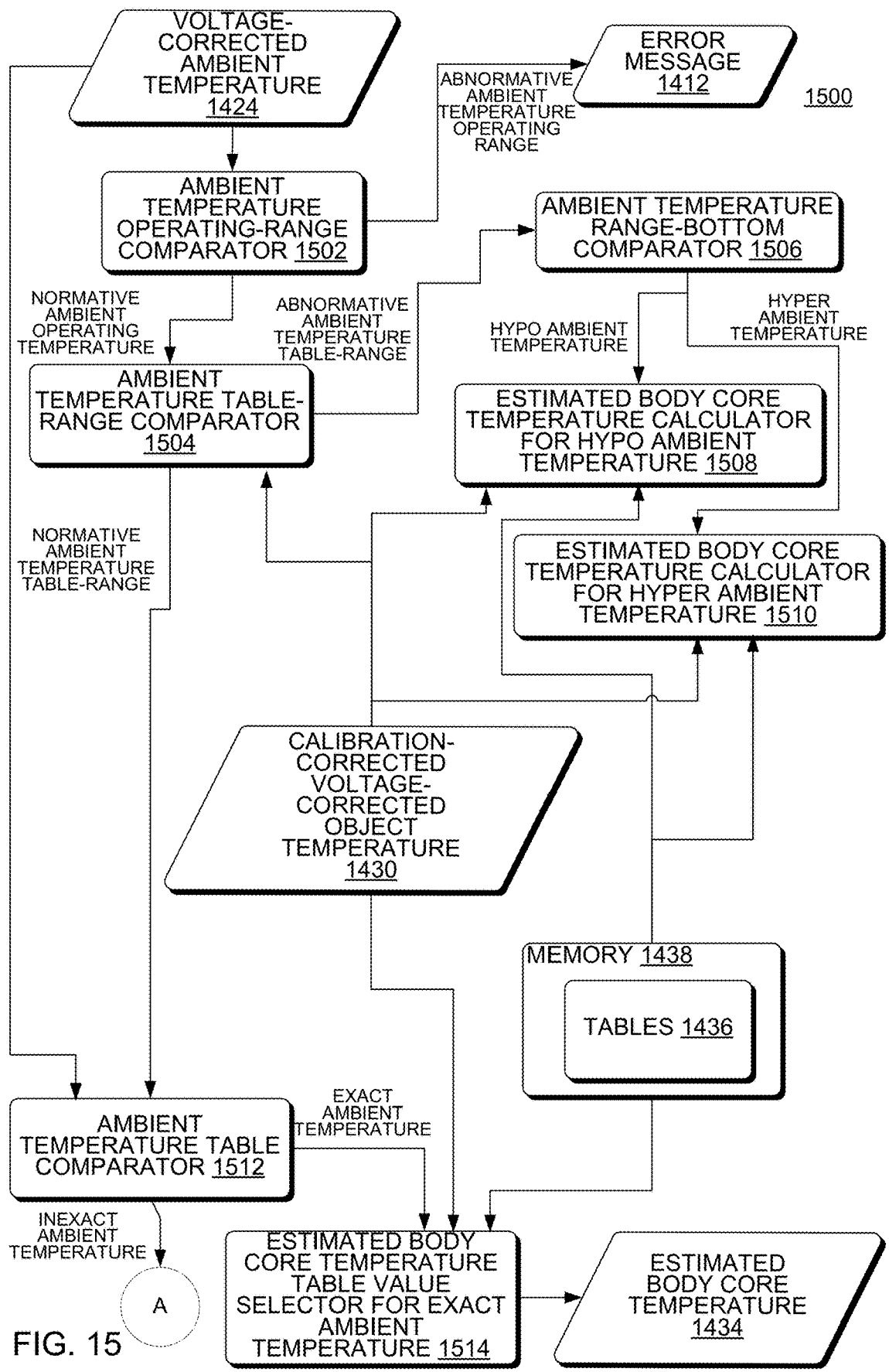
FIG. 15-16 are block diagrams of an apparatus to derive an estimated body core temperature from one or more tables that are stored in a memory that correlate a calibration-corrected voltage-corrected object temperature to the body core temperature in reference to the corrected ambient temperature.
Figure 16:
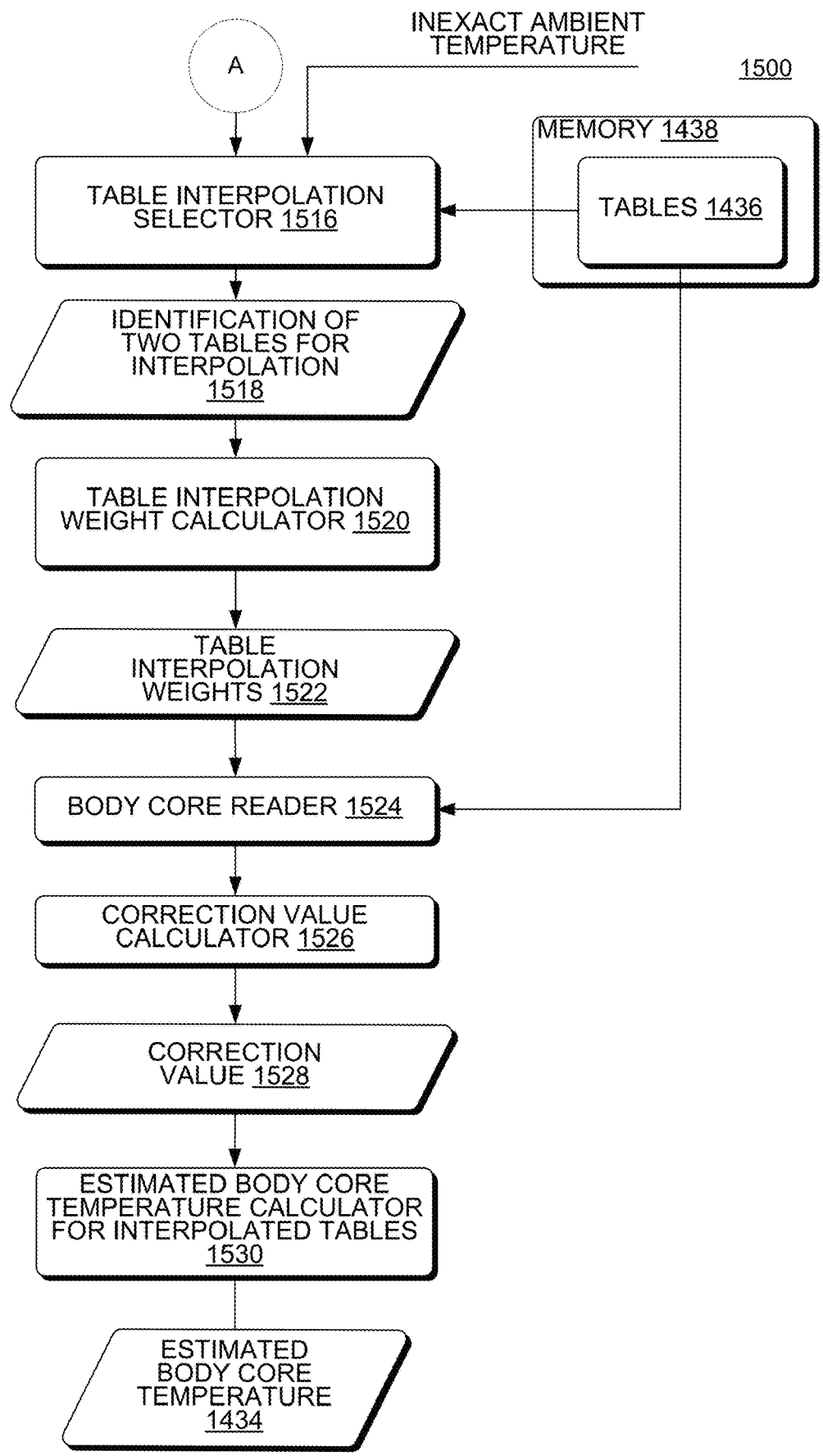

FIG. 15-16 are block diagrams of an apparatus 1500 to derive an estimated body core temperature from one or more tables that are stored in a memory that correlate a calibration-corrected voltage-corrected object temperature to the body core temperature in reference to the corrected ambient temperature, according to an implementation. Apparatus 1500 is one implementation of the estimated body core temperature generator 1832 in FIG. 18.

Figure 27:
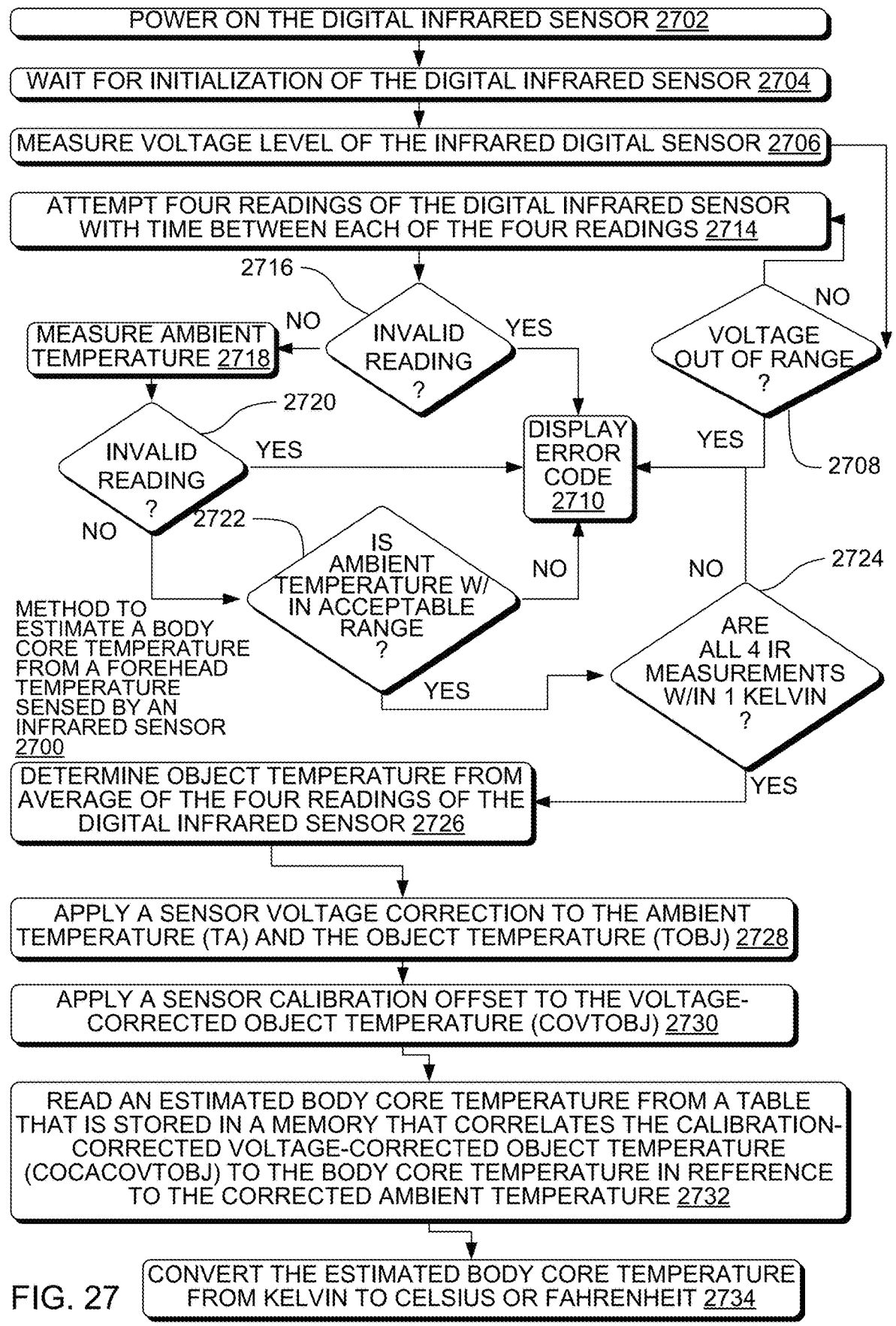
FIG. 27 is a flowchart of a method to estimate a body core temperature from a forehead temperature sensed by an infrared sensor.

Apparatus 1500 includes an ambient temperature operating-range comparator 1902 that is configured to compare the voltage-corrected ambient temperature (COvTa) (1824 in FIG. 18) to an operational temperature range of the apparatus to determine whether or not the voltage-corrected ambient temperature (COvTa) 1824 is outside of the operational temperature range of the apparatus. The operational temperature range is from the lowest operational temperature of the apparatus 1500 to the highest operational temperature of the MVS system 400. The ambient temperature operating-range comparator 1902 performs block 2722 in FIG. 27. In one example, the operational temperature range is 10.0° C. to 40.0° C.

In a further example, if the voltage-corrected ambient temperature (COvTa) is 282.15° K (9.0° C.), which is less than the exemplary lowest operational temperature (10.0° C.), then the voltage-corrected ambient temperature (COvTa) is outside of the operational temperature range.

Figure 28:
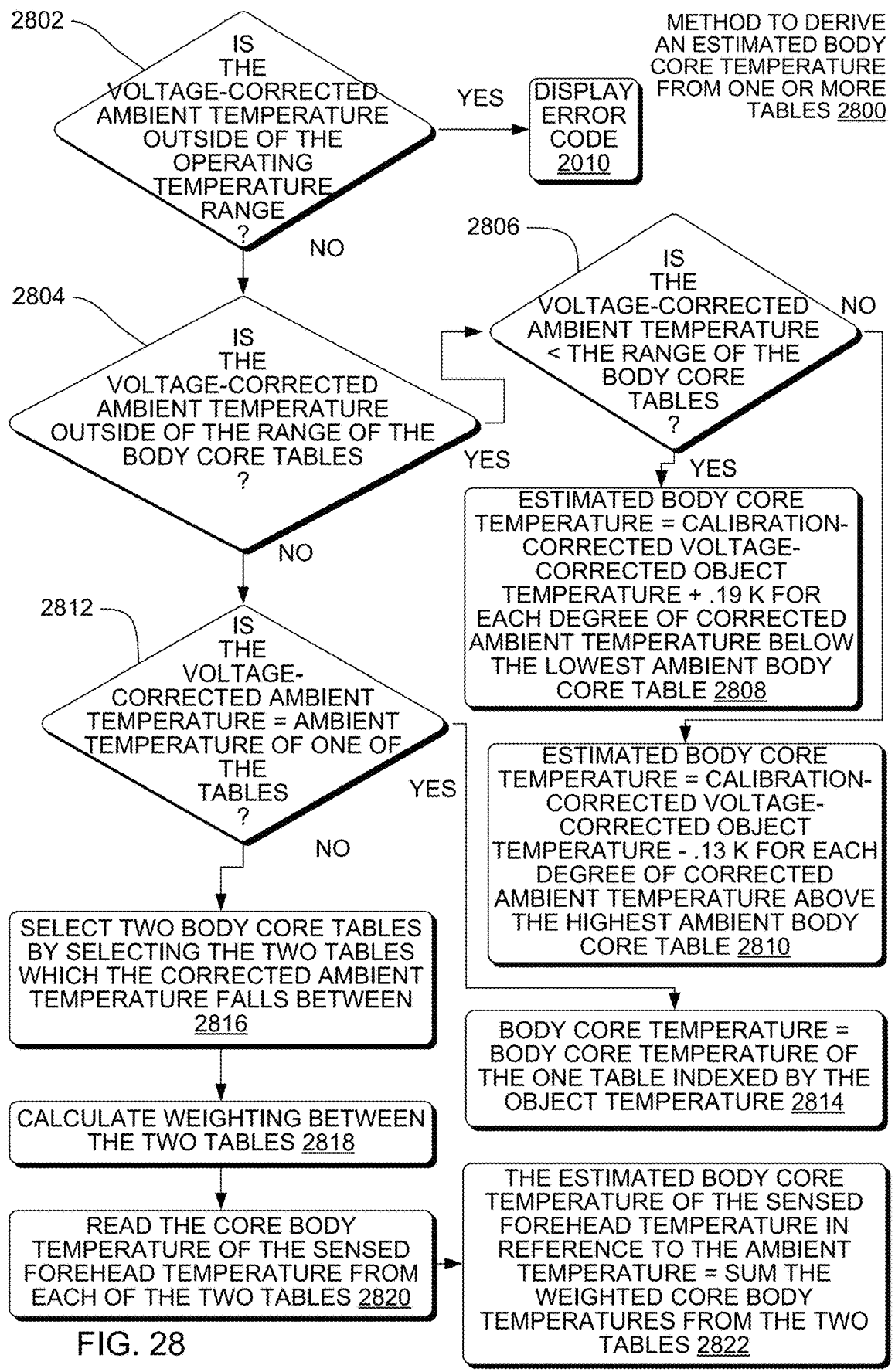
FIG. 28 is a flowchart of a method to derive an estimated body core temperature from one or more tables that are stored in a memory that correlates the calibrated object temperature to the body core temperature in reference to the corrected ambient temperature.

Apparatus 1500 includes an ambient temperature table-range comparator 1504 that determines whether or not the voltage-corrected ambient temperature (COvTa) 1824 is outside of the range of the tables. The ambient temperature table-range comparator 1504 performs action 2804 in FIG. 28. For example, if the voltage-corrected ambient temperature (COvTa) is 287.15° K (14.0° C.), which is less than the lowest ambient temperature the tables, then the voltage-corrected ambient temperature (COvTa) is outside of the range of the tables. In another example, if the voltage-corrected ambient temperature (COvTa) is 312.25° K (39.1° C.), which is greater than the highest ambient temperature (37.9° C.) of all of the tables, then the voltage-corrected ambient temperature (COvTa) is outside of the range of the tables.

When the ambient temperature table-range comparator 1504 determines that the voltage-corrected ambient temperature (COvTa) 1824 is outside of the range of the tables, then control passes to an ambient temperature range-bottom comparator 1506 that is configured to compare the voltage-corrected ambient temperature (COvTa) (1824 in FIG. 18) to the bottom of the range of the tables to determine whether or not the voltage-corrected ambient temperature (COvTa) 1824 is less than the range of the tables. The bottom of the range of the tables is the lowest ambient temperature of all of the tables, such as 14.6° C. Ambient temperature range-bottom comparator 1506 performs block 2806 in FIG. 28. In a further example, if the voltage-corrected ambient temperature (COvTa) is 287.15° K (14.0° C.), which is less than the lowest ambient temperature (14.6° C.) of the tables, then the voltage-corrected ambient temperature (COvTa) is less than the bottom of the range of the tables.

When the ambient temperature range-bottom comparator 1506 determines that the voltage-corrected ambient temperature (COvTa) 1824 is less than the range of the tables, control passes to an estimated body core temperature calculator for hypo ambient temperatures 1508 sets the estimated body core temperature 1834 to the calibration-corrected voltage-corrected object temperature (COcaCOvTobj) 1830+0.19° K for each degree that the voltage-corrected ambient temperature (COvTa) is below the lowest ambient body core table. The estimated body core temperature calculator for hypo ambient temperatures 1508 performs block 2808 in FIG. 28.

For example, when the voltage-corrected ambient temperature (COvTa) is 12.6° C., which is less than the range of the tables, 14.6° C., and the calibration-corrected voltage-corrected object temperature (COcaCOvTobj) 1830 is 29° C. (302.15° K) then the estimated body core temperature calculator for hypo ambient temperatures 1508 sets the estimated body core temperature 1834 to 302.15° K+(0.19° K*(14.6° C.-12.6° C.)), which is 302.53° K.

When the ambient temperature range-bottom comparator 1506 determines that the voltage-corrected ambient temperature (COvTa) 1824 is not less than the range of the tables, control passes to an estimated body core temperature calculator 1510 for hyper ambient temperatures that sets the estimated body core temperature 1834 to the calibration-corrected voltage-corrected object temperature (COcaCOvTobj) 1830-0.13° K for each degree that the voltage-corrected ambient temperature (COvTa) is above the highest ambient body core table. The estimated body core temperature calculator 1510 for hyper ambient temperatures performs block 2810 in FIG. 28.

For example, when the voltage-corrected ambient temperature (COvTa) is 45.9° C., which is above the range of all of the tables, (43.9° C.), and the calibration-corrected voltage-corrected object temperature (COcaCOvTobj) 1830 is 29° C. (302.15° K) then the estimated body core temperature calculator 1510 for hyper ambient temperatures sets the estimated body core temperature 1834 to 302.15° K−(0.13° K*(45.9° C.-43.9° C.)), which is 301.89° K.

When the ambient temperature table-range comparator 1504 determines that the voltage-corrected ambient temperature (COvTa) 1824 is not outside of the range of the tables, then control passes to an ambient temperature table comparator 1512 that determines whether or not the voltage-corrected ambient temperature (COvTa) is exactly equal to the ambient temperature of one of the tables, when the estimated body core temperature calculator 1510 for hyper ambient temperatures determines that the voltage-corrected ambient temperature (COvTa) is within of the range of the tables. The ambient temperature table comparator 1512 performs block 3212 in FIG. 28. When the ambient temperature table comparator 1512 determines that the voltage-corrected ambient temperature (COvTa) is exactly equal to the ambient temperature of one of the tables, then the estimated body core temperature table value selector for exact ambient temperatures 1514 sets the estimated body core temperature 1834 to the body core temperature of that one table, indexed by the calibration-corrected voltage-corrected object temperature (COcaCOvTobj) 1830.

For example, when the voltage-corrected ambient temperature (COvTa) is 34.4° C. (the ambient temperature of Table D) and the calibration-corrected voltage-corrected object temperature (COcaCOvTobj) 1830 is 29.1° C., then the estimated body core temperature table value selector for exact ambient temperatures 1514 sets the estimated body core temperature 1834 to 29.85 C, which is the body core temperature of Table D indexed at the calibration-corrected voltage-corrected object temperature (COcaCOvTobj) 1830 of 29.1° C.

Apparatus 1500 includes a table interpolation selector 1516. When the ambient temperature table comparator 2812 determines that the voltage-corrected ambient temperature (COvTa) is not exactly equal to the ambient temperature of one of the tables, then the table interpolation selector 1516 identifies the two tables which the voltage-corrected ambient temperature (COvTa) falls between. The table interpolation selector 1516 performs block 2816 in FIG. 28.

For example, if the voltage-corrected ambient temperature (COvTa) is 293.25° K (20.1° C.), this ambient value falls between the tables for ambient temperatures of 19.6° C. and 24.6° C., in which case, the 19.6° C. table is selected as the Lower Body Core Table and the 24.6° C. table is selected as the Higher Body Core Table.

Thereafter, apparatus 1500 includes a table interpolation weight calculator 1520 that calculates a weighting between the lower table and the higher table, the table interpolation weights 1522. The table interpolation weight calculator 1520 performs block 2818 in FIG. 28.

For example, when Tamb_bc_low (the voltage-corrected ambient temperature (COvTa) for the Lower Body Core Table)=19.6° C. and T amb_bc_high (the voltage-corrected ambient temperature (COvTa) for the Higher Body Core Table)=24.6 C, then the amb_diff=(Tamb_bc_high−Tamb_bc_low/100)=(24.6−19.6)/100=0.050° C. Further, the Higher Table Weighting=100/((Tamb−Tamb_bc_low)/amb_diff)=100/((20.1−19.6)/0.050)=10% and the Lower Table Weighting=100−Higher Table Weighting=100−10=90%.

Apparatus 1500 includes a body core temperature reader 1524 that reads the core body core temperature that is associated with the sensed forehead temperature from each of the two tables, the Lower Body Core Table and the Higher Body Core Table. The body core temperature reader 1524 performs block 2820 in FIG. 28. The calibration-corrected voltage-corrected object temperature (COcaCOvTobj) 1830 is used as the index into the two tables.

Apparatus 1500 also includes a correction value calculator 1526 that calculates a correction value 1528 for each of the Lower Body Core Table and the Higher Body Core Table. For example, where each of the tables has an entry of calibration-corrected voltage-corrected object temperature (COcaCOvTobj) 1830 for each 0.1° Kelvin, to calculate to a resolution of 0.01° Kelvin, the linear difference is applied to the two table values that the calibration-corrected voltage-corrected object temperature (COcaCOvTobj) 1830 falls between.

For example, when the calibration-corrected voltage-corrected object temperature (COcaCOvTobj) 1830 is 309.03° K, then the calibration-corrected voltage-corrected object temperature (COcaCOvTobj) 1830 falls between 309.00 and 309.10. The correction value 1528 is equal to a+((b−a)*0.03), where a=body core correction value for 309.0° K and b=body curve correction value for 309.1° K.

Thereafter, apparatus 1500 includes an estimated body core temperature calculator for interpolated tables 1530 that determines the body core temperature of the sensed forehead temperature in reference to the ambient temperature by summing the weighted body core temperatures from the two tables. The estimated body core temperature calculator for interpolated tables 1530 performs block 2822 in FIG. 28. The estimated body core temperature is determined to equal (Tcor_low*Lower Table Weighting/100)+(Tcor_high* Higher Table Weighting/100).

For example, when the voltage-corrected ambient temperature (COvTa) is 293.25° K (20.10° C.), then in this case 90% (90/100) of the Table) and 10% (10/100) are summed to set the estimated body core temperature 1834.

The comparators (1502, 1504 and 1506) can be arranged in any order relative to each other.

Implementation Alternatives

Operational Features and Implementation Capability

Some implementations of the EMR data capture systems 100, 200 and 300 have limited operational features and implementation capability. A significant function of the EMR data capture systems 100, 200 and 300 with the limited operational features and implementation capability in the bridge 120 is to accept data from a multi-vital-sign smartphone system(s) 104 and update the EMR/Clinical Data Repository 144. The EMR/Clinical Data Repository 144 can be one or more of the following: Electronic Medical Records System (EMR) 146, Electronic Health Record System (148), Patient Portal Medical Records 150, Clinical Monitoring System 152, and Clinical Data Repository 154.

The following limited feature set in some implementations is supported by the EMR data capture systems 100, 200 and 300 for the demonstrations:

Implementation to a local IT network on a server of the local IT network, OR located on a remote-hosted network, whichever meets the operational requirements for healthcare system.

Acceptance of patient medical records from a multi-vital-sign smartphone system(s) 104:
 a. Date and Time
 b. Operator identification
 c. Patient identification
 d. Vital Sign measurement(s)
 e. Device manufacturer, model number and firmware revision Acceptance of limited status information from a multi-vital-sign smartphone system(s) 104:
 a. Battery Level
 b. Hospital reference
 c. location reference
 d. Manufacturer identification, serial number and firmware revision
 e. Unique identification number Transfer of patient records from a multi-vital-sign smartphone system(s) 104 to a third party EMR capture system and to the EMR data capture systems 100, 200 and 300, respectively in that order.

User interface for status review of known multi-vital-sign smartphone system(s) 104.

Configuration update control for active devices providing configuration of:
   a. Hospital reference
   b. Unit location reference Limited Operational Features and Implementation Capability The following features are supported limited operational capability:

A Patient Record Information and measurement display interface for use without submission of that data to an EMR/Clinical Data Repository 144.

Update of device firmware over the wireless network.

Operational Use

Local Network Based—Single Client

In some implementations, the multi-vital-sign smartphone system(s) 104 are deployed to a local hospital, or other location, wireless IT network that supports WiFi® enabled devices. The multi-vital-sign smartphone system(s) 104 supports all local network policy's including any local security policy/protocols, such as WEP, WPA, WPA2, WPA-EPA as part of the connection process for joining the network. In some implementations, the multi-vital-sign smartphone system(s) 104 operates on both physical and virtual wireless LAN's, WAN's, and the multi-vital-sign smartphone system(s) 104 are configured for operation on a specific segment of the network. Depending on the IT network structure, when the multi-vital-sign smartphone system(s) 104 is configured for operation on a specific segment of the network, the multi-vital-sign smartphone system(s) 104 network connection ability is limited to the areas of the operational environment for which it as be configured. Therefore, the multi-vital-sign smartphone system(s) 104 in network environments that have different network configurations are configured to ensure that when the multi-vital-sign smartphone system(s) 104 are used in various locations throughout the environment that the multi-vital-sign smartphone system(s) 104 has access in all required areas.

In some implementations the bridge 120 system is located on the same IT network and deployed in accordance with all local IT requirements and policy's and that the multi-vital-sign smartphone system(s) 104 on this network are able to determine a routable path to the bridge 120. The multi-vital-sign smartphone system(s) 104 and the server are not required to implement any network name discovery protocols and therefore the bridge 120 is required to be allocated static IP address on the network. In the case where a secondary bridge device is deployed to the network as a backup for the primary, or the bridge 120 supports a dual networking interface capability, then the secondary bridge IP address is also required to be allocated a static IP address.

A benefit of this bridge 120 implementation to the local IT network infrastructure is the reduction in latency times for data sent between the multi-vital-sign smartphone system(s) 104 and the bridge 120.

It is important to note that this is a single organization implementation and as such the bridge 120 is configured to meet the security and access requirements of a single organization.

FIG. 3 is a block diagram of an overview of an electronic medical records (EMR) capture system 300 having a remote cloud based bridge 120, according to an implementation.

An implementation of a remote cloud-based bridge 120 for a single client is similar to the local network case described at the end of the description of FIG. 3, with the exception that the bridge 120 may not be physically located at the physical site of the multi-vital-sign smartphone system(s) 104.

The multi-vital-sign smartphone system(s) 104 include a temperature estimation table (not shown in FIG. 3). The temperature estimation table is stored in memory. The temperature estimation table is a lookup table that correlates a sensed surface temperature to a body core temperature.

The physical locale of the bridge 120 is transparent to the multi-vital-sign smartphone system(s) 104.

Again as in the local install case, the same user access and security policies are in place for the single operating organization.

Remote Based—Multiple Client Support

In some implementations for smaller organizations or for organizations that do not have a supporting IT infrastructure or capability that a remote bridge 120 system is deployed to support more than one organization. Where the bridge 120 is deployed to support more than one organization, the bridge 120 can be hosted as a cloud based system. In this case the multi-vital-sign smartphone system(s) 104 are located at the operational site for the supported different geographical location organizations and tied to the bridge 120 via standard networking methods via either private or public infrastructure, or a combination thereof.

Where a remote, i.e. non-local IT network, system is deployed to support more than one hospital or other organization EMR data capture systems 100, 200 and 300 includes components that isolate each of the supported organizations security and user access policy's and methods along with isolating all data transfers and supporting each organizations data privacy requirements. In addition system performance is required to be balanced evenly across all organizations. In this case each organization can require their specific EMR data capture systems 100, 200 and 300 be used and their EMR data capture systems 100, 200 and 300 are concurrently operational with many diverse EMR/Clinical Repository systems such as Electronic Medical Record System EMR 146, Electronic Health Record 148, Patient Portal Medical Records 150, Clinical Monitoring System 152, and Clinical Data Repository 154.

Single Measurement Update

The primary function of the multi-vital-sign smartphone system(s) 104 is to take vital sign measurements, for example, a patient body core temperature, display the result to the operator and to save the patient information and body core temperature to an EMR/Clinical Data Repositiory 144.

Normally the multi-vital-sign smartphone system(s) 104 are in a low power state simply waiting for an operator to activate the unit for a patient measurement. Once activated by the operator EMR data capture systems 100, 200 and 300 will power up and under normal operating conditions guide the operator through the process of patient body core temperature measurement and transmission of the patient record to the bridge 120 for saving using the EMR data capture systems 100, 200 and 300.

Confirmation at each stage of the process to the operator is required, to ensure a valid and identified patient result is obtained and saved to the EMR, the key last confirmation point is: Saving of data to the bridge 120.

In some implementations, the confirmation at each stage in some implementations is provided by the operator through either the bridge 120, multi-vital sign capture system(s) 104, or the EMR/Clinical Data Repository 144.

When confirmation is provided by the bridge 120 it is an acknowledgment to the multi-vital-sign smartphone system(s) 104 that the bridge 120 has accepted the information for transfer to the EMR/Clinical Data Repository 144 in a timely manner and is now responsible for the correct management and transfer of that data.

When confirmation is provided by the EMR, the bridge 120 is one of the mechanism via which the confirmation is returned to the multi-vital-sign smartphone system(s) 104. That is the multi-vital-sign smartphone system(s) 104 sends the data to the bridge 120 and then waits for the bridge 120 to send the data to the EMR and for the EMR to respond to the bridge 120 and then the bridge 120 to the multi-vital-sign smartphone system(s) 104, In some implementations depending on the operational network and where the bridge 120 is physically located, i.e. local or remote, that the type of confirmation is configurable.

In some implementations, the multi-vital-sign smartphone system(s) 104 maintains an internal non-volatile storage mechanism for unsaved patient records if any or all of these conditions occur: The multi-vital-sign smartphone system(s) 104 cannot join the network. The multi-vital-sign smartphone system(s) 104 cannot communicate with the bridge 120. The multi-vital-sign smartphone system(s) 104 does not receive level confirmation from either the bridge 120 or the EMR/Clinical Data Repository 144. The multi-vital-sign smartphone system(s) 104 must maintain the internal non-volatile storage mechanism in order to fulfill its primary technical purpose in case of possible operational issues. When the multi-vital-sign smartphone system(s) 104 has saved records present in internal memory of the multi-vital-sign smartphone system(s) 104, then the multi-vital-sign smartphone system(s) 104 attempts to transfer the saved records to the bridge 120 for processing in a timely automatic manner.

Periodic Connectivity

The multi-vital-sign smartphone system(s) 104 in order to obtain date/time, configuration setting, provides status information to the bridge 120, transfers saved patient records and checks for a firmware update to provide a mechanism on a configured interval automatically that powers up and communicates to the configured bridge 120 without operator intervention.

Accordingly and outside of the normal clinical use activation for the multi-vital-sign smartphone system(s) 104, the multi-vital-sign smartphone system(s) 104 can both update its internal settings, and provide status information to the bridge 120 system.

If these actions were left to the operator, startup case of the multi-vital-sign smartphone system(s) 104 for operational clinical use then there may be an unacceptable delay to the operator in proceeding to the measurement action of the multi-vital-sign smartphone system(s) 104.

Automatic Transfer of Saved Patient Measurement Records (PMRs)

If the multi-vital-sign smartphone system(s) 104 for an unknown reason has been unable to either join the network or connect to the bridge 120 or receive a bridge 120 or EMR data level acknowledge that data has been saved the multi-vital-sign smartphone system(s) 104 allows the primary clinical body core temperature measurement function to be performed and saves the resultant PMR in non-volatile internal memory up to a supported, configured, maximum number of saved patient records on the multi-vital-sign smartphone system(s) 104.

When the multi-vital-sign smartphone system(s) 104 are started for a measurement action the multi-vital-sign smartphone system(s) 104 determines if the multi-vital-sign smartphone system(s) 104 contains any saved patient records in its internal memory. If one or more saved patient records are detected then the multi-vital-sign smartphone system(s) 104 attempts to join the network immediately, connect to the bridge 120 and send the patient records one at a time to the bridge 120 device while waiting for the required confirmation that the bridge 120 has accepted the patient record. Note in this case confirmation from the EMR is not required. On receipt of the required validation response from the remote system the multi-vital-sign smartphone system(s) 104 deletes the patient record from its internal memory. Any saved patient record that is not confirmed as being accepted by the remote device is maintained in the multi-vital-sign smartphone system(s) 104 internal memory for a transfer attempt on the next power up of the multi-vital-sign smartphone system(s) 104.

The multi-vital-sign smartphone system(s) 104 on a configured interval will also carry out this function. In some implementations the multi-vital-sign smartphone system(s) 104 reduces the interval when saved patient records are present on the multi-vital-sign smartphone system(s) 104 in order to ensure that the records are transferred to the bridge 120, and subsequently the EMR/Clinical Data Repository 144, in a timely manner once the issue has been resolved. When this transfer mechanism is active status information is presented to the operator on the multi-vital-sign smartphone system(s) 104 screen.

Under this operation it is possible for the bridge 120 device to receive from a single multi-vital-sign smartphone system(s) 104 multiple patient record transfer requests in rapid sequence.

Device Configuration

The multi-vital-sign smartphone system(s) 104 upon 1) connection to the bridge 120, 2) configured interval or 3) operator initiation, transmits to the bridge 120 with the model number and all appropriate revisions numbers and unique identification of the multi-vital-sign smartphone system(s) 104 to allow the bridge 120 to determine the multi-vital-sign smartphone system(s) 104 capabilities and specific configurations for that multi-vital-sign smartphone system(s) 104.

The bridge 120 acts as the central repository for device configuration, either for a single device, a group of defined devices or an entire model range in which the multi-vital-sign smartphone system(s) 104 queries the bridge 120 for the device parameters of the multi-vital-sign smartphone system(s) 104 and if the queried device parameters are different from the multi-vital-sign smartphone system(s) 104, the multi-vital-sign smartphone system(s) 104 updates the current setting to the new setting values as provided by the bridge 120.

Device Date/Time Update

In implementations where there is no mechanism on the multi-vital-sign smartphone system(s) 104 for the user to configure date and time on the multi-vital-sign smartphone system(s) 104 via its user interface.

The real time clock of the multi-vital-sign smartphone system(s) 104 may drift with time. Therefore each multi-vital-sign smartphone system(s) 104 connected to the bridge 120 will query the bridge 120 for the current date and time and update the multi-vital-sign smartphone system(s) 104 internal clock based on the current date and time provided by the bridge 120.

In some implementations, the multi-vital-sign smartphone system(s) 104 query the bridge 120 on the defined interval or when the multi-vital-sign smartphone system(s) 104 are started by the operator upon joining the network. Therefore the bridge supports an accurate date and time mechanism, with leap year capability, as per the local IT policy. If no local IT policy is in place then the bridge 120 maintains date and time against a known accurate source, e.g. a web based time server.

Accordingly, in some implementations all devices are maintained at the same date and time across the operation of EMR data capture systems 100, 200 and 300 and the capabilities of the multi-vital-sign smartphone system(s) 104.

Device Status Management

In some implementations the bridge 120 provides a level of device management for the multi-vital-sign smartphone system(s) 104 being used with EMR data capture systems 100, 200 and 300. In some implementations, the bridge 120 is able to report and determine at least the following:

Group and sort devices by manufacture, device model, revisions information and display devices serial numbers, unique device identification, asset number, revisions, etc. and any other localized identification information configured into the multi-vital-sign smartphone system(s) 104, e.g. ward location reference or Hospital reference.

The last time a specific unit connected to EMR data capture systems 100, 200 and 300.

The current status of the given device, battery level, last error, last date of re-calibration of check, or any other health indicator supported by the multi-vital-sign smartphone system(s) 104.

Report devices out of their calibration period, or approaching their calibration check.

Report devices that require their internal battery replaced.

Report devices that require re-checking due to a detected device failure or error condition, or that have been treated in a harsh manner or dropped.

Determine if a multi-vital-sign smartphone system(s) 104 has not connected for a period of time and identify the multi-vital-sign smartphone system(s) 104 as lost or stolen. If the multi-vital-sign smartphone system(s) 104 reconnects to the network after this period of time then the multi-vital-sign smartphone system(s) 104 in some implementations is highlighted as requiring an accuracy check to ensure that it is operational. In some implementations, the multi-vital-sign smartphone system(s) 104 also supports this capability and after a pre-determined time disconnects from the network to inhibit the measurement function of the multi-vital-sign smartphone system(s) 104 until a multi-vital-sign smartphone system(s) 104 level recheck is carried out.

Provide a mechanism to commission and decommission devices onto and off of the network. If a multi-vital-sign smartphone system(s) 104 has not been specifically commissioned for operation on the network then it in some implementations is not be allowed to access the core services supported by the bridge 120 even if it has configured for operation on the EMR data capture systems 100, 200 and 300.

Firmware Update

In some implementations a firmware update for a given device model is scheduled on the network as opposed to simply occurring. When a multi-vital-sign smartphone system(s) 104 is activated for a patient measurement firmware updates are blocked because the update process delays the patient biological vital sign measurement. Instead the bridge 120 system includes a firmware update roll out mechanism where the date and time of the update can be scheduled and the number of devices being updated concurrently can be controlled.

In some implementations, when a multi-vital-sign smartphone system(s) 104 connects to the bridge 120 due to a heartbeat event that the multi-vital-sign smartphone system(s) 104 queries the bridge 120 to determine if a firmware update for that model of device is available and verify if its firmware, via revision number, is required to be updated. The bridge 120 responds to the query by the multi-vital-sign smartphone system(s) 104 based on whether or not a firmware update is available and the defined schedule for the update process. If an update is available at the bridge 120 but the current time and date is not valid for the schedule then the bridge 120 transmits a message to the multi-vital-sign smartphone system(s) 104 that there is an update but that the update process is delayed and update the multi-vital-sign smartphone system(s) 104 firmware check interval configuration. The firmware check interval setting will then be used by the multi-vital-sign smartphone system(s) 104 to reconnect to the bridge 120 on a faster interval than the heartbeat interval in order to facilitate a more rapid update. For e.g. the firmware update schedule on the bridge 120 in some implementations is set to every night between 2 am and 4 am and the interval timer in some implementations is set to for example, every 15 minutes.

In some implementations the bridge 120 manages the firmware update process for many different multi-vital-sign smartphone systems 104 each with their specific update procedure, file formats, and verification methods and from a date and time scheduling mechanism and the number of devices being update concurrently. In addition in some implementations the bridge 120 will provide a mechanism to manage and validate the firmware update files maintained on the bridge 120 for use with the multi-vital-sign smartphone system(s) 104.

This section concludes with short notes below on a number of different aspects of the EMR data capture systems 100, 200 and 300 follow on numerous topics:

Remote—single client operation: The bridge 120 architecture provide remote operation on a hospital network system. Remote operation is seen as external to the network infrastructure that the multi-vital-sign smartphone system(s) 104 are operational on but considered to be still on the organizations network architecture. This can be the case where a multiple hospital-single organization group has deployed EMR data capture systems 100, 200 and 300 but one bridge 120 device services all hospital locations and the bridge 120 is located at one of the hospital sites or their IT center.

Remote—multiple client operation: The bridge 120 architecture in some implementations is limited to remote operation on a cloud based server that supports full functionality for more than one individual separate client concurrently when a cloud based single or multiple server system is deployed to service one or more individual hospital/clinical organizations.

Multiple concurrent EMR support: For a single remote bridge 120 servicing multiple clients EMR data capture systems 100, 200 and 300 supports connectivity to an independent EMR, and a different EMR vendor, concurrently for each support client. With one bridge 120 servicing multiple clients in some implementations, each client requires the configuration to send data securely to different EMR/Clinical Data Repositories.

Support Different EMR for same client: The bridge 120 architecture for operation in a single client organization supports the user by the organization of different EMR/Clinical Data Repository 144 from different departments of wards in the operational environment. It is not uncommon for a single organization to support multiple different EMR/Clinical Data Repository 144 for different operational environments, for example, Cardiology and ER. EMR data capture systems 100, 200 and 300 in some implementations takes this into account and routes the patient data to the correct EMR/Clinical Data Repository 144. Therefore the bridge 120 is informed for a given multi-vital-sign smartphone system(s) 104 which indicates to the EMR the medical data has to be routed to.

Segregation of operations for multiple client operations on a single bridge 120:

EMR data capture systems 100, 200 and 300 supports per client interfaces and functionality to ensure that each client's configurations, performance, user accounts, security, privacy and data protection are maintained. For single server implementations that service multiple independent hospital groups the bridge 120 in some implementations maintain all functionality, and performance per client separately and ensure that separate user accounts, bridge 120 configuration, device operation, patient and non-patient data, interfaces etc. are handled and isolated per client. A multiple cloud based implementation obviates this function as each client includes their own cloud based system.

Multiple organization device support: The bridge 120 supports at least 1 million+ multi-vital-sign smartphone system(s) 104 for a remote implementations that services multiple separate hospital systems. The supported multi-vital-sign smartphone system(s) 104 can be multi-vital-sign smartphone system(s) 104 from different manufacturers.

EMR capture system support: The multi-vital-sign smartphone system(s) 104 supports a wide range implementations of the EMR data capture system(s) 300 and is capable of interfacing to any commercially deployed EMR/Clinical Data Repository 144.

EMR capture system interface and approvals: The bridge 120 device provides support for all required communication, encryption, security protocols and data formats to support the transfer of PMR information in accordance with all required operational, standards and approval bodies for EMR/Clinical Data Repository 144 supported by the EMR data capture systems 100, 200 and 300.

Remote EMR capture system(s): The bridge 120 supports interfacing to the required EMR/Clinical Data Repository 144 independent of the EMR data capture system(s) 300 location, either locally on the same network infrastructure or external to the network that the bridge 120 is resided on or a combination of both. The EMR data capture systems 100, 200 and 300, or systems, that the bridge 120 is required to interact with and save the patient to can not be located on the same network or bridge 120 implementation location, therefore the bridge 120 implementation in some implementations ensure that the route to the EMR exists, and is reliable.

Bridge buffering of device patient records: The bridge 120 device provides a mechanism to buffer received PMRs from connected multi-vital-sign smartphone system(s) 104 in the event of a communications failure to the EMR/Clinical Data Repository 144, and when communications has been reestablished subsequently transfer the buffered measurement records to the EMR. From time to time in normal operation, the network connection from the bridge 120 is lost. If communications has been lost to the configured EMR data capture system(s) 300 then the bridge 120 in some implementations accepts measurement records from the multi-vital-sign smartphone system(s) 104 and buffers the measurement records until communications has be reestablished. Buffering the measurement records allows the medical facility to transfer the current data of the medical facility to the bridge 120 for secure subsequent processing. In this event the bridge 120 will respond to the multi-vital-sign smartphone system(s) 104 that either 1. Dynamic validation of EMR acceptance is not possible, or 2. The bridge 120 has accepted the data correctly.

Bridge 120 real time acknowledge of EMR save to device: The bridge 120 provides a mechanism to pass to the multi-vital-sign smartphone system(s) 104 confirmation that the EMR has accepted and saved the PMR. The bridge 120 when configured to provide the multi-vital-sign smartphone system(s) 104 with real time confirmation that the EMR/Clinical Data Repository 144 (s) have accepted and validated the PMR. This is a configuration option supported by the bridge 120.

Bridge 120 real time acknowledgement of acceptance of device PMR: The bridge 120 provides a mechanism to pass to the multi-vital-sign smartphone system(s) 104 confirmation that the bridge 120 has accepted the PMR for subsequent processing to the EMR. The multi-vital-sign smartphone system(s) 104 in some implementations verifies that the bridge 120 has accepted the PMR and informs the operator of the multi-vital-sign smartphone system(s) 104 that the data is secure. This level of confirmation to the multi-vital-sign smartphone system(s) 104 is considered the minimum level acceptable for use by the EMR data capture systems 100, 200 and 300. Real time acknowledgement by the bridge 120 of acceptance of the PMR from the device is a configuration option supported by the bridge 120.

Bridge Date and Time: The bridge 120 maintains internal date and time against the local network time source or a source recommended by the IT staff for the network. All transitions and logging events in some implementations are time stamped in the logs of the bridge 120. The multi-vital-sign smartphone system(s) 104 will query the bridge 120 for the current date and time to update its internal RTC. The internal time of multi-vital-sign smartphone system(s) 104 can be maintained to a +/−1 second accuracy level, although there is no requirement to maintain time on the multi-vital-sign smartphone system(s) 104 to sub one-second intervals.

Graphical User Interface: The bridge 120 device provides a graphical user interface to present system information to the operator, or operators of EMR data capture systems 100, 200 and 300. The user interface presented to the user for interaction with EMR data capture systems 100, 200 and 300 in some implementations can be graphical in nature and use modern user interface practices, controls and methods that are common use on other systems of this type. Command line or shell interfaces are not acceptable for operator use though can be provided for use by system admin staff.

Logging and log management: The bridge 120 is required to provide a logging capability that logs all actions carried out on the bridge 120 and provides a user interface to manage the logging information. Standard logging facilities are acceptable for this function for all server and user actions. Advanced logging of all device communications and data transfers in some implementations is also provided, that can be enabled/disable per multi-vital-sign smartphone system or for product range of multi-vital-sign smartphone system.

User Accounts: The bridge 120 device provides a mechanism to support user accounts on the multi-vital-sign smartphone system(s) 104 for access control purposes. Standard methods for user access control are acceptable that complies with the operational requirements for the install/implementation site.

User Access Control: The bridge 120 device supports multiple user access control that defines the access control privileges for each type of user. Multiple accounts of each supported account type are to be support. Access to EMR data capture systems 100, 200 and 300 in some implementations be controlled at a functional level, In some implementations, the following levels of access is provided:

System Admin: provides access to all features and functions of EMR data capture systems 100, 200 and 300, server and device based.

Device Admin: provides access only to all device related features and functions supported by the EMR data capture systems 100, 200 and 300.

Device Operator: provides access only to device usage.

Device Installer: provides access only to device commissioning and test capabilities.

A user account can be configured for permissions for one or more account types. >>>>>>>>>recommend getting rid of this line.

Multi-User Support: The bridge 120 device is required to provide concurrent multi-user support for access and management of the bridge 120 system across all functions. Providing multiple user access is deemed a necessary operational feature to support.

Modify User Accounts: The bridge 120 provides a method to create, delete, and edit the supported user accounts and supported access privileges per account.

Bridge Data Corruption/Recovery: The bridge 120 architecture and implementation in some implementations ensure that under an catastrophic failure of EMR data capture systems 100, 200 and 300 or a storage component that no data is lost that has not been confirmed as saved to the either the EMR for PMRs or localize storage for operational data pertaining to the non-patient data maintained by the EMR data capture systems 100, 200 and 300. The bridge 120 supports a method to ensure zero data lost under critical and catastrophic system failure of the bridge 120 or any of the bridge 120 components, network interfaces, storage systems, memory contents, etc. for any data handled by the EMR data capture systems 100, 200 and 300. In the event of a recovery action where a catastrophic failure has occurred EMR data capture systems 100, 200 and 300 supports both the recovery action and its normal operational activities to ensure that EMR data capture systems 100, 200 and 300 is active for clinical use.

Bridge availability: The bridge 120 device is a high availably system for fail safe operation 24/7/365, with 99.99% availability, i.e. "four nines" system. The bridge 120 implementation meets an availability metric of 99.99%, i.e. a "four nines" system because the bridge 120 hardware in some implementations is implemented with a redundant dual server configuration to handle single fault conditions. The bridge 120 has an independent power source or when the installation site has a policy for power loss operation the bridge 120 installation in some implementations complies with the policy requirements.

Bridge Static IP address and port Number: The bridge 120 provides a mechanism to configure the bridge 120 for a primary use static IP address and port number. For multi-vital-sign smartphone system(s) 104 connection to the bridge 120, the bridge 120 in some implementations has a static IP address and that IP address in some implementations is known by the multi-vital-sign smartphone system(s) 104.

Bridge Dual network capability: The bridge 120 system provides a mechanism to support a dual operational network interface to allow for failure of the primary network interface. This secondary network interface supports a configurable static IP address and port number. A redundant network connection in some implementations is provided to cover the event that the primary network interface has failed. Note if the bridge 120 implementation for EMR data capture systems 100, 200 and 300 employs two separate bridges 120 or other redundant mechanism to provide a backup system then this requirement can be relaxed from an operational view point, however EMR data capture systems 100, 200 and 300 in some implementations support this mechanism.

Local WiFi® commissioning network: The bridge 120 provides a mechanism on the local operational network to commission new multi-vital-sign smartphone system(s) 104 for operational use. EMR data capture systems 100, 200 and 300 supplies a localized isolated network for the use of commissioning new devices onto the operational network. The bridge 120 has a known default IP address on this network and provides a DHCP server for the allocation of IP address to devices on EMR data capture systems 100, 200 and 300. The commissioning of new devices is to be considered a core aspect of the bridge 120 functions. However it is acceptable that a separate non server based application in some implementations will manage the configuration process provided the same user interface is presented to the user and the same device level configuration options are provided. In some implementations, the configuration of a new multi-vital-sign smartphone system(s) 104 on the network is carried out in two stages: Stage 1: network configuration from the commissioning network to the operational network. Stage 2: Once joined on the operational network specific configuration of the multi-vital-sign smartphone system(s) 104 for clinical/system function operation.

Remote commissioning of devices: EMR data capture systems 100, 200 and 300 provides a mechanism where the bridge 120 device is not present on the local network for a new device is to be commissioned on the operational network. Even when the bridge 120 is on a cloud server external to the operational site network new devices in some implementations can be commissioned onto the network in the same manner as if the bridge 120 was a local server. This does not preclude the installation of a commission relay server on to the operational network that supports this mechanism.

Device setup: The bridge 120 supports the configuration of a device level network operation and security settings for an existing or new multi-vital-sign smartphone system(s) 104 on either the commissioning network or the operational network. New devices are configured on the commissioning network. Existing devices on the operational network are also configurable for network and security requirements independent of the network that the multi-vital-sign smartphone system(s) 104 are currently connected to the bridge 120 provides the required user interface for the configuration of the network operational and security settings by the operator. Once configured, a method of verifying that the multi-vital-sign smartphone system(s) 104 have been configured correctly but be presented to the operator to prove that the multi-vital-sign smartphone system(s) 104 are operational. Devices support a network command to reboot and rejoin the network for this verification purpose.

Bridge Configuration: The bridge provides a mechanism to support configuration of all required specific control options of the bridge 120. A method to configure the bridge 120 functions in some implementations is provided for all features where a configuration option enable, disable or a range of parameters are required.

Bridge multi-vital-sign smartphone system acknowledgement method: The bridge 120 provides a configuration method to control the type of acknowledgement required by the EMR data capture systems 100, 200 and 300, one of: device configuration dependent, EMR level acknowledgment, bridge 120 level acknowledgement. In some implementations, a multi-vital-sign smartphone system 104 requires from the bridge an acknowledgement that the PMR has been saved by the EMR data capture systems 100, 200 and 300 or accepted for processing by the bridge 120.

EMR Level: Bridge 120 confirms save by EMR data capture systems 100, 200 and 300.

Bridge Level: bridge 120 controlled, accepted for processing by the bridge 120.

Enabled/Disable of firmware updated mechanism: The bridge 120 provides a method to globally enable or disable the supported multi-vital-sign smartphone system(s) 104 firmware updated feature. A global enable/disable allows the control of the firmware update process.

Server Management: The bridge 120 is required to provide a user interface that provides configuration and performance monitoring of the bridge 120 and platform functions.

System Reporting: The bridge 120 is required to provide a mechanism to provide standard reports to the operator on all capabilities of the bridge 120 system. Standard reporting in some implementations includes selection of report parameter, sorting of report parameters, printing of reports, export of reports to known formats, WORD, excel, PDF etc., identification of reports, organization name, location, page numbers, name of report etc., date and time of log, generate by user type and extent of provides full reporting for all system features and logs, examples are: List of devices known to EMR data capture systems 100, 200 and 300, with location reference and date and time of last connection Report on the battery status for all known multi-vital-sign smartphone system(s) 104. Report on any devices that reported an error Report on devices that have expired there calibration dates. Report on devices that are approaching their calibration dates.

Demo Patient Interface: The bridge 120 provides a mechanism for demo only purposes where an EMR data capture systems 100, 200 and 300 is not available for interfacing to EMR data capture systems 100, 200 and 300 to allow patient records received from a given device to be viewed and the biological vital sign data presented. For demonstrations of EMR data capture systems 100, 200 and 300 where there is no EMR data capture systems 100, 200 and 300 to connect the bridge 120 the system provides a user interface method to present the data sent to the bridge 120 by the connected multi-vital-sign smartphone system(s) 104. In some implementations this patient data interface manages and stores multiple patients and multiple record readings per patient and present the information to the operator in an understandable and consistent manner.

Interface to EMR/clinical data repository 144: The bridge 120 device provides an interface to the EMR/clinical data repository 144 for the purpose of storing patient records. Also, anonymous PMRs are stored for the purposes of data analysis as well as provide a mechanism to monitor the operation of the multi-vital-sign smartphone system(s) 104.

Device PMRs: The bridge 120 in some implementations accepts propriety formatted measurement records from multi-vital-sign smartphone system(s) 104 connected and configured to communicate with the bridge 120 and translate the received measurement record into a suitable format for transfer to a EMR data capture systems 100, 200 and 300. The bridge 120 is the multi-vital-sign smartphone system(s) 104 that will take the multi-vital-sign smartphone system(s) 104 based data and translate that data into a format suitable to pass along to a local or remote EMR/Clinical Data Repository 144 system using the required protocols of that EMR/Clinical Data Repository 144.

Device non patient measurement data: The bridge 120 in some implementations accepts data from connected multi-vital-sign smartphone system(s) 104 and provides data to a connected device. This is data or setting parameters associated with the multi-vital-sign smartphone system(s) 104 that in some implementations is managed by the bridge 120, e.g. device configuration settings, firmware images, status information etc.

Device to Bridge 120 interface protocol: The bridge 120 supports a multi-vital-sign smartphone system(s) 104 to bridge 120 interface protocol, BRIP, for all communications between the multi-vital-sign smartphone system(s) 104 and the bridge 120 device. Each device supports a single interface protocol, BRIF and individual device or manufacture level protocols can be supported by the bridge 120.

Network communications method: The bridge 120 supports a LAN based interface for processing connection requests and data transfers from remote multi-vital-sign smartphone system(s) 104. Standard communications methods such as UDP/TCP/IP etc. are supported but the interface is not restricted to this transfer mechanism, the architecture of EMR data capture systems 100, 200 and 300 in some implementations support other transfer methods such as UDP. Where more than one multi-vital-sign smartphone system(s) 104 type is supported in EMR data capture systems 100, 200 and 300 the bridge 120 supports different transfer mechanism concurrently Multi-vital-sign smartphone system(s) 104: The bridge 120 in some implementations accept connections and measurement data records from multi-vital-sign smartphone system(s) 104.

Non-conforming Multi-vital-sign smartphone system: The bridge 120 in some implementations accepts connections and measurement data records from non-multi-vital-sign smartphone system(s) 104 multi-vital-sign smartphone system(s) 104 using device interface protocols specific to a given device or manufacture of a range of device. The EMR data capture systems 100, 200 and 300 support third party multi-vital-sign smartphone system(s) 104 to provide the same core features and functions as those outlined in this document. In some implementations, a core system supports all multi-vital-sign smartphone system(s) 104 connected to EMR data capture systems 100, 200 and 300, for the purposes of measurement data, body core temperature, ECG, blood pressure, plus other biological vital signs, both single and continuous measurement based, for transfer to the selected EMR/Clinical Data Repository 144, along with per device configuration and status monitoring.

Single Parameter Measurement Data: The bridge 120 in some implementations accept and processes for transfer to the configured EMR/Clinical Data Repository 144, single event measurement data. Single event measurement data is defined as a patient biological vital sign single point measurement such as a patient body core temperature, blood pressure, heart rate or other data that is considered a one-time measurement event for a single measurement parameter This type of data is generated from a multi-vital-sign smartphone system(s) 104 that supports a single biological vital sign reading.

Multiple Parameter Measurement Data: The bridge 120 in some implementations accept and process for transfer to the EMR multiple event measurement data. Multiple event measurement data is defined as a patient biological vital sign single point measurement such as a patient body core temperature, blood pressure, heart rate or other parameter that is considered a one-time measurement event for more than one parameter This type of data is generated from a multi-biological vital sign multi-vital-sign smartphone system(s) 104.

Continuous Parameter Measurement Data: The bridge 120 in some implementations accept and process for transfer to the EMR single parameter continuous measurement data. Continuous measurement data is defined as a stream of measurement samples representing a time domain signal for a single or multiple biological vital sign parameter.

Unique Multi-vital-sign smartphone system identification: The bridge 120 supports a unique identifier per multi-vital-sign smartphone system(s) 104, across all vendors and device types, for the purposes of device identification, reporting and operations. Each multi-vital-sign smartphone system(s) 104 that is supported by the EMR data capture systems 100, 200 and 300 provides a unique identification based on the manufacture, product type, and serial number or other factors such as the FDA UID. The bridge 120 is required to track, take account of, and report this number in all interactions with the multi-vital-sign smartphone system(s) 104 and for logging. This device identification can also be used in the authentication process when a multi-vital-sign smartphone system(s) 104 connects to the bridge 120.

Device connection authentication: The bridge 120 provides a mechanism to authenticate a given multi-vital-sign smartphone system(s) 104 on connection to ensure that the multi-vital-sign smartphone system(s) 104 are known and allowed to transfer information to the bridge 120. Access to the bridge 120 functions in some implementations is controlled in order to restrict access to currently allowed devices only. Acceptance of a multi-vital-sign smartphone system(s) 104 making connection the bridge 120 for 2 main rationales. 1. The multi-vital-sign smartphone system(s) 104 are known to the bridge 120, and that 2. A management function to control access for a given device, i.e. allow or bar access.

Device date and time update: The bridge 120 device can provide a mechanism to allow a connected multi-vital-sign smartphone system(s) 104 to update its internal date and time settings against the bridge 120's current date and time. The multi-vital-sign smartphone system(s) 104 are to update their internal real time clocks on connection to the bridge 120, accordingly, a time reference across all devices used with EMR data capture systems 100, 200 and 300 is obtained from a central source. All embedded systems real time clock functions drift with time, this mechanism will form the basis of both time and date configuration on the multi-vital-sign smartphone system(s) 104 and dynamic update of time and date for the multi-vital-sign smartphone system(s) 104 thereby removing the need to set time and date on a given device. An accuracy of +/−1 second is acceptable for maintaining the time on a multi-vital-sign smartphone system(s) 104. Bridge 120 to device backwards compatibility: The bridge 120 device is required to be backwards compatible with all released versions of multi-vital-sign smartphone system(s) 104 firmware, interface protocols, and data formats supported by the bridge 120 device from first release of the bridge 120 system. Backwards compatibly of the bridge 120 with all released revisions of multi-vital-sign smartphone system(s) 104 in some implementations for the normal operation of EMR data capture systems 100, 200 and 300. It cannot be guarantee that all devices of a given product are at the same revision level or that different products from a single manufacture or from different manufactures will support the same interface protocol or other critical component revision.

Last connection of device: The bridge 120 is required maintain a history of the connection dates and times for a given multi-vital-sign smartphone system(s) 104. This is required from a reporting and logging viewpoint. In some implementations will also be used to determine if a multi-vital-sign smartphone system(s) 104 are lost/stolen or failed.

Calibration/Checker Monitoring: The bridge 120 is required to track the valid calibration dates for a given device and present to the operator those devices that are out of calibration or approaching calibration. All multi-vital-sign smartphone system(s) 104 in some implementations be checked for operation and accuracy on a regular bases. EMR data capture systems 100, 200 and 300 can provide the facility to generate a report and high light devices that are either out of calibration and those approaching calibration. The check carried out by the bridge 120 is on the expiry date exposed by the multi-vital-sign smartphone system(s) 104. The bridge 120 is not required to actually check the multi-vital-sign smartphone system(s) 104 for calibration, only report if the multi-vital-sign smartphone system(s) 104 are out of calibration based on the multi-vital-sign smartphone system(s) 104 expiry date. In some implementations the expiry date is updated at the time of the multi-vital-sign smartphone system(s) 104 recalibration check.

Error/Issue monitoring: The bridge 120 is required to track the issues/errors reported by a given device and present that information to the operator in terms of a system report. Reporting of device level errors dynamically for a given device is diagnostics tool for system management. Providing the issue/error history for a given device provides core system diagnostic information for the multi-vital-sign smartphone system(s) 104.

Battery Life monitoring: The bridge 120 is required to track the battery level of a given device and report the battery level information to the operator. EMR data capture systems 100, 200 and 300 is to highlight to the operator that a given device has an expired or nearly expired or failed internal battery based on the information exposed by the multi-vital-sign smartphone system(s) 104. It is the multi-vital-sign smartphone system(s) 104 responsibility to determine its own internal power source charge level or battery condition. The bridge 120 can provide a mechanism to report the known battery condition for all devices, e.g. say all devices that have 10% battery level remaining.

Lost/Stolen/Failed monitoring: The bridge 120 is required to determine for a given multi-vital-sign smartphone system(s) 104 if it has been lost/stolen/or failed and disable the multi-vital-sign smartphone system(s) 104 for system operation. Being able to determine if a system has not connected to the bridge 120 for a period of time is a feature for failed, lost or stolen reporting to the operator. If a multi-vital-sign smartphone system(s) 104 has not connected to EMR data capture systems 100, 200 and 300 for a period of time, EMR data capture systems 100, 200 and 300 determines that the multi-vital-sign smartphone system(s) 104 has been stolen or lost, in this event the operator is informed in terms of a system report and the multi-vital-sign smartphone system(s) 104 removed from the supported devices list. If and when the multi-vital-sign smartphone system(s) 104 reconnects to EMR data capture systems 100, 200 and 300 the multi-vital-sign smartphone system(s) 104 are to be lighted as "detected" and forced to be rechecked and re-commissioned again for use on the network.

Device Keep Alive: The bridge 120 provides a mechanism to inform a target multi-vital-sign smartphone system(s) 104 upon connection to the bridge 120 to stay connected to the bridge 120 until released by the bridge 120.

A multi-vital-sign smartphone system(s) 104 keep alive method in some implementations is provided so that the bridge 120 when a multi-vital-sign smartphone system(s) 104 connects can inform the multi-vital-sign smartphone system(s) 104 to stay powered and connected to the bridge 120 for the purposes of reconfiguration, status monitoring or diagnostics.

Reset device to network default: A method to reset a target device or group of selected devices to factory settings for all network parameters in some implementations.

Reset device to factory default: A method to reset a target device or group of selected devices to their factory default settings in some implementations is supported.

Dynamic Device Parameter Configuration: The bridge 120 provides a mechanism to provide configuration information to a multi-vital-sign smartphone system(s) 104 when requested by the multi-vital-sign smartphone system(s) 104 on connection to the bridge 120 or via the keep device alive mechanism. Upon connecting to a bridge 120 a multi-vital-sign smartphone system(s) 104 as part of the communications protocol determines if its current configuration is out of date, if any aspect of the multi-vital-sign smartphone system(s) 104 configuration is out of date and is required to be updated then the bridge 120 provides the current configuration information for the multi-vital-sign smartphone system(s) 104 model and revision This is intended to be as simple as the multi-vital-sign smartphone system(s) 104 getting the configuration setting for each of its supported parameters. The bridge 120 is responsible to ensure that the supplied information is correct for the multi-vital-sign smartphone system(s) 104 model and revision level.

Device Configuration Grouping: Single device: The bridge 120 provides a mechanism to configure a single device, based on unique device id, to known configuration parameters. The bridge 120 in some implementations allows a single multi-vital-sign smartphone system(s) 104 to be updated when it connects to the bridge 120 either via the heart beat method or via operator use. This effectively means that the bridge 120 provides a method to manage and maintain individual device configuration settings and have those settings available dynamically for when the multi-vital-sign smartphone system(s) 104 connects. Further the bridge 120 supports per device configurations for different revisions of device firmware, for example revision 1 of device A has configuration parameters x, y and z, but revision 2 of the multi-vital-sign smartphone system(s) 104 has configuration parameters has x, y, z and k and the valid allowed range for the y parameter has been reduced.

Device Configuration Grouping—Multi-vital-sign smartphone system(s) 104 model group: The bridge 120 provides a mechanism to configure all devices within a model range to known configuration parameters. The facility to reconfigure a selected sub-group of devices that are model x and at revision level all with the same configuration information.

Device Configuration Grouping—selected group within model range: The bridge 120 provides a mechanism to configure a selected number of devices within the same model range to known configuration parameters. The facility to reconfigure a selected sub-group of devices that are model x and at revision level y Device Configuration Grouping—defined sub group: The bridge 120 provides a mechanism to configure a selected number of devices with the same model based on device characteristics e.g. revision level, operational location etc. The facility to reconfigure all devices that are model x and at revision level y, OR all model x devices that are in operation in Ward 6 is a feature.

Device Configuration files: The bridge 120 provides a method to save, load, update and edit a configuration file for a multi-vital-sign smartphone system(s) 104 model number and/or group settings. The ability to save and load configuration files and change the configuration content in the file is a required feature for EMR data capture systems 100, 200 and 300. A file management mechanism in some implementations is also provided for the saved configuration files.

Dynamic configuration content: The bridge 120 in some implementations dynamically per multi-vital-sign smartphone system(s) 104 connection determine upon request by the multi-vital-sign smartphone system(s) 104 the new configuration settings for that device, given that the medical devices connect in a random manner to the bridge 120, the bridge 120 is required for the connected device, model, revision, unique identification etc. to maintain the configuration settings for that device.

Association of multi-vital-sign smartphone system(s) 104 to target EMR/Clinical Data Repository 144 The bridge 120 provides a mechanism to control the patient record received from a multi-vital-sign smartphone system(s) 104 to transfer the record to one or more of the supported EMR/Clinical Data Repository 144. Where more than one EMR/Clinical Data Repository 144 is maintained by a single organization, e.g. one for ER, cardiology use and possibility one for outpatients etc. EMR data capture systems 100, 200 and 300 in some implementations manage either by specific device configuration or bridge 120 configuration which EMR the patient record is to be transmitted to by the bridge 120.

Device Configuration and Status Display: In some implementations, when a multi-vital-sign smartphone system(s) 104 connects to the bridge 120 that the multi-vital-sign smartphone system(s) 104 queries its current configuration settings against the bridge 120 settings for that specific device type and device as outlined below: 1. A given device based on a unique id for that device. Note each device is required to be uniquely identified in EMR data capture systems 100, 200 and 300. 2. A group of devices allocated to a physical location in the hospital, i.e. Based on a ward number of other unique location reference. Accordingly, in some implementations a group of devices in a given location in some implementations is updated separately from other devices of the same type located in a different location in the same hospital environment, i.e. a recovery ward 1 as opposed to an emergency room. A group of devices based on product type, i.e. all multi-vital-sign smartphone system(s) 104, updated with the same settings. Bridge 120 device configuration options adjusted based on multi-vital-sign smartphone system(s) 104. The bridge 120 in some implementations adjusts the configuration options presented to the operator based on the capabilities of the multi-vital-sign smartphone system(s) 104 being configured. Where multiple different multi-vital-sign smartphone system(s) 104 are supported by the EMR data capture systems 100, 200 and 300 it cannot be assumed that each device from a different manufacture or from the same manufacture but a different model of the same device level configuration parameters. Therefore the bridge 120 in some implementations determine the configuration capabilities for the multi-vital-sign smartphone system(s) 104 to be configured and present only valid configuration options for that device with valid parameter ranges for these options.

Device parameter Validation: The bridge 120 provides a mechanism for a given model of multi-vital-sign smartphone system(s) 104 to validate that a given configuration parameter is set within valid parameter ranges for that device model and revision. The bridge 120 is required based on the multi-vital-sign smartphone system(s) 104 model and revision level to present valid parameter ranges for the operator to configure a multi-vital-sign smartphone system(s) 104 level parameter with. Device patient record acceptance check response source. The bridge 120 provides a mechanism to configure the multi-vital-sign smartphone system(s) 104 to require either: 1) a confirmation from the bridge 120 device only that a patient record has been received for processing or 2) a confirmation from the bridge 120 device that the EMR data capture systems 100, 200 and 300 has received and saved the patient information. In some implementations of the configuration of the multi-vital-sign smartphone system(s) 104 the multi-vital-sign smartphone system(s) 104 reports to the operator a status indicator.

Device Hospital/Clinic Reference: A device setting to allow an organization identifier to be configured on the multi-vital-sign smartphone system(s) 104. The multi-vital-sign smartphone system(s) 104 can be configured with an alphanumeric identification string, max 30 characters that allows the organization to indicate to the hospital/clinic that the multi-vital-sign smartphone system(s) 104 are in use with, e.g. "Boston General".

Device Ward Location reference: A device setting to allow an operational location identifier to be configured on the multi-vital-sign smartphone system(s) 104. The multi-vital-sign smartphone system(s) 104 are to be configured with an alphanumeric identification string, max 30 characters that allows the organization to indicate an operational area within the organization, e.g. "General Ward #5".

Device Asset Number: A device setting to allow an organization asset number to be configured on the multi-vital-sign smartphone system(s) 104. The multi-vital-sign smartphone system(s) 104 are to be configured with an alphanumeric identification string, max 30 characters to allow the organization to provide an asset tag for the multi-vital-sign smartphone system(s) 104.

Display device Manufacture Name, Device Model and Serial Number: A method to display the manufacture name, device model number and device serial number for the unit is provided. EMR data capture systems 100, 200 and 300 can provide a method to determine the manufacturer name, model number and device level serial number of for the multi-vital-sign smartphone system 100. Alphanumeric identification string, max 60 characters in length for each of the three parameters.

Display multi-vital-sign smartphone system(s) 104 unique identification reference tag: A method to display the device level unique identifier for the unit. For regulatory traceability reasons each device is to support a unique identification number this number in some implementations be displayed by the EMR data capture systems 100, 200 and 300. In some implementations, an alphanumeric identification string is a maximum of 120 characters. This parameter is not to be updateable by the EMR data capture systems 100, 200 and 300.

Device last Check/Calibration Date: A method to display and set the date of the last check or re-calibration action for the multi-vital-sign smartphone system(s) 104. This allows the bridge 120 to determine which devices are required to be re-checked and present that information to the operator of EMR data capture systems 100, 200 and 300. All multi-vital-sign smartphone system(s) 104 with a measurement function are required to be checked for accuracy on a regular basis. EMR data capture systems 100, 200 and 300 provides a mechanism to update the multi-vital-sign smartphone system(s) 104 date of last check/calibration when a device level check has been carried out.

Device Temperature Display units: Configuration option for the displayed body core temperature units for the multi-vital-sign smartphone system(s) 104, Centigrade or Fahrenheit. For detection of patient body core temperature, the unit in some implementations is configured for reporting body core temperatures in degrees centigrade or Fahrenheit. Default is: Fahrenheit The bridge 120 also requires a configuration parameter for the display of any temperature results.

Operator scan enable/disable: The bridge 120 can provide a mechanism to enable or disable the multi-vital-sign smartphone system(s) 104 level operator identification scan action. The operator identification scan capability is to be configurable on a per device basis so that it can be enabled or disabled. Allow Operator Scan Repeat for more than one patient scan: The bridge 120 can provide a mechanism to enable/disable the multi-vital-sign smartphone system(s) 104 to take a single operator identification scan and associate that identification with multiple patient measurements. Where the clinical work flow allows for a known number of patient scan(s), or predetermined time frame(s), to be taken by a single operator an enable/disable feature for the multi-vital-sign smartphone system(s) 104 is provided. Default is: disabled Max number of patient scans per operator scan: The bridge 120 can provide a configuration parameter for controlling the number of patient id scans after an operator identification scan before the operator identification scan has to be taken again by the multi-vital-sign smartphone system(s) 104. The number of patient scans that are allowed to be taken by the multi-vital-sign smartphone system(s) 104 and assigned the same operator is set to a default value of 1. The bridge 120 can provide a configuration parameter for controlling the time frame in seconds that a single operator identification scan can be used for multiple patient identification scans. A time limit in seconds ranging from 0 to 1800 seconds can be set to allow a multi-vital-sign smartphone system(s) 104 to associate a single operator identification with multiple patient records in this time. In some implementations, a parameter of 0 disables the time limit range checking. The default is 0.

3. Multi-Vital-Sign Smartphone System

Figure 17:
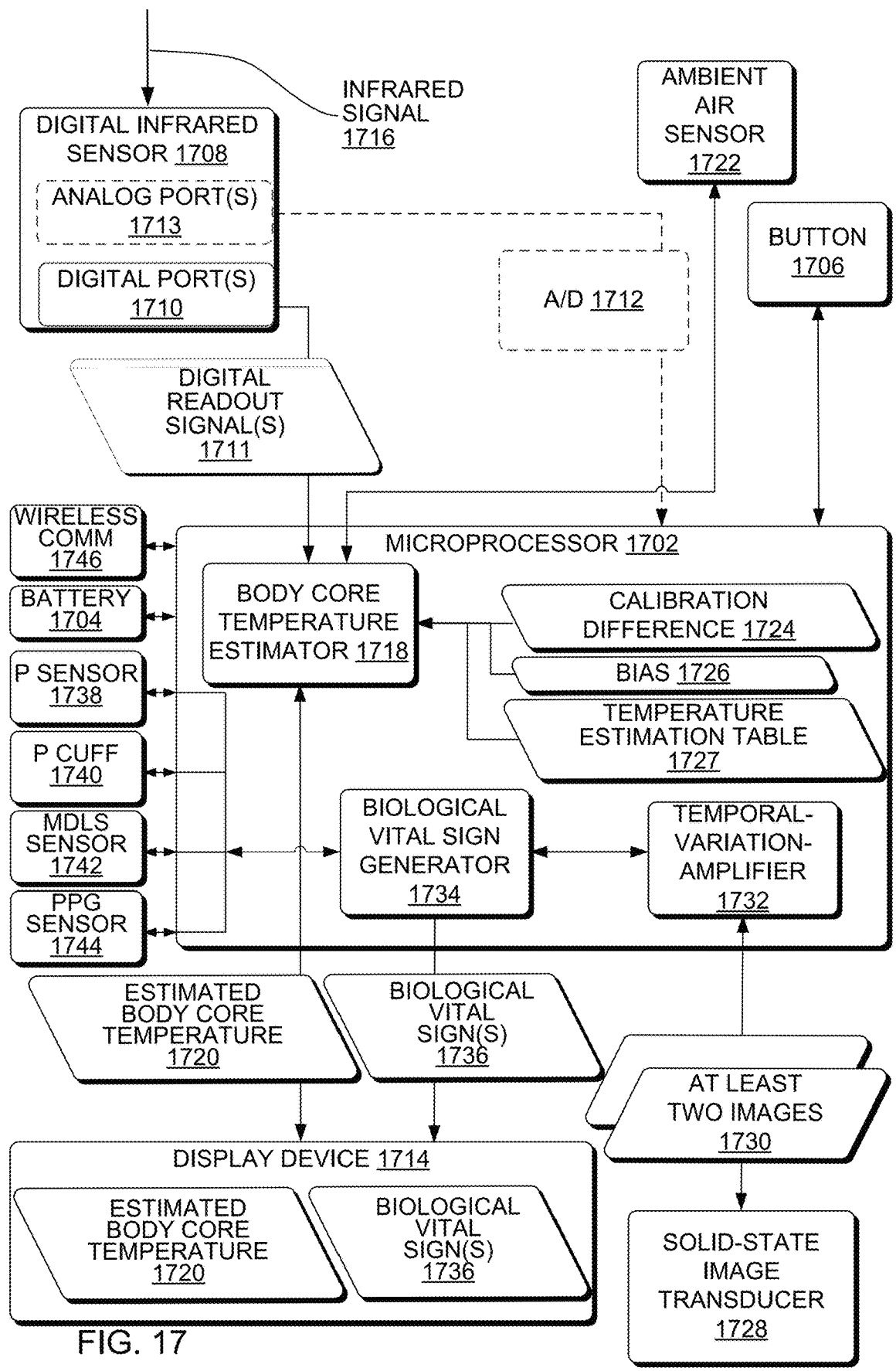
FIG. 17 is a block diagram of a multi-vital-sign smartphone system that includes a digital infrared sensor, a biological vital sign generator and a temporal variation amplifier.

FIG. 17 is a block diagram of a multi-vital-sign smartphone system 1700 that includes a digital infrared sensor, a biological vital sign generator and a temporal variation amplifier, according to an implementation. Multi-vital-sign smartphone system 1700 is an apparatus to measure body core temperature and other biological vital signs. The multi-vital-sign smartphone system 1700 is one example of the multi-vital-sign smartphone system 104 and one example of the multi-vital-signs finger cuff smartphone accessory (MVSFCSA) 502.

The multi-vital-sign smartphone system 1700 includes a microprocessor 1702. The multi-vital-sign smartphone system 1700 includes a battery 1704, in some implementations a single button 1706, and a digital infrared sensor 1708 that is operably coupled to the microprocessor 1702. The digital infrared sensor 1708 includes digital ports 1710 that provide only digital readout signal 1711. In some implementations the multi-vital-sign smartphone system 1700 includes a display device 1714 that is operably coupled to the microprocessor 1702. In some implementations, the display device 1714 is a LCD color display device or a LED color display device, which are easy to read in a dark room, and some pixels in the display device 1714 are activated (remain lit) for about 5 seconds after the single button 1706 is released. After the display has shut off, another body core temperature reading can be taken by the apparatus. The color change of the display device 1714 is to alert the operator of the apparatus of a potential change of body core temperature of the human or animal subject. The body core temperature reported on the display device 1714 can be used for treatment decisions.

The microprocessor 1702 is configured to receive from the digital ports 1710 that provide only digital readout signal 1711. In some implementations, the digital readout signal 1711 is representative of an infrared signal 1716 of a forehead surface temperature that is detected by the digital infrared sensor 1708. In other implementations, the digital readout signal 1711 is representative of an infrared signal 1716 of a surface temperature of a human other than the forehead surface that is detected by the digital infrared sensor 1708. A body core temperature estimator 1718 in the microprocessor 1702 is configured to estimate the body core temperature 1720 from the digital readout signal 1711 that is representative of the infrared signal 1716 of the forehead (or other surface), a representation of an ambient air temperature reading from an ambient air sensor 1722, a representation of a calibration difference from a memory location that stores a calibration difference 1724 and a memory location that stores a representation of a bias 1726 in consideration of a temperature sensing mode. In some implementations, the multi-vital-sign smartphone system 1700 does not include an analog-to-digital converter 1712 operably coupled between the digital infrared sensor 1708 and the microprocessor 1702. Furthermore, the digital infrared sensor 1708 also does not include analog readout ports 1713. The dashed lines of the A/D converter 1712 and the analog readout ports 1713 indicates absence of the A/D converter 1712 and the analog readout ports 1713 in the multi-vital-sign smartphone system 1700 and the apparatus 2100. One implementation of the digital infrared sensor 1708 is digital infrared sensor 2100 in FIG. 21.

The multi-vital-sign smartphone system(s) 104 includes a temperature estimation table 1727 in a memory. The temperature estimation table 1727 is a lookup table that correlates a sensed forehead temperature to an estimated body core temperature 1720. The sensed forehead temperature is derived from the digital readout signal 1711.

Figure 18:
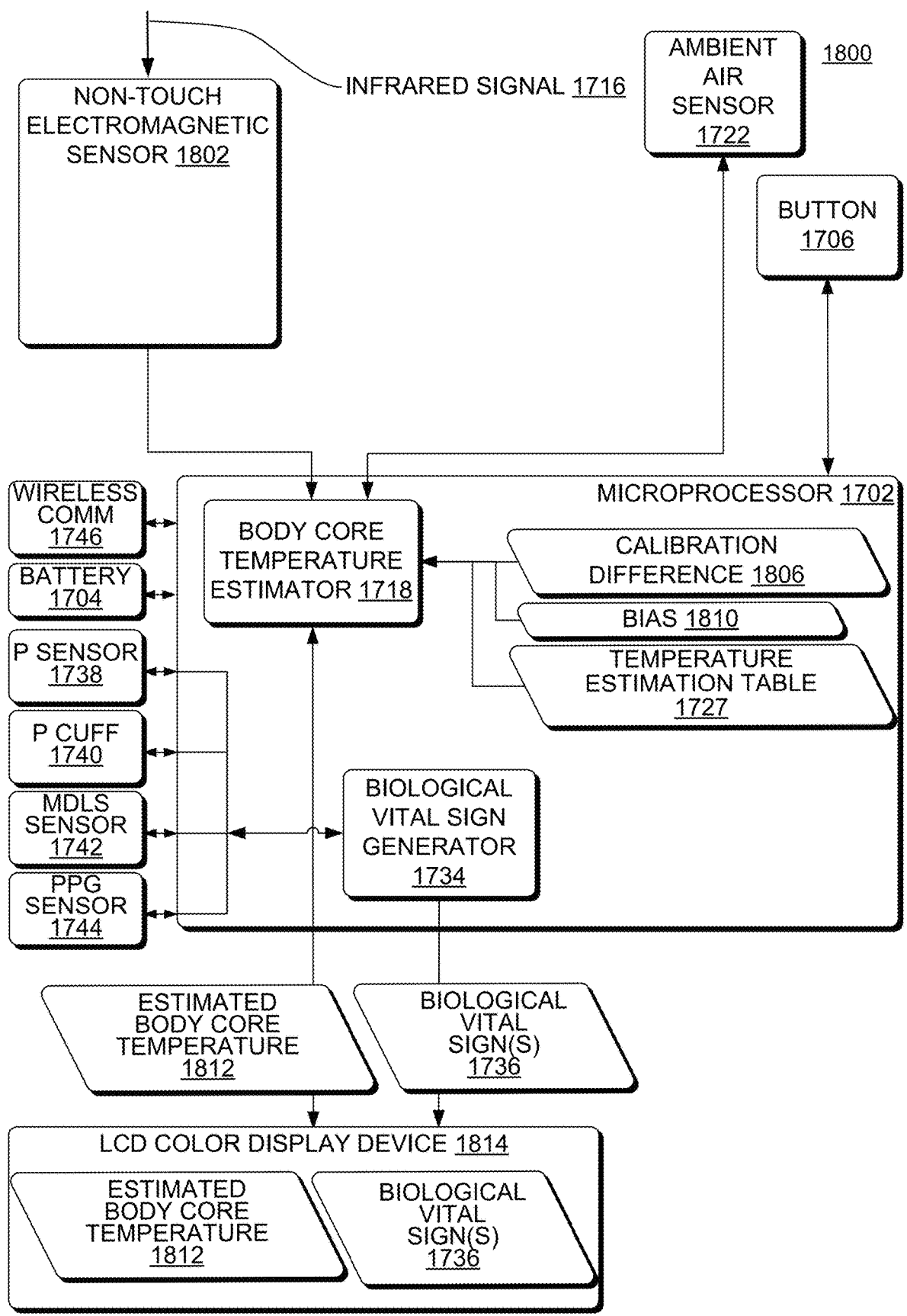
FIG. 18 is a block diagram of a multi-vital-sign smartphone system that includes a no-touch electromagnetic sensor with no temporal variation amplifier.

The temperature estimation table 1727 is stored in a memory. In FIG. 17-18, the temperature estimation table 1727 is shown as a component of the microprocessor 1702. The memory that stores the temperature estimation table 1727 can be separate from the microprocessor 1702 or the memory can be a part of the microprocessor 1702, such as cache on the microprocessor 1702. Examples of the memory include Random Access Memory (RAM) 3206 and flash memory 3208 in FIG. 32. In implementations of the multi-vital-sign smartphone systems in FIG. 17-18, the apparatus that estimates a body core temperature in FIG. 17-18 the multi-vital-sign smartphone system 3200 in which speed of the multi-vital-sign smartphone systems in FIG. 17-18 and the apparatus that estimate a body core temperature of an external source point in FIG. 17-18 is very important, storing the temperature estimation table 1727 in memory that is a part of the microprocessor 1702, such as cache on the microprocessor 1702, is very important.

The correlation between the sensed forehead temperature to an estimated body core temperature varies based on age, sex, and a febrile (pyretic) or hypothermic condition of the patient and intraday time of the reading. Accordingly, in some implementations, the multi-vital-sign smartphone system(s) 104 includes temperature estimation tables 1727 that are specific to the combinations and permutations of the various situations of the age, sex, and a febrile (pyretic) or hypothermic condition of the patient and the intraday time of the reading. For example, in one implementation, the multi-vital-sign smartphone system(s) 104 include a temperature estimation table 1727 for male humans of 3-10 years old, that are neither febrile nor hypothermic, for temperature readings taken between 10 am-2 pm. In another example, in another implementation, the multi-vital-sign smartphone system(s) 104 include a temperature estimation table 1727 for female humans of greater than 51 years of age, that are febrile and for temperature readings taken between 2 am-8 am.

Some implementations of the multi-vital-sign smartphone system 1700 include a solid-state image transducer 1728 that is operably coupled to the microprocessor 1702 and is configured to provide two or more images 1730 to a temporal-variation-amplifier 1732 and a biological vital sign generator 1734 in the microprocessor 1702 to estimate one or more biological vital signs 1736 that are displayed on the display device 1714.

The multi-vital-sign smartphone system 1700 includes any one of a pressure sensor 1738, a pressure cuff 1740, a micro dynamic light scattering (mDLS) sensor 1742 and/or a photoplethysmogram (PPG) sensor 1744 that provide signals to the biological vital sign generator 1734. The mDLS sensor uses a laser beam (singular wavelength) of light and a light detector on the opposite side of the finger to detect the extent of the laser beam that is scattered in the flesh of the finger, which indicates the amount of oxygen in blood in the fingertip. The PPG sensor uses projected light and a light detector on the opposite side of the finger to detect the extent of the laser beam that is absorbed in the flesh of the finger, which indicates the amount of oxygen in blood in the fingertip, which is also known as pulse oximetry. The pressure sensor 1738 is directly linked to the pressure cuff 1740. In some implementations, the multi-vital-sign smartphone system 1700 includes two mDLS sensors to ensure that at least one of the mDLS sensors provides a good quality signal. In some implementations, the biological vital sign generator 1734 generates blood pressure measurement (systolic and diastolic) from signals from the pressure sensor 1738, the finger pressure cuff 1740 and the mDLS sensor 1742. In some implementations, the biological vital sign generator 1734 generates SpO2 measurement and heart rate measurement from signals from the PPG sensor 1744. In some implementations, the biological vital sign generator 1734 generates respiration (breathing rate) measurement from signals from the mDLS sensor 1742. In some implementations, the biological vital sign generator 1734 generates blood flow measurement from signals from the mDLS sensor 1742. In some implementations, the biological vital sign generator 1734 generates heartrate variability from signals from the PPG sensor 1744. In some implementations, the body core temperature estimator 1718 is implemented in the biological vital sign generator 1734.

The multi-vital-sign smartphone system 1700 also includes a wireless communication subsystem 1746 or other external communication subsystem, such as an Ethernet port, that provides communication to the EMR data capture systems 100, 200 and 300 or other devices. In some implementations, the wireless communication subsystem 1746 is communication subsystem 1746 in FIG. 34. The wireless communication subsystem 1746 is operable to receive and transmit the estimated body core temperature 1720 and/or the biological vital sign(s) 1736.

In some implementations, the digital infrared sensor 1708 is a low noise amplifier, 17-bit ADC and powerful DSP unit through which high accuracy and resolution of the estimated body core temperature 1720 by the multi-vital-sign smartphone systems in FIG. 17-18, the apparatus that estimates a body core temperature in FIG. 17-18 and the multi-vital-sign smartphone system 3200.

In some implementations, the digital infrared sensor 1708, 10-bit pulse width modulation (PWM) is configured to continuously transmit the measured temperature in range of −20 . . . 120° C., with an output resolution of 0.14° C. The factory default power on reset (POR) setting is SMBus.

In some implementations, the digital infrared sensor 1708 is packaged in an industry standard TO-39 package.

In some implementations, the generated object and ambient temperatures are available in RAM of the digital infrared sensor 1708 with resolution of 0.01° C. The temperatures are accessible by 2 wire serial SMBus compatible protocol (0.02° C. resolution) or via 10-bit PWM (Pulse Width Modulated) output of the digital infrared sensor 1708.

In some implementations, the digital infrared sensor 1708 is factory calibrated in wide temperature ranges: −40 . . . 85° C. for the ambient temperature and −70 . . . 380° C. for the object temperature.

In some implementations of the digital infrared sensor 1708, the measured value is the average temperature of all objects in the Field Of View (FOV) of the sensor. In some implementations, the digital infrared sensor 1708 has a standard accuracy of ±0.5° C. around room temperatures, and in some implementations, the digital infrared sensor 1708 has an accuracy of ±0.2° C. in a limited temperature range around the human body core temperature.

These accuracies are only guaranteed and achievable when the sensor is in thermal equilibrium and under isothermal conditions (there are no temperature differences across the sensor package). The accuracy of the detector can be influenced by temperature differences in the package induced by causes like (among others): Hot electronics behind the sensor, heaters/coolers behind or beside the sensor or by a hot/cold object very close to the sensor that not only heats the sensing element in the detector but also the detector package. In some implementations of the digital infrared sensor 1708, the thermal gradients are measured internally and the measured temperature is compensated in consideration of the thermal gradients, but the effect is not totally eliminated. It is therefore important to avoid the causes of thermal gradients as much as possible or to shield the sensor from the thermal gradients.

In some implementations, the digital infrared sensor 1708 is configured for an object emissivity of 1, but in some implementations, the digital infrared sensor 1708 is configured for any emissivity in the range 0.1 . . . 1.0 without the need of recalibration with a black body.

In some implementations of the digital infrared sensor 1708, the PWM can be easily customized for virtually any range desired by the customer by changing the content of 2 EEPROM cells. Changing the content of 2 EEPROM cells has no effect on the factory calibration of the device. The PWM pin can also be configured to act as a thermal relay (input is To), thus allowing for an easy and cost effective implementation in thermostats or temperature (freezing/boiling) alert applications. The temperature threshold is programmable by the microprocessor 1702 of the multi-vital-sign smartphone system. In a multi-vital-sign smartphone system having a SMBus system the programming can act as a processor interrupt that can trigger reading all slaves on the bus and to determine the precise condition.

In some implementations, the digital infrared sensor 1708 has an optical filter (long-wave pass) that cuts off the visible and near infra-red radiant flux is integrated in the package to provide ambient and sunlight immunity. The wavelength pass band of the optical filter is from 5.5 to 14 µm.

In some implementations, the digital infrared sensor 1708 is controlled by an internal state machine, which controls the measurements and generations of the object and ambient temperatures and does the post-processing of the temperatures to output the body core temperatures through the PWM output or the SMBus compatible interface.

Some implementations of the multi-vital-sign smartphone system includes 2 IR sensors, the output of the IR sensors being amplified by a low noise low offset chopper amplifier with programmable gain, converted by a Sigma Delta modulator to a single bit stream and fed to a DSP for further processing. The signal is treated by programmable (by means of EEPROM contend) FIR and IIR low pass filters for further reduction of the bandwidth of the input signal to achieve the desired noise performance and refresh rate. The output of the IIR filter is the measurement result and is available in the internal RAM. 3 different cells are available: One for the on-board temperature sensor and 2 for the IR sensors. Based on results of the above measurements, the corresponding ambient temperature Ta and object temperatures To are generated. Both generated body core temperatures have a resolution of 0.01° C. The data for Ta and To is read in two ways: Reading RAM cells dedicated for this purpose via the 2-wire interface (0.02° C. resolution, fixed ranges), or through the PWM digital output (10 bit resolution, configurable range). In the last step of the measurement cycle, the measured Ta and To are rescaled to the desired output resolution of the PWM) and the regenerated data is loaded in the registers of the PWM state machine, which creates a constant frequency with a duty cycle representing the measured data.

In some implementations, the digital infrared sensor 1708 includes a SCL pin for Serial clock input for 2 wire communications protocol, which supports digital input only, used as the clock for SMBus compatible communication. The SCL pin has the auxiliary function for building an external voltage regulator. When the external voltage regulator is used, the 2-wire protocol for a power supply regulator is overdriven.

In some implementations, the digital infrared sensor 1708 includes a slave deviceA/PWM pin for Digital input/output. In normal mode the measured object temperature is accessed at this pin Pulse Width Modulated. In SMBus compatible mode the pin is automatically configured as open drain NMOS. Digital input/output, used for both the PWM output of the measured object temperature(s) or the digital input/output for the SMBus. In PWM mode the pin can be programmed in EEPROM to operate as Push/Pull or open drain NMOS (open drain NMOS is factory default). In SMBus mode slave deviceA is forced to open drain NMOS I/O, push-pull selection bit defines PWM/Thermal relay operation. The PWM/slave deviceA pin the digital infrared sensor 1708 operates as PWM output, depending on the EEPROM settings. When WPWM is enabled, after POR the PWM/slave deviceA pin is directly configured as PWM output. When the digital infrared sensor 1708 is in PWM mode, SMBus communication is restored by a special command. In some implementations, the digital infrared sensor 1708 is read via PWM or SMBus compatible interface. Selection of PWM output is done in EEPROM configuration (factory default is SMBus). PWM output has two programmable formats, single and dual data transmission, providing single wire reading of two temperatures (dual zone object or object and ambient). The PWM period is derived from the on-chip oscillator and is programmable.

In some implementations, the digital infrared sensor 1708 includes a VDD pin for External supply voltage and a VSS pin for ground.

The microprocessor 1702 has read access to the RAM and EEPROM and write access to 9 EEPROM cells (at addresses 0x00, 0x01, 0x02, 0x03, 0x04, 0x05*, 0x0E, 0x0F, 0x09). When the access to the digital infrared sensor 1708 is a read operation, the digital infrared sensor 1708 responds with 16 data bits and 8 bit PEC only if its own slave address, programmed in internal EEPROM, is equal to the SA, sent by the master. A slave feature allows connecting up to 127 devices (SA=0x00 . . . 0x07F) with only 2 wires. In order to provide access to any device or to assign an address to a slave device before slave device is connected to the bus system, the communication starts with zero slave address followed by low R/W bit. When the zero slave address followed by low R/W bit sent from the microprocessor 1702, the digital infrared sensor 1708 responds and ignores the internal chip code information.

In some implementations, two digital infrared sensors 1708 are not configured with the same slave address on the same bus.

In regards to bus protocol, after every received 8 bits, the slave device should issue ACK or NACK. When a microprocessor 1702 initiates communication, the microprocessor 1702 first sends the address of the slave and only the slave device which recognizes the address will ACK, the rest will remain silent. In case the slave device NACKs one of the bytes, the microprocessor 1702 stops the communication and repeat the message. A NACK could be received after the packet error code (PEC). A NACK after the PEC means that there is an error in the received message and the microprocessor 1702 attempts resending the message. PEC generation includes all bits except the START, REPEATED START, STOP, ACK, and NACK bits. The PEC is a CRC-8 with polynomial X8+X2+X1+1. The Most Significant Bit of every byte is transferred first.

In single PWM output mode the settings for PWM1 data only are used. The temperature reading can be generated from the signal timing as:

$$T_{OUT} = \left(\frac{2t_2}{T} \times (T_{O\_MAX} - T_{O\_MIN})\right) + T_{O\_MIN}$$

where Tmin and Tmax are the corresponding rescale coefficients in EEPROM for the selected temperature output (Ta, object temperature range is valid for both Tobj1 and Tobj2 as specified in the previous table) and T is the PWM period. Tout is TO1, TO2 or Ta according to Config Register [5:4] settings.

The different time intervals t1 . . . t4 have following meaning:

t1: Start buffer. During t1 the signal is always high. t1=0.125 s×T (where T is the PWM period)

t2: Valid Data Output Band, 0 . . . 1/2T. PWM output data resolution is 10 bit.

t3: Error band—information for fatal error in EEPROM (double error detected, not correctable).

t3=0.25 s×T. Therefore a PWM pulse train with a duty cycle of 0.875 indicates a fatal error in EEPROM (for single PWM format). FE means Fatal Error.

In regards to a format for extended PWM, the temperature can be generated using the following equation:

$$T_{OUT1} = \left(\frac{4t_2}{T} \times (T_{MAX1} - T_{MIN1})\right) + T_{MIN1}$$

For Data 2 field the equation is:

$$T_{OUT2} = \left(\frac{4t_5}{T} \times (T_{MAX2} - T_{MIN2})\right) + T_{MIN2}$$

Figure 19:
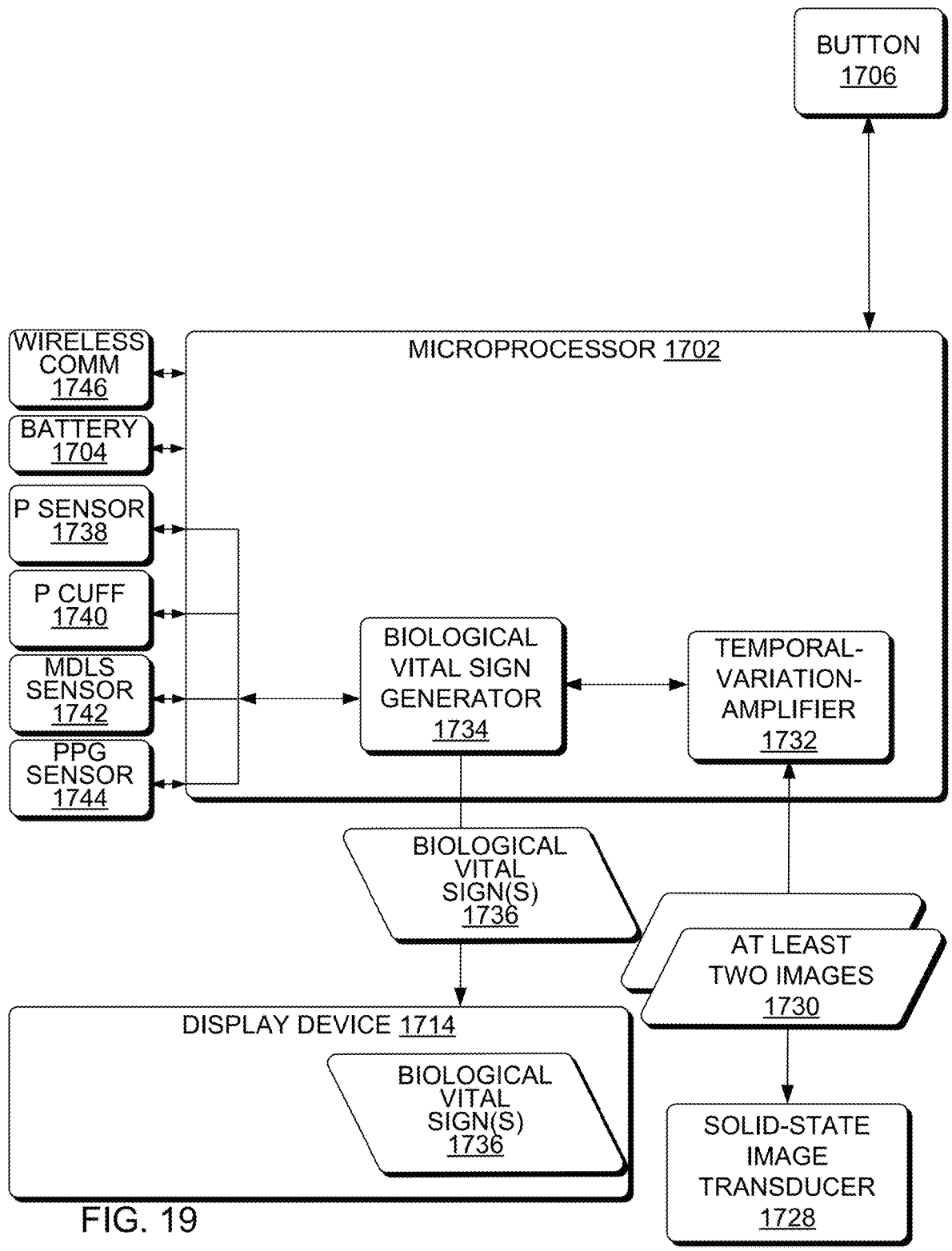
FIG. 19 is a block diagram of a multi-vital-sign smartphone system that includes a non-touch electromagnetic sensor and that detects biological vital-signs from images captured by a solid-state image transducer.

In some implementations of FIG. 17-19, the microprocessor 1702, the image transducer 1728, the pressure sensor 1738, the pressure cuff 1740, the micro dynamic light scattering (mDLS) sensor 1742 and/or the photoplethysmogram (PPG) sensor 1744 are located in the multi-vital-signs finger cuff smartphone accessory and the display devices 1714 and 1814 are located in the multi-vital-sign smartphone.

In some implementations of FIG. 17-19, the image transducer 1728, the pressure sensor 1738, the pressure cuff 1740, the micro dynamic light scattering (mDLS) sensor 1742 and/or the photoplethysmogram (PPG) sensor 1744 are located in the multi-vital-signs finger cuff smartphone accessory and the microprocessor 1702 and the display devices 1714 and 1814 are located in the multi-vital-sign smartphone.

FIG. 18 is a block diagram of a multi-vital-sign smartphone system 1800 that includes a non-touch electromagnetic sensor with no temporal variation amplifier, according to an implementation. The multi-vital-sign smartphone system 1800 is one example of the multi-vital-sign smartphone system 104 and one example of the multi-vital-signs finger cuff smartphone accessory (MVSFCSA) 502. The multi-vital-sign smartphone system 1800 includes a battery 1704, in some implementations a single button 1706, in some implementations a display device 1714, a non-touch electromagnetic sensor 1802 and an ambient air sensor 1722 that are operably coupled to the microprocessor 1702. The microprocessor 1702 is configured to receive a representation of an infrared signal 1716 of the forehead or other external source point from the non-touch electromagnetic sensor 1802. The microprocessor 1702 includes a body core temperature estimator 1718 that is configured to estimate the body core temperature 1812 of the subject from the representation of the electromagnetic energy of the external source point.

The multi-vital-sign smartphone system 1800 includes a pressure sensor 1738, a pressure cuff 1740, a mDLS sensor 1742 and a PPG sensor 1744 that provide signals to the biological vital sign generator 1734. The pressure sensor 1738 is directly linked to the pressure cuff 1740. In some implementations, the multi-vital-sign smartphone system 1800 includes two mDLS sensors to ensure that at least one of the mDLS sensors provides a good quality signal. In some implementations, the biological vital sign generator 1734 generates blood pressure measurement (systolic and diastolic) from signals from the pressure sensor 1738, the finger pressure cuff 1740 and the mDLS sensor 1742. In some implementations, the biological vital sign generator 1734 generates SpO2 measurement and heart rate measurement from signals from the PPG sensor 1744. In some implementations, the biological vital sign generator 1734 generates respiration (breathing rate) measurement from signals from the mDLS sensor 1742. In some implementations, the biological vital sign generator 1734 generates blood flow measurement from signals from the mDLS sensor 1742. In some implementations, the biological vital sign generator 1734 generates heartrate variability from signals from the PPG sensor 1744.

The body core temperature correlation table for all ranges of ambient temperatures provides best results because a linear or a quadratic relationship provide inaccurate estimates of body core temperature, yet a quartic relationship, a quintic relationship, sextic relationship, a septic relationship or an octic relationship provide estimates along a highly irregular curve that is far too wavy or twisting with relatively sharp deviations.

The non-touch electromagnetic sensor 1802 detects temperature in response to remote sensing of a surface a human or animal. In some implementations, the multi-vital-sign smartphone system having an infrared sensor is an infrared temperature sensor. All humans or animals radiate infrared energy. The intensity of this infrared energy depends on the temperature of the human or animal, thus the amount of infrared energy emitted by a human or animal can be interpreted as a proxy or indication of the body core temperature of the human or animal. The non-touch electromagnetic sensor 1802 measures the temperature of a human or animal based on the electromagnetic energy radiated by the human or animal. The measurement of electromagnetic energy is taken by the non-touch electromagnetic sensor 1802 which constantly analyzes and registers the ambient temperature. When the operator of apparatus in FIG. 18 holds the non-touch electromagnetic sensor 1802 about 5-8 cm (2-3 inches) from the forehead and activates the radiation sensor, the measurement is instantaneously measured. To measure a temperature using the non-touch electromagnetic sensor 1802, pushing the button 1706 causes a reading of temperature measurement from the non-touch electromagnetic sensor 1802 and in some implementations the measured body core temperature is thereafter displayed on the display device 1714. Various implementations of the non-touch electromagnetic sensor 1802 can be a digital infrared sensor, such as digital infrared sensor 1708 or an analog infrared sensor.

The body core temperature estimator 1718 correlates the temperatures sensed by the non-touch electromagnetic sensor 1802 to another temperature, such as a body core temperature of the subject, an axillary temperature of the subject, a rectal temperature of the subject and/or an oral temperature of the subject. The body core temperature estimator 1718 can be implemented as a component on a microprocessor, such as main processor 3202 in FIG. 32 or on a memory such as flash memory 3208 in FIG. 32.

The multi-vital-sign smartphone system 1800 also detects the body core temperature of a human or animal regardless of the room temperature because the measured temperature of the non-touch electromagnetic sensor 1802 is adjusted in reference to the ambient temperature in the air in the vicinity of the apparatus. The human or animal must not have undertaken vigorous physical activity prior to temperature measurement in order to avoid a misleading high temperature. Also, the room temperature should be moderate, 50° F. to 120° F.

The multi-vital-sign smartphone system 1800 provides a non-invasive and non-irritating means of measuring human or animal body core temperature to help ensure good health.

When evaluating results, the potential for daily variations in body core temperature can be considered. In children less than 6 months of age daily variation is small. In children 6 months to 4 years old the variation is about 1 degree. By age 6 variations gradually increase to 4 degrees per day. In adults there is less body core temperature variation.

The multi-vital-sign smartphone system 1800 also includes a wireless communication subsystem 1746 or other external communication subsystem, such as an Ethernet port, that provides communication to the EMR data capture systems 100, 200 and 300. In some implementations, the wireless communication subsystem 1746 is communication subsystem 1746 in FIG. 34.

FIG. 19 is a block diagram of a multi-vital-sign smartphone system 1900 that includes a non-touch electromagnetic sensor and that detects biological vital-signs from images captured by a solid-state image transducer, according to an implementation. The multi-vital-sign smartphone system 1900 is one example of the multi-vital-sign smartphone system 104 and one example of the multi-vital-signs finger cuff smartphone accessory (MVSFCSA) 502 in FIG. 5. The multi-vital-sign smartphone system 1900 includes a battery 1704, in some implementations a single button 1706, in some implementations a display device 1714, a non-touch electromagnetic sensor 1802 and an ambient air sensor 1722 that are operably coupled to the microprocessor 1702. The microprocessor 1702 is configured to receive a representation of an infrared signal 1716 of the forehead or other external source point from the non-touch electromagnetic sensor 1802. The microprocessor 1702 includes a body core temperature estimator 1718 that is configured to estimate the body core temperature 1812 of the subject from the representation of the electromagnetic energy of the external source point. The multi-vital-sign smartphone system 1900 includes a solid-state image transducer 1728 that is operably coupled to the microprocessor 1702 and is configured to provide two or more images 1730 to the microprocessor 1702.

The multi-vital-sign smartphone system 1900 include a pressure sensor 1738, a pressure cuff 1740, a mDLS sensor 1742 and a PPG sensor 1744 that provide signals to the biological vital sign generator 1734. The pressure sensor 1738 is directly linked to the pressure cuff 1740. In some implementations, the multi-vital-sign smartphone system 1900 includes two mDLS sensors to ensure that at least one of the mDLS sensors provides a good quality signal. In some implementations, the biological vital sign generator 1734 generates blood pressure measurement (systolic and diastolic) from signals from the pressure sensor 1738, the finger pressure cuff 1740 and the mDLS sensor 1742. In some implementations, the biological vital sign generator 1734 generates SpO2 measurement and heart rate measurement from signals from the PPG sensor 1744. In some implementations, the biological vital sign generator 1734 generates respiration (breathing rate) measurement from signals from the mDLS sensor 1742. In some implementations, the biological vital sign generator 1734 generates blood flow measurement from signals from the mDLS sensor 1742. In some implementations, the biological vital sign generator 1734 generates heartrate variability from signals from the PPG sensor 1744.

Figure 20:
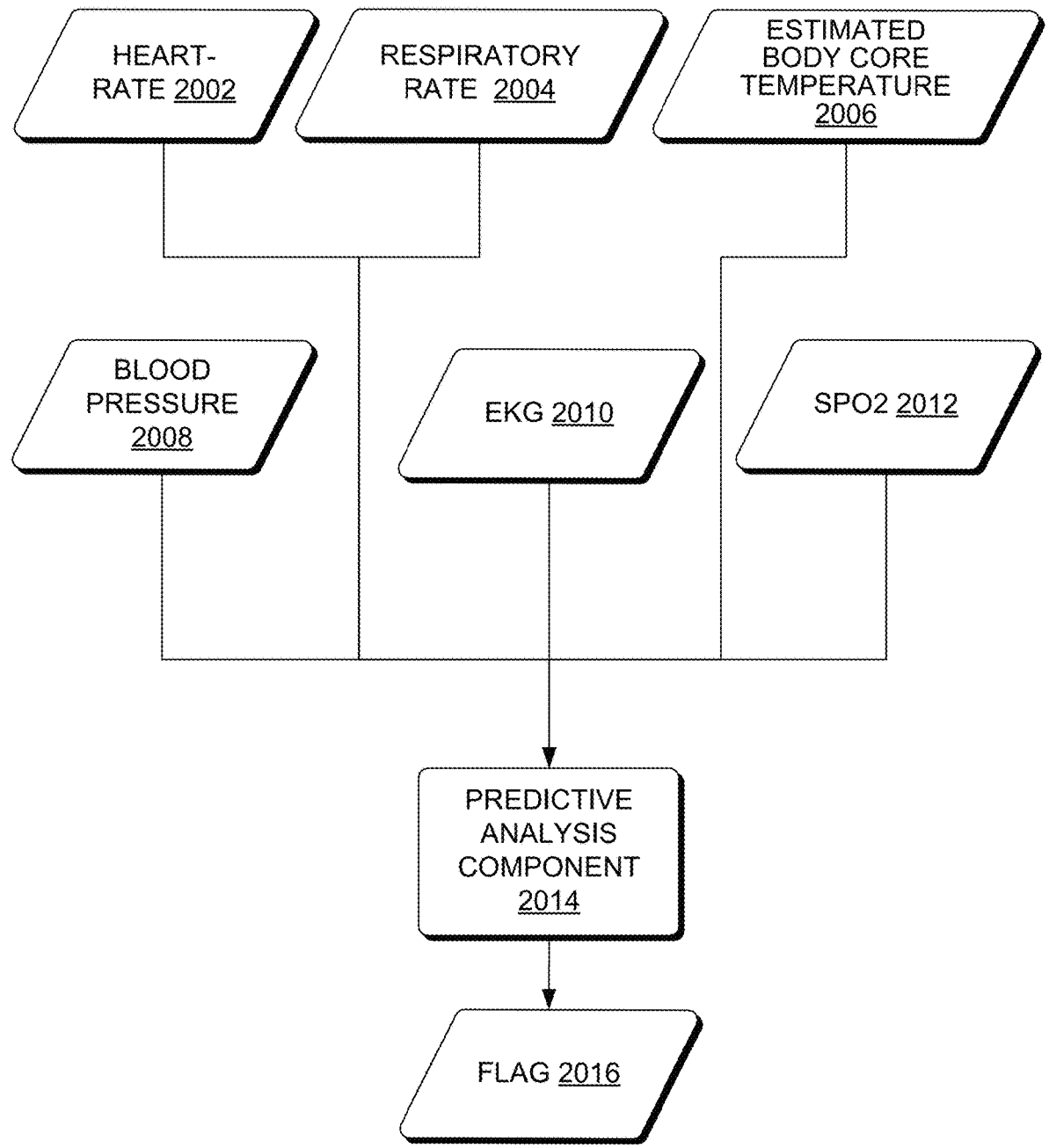
FIG. 20 is a block diagram of an apparatus to generate a predictive analysis of vital signs.

FIG. 20 is a block diagram of an apparatus 2000 to generate a predictive analysis of vital signs, according to an implementation. The apparatus 2000 can be implemented on the multi-vital-signs finger cuff smartphone accessory (MVSFCSA) 402 in FIG. 4, the multi-vital-sign smartphone (MVS Smartphone) 404 in FIG. 4, the multi-vital-signs finger cuff smartphone accessory (MVSFCSA) 502 in FIG. 5 or the multi-vital-sign smartphone (MVS Smartphone) device 503 in FIG. 5, the sensor management component 602 in FIG. 6, the microprocessor 620 in FIG. 6, the multi-vital-sign finger cuff 506 in FIG. 5 and FIG. 7, the microprocessor 702 in FIG. 7, controller 820 in FIG. 8, the microprocessor 1702 in FIG. 17-19 and/or main processor 3202 in FIG. 32. In apparatus 2000, heartrate data 2002 (such as heartrate 3810 in FIG. 38), respiratory rate data 2004 (such as respiratory rate 3816 in FIG. 38), estimated body core temperature data 2006 (such as estimated body core temperature 1720 in FIG. 17 or estimated body core temperature 1812 in FIG. 189), blood pressure data 2008 (such as blood pressure 3822 in FIG. 38), EKG data 2010 (such as EKG 3828 in FIG. 38) and/or SpO2 data 2012 is received by a predictive analysis component 2014 that evaluates the data 2002, 2004, 2006, 2008, 2010 and/or 2012 in terms of percentage change over time. More specifically, the relative change and the rate of change or change in comparison to an established pattern that is described in terms of frequency and amplitude. When the percentage change over time exceeds a predetermined threshold, a flag 2016 is set to indicate an anomaly. The flag 2016 can be transmitted to the EMR/clinical data repository 144, as shown in FIG. 1-3.

4. Non-Touch Table-Based Temperature Correlation Thermometers

Figure 21:
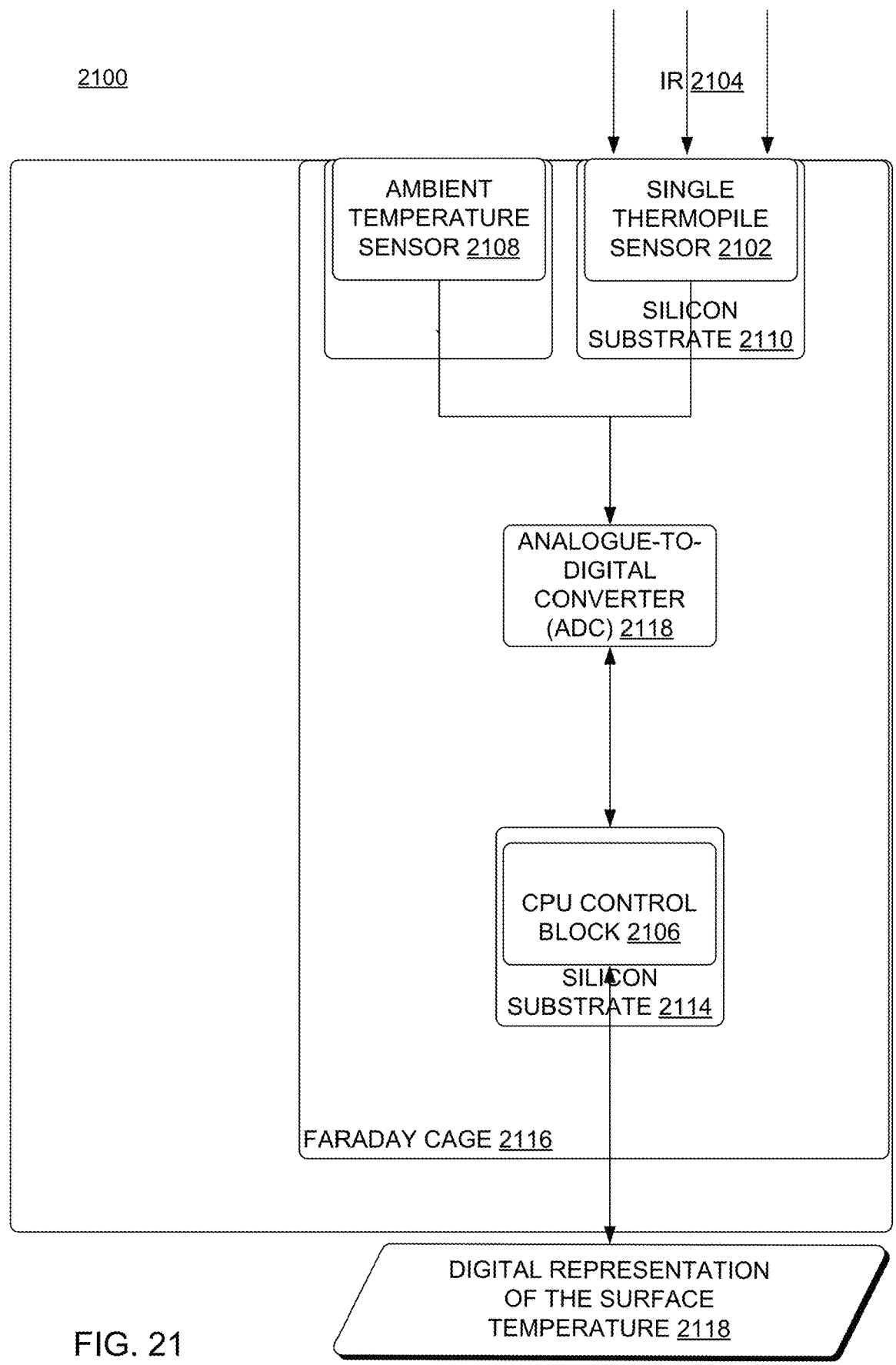
FIG. 21 is a block diagram of a digital infrared sensor, according to an implementation.

FIG. 21 is a block diagram of a digital infrared sensor 2100, according to an implementation. The digital infrared sensor 2100 contains a single thermopile sensor 2102 that senses only infrared electromagnetic energy 2104. The digital infrared sensor 2100 contains a CPU control block 2106 and an ambient temperature sensor 2108, such as a thermocouple. The single thermopile sensor 2102, the ambient temperature sensor 2108 and the CPU control block 2106 are on separate silicon substrates 2110, 2112 and 2114 respectively. The CPU control block 2106 digitizes the output of the single thermopile sensor 2102 and the ambient temperature sensor 2108.

The digital infrared sensor 2100 has a Faraday cage 2116 surrounding the single thermopile sensor 2102, the CPU control block 2106 and the ambient temperature sensor 2108 to prevent electromagnetic (EMF) interference in the single thermopile sensor 2102, the CPU control block 2106 and the ambient temperature sensor 2108 that shields the components in the Faraday cage 2116 from outside electromagnetic interference, which improves the accuracy and the repeatability of a device that estimates body core temperature from the ambient and object temperature generated by the digital infrared sensor 2100. The digital IR sensor 2100 also requires less calibration in the field after manufacturing, and possibly no calibration in the field after manufacturing because in the digital infrared sensor 2100, the single thermopile sensor 2102, the CPU control block 2106 and the ambient temperature sensor 2108 are in close proximity to each other, which lowers temperature differences between the single thermopile sensor 2102, the CPU control block 2106 and the ambient temperature sensor 2108, which minimizes or eliminates calibration drift over time because they are based on the same substrate material and exposed to the same temperature and voltage variations. In comparison, conventional infrared temperature sensors do not include a Faraday cage 2116 that surrounds the single thermopile sensor 2102, the CPU control block 2106 and the ambient temperature sensor 2108. The Faraday cage 2116 can be a metal box or a metal mesh box. In the implementation where the Faraday cage 2116 is a metal box, the metal box has an aperture where the single thermopile sensor 2102 is located so that the field of view of the infrared electromagnetic energy 2104 is not affected by the Faraday cage 2116 so that the infrared electromagnetic energy 2104 can pass through the Faraday cage 2116 to the single thermopile sensor 2102. In the implementation where the Faraday cage 2116 is a metal box, the metal box has an aperture where the ambient temperature sensor 2108 is located so that the atmosphere can pass through the Faraday cage 2116 to the ambient temperature sensor 2108. In other implementations the ambient air temperature sensor 2108 does not sense the temperature of the atmosphere, but instead senses the temperature of the sensor substrate (silicon) material and surrounding materials because the ambient temperature sensor 2108 and the target operating environment temperature are required to be as close as possible in order to reduce measurement error, i.e. the ambient temperature sensor 2108 is to be in thermal equilibrium with the target operating environment.

In some further implementations, the Faraday cage 2116 of the digital infrared sensor 2100 also includes an multichannel analogue-to-digital converter (ADC) 2118 that digitizes an analogue signal from the single thermopile sensor 2102. The ADC 2118 also digitizes an analogue signal from the ambient temperature sensor 2108. In another implementation where the ADC is not a multichannel ADC, separate ADCs are used to digitize the analogue signal from the single thermopile sensor 2102 and the analogue signal from the ambient temperature sensor 2108. There is no ADC between the digital infrared sensor 2100 and microprocessor(s), main processor(s) and controller(s) that are outside the digital IR sensor 2100, such as the microprocessor 1702 in FIG. 17.

The single thermopile sensor 2102 of the digital infrared sensor 2100 is tuned to be most sensitive and accurate to the human body core temperature range, such as forehead surface temperature range of 25° C. to 39° C. The benefits of the digital IR sensor 2100 in comparison to conventional analogue infrared temperature sensors include minimization of the temperature difference between the analogue and digital components effects on calibration parameters (when the temperature differences are close there is a smaller $\Delta T$ which mimics the calibration environment) and reduction of EMC interference in the datalines. The digital infrared sensor 2100 outputs a digital representation of the surface temperature in absolute Kelvin degrees (° K) that is presented at a digital readout port of the digital infrared sensor 2100. The digital representation of the surface temperature is also known as the body surface temperature in FIG. 5-8, digital readout signal 1711 in FIG. 17-19, digital signal that is representative of an infrared signal of a forehead temperature that is detected by the digital infrared sensor in FIG. 24, the body core temperature in FIG. 25, the temperature measurement in FIG. 26, the sensed forehead temperature in FIGS. 15, 17-18, 24 and 27 and the numerical representation of the electromagnetic energy of the external source point in FIG. 31.

The digital infrared sensor 2100 is not an analog device or component, such as a thermistor or a resistance temperature detector (RTD). Because the digital infrared sensor 2100 is not a thermistor, there is no need or usefulness in receiving a reference signal of a resister and then determining a relationship between the reference signal and a temperature signal to compute the surface temperature. Furthermore, the digital infrared sensor 2100 is not an array of multiple transistors as in complementary metal oxide (CMOS) devices or charged coupled (CCD) devices. None of the subcomponents in the digital infrared sensor 2100 detect electromagnetic energy in wavelengths of the human visible spectrum (380 nm-750 nm). Neither does the digital infrared sensor 2100 include an infrared lens.

5. Interoperability Device Manager Component of an EMR System

Figure 22:
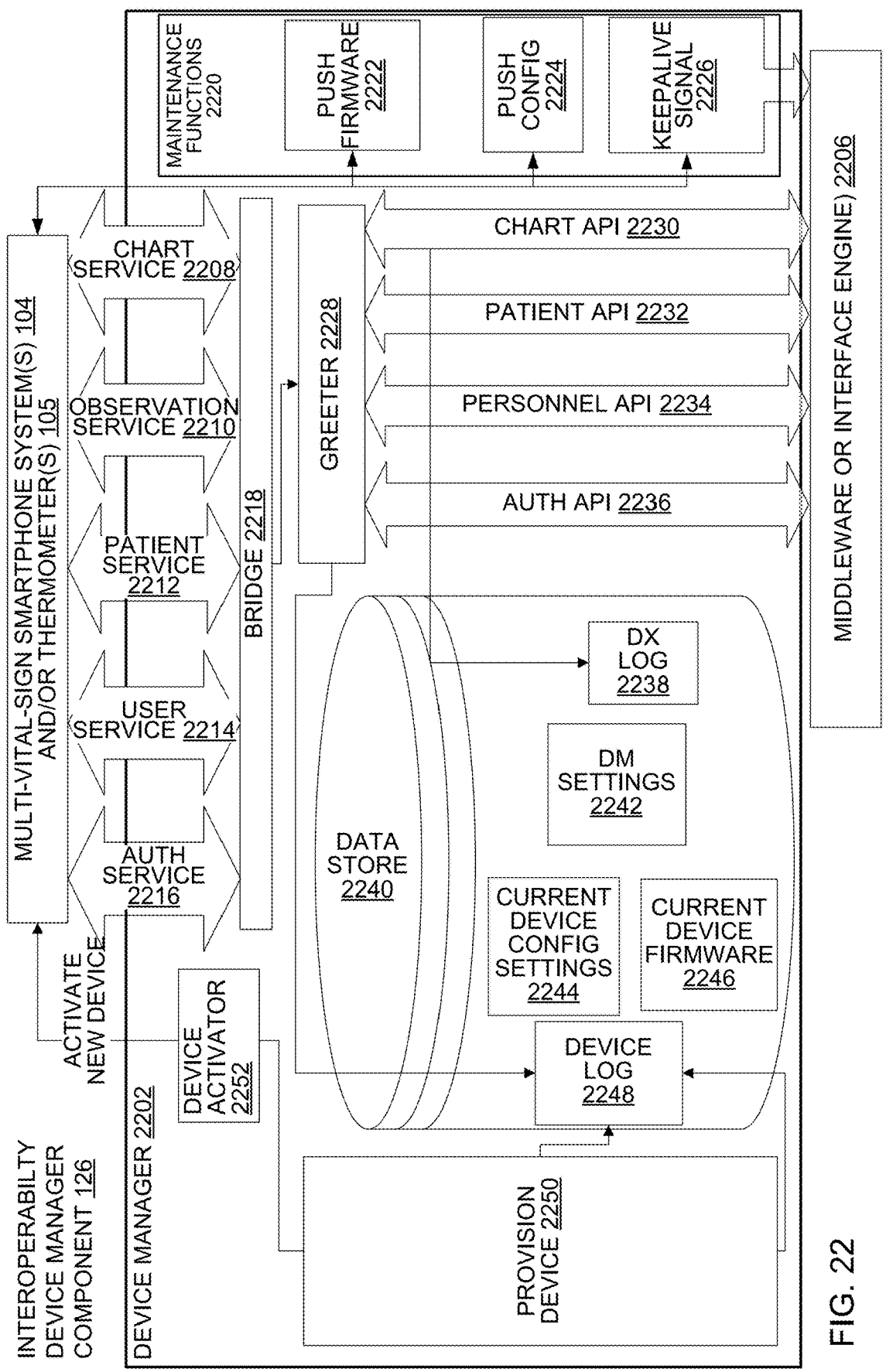
FIG. 22 is a block diagram of a system of interoperation device manager.

FIG. 22 is a block diagram of a system of interoperability device manager component 126, according to an implementation. The interoperability device manager component 126 includes a device manager 2202 that connects one or more multi-vital-sign smartphone system(s) 104 and middleware 2206. The multi-vital-sign smartphone system(s) 104 are connected to the device manager 2202 through via a plurality of services, such as a chart service 2208, an observation service 2210, a patient service 2212, a user service and/or an authentication service 2216 to a bridge 2218 in the interoperability device manager 2202. The multi-vital-sign smartphone system(s) 104 are connected to the device manager 2202 to a plurality of maintenance function components 2220, such as push firmware 2222, a push configuration component 2224 and/or a keepalive signal component 2226. The keepalive signal component 2226 is coupled to the middleware 2206. In some implementations, the APIs 2230, 2232, 2234 and 2236 are health date APIs, observation APIs, electronic health record (EHR) or electronic medical record (EMR) APIs.

The bridge 2218 is operably coupled to a greeter component 2228. The greeter component 2228 synchronizes date/time of the interoperability device manager 2202, checks device log, checks device firmware, checks device configuration and performs additional security. The greeter component 2228 is coupled to the keepalive signal component 2226 through a chart application program interface component 2230, a patient application program interface component 2232, a personnel application program interface component 2234 and/or and authentication application program interface component 2236. All charted observations from the chart application program interface component 2230 are stored in a diagnostics log 2238 of a datastore 2240. The datastore 2240 also includes interoperability device manager settings 2242 for the application program interface components 2230, 2232, 2234 and/or 2236, current device configuration settings 2244, current device firmware 2246 and a device log 2248.

The interoperability device manager 2202 also includes a provision device component 2250 that provides network/WiFi® Access, date/time stamps, encryption keys—once for each of the multi-vital-sign smartphone system(s) 104 for which each multi-vital-sign smartphone system(s) 104 is registered and marked as 'active' in the device log 2248. The provision device component 2250 activates each new multi-vital-sign smartphone system(s) 104 on the interoperability device manager component 126 through a device activator 2252.

6. Methods of Multi-Vital-Sign Smartphone Systems Having an Infrared Sensor

In this section, the particular methods performed by FIG. 17-19 are described by reference to a series of flowcharts.

Figure 23:
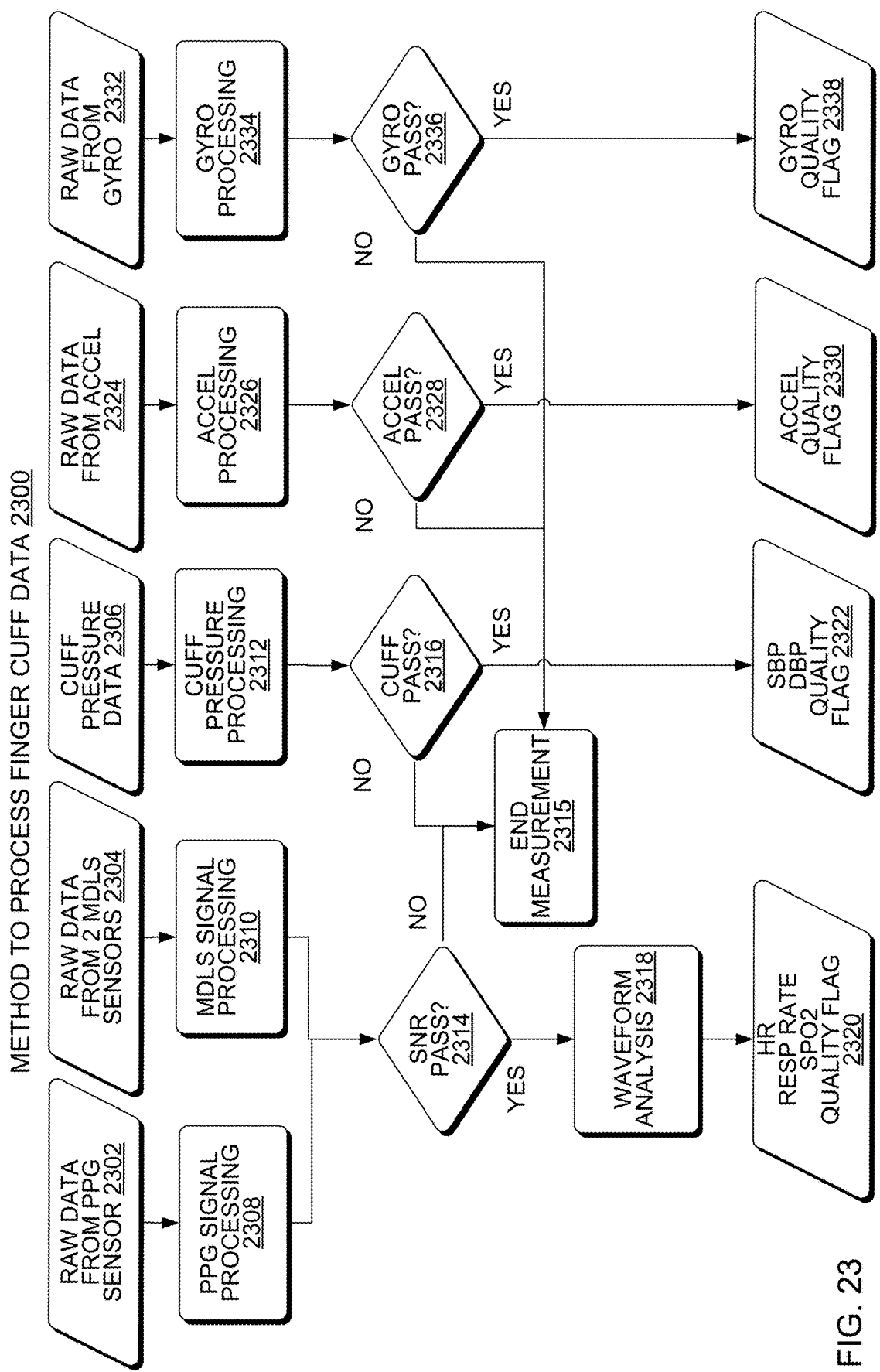
FIG. 23 is a flowchart of a method to perform real time quality check on finger cuff data.

FIG. 23 is a flowchart of a method 2300 to perform real time quality check on finger cuff data, according to an implementation. The method 2300 uses signals from PPG and mDLS sensors to perform quality check. The method 2300 can be performed by the multi-vital-signs finger cuff smartphone accessory (MVSFCSA) 402 in FIG. 4, the MVSFCSA 502 in FIG. 5, the sensor management component 602 in FIG. 6, the microprocessor 620 in FIG. 6, the multi-vital-sign finger cuff 506 in FIG. 5 and FIG. 7, the microprocessor 702 in FIG. 7, controller 820 in FIG. 8, the microprocessor 1702 in FIG. 17-19 and/or main processor 3202 in FIG. 32.

In method 2300, raw data 2302 is received from a PPG sensor, such as PPG sensor in the multi-vital-sign finger cuff 506 in FIG. 5-7, 842 in FIG. 8 and/or 1744 in FIG. 17-19, raw data 2304 is received from two mDLS sensors, such as mDLS sensor in the multi-vital-sign finger cuff 506 in FIG. 5-7, 844 in FIG. 8, and/or 1742 in FIG. 17-19, raw data 2306 is received from pressure cuff, such as multi-vital-sign finger cuff 406 in FIG. 4, pneumatic engine 507 in FIG. 5-7, cuff 850 in FIG. 8, the pressure sensor 908 in FIG. 9, and/or the pressure sensor 1738 in FIG. 17-19, raw data 2324 is received from an accelerometer and raw data 2332 is received from a three-axis gyroscope. The raw data 2306 received from the pressure cuff can be received from the pneumatic pressure sensor 908 in FIG. 9.

The raw data 2302 that is received from the PPG sensor is analyzed in PPG signal processing 2308, the raw data 2304 that is received from the mDLS sensors is analyzed in mDLS signal processing 2310, the raw data 2306 that is received from the pressure cuff is analyzed in cuff pressure processing 2312, the raw data 2324 that is received from the accelerometer is analyzed in accelerometer processing 2326 and the raw data 2332 that is received from the three axis gyroscope is analyzed in gyroscope processing 2334. If the analysis in the PPG signal processing 2308 and the mDLS signal processing 2310 indicates a poor signal-to-noise ratio 2314 in the raw data 2302 that is received from the PPG sensor or the raw data 2304 that is received from the mDLS sensors, the measurement is ended 2315. If the analysis in the PPG signal processing 2308 and the mDLS signal processing 2310 indicates a good signal-to-noise ratio 2314 in both the raw data 2302 that is received from the PPG sensor and the raw data 2304 that is received from the mDLS sensors, then a waveform analysis 2318 is performed on both the raw data 2302 that is received from the PPG sensor and the raw data 2304 that is received from the mDLS sensors. If the analysis in the cuff pressure processing 2312 indicates the bladder of the finger occlusion cuff can not be inflated to a required pressure or that the required amount of pressure can not be maintained in the bladder of the multi-vital-sign finger cuff 2316 then the measurement is ended 2315. If the analysis in the accelerometer processing 2326 indicates unreliable data from the accelerometer, then the measurement is ended 2315. If the analysis in the three axis gyroscope processing 2334 indicates unreliable data from the three axis gyroscope, then the measurement is ended 2315.

From the waveform analysis 2318 that is performed on both the raw data 2302 that is received from the PPG sensor and the raw data 2304 that is received from the mDLS sensors, flags indicating that status of heartrate, respiratory rate and/or are generated 2320. From the cuff pressure processing 2312, flags indicating the blood pressure (diastolic and systolic) are generated 2322. From the accelerometer processing 2326, flags indicating the quality of the accelerometer data 2324 are generated 2330. From the three axis gyroscope processing 2334, flags indicating the quality of the three axis gyroscope data 2332 are generated 2338.

Figure 24:
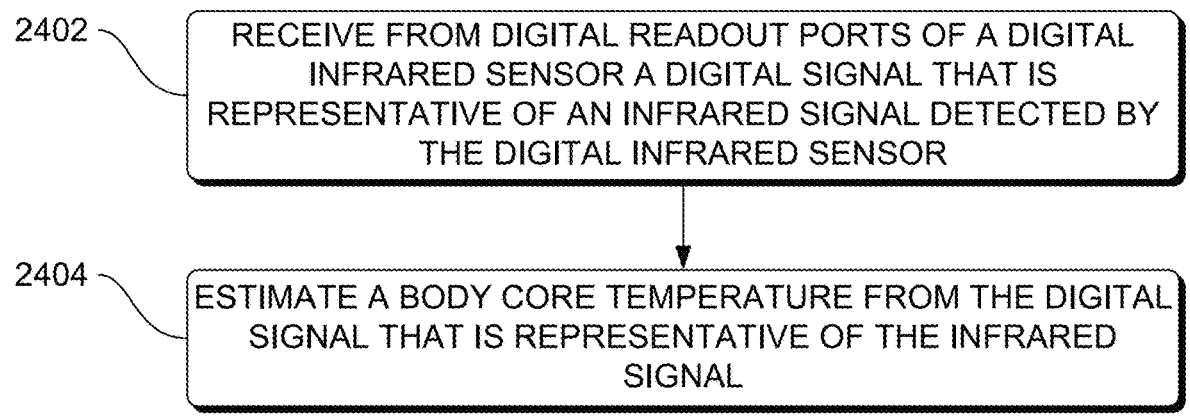
FIG. 24 is a flowchart of a method to estimate a body core temperature from a digital infrared sensor.

FIG. 24 is a flowchart of a method 2400 to estimate a body core temperature from a digital infrared sensor, according to an implementation. Method 2400 includes receiving from the digital readout ports of a digital infrared sensor a digital signal that is representative of an infrared signal of a forehead temperature that is detected by the digital infrared sensor, at block 2402. No signal that is representative of the infrared signal is received from an analog infrared sensor.

Method 2400 also includes estimating a body core temperature from the digital signal that is representative of the infrared signal, at block 2404.

Figure 25:
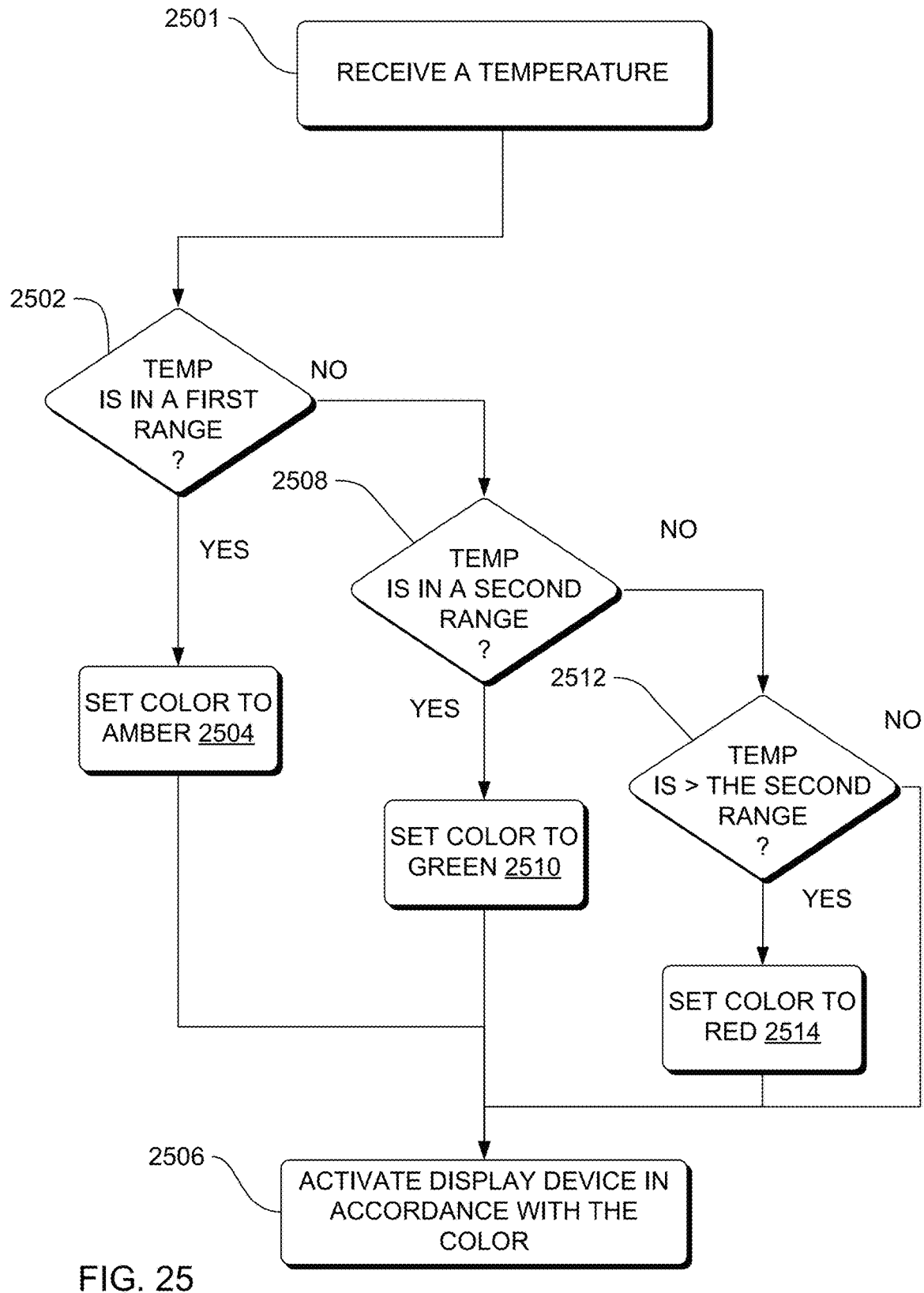
FIG. 25 is a flowchart of a method to display body core temperature color indicators, according to an implementation of three colors.

FIG. 25 is a flowchart of a method 2500 to display body core temperature color indicators, according to an implementation of three colors. Method 2500 provides color rendering to indicate a general range of a body core temperature.

Method 2500 includes receiving the body core temperature (such as digital readout signal 1711 that is representative of the infrared signal 1716 of the forehead in FIG. 17), at block 2501.

Method 2500 also includes determining whether or not the body core temperature is in a first range, such as a range of 32.0° C. and 37.3° C., at block 2502. If the body core temperature is in the first range, then the color is set to 'amber' to indicate a body core temperature that is low, at block 2504 and a lighting emitting diode (LED) or the background of the display is activated in accordance with the color, at block 2506.

If the body core temperature is not the first range, then method 2500 also includes determining whether or not the body core temperature is in a second range that is immediately adjacent and higher than the first range, such as a range of 37.4° C. and 38.0° C., at block 2508. If the body core temperature is in the second range, then the color is set to green to indicate no medical concern, at block 2510 and the LED or the background of the display is activated in accordance with the color, at block 2506.

If the body core temperature is not the second range, then method 2500 also includes determining whether or not the body core temperature is over the second range, at block 2512. If the body core temperature is over the second range, then the color is set to 'red' to indicate alert, at block 2512 and the LED or the background is activated in accordance with the color, at block 2506.

Method 2500 assumes that body core temperature is in gradients of 10ths of a degree. Other body core temperature range boundaries are used in accordance with other gradients of body core temperature sensing.

In some implementations, some pixels in the LED or the display are activated as an amber color when the body core temperature is between a first range of 36.3° C. and 37.3° C. (97.3° F. to 99.1° F.), some pixels in the display are activated as a green when the body core temperature is between a second range of 37.4° C. and 37.9° C. (99.3° F. to 100.2° F.), the LED or some pixels in the display are activated as a red color when the body core temperature is greater than the second range (a least 38° C. (100.4° F.)).

Figure 26:
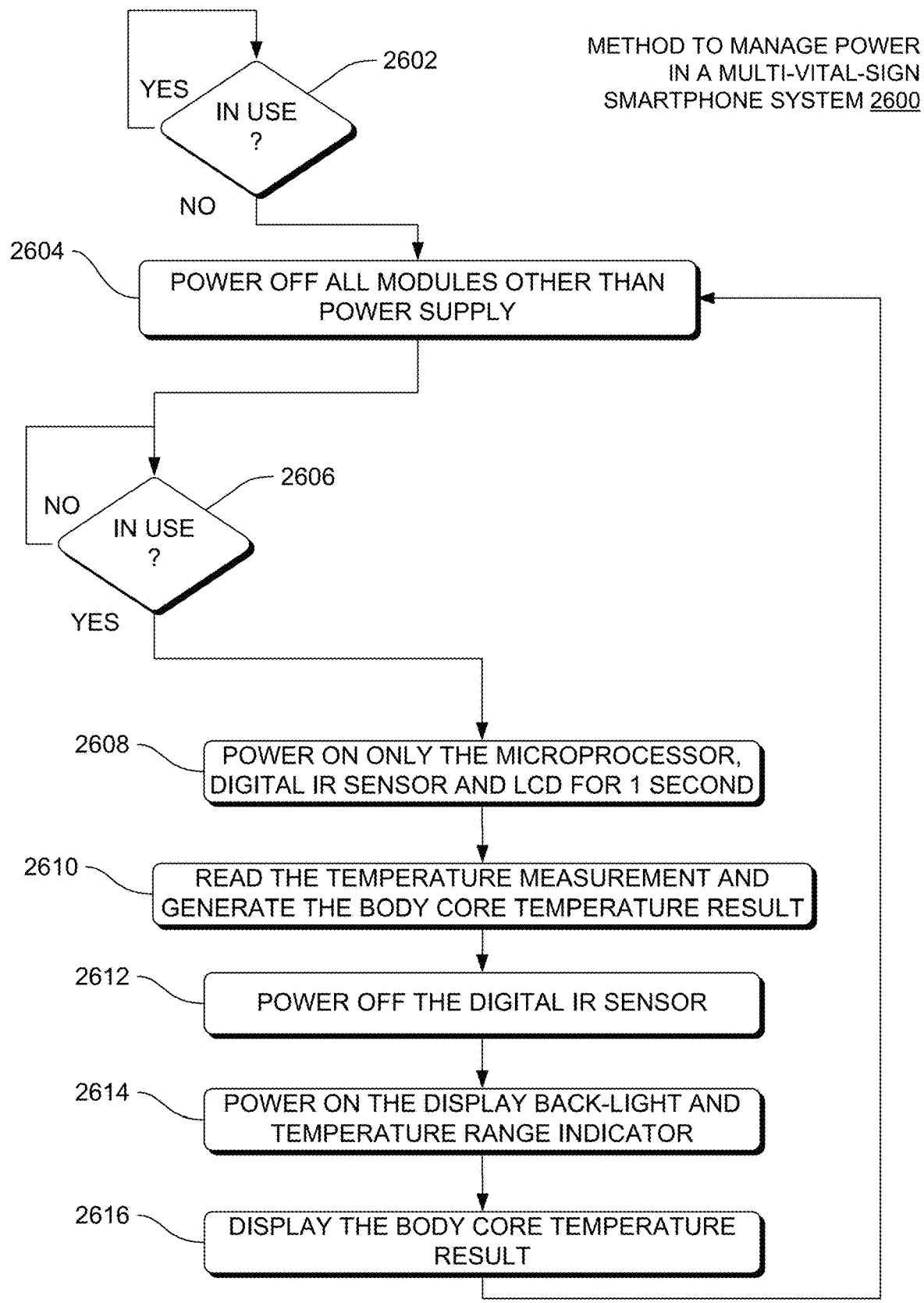
FIG. 26 is a flowchart of a method to manage power in a multi-vital-sign smartphone system having a digital infrared sensor.

FIG. 26 is a flowchart of a method 2600 to manage power in a non-touch device having a digital infrared sensor, according to an implementation. The method 2600 manages power in the device, such as multi-vital-sign smartphone systems and multi-vital-sign smartphone systems in FIGS. 4-8 and 17-19 and FIG. 32, in order to reduce heat pollution in the digital infrared sensor.

Figure 32:
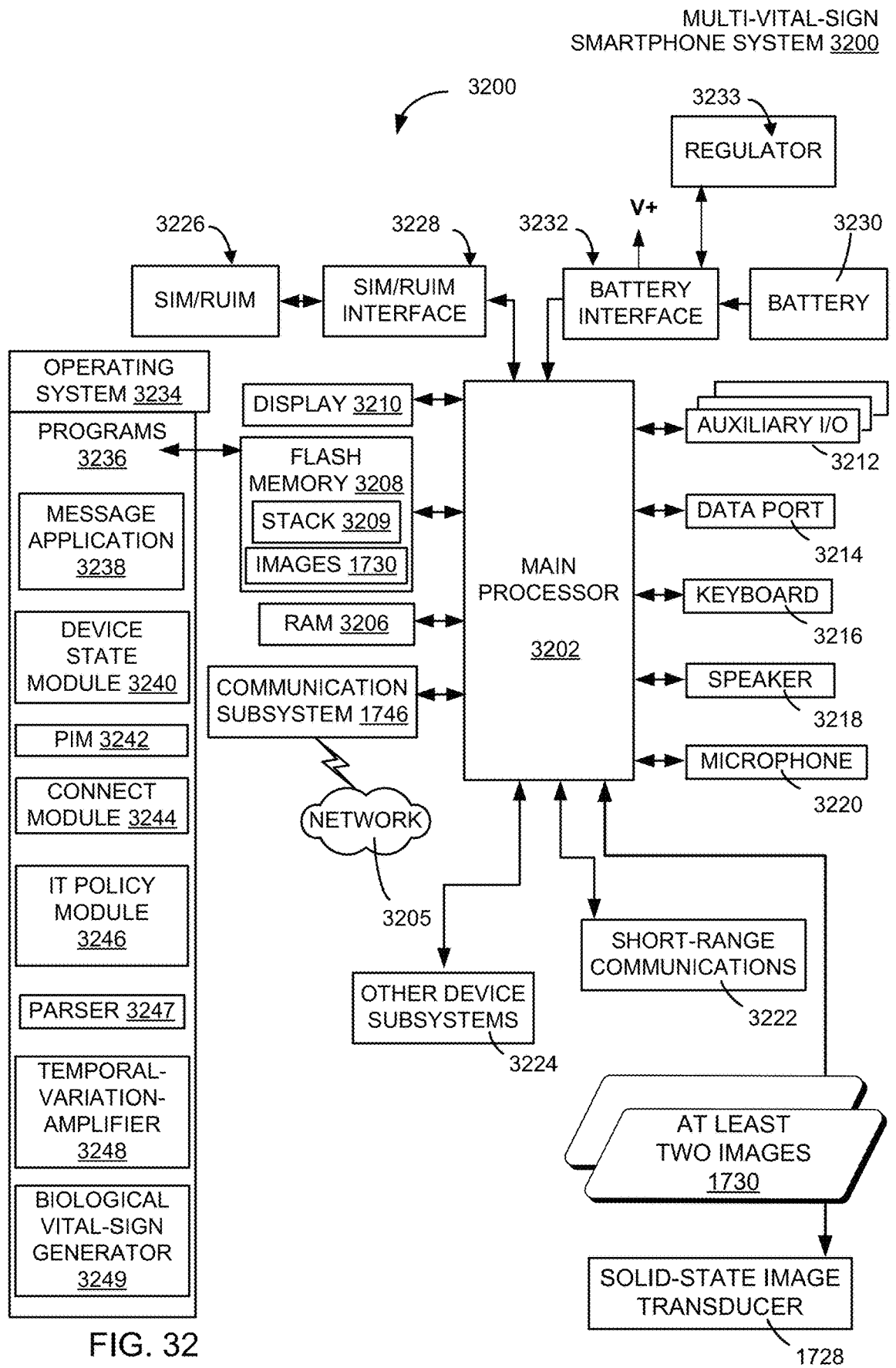
FIG. 32 is a block diagram of a multi-vital-sign smartphone system.

To prevent or at least reduce heat transfer between the digital infrared sensor 1708 and the microprocessor 1702, main processor 3202 in FIG. 32, the components of the multi-vital-sign smartphone systems in FIG. 17-19, the apparatus that estimates a body core temperature in FIG. 17-18 and the multi-vital-sign smartphone system 3200 are power controlled, i.e. sub-systems are turned on and off, and the sub-systems are only activated when needed in the measurement and display process, which reduces power consumption and thus heat generation by the microprocessor 1702, or main processor 3202 in FIG. 32, of the multi-vital-sign smartphone systems in FIG. 17-18, the apparatus that estimates a body core temperature in FIG. 18-19, the multi-vital-sign smartphone system 3200, respectively. When not in use, at block 2602, the multi-vital-sign smartphone systems in FIG. 17-19, the apparatus that estimates a body core temperature in FIG. 17-18 and the multi-vital-sign smartphone system 3200 are completely powered-off, at block 2604 (including the main PCB having the microprocessor 1702, main processor 3202 in FIG. 32 and the sensor PCB having the digital infrared sensor 1708) and not drawing any power, other than a power supply, i.e. a boost regulator, which has the effect that the multi-vital-sign smartphone systems in FIG. 3-16, the apparatus that estimates a body core temperature in FIG. 17-18 and the multi-vital-sign smartphone system 3200 draw only micro-amps from the battery 1704 while in the off state, which is required for the life time requirement of 3 years of operation, but which also means that in the non-use state there is very little powered circuitry in the multi-vital-sign smartphone systems in FIG. 17-18 and the multi-vital-sign smartphone system 3200 and therefore very little heat generated in the multi-vital-sign smartphone systems in FIG. 17-18 and the multi-vital-sign smartphone system 3200.

When the multi-vital-sign smartphone systems in FIG. 17-18, the apparatus that estimates a body core temperature in FIG. 17-19 and the multi-vital-sign smartphone system 3200 are started by the operator, at block 2606, only the microprocessor 1702, microprocessor 1702, main processor 3202. In FIG. 32, main processor 3202 in FIG. 32, digital infrared sensor 1708, and in some implementations low power LCD (e.g. display device 1714) are turned on for the first 1 second, at block 2608, to take the temperature measurement via the digital infrared sensor 1708 and generate the body core temperature result via the microprocessor 1702 in FIG. 17-18, main processor 3202 in FIG. 32, at block 2610. In this way, the main heat generating components (the display device 1714, the main PCB having the microprocessor 1702 and the sensor PCB having the digital infrared sensor 1708), the display back-light and the body core temperature traffic light) are not on and therefore not generating heat during the critical start-up and measurement process, no more than 1 second. After the measurement process of block 2610 has been completed, the digital infrared sensor 1708 is turned off, at block 2612, to reduce current usage from the batteries and heat generation, and also the display back-light and temperature range indicators are turned on, at block 2614.

The measurement result is displayed for 4 seconds, at block 2616, and then the multi-vital-sign smartphone systems in FIG. 17-19, the apparatus that estimates a body core temperature in FIG. 17-18 and the multi-vital-sign smartphone system 3200 are put in low power-off state, at block 2618.

In some implementations of methods and apparatus of FIG. 17-32 an operator can take the temperature of a subject and from the temperatures to estimate the temperature at a number of other locations of the subject.

The correlation of action can include a calculation based on Formula 1:

$$T_{body} = |f_{stb}(T_{surface\ temp} + f_{ntc}(T_{ntc})) + F4_{body}| \qquad \text{Formula 1}$$

where $T_{body}$ is the temperature of a body or subject where $f_{stb}$ is a mathematical formula of a surface of a body where $f_{ntc}$ is mathematical formula for ambient temperature reading where $T_{surface\ temp}$ is a surface temperature estimated from the sensing.

where $T_{ntc}$ is an ambient air temperature reading where $F4_{body}$ is a calibration difference in axillary mode, which is stored or set in a memory of the apparatus either during manufacturing or in the field. The apparatus also sets, stores and retrieves $F4_{oral}$, $F4_{core}$, and $F4_{rectal}$ in the memory.

$f_{ntc}(T_{ntc})$ is a bias in consideration of the temperature sensing mode. For example $f_{axillary}(T_{axillary})=0.2°$ C., $f_{oral}(T_{oral})=0.4°$ C., $f_{rectal}(T_{rectal})=0.5°$ C. and $f_{core}(T_{core})=0.3°$ C.

Figure 29:
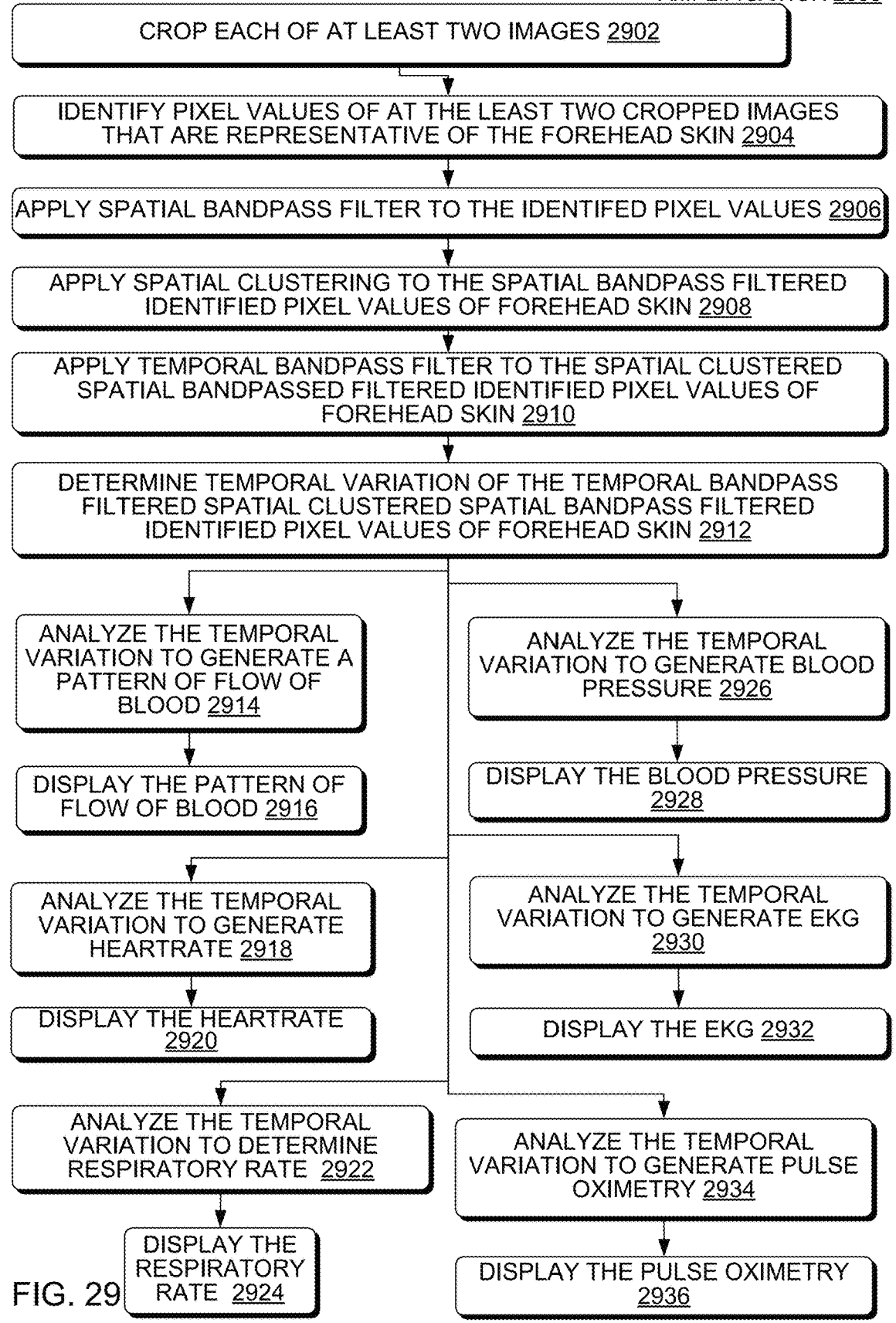
FIG. 29 is a flowchart of a method of variation amplification from which to generate and communicate biological vital signs.

In some implementations the method in FIG. 29 is implemented on the multi-vital-sign smartphone system 3200 in FIG. 32.

8. Biological Vital Sign Amplification Methods

FIG. 29 uses spatial and temporal signal processing to generate biological vital signs from a series of digital images.

FIG. 29 is a flowchart of a method 4700 of variation amplification from which to generate and communicate biological vital signs, according to an implementation. Method 4700 analyzes the temporal and spatial variations in digital images of an animal subject in order to generate and communicate the biological vital signs.

In some implementations, method 4700 includes cropping plurality of images to exclude areas that do not include a skin region, at block 4702. For example, the excluded area can be a perimeter area around the center of each image, so that an outside border area of the image is excluded. In some implementations of cropping out the border, about 72% of the width and about 72% of the height of each image is cropped out, leaving only 7.8% of the original uncropped image, which eliminates about $^{11}/_{12}$ of each image and reduces the amount of processing time for the remainder of the actions in this process by about 12-fold. This one action alone at block 4702 in method 4700 can reduce the processing time of the plurality of images 1730 in comparison to method 4400 from 4 minutes to 32 seconds, which is of significant difference to the health workers who used devices that implement method 4700. In some implementations, the remaining area of the image after cropping in a square area and in other implementation the remaining area after cropping is a circular area. Depending upon the topography and shape of the area in the images that has the most pertinent portion of the imaged subject, different geometries and sizes are most beneficial.

In some implementations, method 4700 includes identifying pixel-values of the plurality of or more cropped images that are representative of the skin, at block 4704. Some implementations of identifying pixel-values that are representative of the skin include performing an automatic seed point based clustering process on the least two images.

In some implementations, method 4700 includes applying a spatial bandpass filter to the identified pixel-values, at block 4402. In some implementations, the spatial filter in block 4706 is a two-dimensional spatial Fourier Transform, a high pass filter, a low pass filter, a bandpass filter or a weighted bandpass filter.

In some implementations, method 4700 includes applying spatial clustering to the spatial bandpass filtered identified pixel-values of skin, at block 4708. In some implementations the spatial clustering includes fuzzy clustering, k-means clustering, expectation-maximization process, Ward's method or seed point based clustering.

In some implementations, method 4700 includes applying a temporal bandpass filter to the spatial clustered spatial bandpass filtered identified pixel-values of skin, at block 4710. In some implementations, the temporal bandpass filter in block 4710 is a one-dimensional spatial Fourier Transform, a high pass filter, a low pass filter, a bandpass filter or a weighted bandpass filter.

In some implementations, method 4700 includes determining temporal variation of the temporal bandpass filtered spatial clustered spatial bandpass filtered identified pixel-values of skin, at block 4712.

In some implementations, method 4700 includes analyzing the temporal variation to generate and visually display a pattern of flow of blood, at block 4714. In some implementations, the pattern flow of blood is generated from motion changes in the pixels and the temporal variation of color changes in the skin. In some implementations, method 4700 includes displaying the pattern of flow of blood for review by a healthcare worker, at block 4716.

In some implementations, method 4700 includes analyzing the temporal variation to generate heartrate, at block 4718. In some implementations, the heartrate is generated from the frequency spectrum of the temporal variation in a frequency range for heart beats, such as (0-10 Hertz). In some implementations, method 4700 includes displaying the heartrate for review by a healthcare worker, at block 4720.

In some implementations, method 4700 includes analyzing the temporal variation to determine respiratory rate, at block 4722. In some implementations, the respiratory rate is generated from the motion of the pixels in a frequency range for respiration (0-5 Hertz). In some implementations, method 4700 includes displaying the respiratory rate for review by a healthcare worker, at block 4724.

In some implementations, method 4700 includes analyzing the temporal variation to generate blood pressure, at block 4726. In some implementations, the blood pressure is generated by analyzing the motion of the pixels and the color changes based on the clustering process and potentially temporal data from the infrared sensor. In some implementations, method 4700 includes displaying the blood pressure for review by a healthcare worker, at block 4728.

In some implementations, method 4700 includes analyzing the temporal variation to generate EKG, at block 4730. In some implementations, method 4700 includes displaying the EKG for review by a healthcare worker, at block 4732.

In some implementations, method 4700 includes analyzing the temporal variation to generate pulse oximetry, at block 4734. In some implementations, the pulse oximetry is generated by analyzing the temporal color changes based in conjunction with the k-means clustering process and potentially temporal data from the infrared sensor. In some implementations, method 4700 includes displaying the pulse oximetry for review by a healthcare worker, at block 4736.

9. Non-Touch Body Core Temperature Correlation Table Methods

Figure 30:
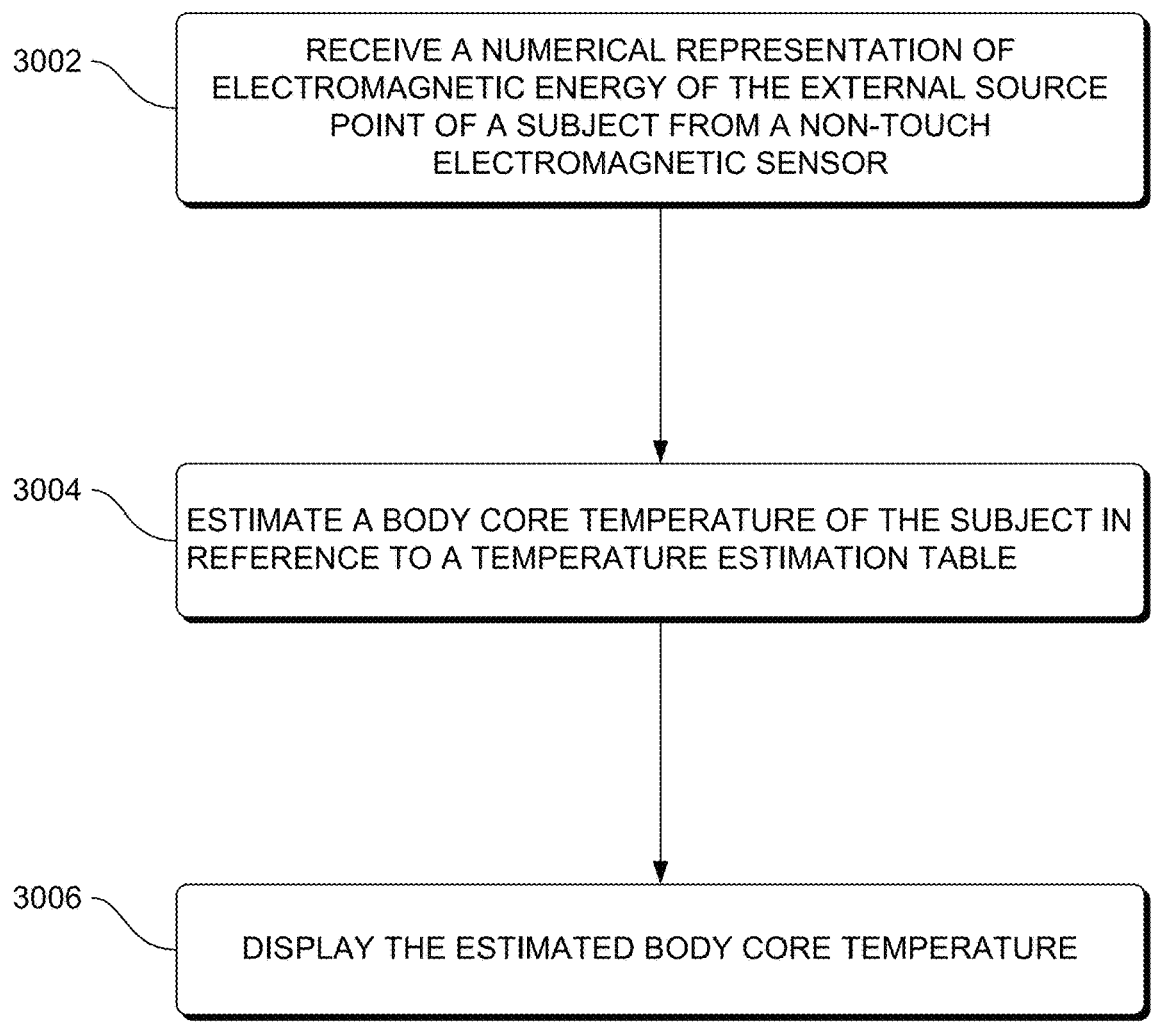
FIG. 30 is a flowchart of a method to estimate a body core temperature from an external source point in reference to a body core temperature correlation table.

FIG. 30 is a flowchart of a method 3000 to estimate a body core temperature from an external source point in reference to a body core temperature correlation table, according to an implementation.

Method 3000 includes receiving from a non-touch electromagnetic sensor a numerical representation of electromagnetic energy of the external source point of a subject, at block 3002.

Method 3000 also includes estimating the body core temperature of the subject from the numerical representation of the electromagnetic energy of the external source point, a representation of an ambient air temperature reading, a representation of a calibration difference, and a representation of a bias in consideration of the temperature sensing mode, at block 3004. The estimating at block 3004 is based on a body core temperature correlation table representing the body core temperature and the numerical representation of the electromagnetic energy of the external source point.

A body core temperature correlation table provides best results because a linear or a quadratic relationship provides inaccurate estimates of body core temperature, yet a quartic relationship, a quintic relationship, sextic relationship, a septic relationship or an octic relationship provide estimates along a highly irregular curve that is far too wavy or twisting with relatively sharp deviations.

Method 3000 also includes displaying the body core temperature, at block 3006.

Figure 31:
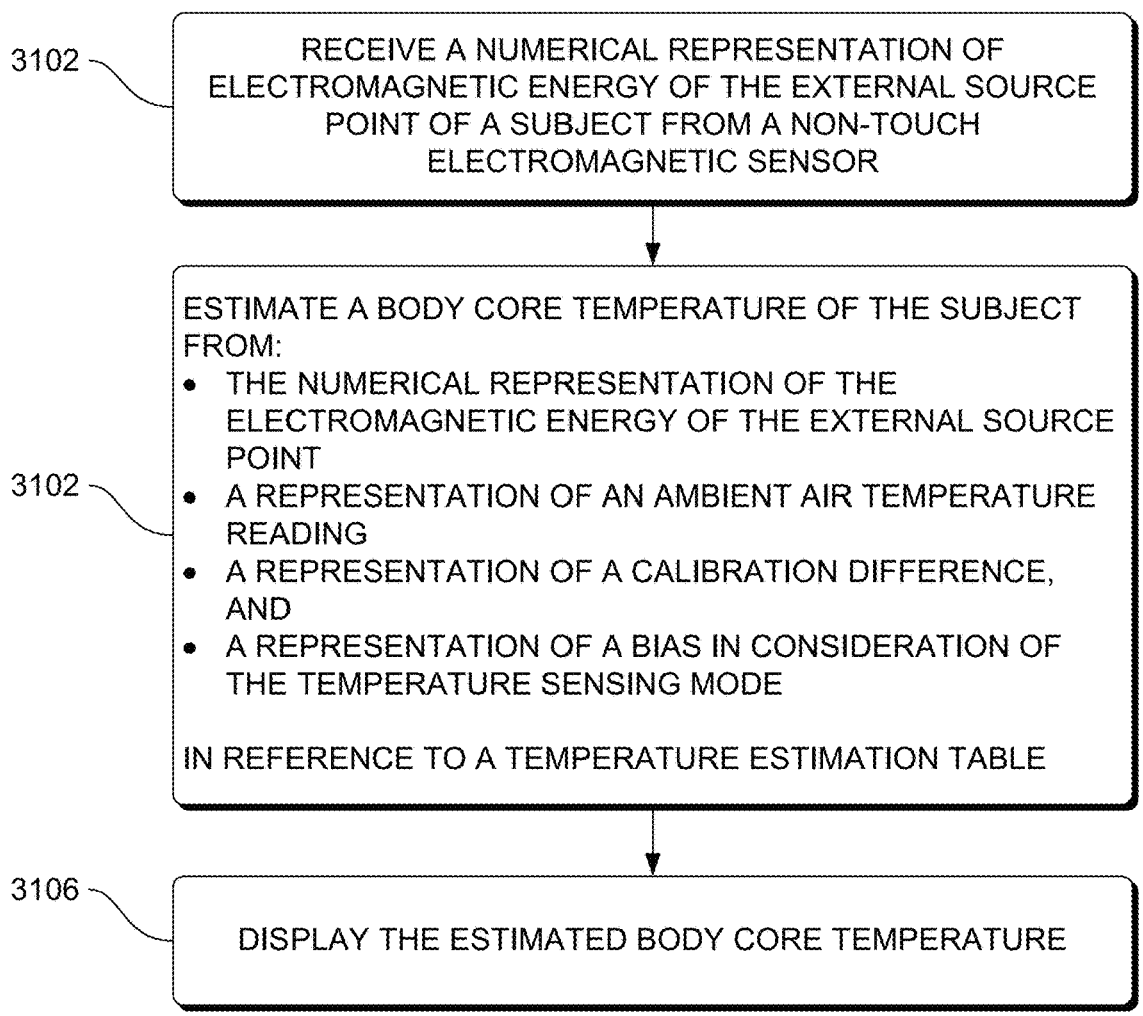
FIG. 31 is a flowchart of a method to estimate a body core temperature from an external source point and other measurements in reference to a body core temperature correlation table.

FIG. 31 is a flowchart of a method 3100 to estimate a body core temperature from an external source point and other measurements in reference to a body core temperature correlation table, according to an implementation. Method 3100 includes receiving from a non-touch electromagnetic sensor a numerical representation of electromagnetic energy of the external source point of a subject, at block 3002.

Method 3100 also includes estimating the body core temperature of the subject from the numerical representation of the electromagnetic energy of the external source point, a representation of an ambient air temperature reading, a representation of a calibration difference, and a representation of a bias in consideration of the temperature sensing mode, at block 3102. The estimating at block 3104 is based on a body core temperature correlation table representing three thermal ranges between the body core temperature and the numerical representation of the electromagnetic energy of the external source point.

Method 3100 also includes displaying the body core temperature, at block 3006.

In some implementations, methods 2900-3100 are implemented as a sequence of instructions which, when executed by a microprocessor 1702 in FIG. 17-19, main processor 3202 in FIG. 32, cause the processor to perform the respective method. In other implementations, methods 2900-3100 are implemented as a computer-accessible medium having computer executable instructions capable of directing a microprocessor, such as microprocessor 1702 in FIG. 17-19 or main processor 3202 in FIG. 32, to perform the respective method. In different implementations, the medium is a magnetic medium, an electronic medium, or an optical medium.

Hardware and Operating Environments

FIG. 32 is a block diagram of a multi-vital-sign smartphone system 3200, according to an implementation. The multi-vital-sign smartphone system 3200 includes a number of modules such as a main processor 3202 that controls the overall operation of the multi-vital-sign smartphone system 3200. Communication functions, including data and voice communications, can be performed through a communication subsystem 1746. The communication subsystem 1746 receives messages from and sends messages to wireless networks 3205. In other implementations of the multi-vital-sign smartphone system 3200, the communication subsystem 1746 can be configured in accordance with the Global System for Mobile Communication (GSM), General Packet Radio Services (GPRS), Enhanced Data GSM Environment (EDGE), Universal Mobile Telecommunications Service (UMTS), data-centric wireless networks, voice-centric wireless networks, and dual-mode networks that can support both voice and data communications over the same physical base stations. Combined dual-mode networks include, but are not limited to, Code Division Multiple Access (CDMA) or CDMA2000 networks, GSM/GPRS networks (as mentioned above), and future third-generation (3G) networks like EDGE and UMTS. Some other examples of data-centric networks include Mobitex™ and DataTAC™ network communication systems. Examples of other voice-centric data networks include Personal Communication Systems (PCS) networks like GSM and Time Division Multiple Access (TDMA) systems.

The wireless link connecting the communication subsystem 1746 with the wireless network 3205 represents one or more different Radio Frequency (RF) channels. With newer network protocols, these channels are capable of supporting both circuit switched voice communications and packet switched data communications.

The main processor 3202 also interacts with additional subsystems such as a Random Access Memory (RAM) 3206, a flash memory 3208, a display 3210, an auxiliary input/output (I/O) subsystem 3212, a data port 3214, a keyboard 3216, a speaker 3218, a microphone 3220, short-range communications subsystem 3222 and other device subsystems 3224. The other device subsystems 3224 can include any one of the micro dynamic light scattering (mDLS) sensor 1742 and/or the photoplethysmogram (PPG) sensor 1744 that provide signals to the biological vital sign generator 3249. In some implementations, the flash memory 3208 includes a hybrid femtocell/WiFi® protocol stack 3209. The hybrid femtocell/WiFi® protocol stack 3209 supports authentication and authorization between the multi-vital-sign smartphone system 3200 into a shared WiFi® network and both a 3G, 4G or 5G mobile networks.

Some of the subsystems of the multi-vital-sign smartphone system 3200 perform communication-related functions, whereas other subsystems may provide "resident" or on-device functions. By way of example, the display 3210 and the keyboard 3216 may be used for both communication-related functions, such as entering a text message for transmission over the wireless network 3205, and device-resident functions such as a calculator or task list.

The multi-vital-sign smartphone system 3200 can transmit and receive communication signals over the wireless network 3205 after required network registration or activation procedures have been completed. Network access is associated with a subscriber or user of the multi-vital-sign smartphone system 3200. To identify a subscriber, the multi-vital-sign smartphone system 3200 requires a SIM card/RUIM 3226 (i.e. Subscriber Identity Module or a Removable User Identity Module) to be inserted into a SIM/RUIM interface 3228 in order to communicate with a network. The SIM card/RUIM or 3226 is one type of a conventional "smart card" that can be used to identify a subscriber of the multi-vital-sign smartphone system 3200 and to personalize the multi-vital-sign smartphone system 3200, among other things. Without the SIM card/RUIM 3226, the multi-vital-sign smartphone system 3200 is not fully operational for communication with the wireless network 3205. By inserting the SIM card/RUIM 3226 into the SIM/RUIM interface 3228, a subscriber can access all subscribed services. Services may include: web browsing and messaging such as e-mail, voice mail, Short Message Service (SMS), and Multimedia Messaging Services (MMS). More advanced services may include: point of sale, field service and sales force automation. The SIM card/RUIM 3226 includes a processor and memory for storing information. Once the SIM card/RUIM 3226 is inserted into the SIM/RUIM interface 3228, the SIM is coupled to the main processor 3202. In order to identify the subscriber, the SIM card/RUIM 3226 can include some user parameters such as an International Mobile Subscriber Identity (IMSI). An advantage of using the SIM card/RUIM 3226 is that a subscriber is not necessarily bound by any single physical mobile device. The SIM card/RUIM 3226 may store additional subscriber information for the multi-vital-sign smartphone system 3200 as well, including datebook (or calendar) information and recent call information. Alternatively, user identification information can also be programmed into the flash memory 3208.

The multi-vital-sign smartphone system 3200 is a battery-powered device and includes a battery interface 3232 for receiving one or more batteries 3230. In one or more implementations, the battery 3230 can be a smart battery with an embedded microprocessor. The battery interface 3232 is coupled to a regulator 3233, which assists the battery 3230 in providing power V+ to the multi-vital-sign smartphone system 3200. Although current technology makes use of a battery, future technologies such as micro fuel cells may provide the power to the multi-vital-sign smartphone system 3200.

The multi-vital-sign smartphone system 3200 also includes an operating system 3234 and modules 3236 to 3249 which are described in more detail below. The operating system 3234 and the modules 3236 to 3249 that are executed by the main processor 3202 are typically stored in a persistent nonvolatile medium such as the flash memory 3208, which may alternatively be a read-only memory (ROM) or similar storage element (not shown). Those skilled in the art will appreciate that portions of the operating system 3234 and the modules 3236 to 3249, such as specific device applications, or parts thereof, may be temporarily loaded into a volatile store such as the RAM 3206. Other modules can also be included.

The subset of modules 3236 that control basic device operations, including data and voice communication applications, will normally be installed on the multi-vital-sign smartphone system 3200 during its manufacture. Other modules include a message application 3238 that can be any suitable module that allows a user of the multi-vital-sign smartphone system 3200 to transmit and receive electronic messages. Various alternatives exist for the message application 3238 as is well known to those skilled in the art. Messages that have been sent or received by the user are typically stored in the flash memory 3208 of the multi-vital-sign smartphone system 3200 or some other suitable storage element in the multi-vital-sign smartphone system 3200. In one or more implementations, some of the sent and received messages may be stored remotely from the multi-vital-sign smartphone system 3200 such as in a data store of an associated host system with which the multi-vital-sign smartphone system 3200 communicates.

The modules can further include a device state module 3240, a Personal Information Manager (PIM) 3242, and other suitable modules (not shown). The device state module 3240 provides persistence, i.e. the device state module 3240 ensures that important device data is stored in persistent memory, such as the flash memory 3208, so that the data is not lost when the multi-vital-sign smartphone system 3200 is turned off or loses power.

The PIM 3242 includes functionality for organizing and managing data items of interest to the user, such as, but not limited to, e-mail, contacts, calendar events, voice mails, appointments, and task items. A PIM application has the ability to transmit and receive data items via the wireless network 3205. PIM data items may be seamlessly integrated, synchronized, and updated via the wireless network 3205 with the multi-vital-sign smartphone system 3200 subscriber's corresponding data items stored and/or associated with a host computer system. This functionality creates a mirrored host computer on the multi-vital-sign smartphone system 3200 with respect to such items. This can be particularly advantageous when the host computer system is the multi-vital-sign smartphone system 3200 subscriber's office computer system.

The multi-vital-sign smartphone system 3200 also includes a connect module 3244, and an IT policy module 3246. The connect module 3244 implements the communication protocols that are required for the multi-vital-sign smartphone system 3200 to communicate with the wireless infrastructure and any host system, such as an enterprise system, with which the multi-vital-sign smartphone system 3200 is authorized to interface. Examples of a wireless infrastructure and an enterprise system are given in FIGS. 32 and 31, which are described in more detail below.

The connect module 3244 includes a set of APIs that can be integrated with the multi-vital-sign smartphone system 3200 to allow the multi-vital-sign smartphone system 3200 to use any number of services associated with the enterprise system. The connect module 3244 allows the multi-vital-sign smartphone system 3200 to establish an end-to-end secure, authenticated communication pipe with the host system. A subset of applications for which access is provided by the connect module 3244 can be used to pass IT policy commands from the host system to the multi-vital-sign smartphone system 3200. This can be done in a wireless or wired manner. These instructions can then be passed to the IT policy module 3246 to modify the configuration of the multi-vital-sign smartphone system 3200. Alternatively, in some cases, the IT policy update can also be done over a wired connection.

The IT policy module 3246 receives IT policy data that encodes the IT policy. The IT policy module 3246 then ensures that the IT policy data is authenticated by the multi-vital-sign smartphone system 3200. The IT policy data can then be stored in the RAM 3206 in its native form. After the IT policy data is stored, a global notification can be sent by the IT policy module 3246 to all of the applications residing on the multi-vital-sign smartphone system 3200. Applications for which the IT policy may be applicable then respond by reading the IT policy data to look for IT policy rules that are applicable.

The IT policy module 3246 can include a parser 3247, which can be used by the applications to read the IT policy rules. In some cases, another module or application can provide the parser. Grouped IT policy rules, described in more detail below, are retrieved as byte streams, which are then sent (recursively) into the parser to determine the values of each IT policy rule defined within the grouped IT policy rule. In one or more implementations, the IT policy module 3246 can determine which applications are affected by the IT policy data and transmit a notification to only those applications. In either of these cases, for applications that are not being executed by the main processor 3202 at the time of the notification, the applications can call the parser or the IT policy module 3246 when the applications are executed to determine if there are any relevant IT policy rules in the newly received IT policy data.

All applications that support rules in the IT Policy are coded to know the type of data to expect. For example, the value that is set for the "WEP User Name" IT policy rule is known to be a string; therefore the value in the IT policy data that corresponds to this rule is interpreted as a string. As another example, the setting for the "Set Maximum Password Attempts" IT policy rule is known to be an integer, and therefore the value in the IT policy data that corresponds to this rule is interpreted as such.

After the IT policy rules have been applied to the applicable applications or configuration files, the IT policy module 3246 sends an acknowledgement back to the host system to indicate that the IT policy data was received and successfully applied.

The programs 3237 can also include a temporal-variation-amplifier 3248 and a biological vital sign generator 3249. In some implementations, the temporal-variation-amplifier 3248 includes a forehead skin-pixel-identification module 3302, a frequency filter 3306, a regional facial clusterial module 3308 and a frequency filter 3310 as in FIGS. 33 and 34. In some implementations, the temporal-variation-amplifier 3248 includes a forehead skin-pixel-identification module 3302, a spatial bandpass filter 3304, regional facial clusterial module 3308 and a temporal bandpass filter 3504 as in FIG. 35. In some implementations, the temporal-variation-amplifier 3248 includes a pixel-examiner 3602, a temporal variation determiner 3606 and signal processor 3608 as in FIG. 36. In some implementations, the temporal-variation-amplifier 3248 includes a forehead-skin pixel identification module 3702, a frequency-filter module 3708, spatial-cluster module 3712 and a frequency filter module 3716 as in FIGS. 37 and 39. In some implementations, the forehead-skin pixel identification module 3702, a spatial bandpass filter module 4002, a spatial-cluster module 3712 and a temporal bandpass filter module 4006 as in FIG. 40. In some implementations, the temporal-variation-amplifier 3248 includes a pixel-examination-module 4102, a temporal variation determiner module 4106 and a signal processing module 4110 as in FIG. 41. The solid-state image transducer 1728 captures images 1730 and the biological vital sign generator 3249 generates the biological vital sign(s) 3316 that is displayed by display 3210 or transmitted by communication subsystem 1746 or short-range communications subsystem 3222, enunciated by speaker 3218 or stored by flash memory 3208.

Other types of modules can also be installed on the multi-vital-sign smartphone system 3200. These modules can be third party modules, which are added after the manufacture of the multi-vital-sign smartphone system 3200. Examples of third party applications include games, calculators, utilities, etc.

The additional applications can be loaded onto the multi-vital-sign smartphone system 3200 through of the wireless network 3205, the auxiliary I/O subsystem 3212, the data port 3214, the short-range communications subsystem 3222, or any other suitable device subsystem 3224. This flexibility in application installation increases the functionality of the multi-vital-sign smartphone system 3200 and may provide enhanced on-device functions, communication-related functions, or both. For example, secure communication applications may enable electronic commerce functions and other such financial transactions to be performed using the multi-vital-sign smartphone system 3200.

The data port 3214 enables a subscriber to set preferences through an external device or module and extends the capabilities of the multi-vital-sign smartphone system 3200 by providing for information or module downloads to the multi-vital-sign smartphone system 3200 other than through a wireless communication network. The alternate download path may, for example, be used to load an encryption key onto the multi-vital-sign smartphone system 3200 through a direct and thus reliable and trusted connection to provide secure device communication.

The data port 3214 can be any suitable port that enables data communication between the multi-vital-sign smartphone system 3200 and another computing device. The data port 3214 can be a serial or a parallel port. In some instances, the data port 3214 can be a USB port that includes data lines for data transfer and a supply line that can provide a charging current to charge the battery 3230 of the multi-vital-sign smartphone system 3200.

The short-range communications subsystem 3222 provides for communication between the multi-vital-sign smartphone system 3200 and different systems or devices, without the use of the wireless network 3205. For example, the short-range communications subsystem 3222 may include an infrared device and associated circuits and modules for short-range communication. Examples of short-range communication standards include standards developed by the Infrared Data Association (IrDA), Bluetooth®, and the 802.11 family of standards developed by IEEE.

Bluetooth® is a wireless technology standard for exchanging data over short distances (using short-wavelength radio transmissions in the ISM band from 2400-2480 MHz) from fixed and mobile devices, creating personal area networks (PANs) with high levels of security. Created by telecom vendor Ericsson in 1594, Bluetooth® was originally conceived as a wireless alternative to RS-232 data cables. Bluetooth® can connect several devices, overcoming problems of synchronization. Bluetooth® operates in the range of 2400-2483.5 MHz (including guard bands), which is in the globally unlicensed Industrial, Scientific and Medical (ISM) 2.4 GHz short-range radio frequency band. Bluetooth® uses a radio technology called frequency-hopping spread spectrum. The transmitted data is divided into packets and each packet is transmitted on one of the 79 designated Bluetooth® channels. Each channel has a bandwidth of 1 MHz. The first channel starts at 2402 MHz and continues up to 2480 MHz in 1 MHz steps. The first channel usually performs 1600 hops per second, with Adaptive Frequency-Hopping (AFH) enabled. Originally Gaussian frequency-shift keying (GFSK) modulation was the only modulation scheme available; subsequently, since the introduction of Bluetooth® 2.0+EDR, $\pi/4$-DQPSK and 8 DPSK modulation may also be used between compatible devices. Devices functioning with GFSK are said to be operating in basic rate (BR) mode where an instantaneous data rate of 1 Mbit/s is possible. The term Enhanced Data Rate (EDR) is used to describe $\pi/4$-DPSK and 8 DPSK schemes, each giving 2 and 3 Mbit/s respectively. The combination of these (BR and EDR) modes in Bluetooth® radio technology is classified as a "BR/EDR radio". Bluetooth® is a packet-based protocol with a master-slave structure. One master may communicate with up to 7 slaves in a piconet; all devices share the master's clock. Packet exchange is based on the basic clock, defined by the master, which ticks at 452.5 µs intervals. Two clock ticks make up a slot of 625 µs; two slots make up a slot pair of 1250 µs. In the simple case of single-slot packets the master transmits in even slots and receives in odd slots; the slave, conversely, receives in even slots and transmits in odd slots. Packets may be 1, 3 or 5 slots long but in all cases the master transmit will begin in even slots and the slave transmit in odd slots. A master Bluetooth® device can communicate with a maximum of seven devices in a piconet (an ad-hoc computer network using Bluetooth® technology), though not all devices reach this maximum. The devices can switch roles, by agreement, and the slave can become the master (for example, a headset initiating a connection to a phone will necessarily begin as master, as initiator of the connection; but may subsequently prefer to be slave). The Bluetooth® Core Specification provides for the connection of two or more piconets to form a scatternet, in which certain devices simultaneously play the master role in one piconet and the slave role in another. At any given time, data can be transferred between the master and one other device (except for the little-used broadcast mode. The master chooses which slave device to address; typically, the master switches rapidly from one device to another in a round-robin fashion. Since the master chooses which slave to address, whereas a slave is (in theory) supposed to listen in each receive slot, being a master is a lighter burden than being a slave. Being a master of seven slaves is possible; being a slave of more than one master is difficult. Many of the services offered over Bluetooth® can expose private data or allow the connecting party to control the Bluetooth® device. For security reasons it is necessary to be able to recognize specific devices and thus enable control over which devices are allowed to connect to a given Bluetooth® device. At the same time, it is useful for Bluetooth® devices to be able to establish a connection without user intervention (for example, as soon as the Bluetooth® devices of each other are in range). To resolve this conflict, Bluetooth® uses a process called bonding, and a bond is created through a process called pairing. The pairing process is triggered either by a specific request from a user to create a bond (for example, the user explicitly requests to "Add a Bluetooth® device"), or the pairing process is triggered automatically when connecting to a service where (for the first time) the identity of a device is required for security purposes. These two cases are referred to as dedicated bonding and general bonding respectively. Pairing often involves some level of user interaction; this user interaction is the basis for confirming the identity of the devices. Once pairing successfully completes, a bond will have been formed between the two devices, enabling those two devices to connect to each other in the future without requiring the pairing process in order to confirm the identity of the devices. When desired, the bonding relationship can later be removed by the user. Secure Simple Pairing (SSP): This is required by Bluetooth® v2.1, although a Bluetooth® v2.1 device may only use legacy pairing to interoperate with a v2.0 or earlier device. Secure Simple Pairing uses a form of public key cryptography, and some types can help protect against man in the middle, or MITM attacks. SSP has the following characteristics: Just works: As implied by the name, this method just works. No user interaction is required; however, a device may prompt the user to confirm the pairing process. This method is typically used by headsets with very limited IO capabilities, and is more secure than the fixed PIN mechanism which is typically used for legacy pairing by this set of limited devices. This method provides no man in the middle (MITM) protection. Numeric comparison: If both devices have a display and can accept a binary Yes/No user input, both devices may use Numeric Comparison. This method displays a 6-digit numeric code on each device. The user should compare the numbers to ensure that the numbers are identical. If the comparison succeeds, the user(s) should confirm pairing on the device(s) that can accept an input. This method provides MITM protection, assuming the user confirms on both devices and actually performs the comparison properly. Passkey Entry: This method may be used between a device with a display and a device with numeric keypad entry (such as a keyboard), or two devices with numeric keypad entry. In the first case, the display is used to show a 6-digit numeric code to the user, who then enters the code on the keypad. In the second case, the user of each device enters the same 6-digit number. Both of these cases provide MITM protection. Out of band (OOB): This method uses an external means of communication, such as Near Field Communication (NFC) to exchange some information used in the pairing process. Pairing is completed using the Bluetooth® radio, but requires information from the OOB mechanism. This provides only the level of MITM protection that is present in the OOB mechanism. SSP is considered simple for the following reasons: In most cases, SSP does not require a user to generate a passkey. For use-cases not requiring MITM protection, user interaction can be eliminated. For numeric comparison, MITM protection can be achieved with a simple equality comparison by the user. Using OOB with NFC enables pairing when devices simply get close, rather than requiring a lengthy discovery process.

In use, a received signal such as a text message, an e-mail message, or web page download will be processed by the communication subsystem 1746 and input to the main processor 3202. The main processor 3202 will then process the received signal for output to the display 3210 or alternatively to the auxiliary I/O subsystem 3212. A subscriber may also compose data items, such as e-mail messages, for example, using the keyboard 3216 in conjunction with the display 3210 and possibly the auxiliary I/O subsystem 3212. The auxiliary I/O subsystem 3212 may include devices such as: a touch screen, mouse, track ball, infrared fingerprint detector, or a roller wheel with dynamic button pressing capability. The keyboard 3216 is preferably an alphanumeric keyboard and/or telephone-type keypad. However, other types of keyboards may also be used. A composed item may be transmitted over the wireless network 3205 through the communication subsystem 1746.

For voice communications, the overall operation of the multi-vital-sign smartphone system 3200 is substantially similar, except that the received signals are output to the speaker 3218, and signals for transmission are generated by the microphone 3220. Alternative voice or audio I/O subsystems, such as a voice message recording subsystem, can also be implemented on the multi-vital-sign smartphone system 3200. Although voice or audio signal output is accomplished primarily through the speaker 3218, the display 3210 can also be used to provide additional information such as the identity of a calling party, duration of a voice call, or other voice call related information.

Figure 33:
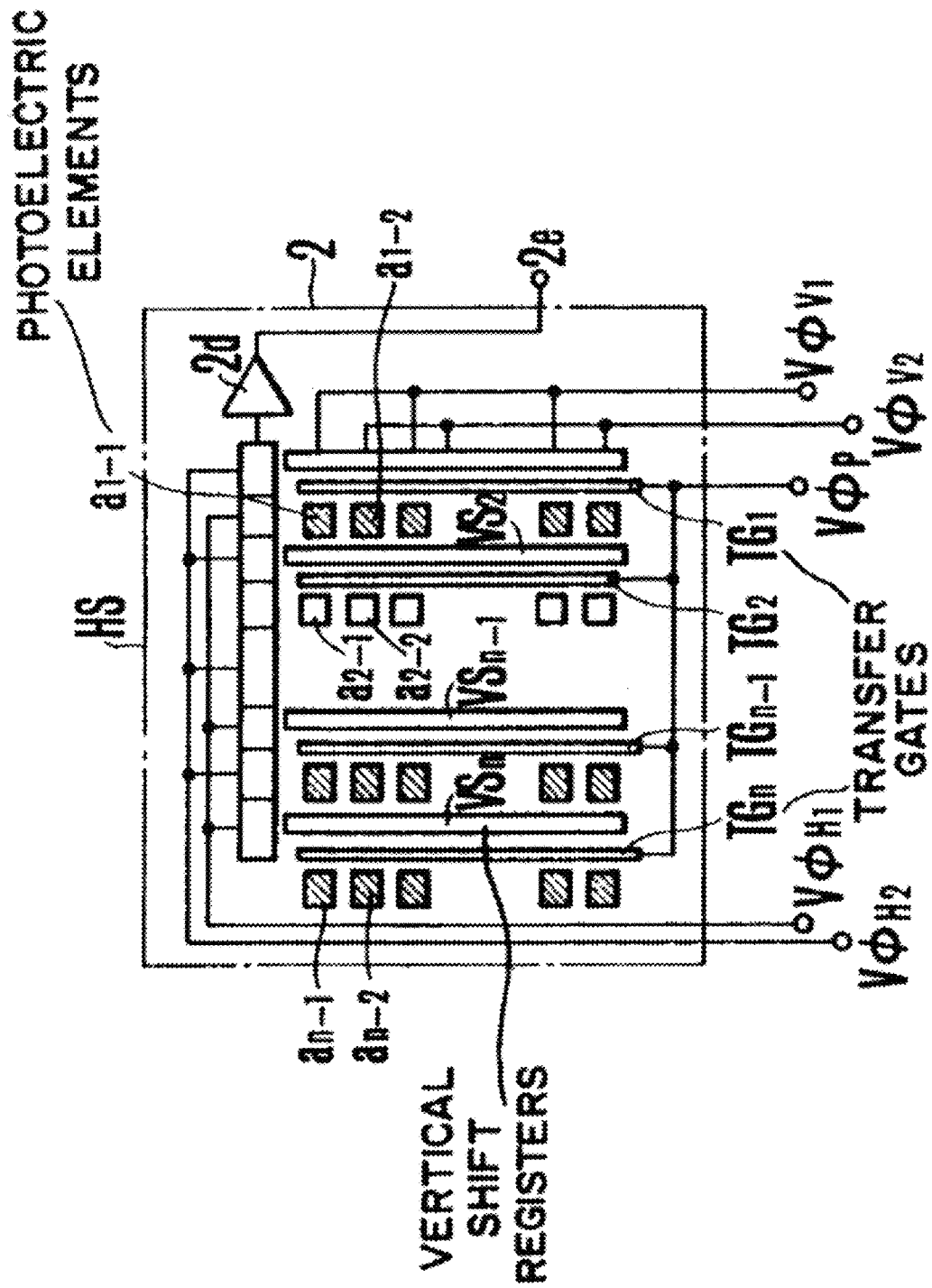
FIG. 33 is a block diagram of a solid-state image transducer.

FIG. 33 is a block diagram of a solid-state image transducer 3300, according to an implementation. The solid-state image transducer 3300 includes a great number of photoelectric elements, $a_1 \ldots sub.1$, $a_2 \ldots sub.1, \ldots, a.sub.mn$, in the minute segment form, transfer gates TG1, TG2, . . . , TGn responsive to a control pulse $V_{\varphi P}$ for transferring the charges stored on the individual photoelectric elements as an image signal to vertical shift registers VS1, VS2, . . . , VSn, and a horizontal shift register HS for transferring the image signal from the vertical shift registers VSs, through a buffer amplifier 2*d* to an outlet 2*e*. After the one-frame image signal is stored, the image signal is transferred to vertical shift register by the pulse $V_{\varphi P}$ and the contents of the vertical shift registers VSs are transferred upward line by line in response to a series of control pulses V.sub.φV1, V.sub.φV2. During the time interval between the successive two vertical transfer control pulses, the horizontal shift register HS responsive to a series of control pulses V.sub.φH1, V.sub.φH2 transfers the contents of the horizontal shift registers HSs in each line row by row to the right as viewed in FIG. 33. As a result, the one-frame image signal is formed by reading out the outputs of the individual photoelectric elements in such order.

Figure 34:
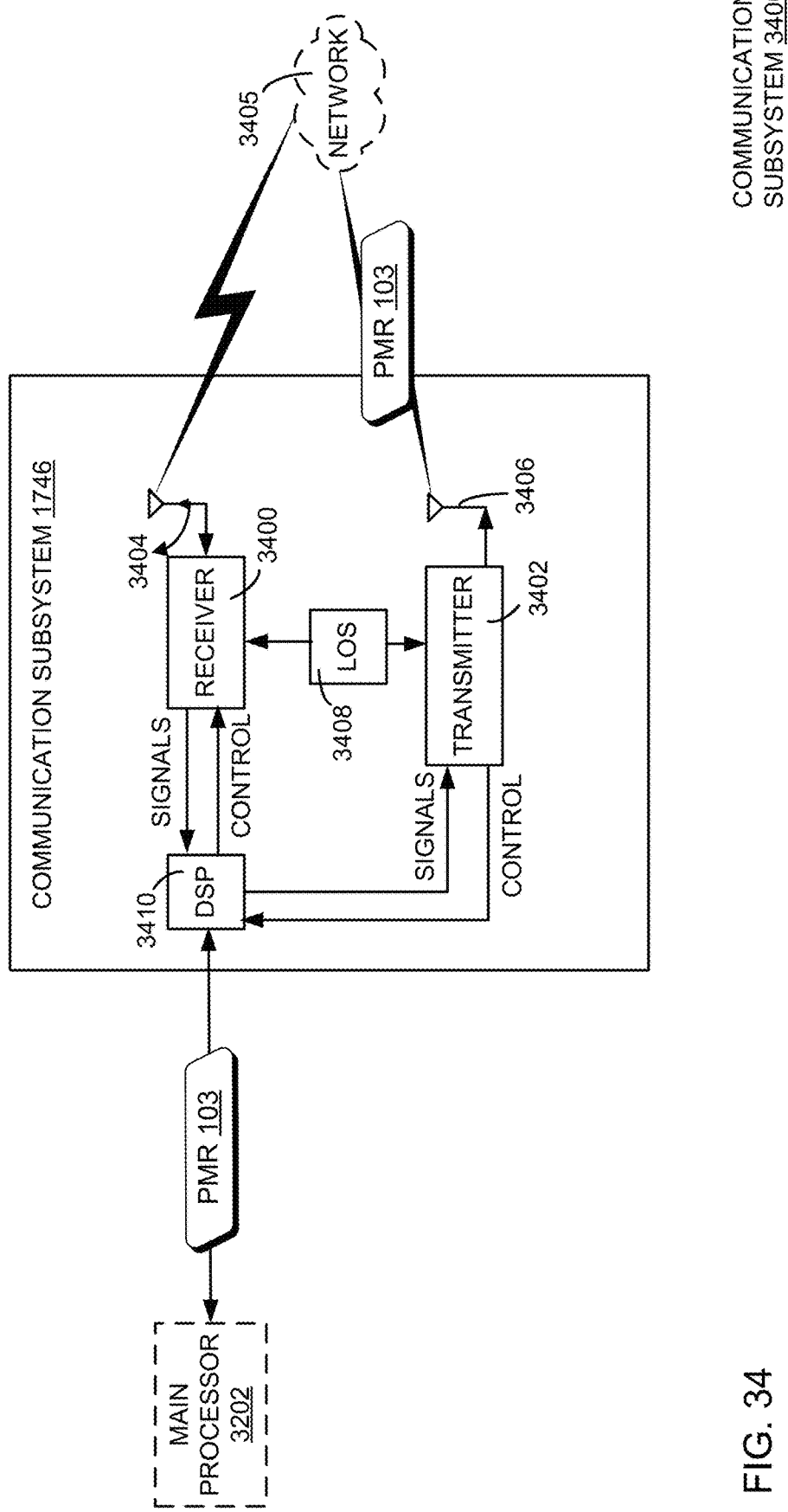
FIG. 34 is a block diagram of a communication subsystem.

FIG. 34 is a block diagram of the wireless communication subsystem 1746, according to an implementation. The wireless communication subsystem 1746 includes a receiver 3400, a transmitter 3402, as well as associated components such as one or more embedded or antennas 3404 and 3406, Local Oscillators (LOs) 3408, and a processing module such as a digital signal processor (DSP) 3410. The particular implementation of the wireless communication subsystem 1746 is dependent upon communication protocols of a wireless network 3405 with which the mobile device is intended to operate. Thus, it should be understood that the implementation illustrated in FIG. 34 serves only as one example. Examples of the multi-vital-sign smartphone system 444 include multi-vital-sign smartphone system 3200, multi-vital-sign smartphone system in FIGS. 4-8 and 7-9, apparatus that estimates a body core temperature 17-18 and multi-vital-sign smartphone system 3200. Examples of the wireless network 3405 include network 3205 in FIG. 32.

Signals received by the antenna 3404 through the wireless network 3405 are input to the receiver 3400, which may perform such common receiver functions as signal amplification, frequency down conversion, filtering, channel selection, and analog-to-digital (A/D) conversion. A/D conversion of a received signal allows more complex communication functions such as demodulation and decoding to be performed in the DSP 3410. In a similar manner, signals to be transmitted are processed, including modulation and encoding, by the DSP 3410. These DSP-processed signals are input to the transmitter 3402 for digital-to-analog (D/A) conversion, frequency up conversion, filtering, amplification and transmission over the wireless network 3405 via the antenna 3406. The DSP 3410 not only processes communication signals, but also provides for receiver and transmitter control. For example, the gains applied to communication signals in the receiver 3400 and the transmitter 3402 may be adaptively controlled through automatic gain control algorithms implemented in the DSP 3410.

The wireless link between the multi-vital-sign smartphone system(s) 104 and the wireless network 3405 can contain one or more different channels, typically different RF channels, and associated protocols used between the multi-vital-sign smartphone system(s) 104 and the wireless network 3405. An RF channel is a limited resource that must be conserved, typically due to limits in overall bandwidth and limited battery power of the multi-vital-sign smartphone system(s) 104.

When the multi-vital-sign smartphone system(s) 104 are fully operational, the transmitter 3402 is typically keyed or turned on only when it is transmitting to the wireless network 3405 and is otherwise turned off to conserve resources. Similarly, the receiver 3400 is periodically turned off to conserve power until the receiver 3400 is needed to receive signals or information (if at all) during designated time periods.

The PMR 103 is received by the wireless communication subsystem 1746 from the main processor 3202 at the DSP 3410 and then transmitted to the wireless network 3405 through the antenna 3404 of the receiver 3400.

Figure 35:
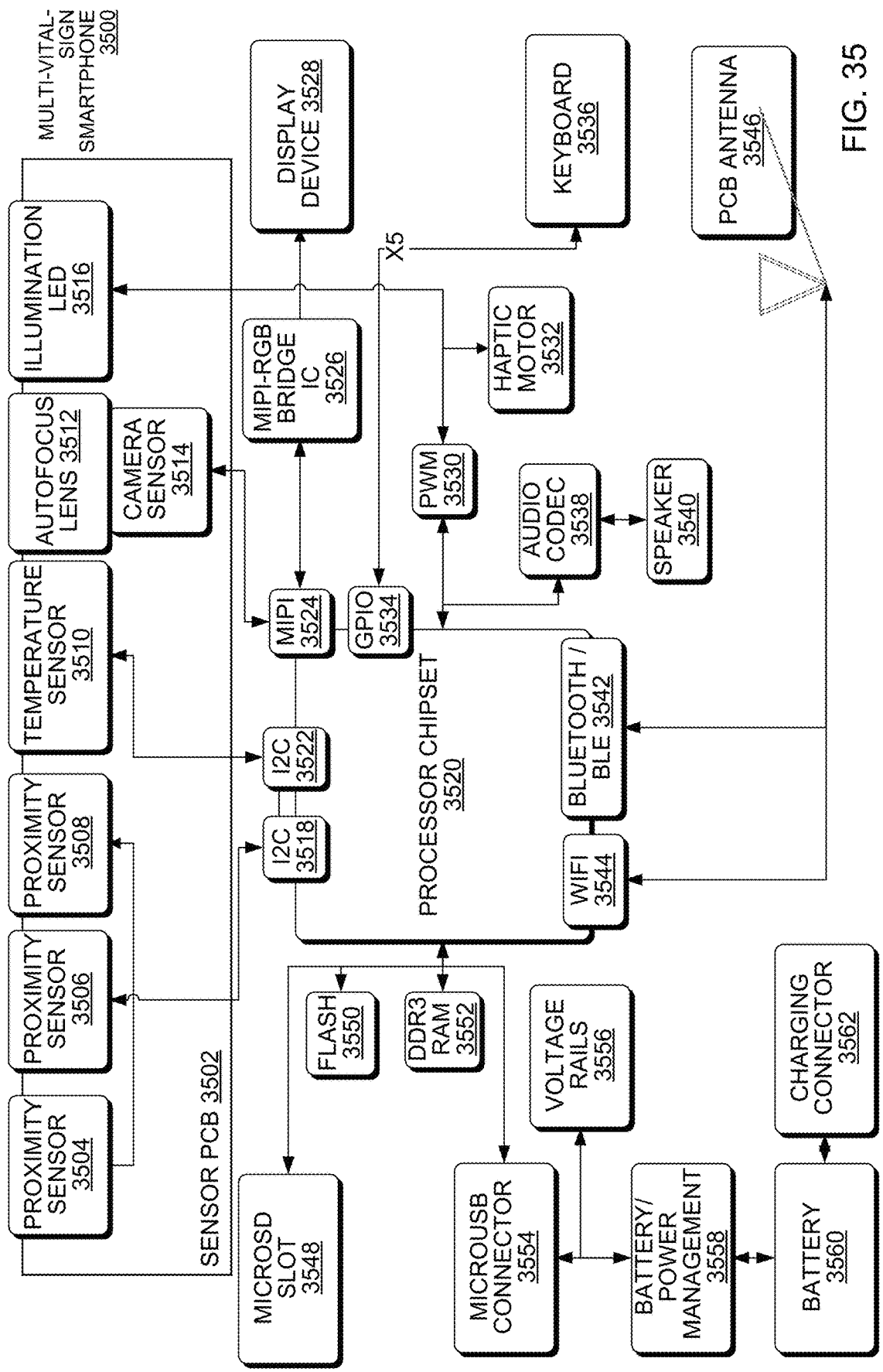
FIG. 35 is a block diagram of a multi-vital-sign smartphone.

FIG. 35 is a block diagram of a multi-vital-sign smartphone (MVS Smartphone) device 3500, according to an implementation. MVS Smartphone 3500 is one implementation of MVS Smartphone 404 in FIG. 4. The MVS Smartphone 3500 includes a sensor printed circuit board (PCB) 3502. The sensor PCB 3502 includes proximity sensors 3504, 3506 and 3508, and temperature sensor 3510, autofocus lens 3512 in front of camera sensor 3514 and an illumination light emitting diode (LED) 3516. The includes proximity sensors 3504, 3506 and 3508 are operably coupled to a first I$^2$C port 3518 of a microprocessor 3520. One example of the microprocessor 3520 is a Qualcomm Snapdragon microprocessor chipset. The temperature sensor 3510 is operably coupled to a second I$^2$C port 3522 of the microprocessor 3520. The I$^2$C standard is a multi-master, multi-slave, single-ended, serial computer bus developed by Philips Semiconductor (now NXP Semiconductors) for attaching lower-speed peripheral ICs to processors and microcontrollers in short-distance, intra-board communication. The camera sensor 3514 is operably coupled to a MIPI port 3524 of the microprocessor 3520. The MIPI standard is defined by the MIPI standard is defined by the MIPI Alliance, Inc. of Piscataway, N.J. The a MIPI port 3524 is also operably coupled to a MIPI RGB bridge 3526, and the MIPI RGB bridge 3526 is operably coupled to a display device 3528 such as a TFT Color Display (2.8"). The illumination LED 3516 is operably coupled to a pulse-width modulator (PWM) 3530 of the microprocessor 3520. The PWM 3530 is also operably coupled to a haptic motor 3532. The microprocessor 3520 also includes a GPIO port 3534, the GPIO port 3534 being a general-purpose input/output that is a generic pin on an integrated circuit or computer board whose behavior—including whether GPIO port 3534 is an input or output pin—is controllable by the microprocessor 3520 at run time. The GPIO port 3534 is operably coupled to a keyboard 3536, such as a membrane keypad (3× buttons). The microprocessor 3520 is also operably coupled to an audio codec 3538 with is operably coupled to a speaker 3540. The microprocessor 3520 also includes a Bluetooth® communication port 3542 and a WiFi® communication port 3544, that are both capable of communicating with a PCB antenna 3546. The microprocessor 3520 is also operably coupled to a micro SD slot (for debugging purposes), a flash memory unit 3550, a DDR3 random access memory unit 3552 and a micro USB port 3554 (for debugging purposes). The micro USB port 3554 is operably coupled to voltage rails and a battery power/management component 3558. The battery power/management component 3558 is operably coupled to a battery 3560, which is operably coupled to a charger connector 3562.

FIG. 36-43 are drawings of various views of a multi-vital-sign finger cuff, according to an implementation. SpO2 subsystem 3602 in FIG. 36-43 is one example of the SpO2 subsystem 418. The mDLS sensors 4302 is the same as the multi-vital-sign finger cuff 506 in FIGS. 5-7, 844 and 846 in FIG. 8, and/or 1742.

Figure 44:
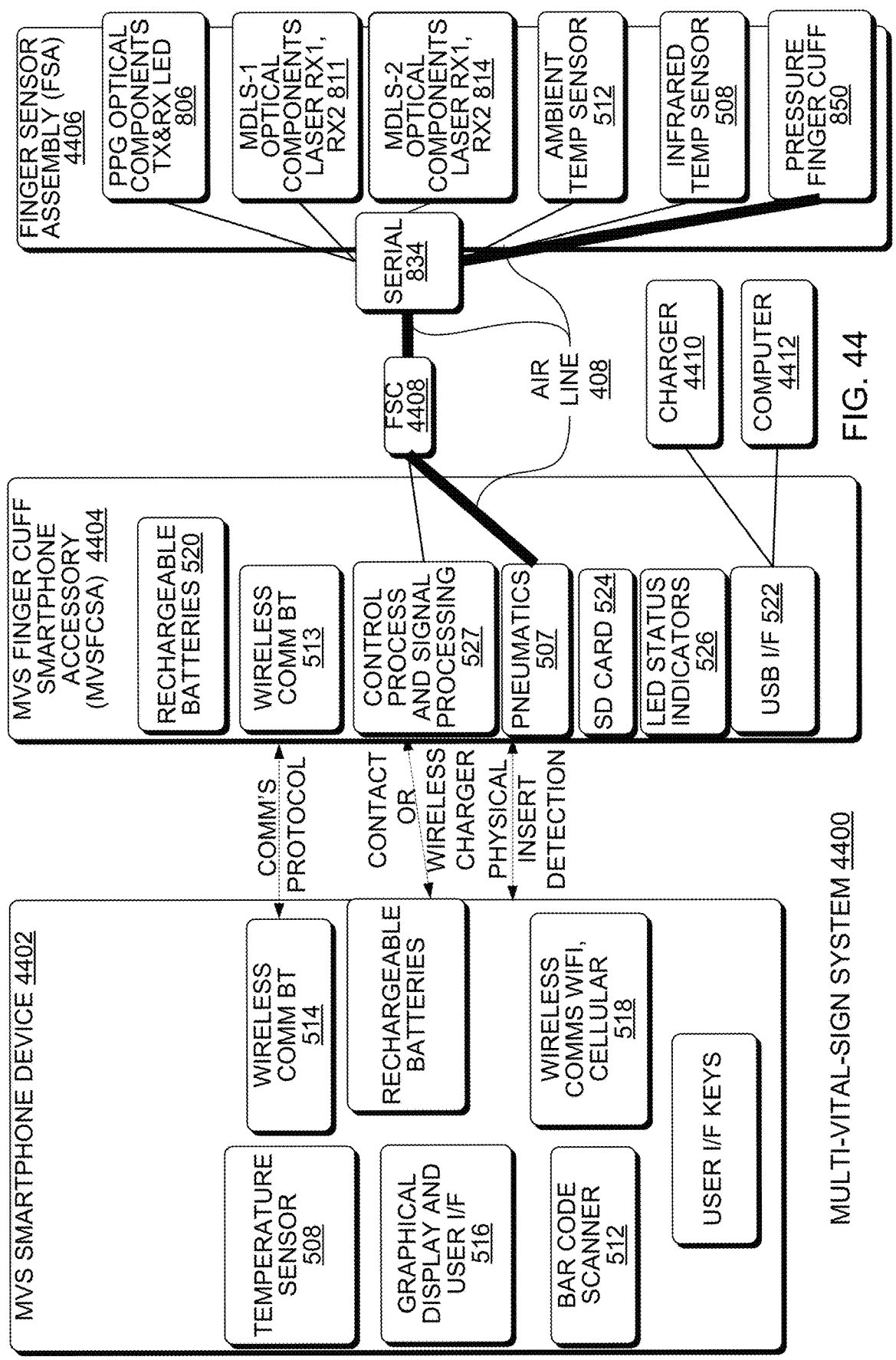
FIG. 44 is a block diagram of a multi-vital-sign smartphone system.

FIG. 44 is a block diagram of a multi-vital-sign smartphone system, according to an implementation. The MVS smartphone system 4400 includes two communicatively coupled devices; a MVS smartphone device 4402 and a MVS Finger Cuff Smartphone Accessory (MVSFCSA) 4404. MVS smartphone device 4402 is one implementation of non-contact human multi-vital sign device 6900 in FIG. 69, MVS Smartphone 404 in FIG. 4, MVS Smartphone 503 in FIG. 5 and MVS Smartphone 1000 in FIG. 10. MVS-FCSA 4404 is one implementation of multi-vital-signs finger cuff smartphone accessory (MVSFCSA) 402 in FIG. 4, MVSFCSA 502 in FIG. 2, MVSFCSA 600 in FIG. 6 and MVSFCSA 700 in FIG. 7. The MVS smartphone system 4400, the MVSFCSA 4404 and the MVS smartphone device 4402 are all examples of the multi-vital-sign capture system(s) 104. The MVS smartphone device 4402 captures, stores and exports raw data from all supported sensors in the MVS smartphone system 4400. More specifically, the MVS smartphone device 4402 extracts the vital signs through the MVSFCSA 4404, displays the vital signs and transfers the vital signs to either a remote third party, hub, bridge etc., or a device manager, or directly to remote EMR/HER/Hospital systems or other third party local or cloud based systems. MVS smartphone system 4400 provides a flexible human vital sign measurement methodology that supports different measurement methods and techniques. The MVS smartphone system 4400 can be used in a clinical setting for the collection of human vital signs.

The MVSFCSA 4404 include a finger sensor assembly (FSA) 4406 that is fixed into the MVSFCSA 4404, rather than the replaceable, detachable and removable multi-vital-sign finger cuff 406 in FIG. 4, the multi-vital-sign finger cuff 506 in FIG. 5, the multi-vital-sign finger cuff 800 in FIG. 8, the multi-vital-sign finger cuff 4700 in FIG. 47-52. The FSA 4406 includes a PPG sensor 806 and at least one mDLS sensor 811 and/or 814. The FSA 4406 is powered by and connected to a finger sensor cable (FSC) 4408 that includes an air line (e.g. 408 in FIG. 4), the air line being powered by a pneumatic engine 507 in the MVSFCSA 4404 that provides air pressure to inflate a cuff bladder of the finger pressure cuff 850 and the controlled release of that air pressure.

In some implementations, a body surface temperature of a human is also sensed by an infrared finger temperature sensor 508 that is integrated into the FSA 4406 in which the body surface temperature is collected and managed by the FSA 4406.

In some implementations, a single stage measurement process is required to measure all vital signs in one operation by the MVS smartphone device 4402, the MVSFCSA 4404 and the FSA 4406 working cooperatively. However, in some implementations, a two stage measurement process is performed in which the MVSFCSA 4404 measures some vital signs through the FSA 4406; and in the second stage, the body surface temperature is measured through an infrared finger temperature sensor 508 in the MVS smartphone device 4402. One implementation of the infrared finger temperature sensor 508 is digital infrared sensor 2100 in FIG. 21.

The MVSFCSA 4404 operates in two primary modes, the modes of operation based on who takes the measurements, a patient or an operator. The two modes are: 1) Operator Mode in which an operator operates the MVSFCSA 4404 through the MVS smartphone device 4402 to take a set of vital sign measurements of another human. The operator is typically clinical staff or a home care giver. 2) Patient Mode in which a patient uses the MVSFCSA 4404 through the MVS smartphone device 4402 to take a set of vital sign measurements of themselves. In some implementations, the MVSFCSA 4404 provides both the main measurement modes for patient and operator. The primary measurement areas on the human to be measured are 1) Left hand, index and middle finger, 2) right hand, index and middle finger, and 3) human forehead temperature (requires the MVS smartphone device 4402 to perform temperature measurement). The MVSFCSA 4404 is portable, light weight, handheld and easy to use in primary and secondary modes of operation in all operational environments.

Given the complex nature of integration into hospital networks, in some implementations, in some implementations the MVSFCSA 4404 does not include site communication infrastructure, rather the collected data (vital sign) is extracted from the MVSFCSA 4404 via a USB port 522 or by a USB mass storage stick that is inserted into the MVSFCSA 4404 or by connecting the MVSFCSA 4404 directly to a PC system as a mass storage device itself.

The MVSFCSA 4404, when connected to a wireless Bluetooth® communication component 514 of the MVS smartphone device 4402 via a wireless Bluetooth® communication component 513, can be a slave to the MVS smartphone device 4402. The MVSFCSA 4404 reports status, measurement process, and measurement measurements to the user via the MVS smartphone device 4402. The MVS smartphone device 4402 provides a user input method to the MVSFCSA 4404 via a graphical user interface on a LCD display 516 which displays data representative of the measurement process and status. In one implementation, the wireless Bluetooth® communication component 514 of the MVS smartphone device 4402 includes communication capability with cellular communication paths (3G, 4G and/or 5G) and/or WiFi® communication paths, the MVS smartphone device 4402 is not a slave to the MVSFCSA 4404 and the MVSFCSA 4404 captures vital sign data and transmits the vital sign data via the wireless Bluetooth® communication component 514 in the MVS smartphone device 4402 and the MVS smartphone device 4402 transmits the vital sign data to the middle layer 106 in FIG. 1 or the MVSFCSA 4404 transmits the vital sign data via the wireless Bluetooth® communication component 513 of the MVSFCSA 4404 to the bridge 120, a WiFi® access point, a cellular communications tower or a bridge 120 in FIG. 1.

In some implementations, the MVS smartphone device 4402 provides communications with other devices via a communication component 517 of the MVS smartphone device 4402. The communication component 517 has communication capability with cellular communication paths (3G, 4G and/or 5G) and/or WiFi® communication paths. For example, the MVSFCSA 4404 captures vital sign data and transmits the vital sign data via the wireless Bluetooth® communication component 513 in the MVSFCSA 4404 to the wireless Bluetooth® communication component 514 in the MVS smartphone device 4402, and the MVS smartphone device 4402 transmits the vital sign data via the communication component 517 of the MVS smartphone device 4402 to the middle layer 106 in FIG. 1 or the MVS smartphone device 4402 transmits the vital sign data via the communication component 517 of the MVS smartphone device 4402 to the bridge 120, a WiFi® access point, a cellular communications tower or a bridge 120 in FIG. 1.

In some implementations, when the MVS smartphone device 4402 is connected to the MVSFCSA 4404, the MVS smartphone device 4402 performs human bar code scan by a bar code scanner 515 or identification entry as requested by MVSFCSA 4404, the MVS smartphone device 4402 performs an operator bar code scan or identification entry as requested by MVSFCSA 4404, the MVS smartphone device 4402 displays information that is related to the MVSFCSA 4404, the MVS smartphone device 4402 starts when the MVSFCSA 4404 is started, and the MVS smartphone device 4402 is shutdown under the direction and control of the MVSFCSA 4404, and the MVS smartphone device 4402 has a self-test mode that determines the operational state of the MVSFCSA 4404 and sub systems, to ensure that the MVSFCSA 4404 is functional for the measurement. In other implementations, In some implementations, when the MVS smartphone device 4402 is connected to the MVSFCSA 4404, the MVS smartphone device 4402 performs human bar code scan by a bar code scanner 515 or identification entry as requested by the MVSFCSA 4404, the MVS smartphone device 4402 performs an operator bar code scan or identification entry as requested by the MVSFCSA 4404, and the MVS smartphone device 4402 displays information that is related to the MVSFCSA 4404. In some implementations, the information displayed by the MVS smartphone device 4402 includes date/time, human identification number, human name, vitals measurement such as blood pressure (diastolic and systolic), SpO2, heart rate, temperature, respiratory rate, MVSFCSA 4404 free memory slots, battery status of the MVS smartphone device 4402, battery status of the MVSFCSA 4404, device status of the MVSFCSA 4404, errors of the MVS smartphone device 4402, device measurement sequence, measurement quality assessment measurement, mode of operation, subject and operator identification, temperature, measurement, display mode and device revision numbers of the MVS smartphone device 4402 and the MVSFCSA 4404. In some implementations, when a body surface temperature of a human is also sensed by an infrared sensor in the MVS smartphone device 4402, the body surface temperature is collected and managed by the MVSFCSA 4404. In other implementations, when a body surface temperature of a human is sensed by an infrared sensor in the MVS smartphone device 4402, the body surface temperature is not collected and managed by the MVSFCSA 4404.

In some implementations, the MVS Finger Cuff Smartphone Accessory (MVSFCSA) 4404 includes the following sensors and sensor signal capture and processing components that are required to extract the required primary and secondary human vital signs measurements: the finger pressure cuff 850, the PPG sensor 806 and two mDLS sensors 844 and 846, the infrared finger temperature sensor 508 and an ambient temperature sensor 512, and in some further implementations, non-disposable sensors for other human vital sign measurements. In some implementations, data sample rates for the PPG sensor 806 is 2×200 Hz×24 bit=9600 bits/sec, for each of the mDLS sensors 844 and 846 is 32 kHz×24 bit=1,572,864 bit/sec and for the ambient temperature sensor is less than 1000 bps. Two mDLS sensors 844 and 846 are included in the FSA 4406 to ensure that one or both sensors 844 and 846 delivers a good quality signal, thus increasing the probability of obtaining a good signal from at least one of the mDLS sensors 844 and 846.

The MVS smartphone device 4402 performs concurrent two stage measurement processes for all measurements. The measurement process performed by the MVSFCSA 4404 is controlled and guided from the MVS smartphone device 4402 via the GUI on the MVSFCSA 4404. The measurements are sequenced and configured to minimize time required to complete all measurements. In some implementations, the MVS smartphone device 4402 calculates the secondary measurements of heart rate variability and blood flow from signals from the PPG sensor 806 and the MDLS sensors 811 and 814. The MVS smartphone device 4402 commands and controls the MVSFCSA 4404 via a wireless Bluetooth® protocol communication line and in some further implementations, the MVSFCSA 4404 communicates to other devices through Bluetooth® protocol communication line (not shown), in addition to the communications with the MVS smartphone device 4402, which could also be concurrent. In some further implementations, the MVS smartphone device 4402 communicates to other devices through Bluetooth® protocol communication line (not shown), in addition to the communications with the MVSFCSA 4404 device, which could also be concurrent.

MVSFCSA 4404 includes USB port 522 to perform the following functions: recharge the internal rechargeable batteries 520 of the MVSFCSA 4404, export sensor data sets to a windows based computer system 4412, firmware update of the MVSFCSA 4404 via an application to control and manage the firmware update of the MVSFCSA 4404 and configuration update of the MVSFCSA 4404. The MVSFCSA 4404 does not update the MVS smartphone device 4402 firmware. The internal rechargeable batteries 520 can be recharged via a USB port 522, which provides charge, and the MVSFCSA 4404 can also include an external direct DC input providing a fast recharge. The internal batteries 520 of the MVSFCSA 4404 can be recharged when the MVSFCSA 4404 is powered-off but while connected to USB or DC input. In some implementations, the MVSFCSA 4404 can recharge the MVS smartphone device 4402 from its internal power source over a wireless charging connection. In some implementations, the internal rechargeable batteries 520 provide sufficient operational life of the MVSFCSA 4404 on a single charge to perform at least 2 days of full measurements before recharging of the internal rechargeable batteries 520 of the MVSFCSA 4404 is required.

In some implementations, the MVSFCSA 4404 includes an internal non-volatile, non-user removable, data storage device 524 for up to 20 human raw measurement data sets. The data storage device 524 can be removed by a technician when the data storage device 524 is determined to be faulty. A human measurement set contains all measurement data and measurements acquired by the MVSFCSA 4404, including the temperature measurement from the MVS smartphone device 4402. The internal memory is protected against data corruption in the event of an abrupt power loss event. The MVSFCSA 4404 and the FSA 4406 have a human-form fit function. The MVSFCSA 4404 also includes anti-microbial exterior material to and an easy clean surface for all sensor and device surfaces. The MVSFCSA 4404 stores in the data storage device 524 an "atomic" human record structure that contains the entire data set recording for a single human measurement containing all human raw sensor signals and readings, extracted human vitals, and system status information. The MVSFCSA 4404 includes self-test components that determine the operational state of the MVSFCSA 4404 and sub systems, to ensure that the MVSFCSA 4404 is functional for measurement. The MVSFCSA 4404 includes a clock function for date and time. In some implementations. The date and time of the MVSFCSA 4404 is updated from the MVS smartphone device 4402. In some implementations, the MVSFCSA 4404 includes user input controls, such as a power on/off switch (start/stop), an emergency stop control to bring the finger pressure cuff 850 to a deflated condition. In some implementations, all other input is supported via the MVS smartphone device 4402 via on screen information of the MVS smartphone device 4402. In some implementations, the MVSFCSA 4404 includes visual indicators 526 such as a fatal fault indicator that indicates device has failed and will not power up, a device fault indicator (that indicates the MVSFCSA 4404 has a fault that would affect the measurement function), battery charging status indicator, battery charged status indicator or a battery fault status indicator.

The components (e.g. 507, 513, 520, 522, 524 and 526) in the MVSFCSA 4404 are controlled by a control process and signal processing component 527. The control process and signal processing component 527 be can implemented in a microprocessor or by a FPGA.

The external USB charger 4410 provides electrical power to recharge the MVSFCSA 4404. The external USB charger 4410 can provide electrical power to recharge the batteries of the MVSFCSA 4404 either via a physical wired connection or via a wireless charger. In some implementations, the external USB charger 4410 does not provide electrical power to the MVSFCSA 4404 because the MVSFCSA 4404 includes internal rechargeable batteries 520 that can be recharged via either USB port 522 or a DC input.

The MVSFCSA 4404 is hand held and portable. The MVSFCSA 4404 includes non-slip/slide exterior surface material.

CONCLUSION

A multi-vital-sign smartphone system that senses temperature, heart rate at rest, heart rate variability, respiration, SpO2, blood flow and blood pressure through a device, and transmits the vital signs to an electronic medical record system. A technical effect of the apparatus and methods disclosed herein is electronic transmission of a body core temperature that is estimated from signals from the non-touch electromagnetic sensor to an electronic medical record system and combination of sensing heart rate at rest, heart rate variability, respiration, SpO2, blood flow and blood pressure. Another technical effect of the apparatus and methods disclosed herein is generating a temporal variation of images from which a biological vital sign can be transmitted to an electronic medical record system. Although specific implementations are illustrated and described herein, it will be appreciated by those of ordinary skill in the art that any arrangement which is generated to achieve the same purpose may be substituted for the specific implementations shown. This application is intended to cover any adaptations or variations. Further implementations of power supply to all devices includes A/C power both as a supplemental power supply to battery power and as a substitute power supply.

In particular, one of skill in the art will readily appreciate that the names of the methods and apparatus are not intended to limit implementations. Furthermore, additional methods and apparatus can be added to the modules, functions can be rearranged among the modules, and new modules to correspond to future enhancements and physical devices used in implementations can be introduced without departing from the scope of implementations. One of skill in the art will readily recognize that implementations are applicable to future vital sign and non-touch temperature sensing devices, different temperature measuring sites on humans or animals, new communication protocols for transmission (of user service, patient service, observation service, and chart service and all current and future application programming interfaces and new display devices.

The terminology used in this application meant to include all temperature sensors, processors and operator environments and alternate technologies which provide the same functionality as described herein.

The invention claimed is:

1. An apparatus comprising:
   a microprocessor;
   a digital infrared sensor operably coupled to the microprocessor;
   an ambient temperature sensor operably coupled to the microprocessor;
   a wireless communication subsystem operably coupled to the microprocessor;
   a battery operably coupled to the microprocessor;
   a pneumatic engine operably coupled to the microprocessor;
   a multi-vital-sign finger cuff that is detachable and removable from the apparatus and that includes:
      a printed circuit board;
      a SpO2 subsystem that is operably coupled to the printed circuit board and that includes a photoplethysmogram sensor and that is operably coupled to the printed circuit board, the photoplethysmogram sensor includes one infrared detector that detects infrared energy at two different transmitted wavelengths, red and near infrared; and
      a finger occlusion cuff including a micro dynamic light scattering sensor, the micro dynamic light scattering sensor includes two photo diode receivers and one laser transmitter, the finger occlusion cuff including a cuff bladder that is transparent to wavelengths of the laser transmitter of the micro dynamic light scattering sensor, and the finger occlusion cuff operably coupled to the printed circuit board; and
   an air-line operably between the finger occlusion cuff of the multi-vital-sign finger cuff and the pneumatic engine,
   the microprocessor is configured to estimate a plurality of vital signs from the micro dynamic light scattering sensor and the photoplethysmogram sensor,
   the apparatus operably couples to a smartphone via the wireless communication subsystem, and
   the apparatus transmits the plurality of vital signs to the smartphone via the wireless communication subsystem.

2. The apparatus of claim 1 wherein the digital infrared sensor further comprises: having only digital readout ports, the digital infrared sensor including a Faraday cage surrounding a single thermopile sensor, a central processing unit and a control block, and generating digital readout signals that are representative of an infrared signal, the vital signs includes a body core temperature and the microprocessor is configured to estimate the body core temperature from the digital readout signals that are representative of the infrared signal in reference to a plurality of tables that are stored in a memory that correlate the digital readout signals that are representative of the infrared signal to the body core temperature.

3. The apparatus of claim 1 further comprising: the digital infrared sensor having no analog sensor readout ports and wherein no analog-to-digital converter is operably coupled between the digital infrared sensor and the microprocessor.

4. The apparatus of claim 1 further comprising:
   a camera that is operably coupled to the microprocessor and configured to provide a plurality of images to the microprocessor; and
   the microprocessor including a cropper module that is configured to receive the plurality of images and configured to crop the plurality of images to exclude a border area of the plurality of images, generating a plurality of cropped images, the microprocessor also including a temporal-variation-amplifier of the plurality of cropped images that is configured to generate a temporal variation, the microprocessor also including a biological vital sign generator that is operably coupled to the temporal-variation-amplifier that is configured to generate a biological vital sign from the temporal variation and the microprocessor also operably coupled to the biological vital sign generator.

5. The apparatus of claim 4, wherein the temporal-variation-amplifier further comprises a forehead skin-pixel-identification module.

6. The apparatus of claim 4, wherein the temporal-variation-amplifier further comprises a regional facial clusterial module.

7. The apparatus of claim 4, wherein the temporal-variation-amplifier further comprises a first frequency filter module.

8. The apparatus of claim 4 wherein the plurality of vital signs includes a blood pressure systolic is estimated from data from the micro dynamic light scattering sensor.

9. The apparatus of claim 8 wherein the plurality of vital signs includes a SpO2 and a heart rate at rest that is estimated from data from the photoplethysmogram sensor, and the plurality of vital signs further includes a respiration rate, a heart rate variability and a blood pressure diastolic that is estimated from data from the micro dynamic light scattering sensor.

10. The apparatus of claim 8 further comprising a storage device that is operably coupled to the biological vital sign generator and that is configured to store the plurality of vital signs.

11. The apparatus of claim 1 wherein the wireless communication subsystem transmits via a short distance wireless communication path and wherein the wireless communication subsystem transmits through an Internet Protocol tunnel.

12. The apparatus of claim 1 wherein the plurality of vital signs includes total hemoglobin (SpHb), PVi, methemoglobin (SpMet), acoustic respiration rate (RRa), carboxyhemoglobin (SpCO), oxygen reserve index (ORi), oxygen content (SpOC) and EEG.

13. The apparatus of claim 1 wherein a connection is established and the plurality of vital signs are pushed from the apparatus through the wireless communication subsystem, thereafter an external device controls flow of the plurality of vital signs between the apparatus and the external device, wherein the connection further comprises an authenticated communication channel.

14. The apparatus of claim 1, wherein the digital infrared sensor further comprises an analog-to-digital converter.

15. The apparatus of claim 1, wherein the apparatus receives control signals from the smartphone via the wireless communication subsystem.

16. An apparatus comprising:
a first microprocessor;
a digital infrared sensor operably coupled to the first microprocessor;
an ambient temperature sensor operably coupled to the first microprocessor;
a battery operably coupled to the first microprocessor;
a multi-vital-sign finger cuff that is detachable and removable from the apparatus and that includes:
 a printed circuit board;
 a SpO2 subsystem that is operably coupled to the printed circuit board and that includes a photoplethysmogram sensor and that is operably coupled to the printed circuit board, the photoplethysmogram sensor includes one infrared detector that detects infrared energy at two different transmitted wavelengths, red and near infrared; and
 a micro dynamic light scattering sensor, the micro dynamic light scattering sensor includes two photo diode receivers and one laser transmitter.

17. The apparatus of claim 16, further comprising
a second microprocessor that is operably coupled to the first microprocessor; and
a wireless communication subsystem that is operably coupled to the second microprocessor,
the apparatus is operable to couple to an other apparatus via the wireless communication subsystem, and
the apparatus is operable to transmit a plurality of vital signs to the other apparatus via the wireless communication subsystem.

18. The apparatus of claim 17,
wherein the second microprocessor is configured to estimate the plurality of vital signs from the micro dynamic light scattering sensor and the photoplethysmogram sensor,
wherein the plurality of vital signs includes a SpO2 and a heart rate at rest that is estimated from data from the photoplethysmogram sensor, and
wherein the plurality of vital signs further includes a respiration rate, a heart rate variability and a blood pressure diastolic that is estimated from data from the micro dynamic light scattering sensor.

19. The apparatus of claim 17 further comprising:
a camera that is operably coupled to the second microprocessor and configured to provide a plurality of images to the second microprocessor; and
the second microprocessor including a cropper module that is configured to receive the plurality of images and configured to crop the plurality of images to exclude a border area of the plurality of images, generating a plurality of cropped images, the second microprocessor also including a temporal-variation-amplifier of the plurality of cropped images that is configured to generate a temporal variation, the second microprocessor also including a biological vital sign generator that is operably coupled to the temporal-variation-amplifier that is configured to generate a biological vital sign from the temporal variation and the second microprocessor also operably coupled to the biological vital sign generator.

20. The apparatus of claim 17 wherein the digital infrared sensor further comprises: having only digital readout ports, the digital infrared sensor including a Faraday cage surrounding a single thermopile sensor, a central processing unit and a control block, and generating digital readout signals that are representative of an infrared signal, the vital signs includes a body core temperature and the second microprocessor is configured to estimate the body core temperature from the digital readout signals that are representative of the infrared signal in reference to a plurality of tables that are stored in a memory that correlate the digital readout signals that are representative of the infrared signal to the body core temperature.

* * * * *